(12) United States Patent
Sommer et al.

(10) Patent No.: US 11,788,085 B2
(45) Date of Patent: *Oct. 17, 2023

(54) TREATING AND PREVENTING MICROBIAL INFECTIONS

(71) Applicant: SNIPR Biome ApS, Copenhagen Ø (DE)

(72) Inventors: Morten Sommer, Copenhagen Ø (DE); Virginia Martinez, Copenhagen Ø (DK); Eric Van Der Helm, Copenhagen Ø (DE); Jakob Krause Haaber, Copenhagen Ø (DK); Ana De Santiago Torio, Copenhagen Ø (DK); Christian Grøndahl, London (GB); Jasper Clube, London (GB)

(73) Assignee: SNIPR Biome ApS, Copenhagen Ø (DK)

( * ) Notice: Subject to any disclaimer, the term of this patent is extended or adjusted under 35 U.S.C. 154(b) by 0 days.

This patent is subject to a terminal disclaimer.

(21) Appl. No.: 17/748,875

(22) Filed: May 19, 2022

(65) Prior Publication Data

US 2022/0290133 A1 Sep. 15, 2022

Related U.S. Application Data

(63) Continuation of application No. 17/029,860, filed on Sep. 23, 2020, now Pat. No. 11,485,973, which is a continuation of application No. 16/700,856, filed on Dec. 2, 2019, now Pat. No. 10,920,222, which is a continuation of application No. 15/967,484, filed on Apr. 30, 2018, now Pat. No. 10,760,075.

(51) Int. Cl.
| | |
|---|---|
| *C12N 15/11* | (2006.01) |
| *A61P 31/04* | (2006.01) |
| *A61K 39/395* | (2006.01) |
| *A61K 38/46* | (2006.01) |
| *C07K 16/28* | (2006.01) |

(52) U.S. Cl.
CPC ............ *C12N 15/11* (2013.01); *A61K 38/465* (2013.01); *A61K 39/3955* (2013.01); *A61K 39/39558* (2013.01); *A61P 31/04* (2018.01); *C07K 16/2818* (2013.01); *C07K 16/2827* (2013.01); *C12N 2310/20* (2017.05); *C12N 2320/30* (2013.01); *C12N 2320/31* (2013.01); *Y02A 50/30* (2018.01)

(58) Field of Classification Search
CPC .................. C12N 15/11; A61P 31/04
See application file for complete search history.

(56) References Cited

U.S. PATENT DOCUMENTS

| | | |
|---|---|---|
| 4,626,504 A | 12/1986 | Puhler |
| 4,870,287 A | 9/1989 | Cole |
| 5,633,154 A | 5/1997 | Schaefer |
| 5,760,395 A | 6/1998 | Johnstone |
| 5,844,905 A | 12/1998 | Mckay |
| 5,885,796 A | 3/1999 | Linsley |
| 6,207,156 B1 | 3/2001 | Kuchroo |
| 7,459,272 B2 | 12/2008 | Morris |
| 8,003,323 B2 | 8/2011 | Morris |
| 8,008,449 B2 | 8/2011 | Korman |
| 8,017,114 B2 | 9/2011 | Korman |
| 8,119,129 B2 | 2/2012 | Jure-kunkel |
| 8,241,498 B2 | 8/2012 | Summer |
| 8,252,576 B2 | 8/2012 | Campbell |
| 8,329,867 B2 | 12/2012 | Lazar |
| 8,354,509 B2 | 1/2013 | Carven |
| 8,735,553 B1 | 5/2014 | Li |
| 8,906,682 B2 | 12/2014 | June |
| 8,911,993 B2 | 12/2014 | June |
| 8,916,381 B1 | 12/2014 | June |
| 8,975,071 B1 | 3/2015 | June |
| 9,101,584 B2 | 8/2015 | June |
| 9,102,760 B2 | 8/2015 | June |
| 9,102,761 B2 | 8/2015 | June |
| 9,113,616 B2 | 8/2015 | Stevens |
| 9,328,156 B2 | 5/2016 | June |
| 9,464,140 B2 | 10/2016 | June |
| 9,481,728 B2 | 11/2016 | June |
| 9,499,629 B2 | 11/2016 | June |
| 9,518,123 B2 | 12/2016 | June |
| 9,540,445 B2 | 1/2017 | June |
| 9,701,964 B2 | 7/2017 | Clube |
| 9,758,583 B2 | 9/2017 | Wang |

(Continued)

FOREIGN PATENT DOCUMENTS

| | | |
|---|---|---|
| CA | 3010891 A1 | 7/2017 |
| EP | 2320940 B1 | 5/2011 |

(Continued)

OTHER PUBLICATIONS

Mancha-Agresti et al., Molecular Therapy: Methods & Clinical Development, 2017; 4: 83-91 (Year: 2017).*

(Continued)

*Primary Examiner* — Brian Gangle
*Assistant Examiner* — Lakia J Jackson-Tongue
(74) *Attorney, Agent, or Firm* — MORRISON & FOERSTER LLP

(57) ABSTRACT

The invention provides methods for treating or preventing microbial (eg, bacterial) infections and means for performing these methods. In particular, treatment of infections requiring rapid and durable therapy is made possible, such as for treating acute conditions such as septicemia, sepsis, SIRS or septic shock. The invention is particularly useful, for example, for treatment of microbes such as for environmental, food and beverage use. The invention relates inter alia to methods of controlling microbiologically influenced corrosion (MIC) or biofouling of a substrate or fluid in an industrial or domestic system. The invention also useful for the treatment of pathogenic bacterial infections in subjects receiving a treatment for a disease or condition, such as a transplant or a treatment for cancer, a viral infection or an autoimmune disease.

28 Claims, 9 Drawing Sheets

Specification includes a Sequence Listing.

(56) References Cited

U.S. PATENT DOCUMENTS

| | | |
|---|---|---|
| 9,822,372 B2 | 11/2017 | Zhang |
| 9,879,269 B2 | 1/2018 | Barrangou |
| 10,066,233 B2 | 9/2018 | Barrangou |
| 10,136,639 B2 | 11/2018 | Wuest |
| 10,136,649 B2 | 11/2018 | Barrangou |
| 10,195,273 B2 | 2/2019 | Clube |
| 10,300,138 B2 | 5/2019 | Clube |
| 10,300,139 B2 | 5/2019 | Clube |
| 10,363,308 B2 | 7/2019 | Clube |
| 10,463,049 B2 | 11/2019 | Clube |
| 10,506,812 B2 | 12/2019 | Clube |
| 10,524,477 B2 | 1/2020 | Clube |
| 10,561,148 B2 | 2/2020 | Clube |
| 10,582,712 B2 | 3/2020 | Clube |
| 10,596,255 B2 | 3/2020 | Clube |
| 10,603,379 B2 | 3/2020 | Clube |
| 10,624,349 B2 | 4/2020 | Clube |
| 10,760,065 B2 | 9/2020 | Lu et al. |
| 10,760,075 B2 | 9/2020 | Sommer et al. |
| 10,765,740 B2 | 9/2020 | Clube et al. |
| 10,920,222 B2 * | 2/2021 | Sommer ............... C12N 15/11 |
| 10,953,090 B2 | 3/2021 | Clube et al. |
| 11,141,481 B2 | 10/2021 | Clube |
| 11,147,830 B2 | 10/2021 | Clube |
| 11,291,723 B2 | 4/2022 | Clube |
| 11,351,252 B2 | 6/2022 | Clube |
| 2003/0049841 A1 | 3/2003 | Short |
| 2004/0096974 A1 | 5/2004 | Herron |
| 2005/0118719 A1 | 6/2005 | Schmidt |
| 2009/0155768 A1 | 6/2009 | Scholl |
| 2010/0076057 A1 | 3/2010 | Sontheimer |
| 2010/0093617 A1 | 4/2010 | Barrangou |
| 2010/0172874 A1 | 7/2010 | Turnbaugh |
| 2011/0002889 A1 | 1/2011 | Barrangou |
| 2011/0008369 A1 | 1/2011 | Finnefrock |
| 2011/0136688 A1 | 6/2011 | Scholl |
| 2011/0143997 A1 | 6/2011 | Henry et al. |
| 2012/0177645 A1 | 7/2012 | Langermann |
| 2012/0269859 A1 | 10/2012 | Minato |
| 2012/0294796 A1 | 11/2012 | Johnson |
| 2013/0011828 A1 | 1/2013 | Barrangou |
| 2013/0109053 A1 | 5/2013 | Macdonald |
| 2013/0121968 A1 | 5/2013 | Quay |
| 2013/0287748 A1 | 10/2013 | June |
| 2013/0288368 A1 | 10/2013 | June |
| 2013/0309258 A1 | 11/2013 | June |
| 2014/0022021 A1 | 1/2014 | Kusachi |
| 2014/0068797 A1 | 3/2014 | Doudna |
| 2014/0105912 A1 | 4/2014 | Noelle |
| 2014/0106449 A1 | 4/2014 | June |
| 2014/0107092 A1 | 4/2014 | Meyerson |
| 2014/0179726 A1 | 6/2014 | Bajaj |
| 2014/0199767 A1 | 7/2014 | Barrangou |
| 2014/0234972 A1 | 8/2014 | Zhang |
| 2014/0294898 A1 | 10/2014 | Miller |
| 2014/0341920 A1 | 11/2014 | Noelle |
| 2014/0349400 A1 | 11/2014 | Jakimo et al. |
| 2014/0370017 A1 | 12/2014 | June |
| 2015/0004705 A1 | 1/2015 | Lu et al. |
| 2015/0031134 A1 | 1/2015 | Zhang |
| 2015/0050699 A1 | 2/2015 | Siksnys |
| 2015/0050729 A1 | 2/2015 | June |
| 2015/0064138 A1 | 3/2015 | Lu |
| 2015/0093822 A1 | 4/2015 | June |
| 2015/0099299 A1 | 4/2015 | June |
| 2015/0118202 A1 | 4/2015 | June |
| 2015/0125463 A1 | 5/2015 | Cogswell |
| 2015/0132419 A1 | 5/2015 | Arvik |
| 2015/0139943 A1 | 5/2015 | Campana |
| 2015/0140001 A1 | 5/2015 | Lee |
| 2015/0184139 A1 | 7/2015 | Zhang |
| 2015/0225730 A1 | 8/2015 | Minshull et al. |
| 2015/0232881 A1 | 8/2015 | Glucksmann |
| 2015/0290244 A1 | 10/2015 | June |
| 2015/0353905 A1 | 12/2015 | Weiss |
| 2016/0009805 A1 | 1/2016 | Kowanetz |
| 2016/0009813 A1 | 1/2016 | Themeli |
| 2016/0024510 A1 | 1/2016 | Bikard |
| 2016/0040215 A1 | 2/2016 | Henn et al. |
| 2016/0081314 A1 | 3/2016 | Thurston |
| 2016/0115488 A1 | 4/2016 | Zhang |
| 2016/0115489 A1 | 4/2016 | Zhang |
| 2016/0130355 A1 | 5/2016 | June |
| 2016/0159905 A1 | 6/2016 | Abdiche |
| 2016/0159907 A1 | 6/2016 | June |
| 2016/0160186 A1 | 6/2016 | Parsley |
| 2016/0194404 A1 | 7/2016 | June |
| 2016/0208012 A1 | 7/2016 | June |
| 2016/0237455 A1 | 8/2016 | Glucksmann |
| 2016/0244784 A1 | 8/2016 | Jacobson et al. |
| 2016/0281053 A1 | 9/2016 | Sorek |
| 2016/0324938 A1 | 11/2016 | Bikard |
| 2016/0333348 A1 | 11/2016 | Clube |
| 2016/0339064 A1 | 11/2016 | Kovarik et al. |
| 2016/0345578 A1 | 12/2016 | Barrangou |
| 2016/0347836 A1 | 12/2016 | Grosso |
| 2016/0354416 A1 | 12/2016 | Gajewski |
| 2017/0022499 A1 | 1/2017 | Lu |
| 2017/0037416 A1 | 2/2017 | Barrangou |
| 2017/0106025 A1 | 4/2017 | Kovarik |
| 2017/0106026 A1 | 4/2017 | Kovarik |
| 2017/0114351 A1 | 4/2017 | Mahfouz |
| 2017/0143772 A1 | 5/2017 | Mulder |
| 2017/0173085 A1 | 6/2017 | Kovarik |
| 2017/0174713 A1 | 6/2017 | Du |
| 2017/0175142 A1 | 6/2017 | Zhang |
| 2017/0196225 A1 | 7/2017 | Clube |
| 2017/0246221 A1 | 8/2017 | Clube |
| 2017/0247690 A1 | 8/2017 | Quake |
| 2017/0304443 A1 | 10/2017 | Lebwohl |
| 2017/0327582 A1 | 11/2017 | Bissonnette |
| 2017/0340733 A1 | 11/2017 | Cao |
| 2018/0015131 A1 | 1/2018 | Gajewski |
| 2018/0055852 A1 | 3/2018 | Kutok |
| 2018/0064114 A1 | 3/2018 | Clube |
| 2018/0064115 A1 | 3/2018 | Clube |
| 2018/0070594 A1 | 3/2018 | Clube |
| 2018/0084785 A1 | 3/2018 | Clube |
| 2018/0084786 A1 | 3/2018 | Clube |
| 2018/0140698 A1 | 5/2018 | Clube |
| 2018/0146681 A1 | 5/2018 | Clube |
| 2018/0147221 A1 | 5/2018 | Von Maltzahn et al. |
| 2018/0155721 A1 | 6/2018 | Lu |
| 2018/0155729 A1 | 6/2018 | Beisel |
| 2018/0161368 A1 | 6/2018 | Odegard |
| 2018/0179547 A1 | 6/2018 | Zhang |
| 2018/0200342 A1 | 7/2018 | Bikard |
| 2018/0273937 A1 | 9/2018 | Beisel et al. |
| 2018/0273940 A1 | 9/2018 | Sommer |
| 2018/0303934 A1 | 10/2018 | Clube |
| 2018/0326057 A1 | 11/2018 | Clube |
| 2018/0355378 A1 | 12/2018 | Krom et al. |
| 2018/0371405 A1 * | 12/2018 | Barrangou ............. C12N 15/113 |
| 2019/0015441 A1 | 1/2019 | Shachar |
| 2019/0021343 A1 | 1/2019 | Barrangou |
| 2019/0070233 A1 | 3/2019 | Yeung |
| 2019/0117709 A1 | 4/2019 | Kovarik |
| 2019/0133135 A1 | 5/2019 | Clube |
| 2019/0134194 A1 | 5/2019 | Clube |
| 2019/0136230 A1 | 5/2019 | Sather |
| 2019/0142881 A1 | 5/2019 | Turner et al. |
| 2019/0160120 A1 | 5/2019 | Haaber |
| 2019/0230936 A1 | 8/2019 | Clube |
| 2019/0240325 A1 | 8/2019 | Clube |
| 2019/0240326 A1 | 8/2019 | Clube |
| 2019/0255084 A1 | 8/2019 | Schentag |
| 2019/0256900 A1 | 8/2019 | Zhang |
| 2019/0298779 A1 | 10/2019 | Falb |
| 2019/0321468 A1 | 10/2019 | Clube et al. |
| 2019/0321469 A1 | 10/2019 | Clube et al. |
| 2019/0321470 A1 | 10/2019 | Clube |
| 2019/0359933 A1 | 11/2019 | Swee |
| 2020/0030444 A1 | 1/2020 | Clube |
| 2020/0046773 A1 | 2/2020 | Borody |

(56) References Cited

U.S. PATENT DOCUMENTS

| | | | |
|---|---|---|---|
| 2020/0068901 A1 | 3/2020 | Clube | |
| 2020/0077663 A1 | 3/2020 | Clube | |
| 2020/0085066 A1 | 3/2020 | Clube | |
| 2020/0087660 A1 | 3/2020 | Sommer | |
| 2020/0102551 A1 | 4/2020 | Barrangou | |
| 2020/0115716 A1 | 4/2020 | Martinez | |
| 2020/0121787 A1 | 4/2020 | Clube | |
| 2020/0128832 A1 | 4/2020 | Clube | |
| 2020/0157237 A1 | 5/2020 | Regev | |
| 2020/0164070 A1 | 5/2020 | Clube | |
| 2020/0179460 A1 | 6/2020 | Kovarik | |
| 2020/0199570 A1 | 6/2020 | Novick | |
| 2020/0205416 A1 | 7/2020 | Clube | |
| 2020/0267992 A1 | 8/2020 | Clube | |
| 2020/0282027 A1 | 9/2020 | Bikard et al. | |
| 2020/0337313 A1 | 10/2020 | Clube | |
| 2020/0354690 A1 | 11/2020 | Garofolo | |
| 2020/0390886 A1 | 12/2020 | Clube | |
| 2021/0009996 A1* | 1/2021 | Sommer | C07K 16/2827 |
| 2021/0113689 A1 | 4/2021 | Clube | |
| 2021/0145006 A1 | 5/2021 | Clube | |
| 2021/0147827 A1 | 5/2021 | Clube | |
| 2021/0147857 A1 | 5/2021 | Clube | |
| 2021/0163960 A1 | 6/2021 | Martinez et al. | |
| 2021/0189406 A1 | 6/2021 | Martinez et al. | |
| 2021/0198665 A1* | 7/2021 | Sommer | A61K 39/3955 |
| 2021/0230559 A1 | 7/2021 | Clube | |
| 2021/0283167 A1 | 9/2021 | Clube | |
| 2021/0290654 A1 | 9/2021 | Clube | |
| 2021/0386773 A1 | 12/2021 | Clube | |
| 2022/0259588 A1 | 8/2022 | Sommer et al. | |
| 2022/0282245 A1 | 9/2022 | Sommer et al. | |

FOREIGN PATENT DOCUMENTS

| | | |
|---|---|---|
| EP | 2325332 A1 | 5/2011 |
| EP | 2840140 A1 | 2/2015 |
| EP | 3461337 A1 | 4/2019 |
| EP | 3132035 B8 | 4/2020 |
| EP | 3132036 B8 | 4/2020 |
| EP | 3630975 A1 | 4/2020 |
| EP | 3633032 A2 | 4/2020 |
| EP | 3634442 A1 | 4/2020 |
| EP | 3634473 A1 | 4/2020 |
| RU | 2531343 C2 | 10/2014 |
| WO | 1995001994 A1 | 1/1995 |
| WO | 1998042752 A1 | 10/1998 |
| WO | 2000037504 A2 | 6/2000 |
| WO | 2000037504 A3 | 6/2000 |
| WO | 2001014424 A2 | 3/2001 |
| WO | 2001014424 A3 | 3/2001 |
| WO | 2005003168 A2 | 1/2005 |
| WO | 2005009465 A1 | 2/2005 |
| WO | 2005003168 A3 | 5/2005 |
| WO | 2005046579 A2 | 5/2005 |
| WO | 2005046579 A3 | 8/2005 |
| WO | 2006003179 A2 | 1/2006 |
| WO | 2006003179 A3 | 5/2006 |
| WO | 2006072625 A2 | 7/2006 |
| WO | 2006072626 A1 | 7/2006 |
| WO | 2006121168 A1 | 11/2006 |
| WO | 2006072625 A3 | 12/2006 |
| WO | 2007025097 A2 | 3/2007 |
| WO | 2007042573 A2 | 4/2007 |
| WO | 2007025097 A3 | 7/2007 |
| WO | 2007042573 A3 | 7/2007 |
| WO | 2008084106 A1 | 7/2008 |
| WO | 2008108989 A2 | 9/2008 |
| WO | 2008132601 A1 | 11/2008 |
| WO | 2008108989 A3 | 3/2009 |
| WO | 2009044273 A2 | 4/2009 |
| WO | 2009101611 A1 | 8/2009 |
| WO | 2008084106 A9 | 9/2009 |
| WO | 2009044273 A3 | 9/2009 |
| WO | 2009114335 A2 | 9/2009 |
| WO | 2010011961 A2 | 1/2010 |
| WO | 2010027827 A2 | 3/2010 |
| WO | 2010027827 A3 | 5/2010 |
| WO | 2009114335 A3 | 6/2010 |
| WO | 2010011961 A1 | 6/2010 |
| WO | 2010065939 A1 | 6/2010 |
| WO | 2010075424 A2 | 7/2010 |
| WO | 2010075424 A3 | 9/2010 |
| WO | 2011014438 A1 | 2/2011 |
| WO | 2011066342 A2 | 6/2011 |
| WO | 2011066342 A3 | 7/2011 |
| WO | 2012071411 A2 | 5/2012 |
| WO | 2012079000 A1 | 6/2012 |
| WO | 2012071411 A3 | 8/2012 |
| WO | 2012079000 A4 | 8/2012 |
| WO | 2012160448 A2 | 11/2012 |
| WO | 2012164565 A1 | 12/2012 |
| WO | 2013006490 A2 | 1/2013 |
| WO | 2013025779 A1 | 2/2013 |
| WO | 2012160448 A3 | 5/2013 |
| WO | 2013063361 A1 | 5/2013 |
| WO | 2013067492 A1 | 5/2013 |
| WO | 2013176772 A1 | 11/2013 |
| WO | 2014012001 A2 | 1/2014 |
| WO | 2014015252 A1 | 1/2014 |
| WO | 2014018423 A2 | 1/2014 |
| WO | 2014018423 A3 | 1/2014 |
| WO | 2013006490 A3 | 5/2014 |
| WO | 2014093595 A1 | 6/2014 |
| WO | 2014093661 A2 | 6/2014 |
| WO | 2014093661 A3 | 8/2014 |
| WO | 2014124226 A1 | 8/2014 |
| WO | WO 2014/124226 A1 * | 8/2014 |
| WO | 2014093661 A9 | 10/2014 |
| WO | 2014204725 A1 | 12/2014 |
| WO | 2015016718 A1 | 2/2015 |
| WO | 2015034872 A2 | 3/2015 |
| WO | 2014012001 A3 | 4/2015 |
| WO | 2015034872 A3 | 4/2015 |
| WO | 2015058018 A1 | 4/2015 |
| WO | 2015069682 A2 | 5/2015 |
| WO | 2015070083 A1 | 5/2015 |
| WO | 2015071474 A2 | 5/2015 |
| WO | 2015075688 A1 | 5/2015 |
| WO | 2015088643 A1 | 6/2015 |
| WO | 2015089351 A1 | 6/2015 |
| WO | 2015089419 A2 | 6/2015 |
| WO | 2015069682 A3 | 7/2015 |
| WO | 2015071474 A3 | 8/2015 |
| WO | 2015089419 A3 | 9/2015 |
| WO | 2015136541 A2 | 9/2015 |
| WO | 2015148680 A1 | 10/2015 |
| WO | 2015153940 A1 | 10/2015 |
| WO | 2015155686 A2 | 10/2015 |
| WO | 2015159068 A1 | 10/2015 |
| WO | 2015159086 A1 | 10/2015 |
| WO | 2015159087 A1 | 10/2015 |
| WO | 2015136541 A3 | 11/2015 |
| WO | 2015155686 A3 | 12/2015 |
| WO | 2016044745 A1 | 3/2016 |
| WO | 2016063263 A2 | 4/2016 |
| WO | 2016063263 A3 | 6/2016 |
| WO | 2016084088 A1 | 6/2016 |
| WO | 2016177682 A1 | 11/2016 |
| WO | 2016196361 A1 | 12/2016 |
| WO | 2016196605 A1 | 12/2016 |
| WO | 2016205276 A1 | 12/2016 |
| WO | 2017009399 A1 | 1/2017 |
| WO | 2017042347 A1 | 3/2017 |
| WO | 2017058751 A1 | 4/2017 |
| WO | 2017112620 A1 | 6/2017 |
| WO | 2017118598 A1 | 7/2017 |
| WO | 2017211753 A1 | 12/2017 |
| WO | 2018064165 A2 | 4/2018 |
| WO | 2018081502 A1 | 5/2018 |
| WO | 2018115519 A1 | 6/2018 |
| WO | 2018217351 A1 | 11/2018 |
| WO | 2018217981 A1 | 11/2018 |
| WO | 2018222969 A1 | 12/2018 |

(56) References Cited

FOREIGN PATENT DOCUMENTS

| | | |
|---|---|---|
| WO | 2018226853 A1 | 12/2018 |
| WO | 2019002218 A2 | 1/2019 |
| WO | 2019002218 A3 | 2/2019 |
| WO | 2018064165 A3 | 6/2019 |
| WO | 2020072248 A1 | 4/2020 |
| WO | 2020072250 A1 | 4/2020 |
| WO | 2020072253 A1 | 4/2020 |
| WO | 2020072254 A1 | 4/2020 |
| WO | 2020152369 A1 | 7/2020 |

OTHER PUBLICATIONS

Sinkunas et al., The EMBO Journal (2011) 30, 1335-1342 (Year: 2011).*
Abedon, S.T. et al. (Dec. 2003). "Experimental Examination of Bacteriophage Latent-Period Evolution as a Response to Bacterial Availability," Applied and Environmental Microbiology 69(12):7499-7506.
Abernethy, J. K. et al., (Mar. 2015, e-pub. Jan. 14, 2015). "Thirty Day All-Cause Mortality In Patients With *Escherichia coli* Bacteraemia In England," Clin. Microbial. Infect. 21:251.e1-251.e8.
Advisory Action, dated Dec. 9, 2021 for U.S. Appl. No. 90/014,705, filed Mar. 23, 2021, 9 pages.
Aklujkar et al. (2010) "Interference With Histidyl-tRNA Synthetase By a CRISPR Spacer Sequence As a Factor In The Evolution Of Pelobacter Carbinolicus," BMC Evolutionary Biology 10:203, 15 pages.
American Lung Association (2019). "Preventing COPD," retrieved from https://www.lung.org/lung-health-and-diseases/lung-disease-lookup/copd/symptoms-causes-risk-factors/preventing-copd.html, last visited Aug. 5, 2019, 1 page.
Anatoliotaki, M. et al. (2004). "Bloodstream Infections in Patients with Solid Tumors: Associated Factors, Microbial Spectrum and Outcome," Infection 2004, 32(2):65-71.
Ang, Y.L.E. et al. (2015). "Best Practice In The Treatment Of Advanced Squamous Cell Lung Cancer," Ther. Adv. Respir. Dis. 9(5):224-235.
Anonymous (Apr. 2016). "Checkpoint Inhibition: A Promising Immunotherapeutic Approach for Colorectal Cancer," Oncology, 5(3):1-5, retrieved from http//www.personalizedmedonc.com/publications/prno/april-2016-vol5-no3/checkpoint-inhibition-a-promising-irmunotherapeutic-approach-for-colorectal-cancer-2/, last visited Aug. 27, 2019, 5 pages.
Arnold, I.C. et al. (Apr. 8, 2015, e-pub. Mar. 4, 2015). "Helicobacter Hepaticus Infection In BALB/c Mice Abolishes Subunit-Vaccine-Induced Protection Against M. Tuberculosis," Vaccine 33(15):1808-1814.
Arslan, Z. et al. (May 7, 2013) "RcsB-BgIJ-Mediated Activation of Cascade Operon Does Not Induce The Maturation of CRISPR RNAs in *E. coli* K12," RNA Biology 10(5):708-715.
Arumugam et al. (May 12, 2011). "Enterotypes of the human gut microbiome," Nature 473(7346):174-180, 16 pages.
Bae, T. et al. (2006). "Prophages of *Staphylococcus aureus* Newman and Their Contribution to Virulence," Molecular Microbiology pp. 1-13.
Barrangou, R. et al. (Mar. 2007). "CRISPR Provides Acquired Resistance Against Viruses in Prokaryotes," Science, 315:1709-1712.
Beisel, C.L. et al. (2014). "A CRISPR Design For Next-Generation Antimicrobials," Genome Biology 15:516, 4 pages.
Belizario, J.E. et al. (Oct. 6, 2015). "Human Microbiomes and Their Roles In Dysbiosis, Common Diseases, and Novel Therapeutic Approaches," Frontiers in Microbiology 6(1050):1-16.
Bellanger, X. et al. (Jul. 1, 2014, e-pub. Jan. 27, 2014). "Conjugative and Mobilizable Genomic Islands in Bacteria: Evolution and Diversity," FEMS Microbiology Reviews 38(20144):720-760.
Bikard, D. et al. (2013, e-pub. Jun. 12, 2013). "Programmable Repression and Activation Of Bacterial Gene Expression Using an Engineered CRISPR-Cas System," Nucleic Acids Research 41(15):7429-7437.
Bikard, D. et al. (2017, e-pub. Sep. 6, 2017). "Using CRISPR-Cas Systems as Antimicrobials," Current Opinion in Microbiology 37:155-160.
Bikard, D. et al. (Aug. 16, 2012). "CRISPR Interference Can Prevent Natural Transformation and Virulence Acquisition during In Vivo Bacterial Infection," Cell Host & Microbe 12(2):177-186.
Bikard, D. et al. (Nov. 2014). "Development of Sequence-Specific Antimicrobials Based On Programmable CRISPR-Cas Nucleases," Nature Biotechnology 32(11):1146-1151, 16 pages.
Broaders, E. et al. (Jul./Aug. 2013). "Mobile Genetic Elements Of The Human Gastrointestinal Tract," Gut Microbes 4(4):271-280.
Brouns, S.J.J. et al. (Aug. 15, 2008). Supplemental Material for "Small CRISPR RNAs Guide Antiviral Defense in Prokaryotes," Science 321:960-964.
Brouns, S.J.J. et al. (Aug. 15, 2008)."Small CRISPR RNAs Guide Antiviral Defense in Prokaryotes," Science 321:960-964.
Bryksin, A.V. et al. (Oct. 8, 2010). "Rational Design Of A Plasmic, Origin That Replicates Efficiently In Both Gram-Positive And Gram Negative Bacteria," PloS One 5(10):e13244, 9 pages.
Bugrysheva, J.V. et al. (Jul. 2011, E-Pub. Apr. 29, 2011). "The Histone-Like Protein Hip Is Essential For Growth Of *Streptococcus pyogenes*: Comparison Of Genetic Approaches To Study Essential Genes," Appl. Environ. Microbiol. 77(13):4422-4428.
Bullman, S. et al. (Nov. 23, 2017). "Analysis of Fusobacterium Persistence and Antibiotic Response In Colorectal Cancer," Science pp. 1443-1448, 10 pages.
Burns, M.B. et al. (2015). "Virulence Genes Are a Signature of the Microbiome in the Colorectal Tumor Microenvironment," Genome Medicine 7:55, 12 pages.
Catalao, M.J. et al. (Jul. 2013, e-pub. Nov. 8, 2012). "Diversity in Bacterial Lysis Systems: Bacteriophages Show the Way," FEMS Microbiology Reviews 37(4):554-571.
Chan, B.K. et al. (2013). "Phage Cocktails and the Future of Phage Therapy," Future Microbiol. 8(6):769-783.
Chan, C.T.Y. et al. (Dec. 2015). "'Deadman' and 'Passcode' Microbial Kill Switches For Bacterial Containment," Nat. Chem. Biol. 12(2):82-86.
Cheadle, E.J. et al. (2012). "Chimeric Antigen Receptors For T-Cell Based Therapy," Methods Mol. Biol. 907:645-666, 36 pages.
Chen, Z. et al. (Aug. 7, 2020). "Akkermansia muciniphila Enhances the Antitumor Effect of Cisplatin in Lewis Lung Cancer Mice," Journal of Immunology Research 2020(2969287):1-13.
Citorik, R.J. et al. (Nov. 2014, e-pub Sep. 21, 2014). "Sequence-Specific Antimicrobials Using Efficiently Delivered RNA-Guided Nucleases," Nat. Biotechnol. 32(11):1141-1145, 18 pages.
Cochrane, K. et al. (2016, e-pub. Nov. 3, 2015). "Complete Genome Sequences and Analysis Of The *Fusobacterium nucleatum* Subspecies Animalis 7-1 Bacteripophage Φfunu1 and Φfunu2," Anaerobe 38:125-129. Abstract Only.
Cong, L. et al. (Feb. 15, 2013, e-pub. Oct. 11, 2013). "Multiplex Genome Engineering Using CRISPR/Cas Systems," Science 339(6121):819-823, 9 pages.
Consumer Updates (2019). "Combating Antibiotic Resistance," retrieved from https://www.fda.gov/ForConsumers/ConsumerUpdates/ucm092810.htm, last visited Jan. 28, 2019.
Coyne, M.J. et al. (2014). "Evidence of Extensive DNA Transfer between *Bacteroidales* Species Within The Human Gut," mBio 5(3):e01305-14, 12 pages.
Cronan, J.E. (Jan. 2013). "Improved Plasmid-Based System for Fully Regulated Off-To-On Gene Expression in *Escherichia coli*: Application to Production of Toxic Proteins," Plasmid 69(1):81-89, 17 pages.
Cui, L. et al. (2016, e-pub. Apr. 8, 2016). "Consequences of Cas9 Cleavage in the Chromosome of *Escherichia coli*," Nucleic Acids Research 44(9):4243-4251.
Daillere, R. et al. (Oct. 18, 2016). "Enterococcus hirae and Barnesiella intestinihominis Facilitate Cyclophosphamide-Induced Therapeutic Immunomodulatory Effects," Immunity 95:931-943.
Datsenko, K.A. et al. (Jul. 10, 2012). "Molecular Memory of Prior Infections Activates the CRISPR/Cas Adaptive Bacterial Immunity System," Nature Communication 3:945, 7 pages.

(56) References Cited

OTHER PUBLICATIONS

De Filippo, C. et al. (Aug. 33 2010). "Impact Of Diet In Shaping Gut Microbiota Revealed By a Comparative Study In Children From Europe and Rural Africa," Proc. Natl. Acad. Sci. USA 107(33):14691-14696, 6 pages.
De Paepe, M. et al. (Mar. 28, 2014). "Bacteriophages: An Underestimated Role In Human and Animal Health?" Frontiers in Cellular and Infection Microbiology 4(39):1-11.
Deeks, E.D. (2014, e-pub. Jul. 15, 2014). "Nivolumab: A Review Of Its Use In Patients With Malignant Melanoma," Drugs 74:1233-1239.
Deghorain, M. et al. (Nov. 23, 2012). "The Staphylococci Phages Family: An Overview," Viruses 4:3316-3335.
Del Castillo, M. et al. (Dec. 1, 2016). The Spectrum of Serious Infections Among Patients Receiving Immune Checkpoint Blockade for the Treatment of Melanoma Clin. Infect. Dis. 63:1490-1493.
Denham, J.D. et al. (2018). "Case Report: Treatment of Enteropathogenic *Escherichia coli* Diarrhea in Cancer Patients: A Series of Three Cases," Case Reports in Infectious Diseases Article ID 8438701:1-3.
Derosa, L. et al. (2018, e-pub. Mar. 30, 2018). "Negative Association Of Antibiotics On Clinical Activity Of Immune Checkpoint Inhibitors In Patients With Advanced Renal Cell and Non-Small-Cell Lung Cancer," Annals of Oncology. 2 pages.
Dhar, A.D. (Jul. 20, 2018). "Overview Of Bacterial Skin Infections," Merck Manual retrieved from https://www.merckmanuals.com/home/skin-disorders/bacterial-skin-infections/overview-of-bacterial-skin-infections, last visited Jul. 20, 2018, 3 pages.
Dickson, R.P. et al. (Jan./Feb. 2017). "Bacterial Topography of the Healthy Human Lower Respiratory Tract," American Society for Microbiology 8(1):e02287-6, 12 pages.
Diez-Villasenor, C. et al. (May 2013). "CRISPR-Spacer Integration Reporter Plasmids Reveal Distinct Genuine Acquisition Specificities Among CROSPR-Cas 1-E Variants of *Escherichia coli*," RNA Biology 10(5):792-802.
Dutilh, B.E. et al. (Jul. 24, 2014). "A Highly Abundant Bacteriophage Discovered In The Unknown Sequences Of Human Faecal Metagenomes," Nature Communications 5(4498):1-10.
Edgar et al. (Dec. 2010). "The *Escherichia coli* CRISPR System Protects From λ Lysogenization, Lysogens, and Prophage Induction," Journal of Bacteriology 192(23):6291-6294, Supplemental Material, 2 pages.
Edgar et al. (Dec. 2010). "The *Escherichia coli* CRISPR System Protects From A Lysogenization, Lysogens, and Prophage Induction," Journal of Bacteriology 192(23):6291-6294.
Ericsson, A.C. et al. (Sep. 10, 2015). "Differential Susceptibility to Colorectal Cancer Due to Naturally Occurring Gut Microbiota," Oncotarget 6(32):33689-33704.
Esvelt, K.M. et al. (Nov. 2013). "Orthogonal Cas9 Proteins for RNA-Guided Gene Regulation and Editing," Nature Methods 10(11):1116-1123.
European Office Action, dated Jun. 29, 2021, for European Patent Application No. 16719873.8, 24 pages.
European Search Report, dated Oct. 4, 2021, for European Patent Application No. 21170379.8, 6 pages.
European Search Report, dated Oct. 8, 2021, for European Patent Application No. 21170380.6, 7 pages.
Ex Parte Re-Exam Communication Transmittal Form, dated Jun. 30, 2021, for U.S. Appl. No. 90/014,705, for Reexamination U.S. Pat. No. 10,953,090, 26 pages.
Ex Parte Re-Exam Communication Transmittal Form, dated May 25, 2022, for Control No. 90/014,705, for Reexamination of U.S. Pat. No. 10,953,090, 19 pages.
Ex Parte Re-Exam, mailed Apr. 21, 2021, for U.S. Appl. No. 90/014,705, filed Mar. 26, 2021, for Reexamination U.S. Pat. No. 10,953,090, 15 pages.
Ex Parte Re-Exam, mailed Apr. 30, 2021, for U.S. Appl. No. 90/014,681, filed Feb. 16, 2021, for Reexamination U.S. Pat. No. 10,920,222, 25 pages.
Ex Parte Re-Exam, mailed Dec. 10, 2018, for U.S. Appl. No. 90/014,184, filed Aug. 10, 2018, for Reexamination U.S. Pat. No. 9,701,964 102 pages.
Ex Parte Re-Exam, mailed Dec. 16, 2021, for U.S. Appl. No. 90/014,877, filed Oct. 6, 2021, for Reexamination U.S. Pat. No. 10,953,090, 12 pages.
Ex Parte Re-Exam, mailed Feb. 22, 2021, for U.S. Appl. No. 16/700,856, filed Dec. 2, 2019, for Reexamination U.S. Pat. No. 10,920,222, 459 pages.
Ex Parte Re-Exam, mailed Mar. 23, 2021, for U.S. Appl. No. 16/453,604, filed Jun. 26, 2019, for Reexamination U.S. Pat. No. 10,953,090, 235 pages.
Ex Parte Re-Exam, mailed Mar. 24, 2021, for U.S. Appl. No. 90/014,681, filed Mar. 24, 2021, for Reexamination U.S. Pat. No. 10,920,222, 18 pages.
Ex Parte Re-Exam, mailed Nov. 15, 2021, for U.S. Appl. No. 90/014,877, 12 pages.
Ex Parte Re-Exam, mailed Sep. 27, 2021, for U.S. Appl. No. 90/014,705, filed Mar. 23, 2021, for Reexamination now U.S. Pat. No. 10,953,090, 16 pages.
Extended European Search Report, dated Jul. 27, 2020, for European Patent Application No. 20155001.9, 9 pages.
Extended European Search Report, dated Sep. 24, 2020, for European Patent Application No. 20154858.3, 12 pages.
Fact Sheet (Oct. 2010). "Antimicrobial Resistance," National Institutes of Health, 1-2.
Foca, A. et al. (2015, e-pub. Apr. 7, 2015). Gut Inflammation and Immunity: What Is The Role Of The Human Gut Virome? Mediators of Inflammation 2015(326032):1-7.
Fujita, K. et al. (2017). "Emerging Concern Of Infectious Diseases In Lung Cancer Patients Receiving Immune Checkpoint Inhibitor Therapy," Eur. Resp. J. 50, OA1478. (Abstract Only).
Galperin, M.Y. (Dec. 2013). "Genome Diversity of Spore-Forming Firmicutes," Microbiology Spectrum 1(2): TBS-0015-2012, 27 pages.
Garneau, J. E. et al. (Nov. 4, 2010). "The CRISPR/Cas Bacterial Immune System Cleaves Phage and Plasmid DNA," Nature 468(7320):67-71, 28 pages.
Garon, E.B. et al. (Oct. 2015). "Current Perspectives In Immunotherapy For Non-Small Cell Lung Cancer," Seminars In Oncology 42(5 Supp. 2):S11-S18.
Garrett W.S. et al. (Oct. 5, 2007). "Communicable Ulcerative Colitis Induced By T-Bet Deficiency In The Innate Immune System," Cell 131(1):33-45, 23 pages.
Gauer, R.L. et al. (Jul. 1, 2013). "Early Recognition and Management of Sepsis in Adults: The First Six Hours," American Family Physician 88(1):44-53.
Geller, L.T. et al. (Sep. 15, 2017). "Potential Role Of Intratumor Bacteria In Mediating Tumor Resistance To The Chemotherapeutic Drug Gemcitabine," Cancer, 1156-1160, 6 pages.
Goldwater, P.N. et al. (2012). "Treatment Of Enterohemorrhagic *Escherichia coli* (EHEC) Infection and Hemolytic Uremic Syndrome (HUS)," BMC Medicine 10:12, 8 pages.
Golubovskaya, V. et al. (Mar. 15, 2016). "Different Subsets of T Cells, Memory, Effector Functions, and CAR-T Immunotherapy," Cancers 8(36), 12 pages.
Gomaa et al. (Jan. 28, 2014). "Programmable Removal Of Bacterial Strains By Use Of Genome-Targeting CRISPR-Cas Systems," mBio, 5(1):e000928-13.
Gomaa, A.A. et al. (Jan./Feb. 2014). Supplemental Material to "Programmable Removal of Bacterial Strains by Use of Genome Targeting CRISPR-Cas Systems," American Society for Microbiology 5(1):1-9.
Goodall, E.C.A. et al. (Feb. 20, 2018). "The Essential Genome of *Escherichia coli* K-12," Am. Society for Microbiology—mBio 9(1):e02096-17, 18 pages.
Gopalakrishnan, V. et al. (Jan. 5, 2018). "Gut Microbiome Modulates Response To Anti-PD-1 Immunotherapy in Melanoma Patients," Science 359:97-103, 20 pages.
Green, J. (Jul. 20, 2018). Colgate https://www.colgate.com/en-us/oral-health/conditions/mouth-sores-and-infections/eight-common-oral-infections-0615, last visited Jul. 20, 2018, 4 pages.
Gudbergsdottir, S. et al. (2011, e-pub. Nov. 18, 2010). "Dynamic Properties of The Sulfolobus CRISPR/Cas and CRISPR/CMR Sys-

(56) References Cited

OTHER PUBLICATIONS tems When Challenged With Vector-Borne Viral and Plasmid Genes and Protospacers," Molecular Microbiology 79(1):35-49.
Gudiol, C. et al. (2016). "Bloodstream Infections In Patients With Solid Tumors," Virulence 7(3):298-308.
Guedan, S. et al. (Aug. 14, 2014). "ICOS-Based Chimeric Antigen Receptors Program Bipolar TH17/TH1 Cells," Blood 124(7):1070-1080.
Guglielmi, G. (2020). "How Gut Bacteria Boost Cancer Immunotherapy," retrieved from the Internet https://microbiomepost.com/how-gut-bacteria-boost-cancer-immunotherapy/, last visited Jul. 25, 2021, 2 pages.
Gupta, R. et al. (2011). "p. 27/HP Endolysin as Antibacterial Agent for Antibiotic Resistant *Staphylococcus aureus* of Human Infections," Curr. Microbiol. 63:39-45.
Gur, C. et al. (Feb. 17, 2015). "Binding of the Fap2 Protein of Fusobacterium nucleatum to Human Inhibitory Receptor TIGIT Protects Tumors from Immune Cell Attack," Immunity 42(2):344-355.
Gutierrez, B. et al. (Apr. 30, 2018). "Genome-Wide CRISPR-Cas9 Screen in *E. coli* Identifies Design Rules for Efficient Targeting," 22 pages.
Ha, Y.E. et al. (2013). "Epidemiology and Clinical Outcomes Of Bloodstream Infections Caused By Extended-Spectrum β-Lactamase-Producing *Escherichia coli* In Patients With Cancer," In.t J. Antimicr. Agen. 42(5):403-409.
Hamanishi, J. et al. (2016, e-pub. Feb. 22, 2016). "PD-1/PD-L1 Blockade In Cancer Treatment: Perspectives and Issues," International Journal of Clinical Oncology 21:462-473.
Hansen, J.J. et al. (Mar. 2015). "Therapeutic Manipulation of the Microbiome in IBD: Current Results and Future Approaches," Curr. T. Options Gastroentrol. 13(1):1-18.
Hargreaves, K.R. et al. (Aug. 26, 2014). "Abundant and Diverse Clustered Regularly Interspaced Short Palindromic Repeat Spacers in Clostridium difficile Strains and Prophages Target Multiple Phage Types within This Pathogen," mBio 5(5):e01045-13.
Harrington, L.E. (Nov. 2005, e-pub. Oct. 2, 2005). "Interleukin 17-producing CD4+ Effector T Cells Develop Via a Lineage Distinct From The T Helper Type 1 and 2 Lineages," Nat Immunol. 6(11):1123-1132.
Hartland, E.L. et al. (Apr. 30, 2013). "Enteropathogenic and Enterohemorrhagic *E. coli*: Ecology, Pathogenesis, and Evolution," Frontiers in Cellular and Infection Microbiology 3(15):1-3.
Hase, K. (Nov. 2014). "Intestinal Microbiota and Immunity," Infectious Disease (in Japanese). 44(6):193-200 22 pages. English Translation.
Healthline (2019). "Cystic Fibrosis," retrieved from https://www.healthline.conn/health/cystic-fibrosis#prevention, last visited Aug. 5, 2019, 14 pages.
Hooper, L.V. et al. (Jun. 8, 2012). "Interactions Between The Microbiota and The Immune System," Science 336(6086):1268-1273, 16 pages.
Horvath, P. et al. (2008, e-pub. Dec. 7, 2007). "Diversity, Activity, and Evolution Of CRISPR Loci In *Streptococcus thermophiles*," Journal of Bacteriology 190(4):1401-1412.
Hotta, K. et al. (2011, e-pub. Sep. 20, 2011). "Prognostic Significance of CD45RO+ Memory T Cells in Renal Cell Carcinoma," British Journal of Cancer 105:1191-1196.
Huddleston, J.R. (Jun. 20, 2014). "Horizontal Gene Transfer In The Human Gastrointestinal Tract: Potential Spread Of Antibiotic Resistance Genes," Infection and Drug Resistance 7:167-176.
Huo, Y. et al. (Sep. 2014). "Structures of CRISPR Cas3 Offer Mechanistic Insights Into Cascade-Activated DNA Unwinding and Degradations," Nat. Struct. Mol. Biol. 21(9):771-777, 21 pages.
Hurwitz, A.A. et al. (Aug. 1998). "CTLA-4 Blockade Synergizes With Tumor-Derived Granulocyte-Macrophage Colony-Stimulating Factor For Treatment Of An Experimental Mammary Carcinoma," Proc. Natl. Acad. Sci. USA 95:10067-10071.

Ichikawa, M. et al. (Dec. 2019). "The Relationship Between Gut Microbiome, Immune System, and Cancer," Jpn. J. Cancer Chemother 16(12):1807-1813. English Abstract.
International Search Report and The Written Opinion of the International Searching Authority for PCT/EP2018/066954, dated Oct. 23, 2018, filed Jun. 25, 2018, 14 pages.
International Search Report and The Written Opinion of the International Searching Authority for PCT/EP2019/057453, dated Aug. 16, 2019, filed Mar. 25, 2019, 21 pages.
International Search Report for PCT/EP2016/059803, dated Jun. 30, 2016, filed May 3, 2016, 6 pages.
International Search Report for PCT/EP2018/082053, dated Mar. 14, 2019, filed Nov. 21, 2018, 9 pages.
Vanov, I.I. et al. (May 2010). "Segmented Filamentous Bacteria Take The Stage," Muscosal Immunol. 3(3):209-212, 7 pages.
Jiang, W. et al. (Jan. 29, 2013). "RNA-Guided Editing of Bacterial Genomes Using CRISPR-Cas Systems," Nat. Biotechnology 31:233-241.
Jiang, W. et al. (Mar. 2013, e-pub. Sep. 1, 2013). "CRISPR-Assisted Editing Of Bacterial Genomes," Nat. Biotechnol. 31(3):233-239.
Jiang, W. et al. (Nov. 2013). "Demonstration Of CRISPR/Cas9/sgRNA-Mediated Targeted Gene Modification In *Arabidopsis*, Tobacco, Sorghum and Rice," Nucleic Acids Research 41(20):e188, 12 pages.
Jin, Y. et al. (2019, e-pub. Apr. 23, 2019). "The Diversity of Gut Microbiome is Associated With Favorable Responses to Anti-Programmed Death 1 Immunotherapy in Chinese Patients With NSCLC," Journal of Thoracic Oncology 14(8):1378-1389.
Jinek et al. (Aug. 17, 2012). "A Programmable Dual-RNA-Guided DNA Endonuclease In Adaptive Bacterial Immunity," Science 337(6096):816-821.
Johnson, C. M. et al. (Nov. 23, 2015). "Integrative and Conjugative Elements (ICEs): What They Do and How They Work," Annual Review of Genetics 49(1):577-601, 33 pages.
Jones, R.B. et al. (2008). "Tim-3 Expression Defines A Novel Population Of Dysfunctional T Cells With Highly Elevated Frequencies In Progressive HIV-1 Infection," J. Exp. Med. 205(12):2763-2779.
Kaiser, J. (Nov. 2, 2017). "Your Gut Bacteria Could Determine How You Respond To Cutting-Edge Cancer Drugs," Science retrieved from Internet https://www.sciencemag.org/news/2017/11/your-gut-bacteria-could-dtermine-how-you-respond-cutting-edge-cancer-drugs, last visited Jul. 25, 2021, 4 pages.
Karch, H. et al. (Jul. 1999). "Epidemiology and diagnosis of Shiga toxin-producing *Escherichia coli* infections," Diagnostic Microbiology and Infectious Disease (34(3):229-243.
Kaulich, M. et al. (2015, e-pub. Jan. 13, 2015). "Efficient CRISPR-rAAV Engineering of Endogenous Genes to Study Protein Function by Allele-Specific RNAi," Nucleic Acids Research 43(7):e45, 8 pages.
Keskin, H. et al. (Nov. 20, 2014). "Transcript-RNA-Templated DNA Recombination and Repair," Nature 515:436-439.
Khoja, L. et al. (2015). "Pembrolizumab," Journal For ImmunoTherapy Of Cancer 3(36):1-13.
Kochenderfer, J.N. et al. (Sep. 2009). "Construction and Pre-clinical Evaluation Of An Anti-CD19 Chimeric Antigen Receptor," J. Immunother. 32(7):689-702, 26 pages.
Koonin, E.V. et al. (2017, e-pub. Jun. 9, 2017). "Diversity, Classification and Evolution of CRISPR-Cas Systems," Current Opinion in Microbiology 37:67-78.
Kosiewicz, M.M. et al. (2014, e-pub. Mar. 26, 2014). "Relationship Between Gut Microbiota and Development of T Cell Associated Disease," FEBS Lett. 588:4195-4206.
Kostic, A.D. et al. (Aug. 14, 2013). "Fusobacterium nucleatum Potentiates Intestinal Tumorigenesis and Modulates The Tumor-Immune Microenvironment," Cell Host Microbe. 14(2):207-215, 18 pages.
Krom, R.J. et al. (Jul. 5, 2015). "Engineered Phagemids for Nonlytic, Targeted Antibacterial Therapies," Nano Letters 15(7):4808-4813.
Kugelberg, E. et al. (Aug. 2005). "Establishment Of A Superficial Skin Infection Model In Mice By Using *Staphylococcus aureus* and *Streptococcus pyogenes*," Antimicrob Agents Chemother. 49(8):3435-3441.

(56) References Cited

OTHER PUBLICATIONS

La Scola, B. et al. (Sep. 4, 2008). "The Virophage as a Unique Parasite of the Giant Mimivirus," Nature Letters 455:100-104.

Leshem, A. et al. (Sep. 29, 2020). "The Gut Microbiome and Individual-Specific Responses to Diet," mSystems 5(5):e00665-20, 12 pages.

Lopez-Sanchez, M.-J. et al. (2012, e-pub. Jul. 27, 2012). "The Highly Dynamic CRISPR1 System Of *Streptococcus agalactiae* Controls The Diversity Of its Mobilome," Molecular Microbiology 85(6):1057-1071.

Lu, T.K. et al. (Jul. 3, 2007). "Dispersing Biofilms With Engineered Enzymatic Bacteriophage," PNAS 104(27):11197-11202.

Ludwig, W. et al. (1985). "The Phylogenetic Position Of *Streptococcus* and Enterococcus," Journal of General Microbiology 131:543-551.

Luo, M.L. et al. (2015, e-pub. Oct. 17, 2014). "Repurposing Endogenous Type I CRISPR-Cas Systems For Programmable Gene Repression," Nucleic Acids Research 43(1):674-681.

López, P. et al. (Apr. 5, 2016). "Th17 Responses and Natural IgM Antibodies Are Related To Gut Microbiota Composition In Systemic Lupus Erythematosus Patients," Sci. Rep. 6:24072, 12 pages.

Macon, B.L. et al. (Jan. 2, 2018). "Acute Nephrities," retrieved from healthline, https://www.healthline.com/health/acute-nephritic-syndrome#ttypes, last visited Jul. 20, 2018, 13 pages.

Magee, M.S. et al. (Nov. 2014). "Challenges To Chimeric Antigen Receptor (CAR)-T Cell Therapy For Cancer," Discov. Med. 18(100):265-271, 6 pages.

Mahoney, K.M. et al. (2015). "The Next Immune-Checkpoint Inhibitors: PD-1/PD-L1 Blockade In Melanoma," Clinical Therapeutics 37(4):764-782.

Makarova, K.S. et al. (Jun. 2011). "Evolution and Classification of the CRISPR-Cas Systems," Nat. Rev. Microbiol. 9(6):467-477, 23 pages.

Mali, P. et al. (Oct. 2013, e-pub. Sep. 27, 2013). "Cas9 as a Versatile Tool for Engineering Biology," Nature Methods 10(10):957-963, 16 pages.

Mancha-Agresti, P. et al. (Mar. 2017). "A New Broad Range Plasmid for DNA Delivery in Eukaryotic Cells Using Lactic Acid Bacteria: In Vitro and In Vivo Assays," Molecular Therapy: Methods & Clinical Development 4:83-91.

Manica, A. et al. (2011, e-pub. Mar. 8, 2011). "In vivo Activity Of CRISPR-Mediated Virus Defence In a Hyperthermophilic Archaeon," Molecular Microbiology 80(2):481-491.

Marin, M. et al. (May 2014). "Bloodstream Infections in Patients With Solid Tumors Epidemiology, Antibiotic Therapy, and Outcomes in 528 Episodes in a Single Cancer Center," Medicine 93:143-149.

Marraffini, L.A. et al. (Dec. 19, 2008). "CRISPR Interference Limits Horizontal Gene Transfer In Staphylococci By Targeting DNA," Science 322(5909):1843-1845, 12 pages.

Martel, B. et al. (2014, e-pub. Jul. 24, 2014). "CRISPR-Cas: AN Efficient Tool For Genome Engineering of Virulent Bacteriophages," Nucleic Acids Research 42(14):9504-9513.

Martinez, R.M. et al. (Aug. 12, 2016). "Bloodstream Infections," Microbial Spectrum 4(4):DMIH2-0031-2016, 34 pages.

Matson, V. et al. (Jan. 5, 2018). "The Commensal Microbiome Is Associated With Anti-PD-1 Efficacy In Metastatic Melanoma Patients," Science 359(6371):104-108.

Matsushiro, A. et al. (Apr. 1999). "Induction of Prophages of Enterohemorrhagic *Escherichia coli* O157:H7 With Norfloxacin," J. Bacteriology 181(7):2257-2260.

Mayo Clinic (2019). "Pulmonary Embolism," retrieved from https://www.nnayoclinic.org/diseases-conditions/pulnnonary-ennbolisnn/synnptonns-causes/syc-20354647, last visited Aug. 5, 2019, 8 pages.

Mayo Clinic (2020). "Infectious Diseases," retrieved from https://www.nnayoclinic.org/diseases-conditions/infectious-diseases/diagnosis-treatnnent/drc-20351179, last visited Jan. 17, 2020, 5 pages.

Mayo Clinic (2020). "Malaria," retrieved from https://www.nnayoclinic.org/diseases-conditions/nnalaria/diagnosis-treatnnent/drc-20351190, last visited Jan. 17, 2020, 3 pages.

Mayo Clinic (2020). "Sexually Transmitted Diseases (STDs)," retrieved from https://www.nnayoclinic.org/diseases-conditions/sexually-transnnitted-diseases-stds/diagnosis-treatnnent/drc-20351246, last visited Jan. 17, 2020, 5 pages.

Mayo Clinic (Jul. 20, 2018). "Bacterial Vaginosis," retrieved from https://www.mayoclinic.org/diseases-conditions/bacterial-vaginosis/symptoms-causes/syc-20352279, last visited Jul. 20, 2018, 3 pages.

Mayo Clinic (Jul. 20, 2018). "Cystitis," retrieved from https://www.mayoclinic.org/diseases-conditions/cystitis/symptoms-causes/syc-20371306, last visited Jul. 20, 2018, 10 pages.

Mayo Clinic (Jul. 20, 2018). "Meningitis," retrieved from https://www.mayoclinic.org/diseases-conditions/meningitis/symptoms-causes/syc-20350508, last visited Jul. 20, 2018, 6 pages.

Mayo Clinic (Jul. 20, 2018). "Pneumonia," retrieved from https://www.mayoclinic.org/diseases-conditions/pneumonia/symptoms-causes/syc-20354204, last visited Jul. 20, 2018, 5 pages.

Mayo Clinic (Mar. 29, 2020). "Liver Disease," retrieved from https://www.mayoclinic.org/diseases-conditions/liver-problems/diagnosis-treatment/drc-20374507, last visited Mar. 29, 2020, 8 pages.

Medina-Aparicio, L. et al. (May 2011, e-pub. Mar. 11, 2011). "The CRI SPR/Cas Immune System Is an Operon Regulated by LeuO, H-NS, and Leucine-Responsive Regulatory Protein in *Salmonella enterica* Serovar *Typhi*," Journal of Bacteriology 193(10):2396-2407.

Mei, J.-M. et al. (1997). "Identification of *Staphylococcus aureus* Virulence Genes in a Murine Model of Bacteraemia Using Signature-Tagged Mutagenesis," Molecular Microbiology 26(2):399-407.

Mercenier, A. (1990). "Molecular Genetics Of Streptococcus Thermophiles," FEMS Microbiology Letters 87(1-2):61-77.

Mick, E. et al. (May 2013). "Holding a Grudge: Persisting Anti-Phage CRISPR Immunity In Multiple Human Gut Microbiomes," RNA Biology 10(5):900-906.

Mills, S. et al. (Jan./Feb. 2013). "Movers and Shakers: Influence Of Bacteriophages In Shaping The Mammalian Gut Microbiota," Gut Microbes 4(1):4-16.

Mima, K. et al. (Aug. 1, 2015, e-pub. Jun. 4, 2014). "Fusobacterium nucleatum and T-Cells in Colorectal Carcinoma," JAMA Oncol. 1(5):653-661.

Mitsuhashi, K. et al. (Mar. 13, 2015). "Association of *Fusobacterium* Species in Pancreatic Cancer Tissues With Molecular Features and Prognosis," Oncotarget 6(9):7209-7220.

Nakamura, S. et al. (Nov. 2008). "Metagenomic Diagnosis Of Bacterial Infections," Emerging Infectious Diseases 14(11):1784-1786.

Nale, J.Y. et al. (2012). "Diverse Temperate Bacteriophage Carriage In Clostridium Difficile 027 Strains," PloS One 7(5):e37263, 9 pages.

Navarre, L. et al. (2007). "Silencing of Xenogeneic DNA by H-NS—Facilitation Of Lateral Gene Transfer In Bacteria By A Defense System That Recognizes Foreign DNA," Genes & Development 21:1456-1471.

Nelson, M.H. et al. (2015). "Harnessing The Microbiome To Enhance Cancer Immunotherapy," Journal of Immunology Research 2015:Article 368736, 12 pages.

News (May 22, 2018). "UK Government and Bill & Melinda Gates Foundation Join Carb-X Partnership in Fight Against Superbugs: Millions Earmarked to Boost Research Into New Life-Saving Products to Address the Global Rise of Drug-Resistant Bacteria," Combating Antibiotic Resistant Bacteria, 7 pages.

Noonan, K.A. et al. (May 20, 2015). "Adoptive Transfer of Activated Marrow-Infiltrating Lymphocytes Induces Measurable Antiumor Immunity in the Bone Marrow in Multiple Myeloma," Science Translational Medicine 7(228):288ra78, 14 pages.

Norris, J.S. et al. (2000). "Prokaryotic Gene Therapy To Combat Multidrug Resistant Bacterial Infection," Gene Therapy 7:723-725.

Notice of Intent to Issue Ex Parte Reexamination Certificate, mailed Aug. 12, 2019, for U.S. Appl. No. 90/014,184, filed Aug. 10, 2018, 26 pages.

Novosiadly, R. et al. (2016, e-pub. Mar. 30, 2016). "High-Content Molecular Profiling of T-Cell Therapy in Oncology," Molecular Therapy—Oncolytics 3:16009, 6 pages.

(56) References Cited

OTHER PUBLICATIONS

Nowak, P. et al. (Nov. 28, 2015). "Gut Microbiota Diversity Predicts Immune Status In HIV-1 Infection," AIDS 29(18):2409-2418.
Office Action, dated Nov. 4, 2021 for U.S. Appl. No. 90/014,705, filed Mar. 23, 2021, 7 pages.
Okazaki, T. et al. (2007). "PD-1 and PD-1 Ligands: From Discovery To Clinical Application," Intern. Immun. 19(7):813-824.
Pardoll, D.M. (Apr. 2012). "The Blockade Of Immune Checkpoints In Cancer Immunotherapy," Nat. Rev. Cancer 12(4): 252-264.
Park, A. (Oct. 18, 2011). "A Surprising Link Between Bacteria and Colon Cancer," Cancer retrieved from http://healthlande.time.com/2011/10/18/a-surprising-link-between-bacteria-and-colon-cancer/, last visited Aug. 27, 2019, 3 pages.
Park, H. et al. (2005). "A Distinct Lineage Of CD4 T Cells Regulates Tissue Inflammation By Producing Interleukin 17," Nat. Immunol. 6(11):1133-1141, 24 pages.
Pastagia, N. et al. (Feb. 2011). "A Novel Chimeric Lysin Shows Superiority to Mupirocin for Skin Decolonization af Methicillin-Resistant and -Sensitive *Staphylococcus aureus* Strains," Antimicrobial Agents and Chemotherapy 55(2):738-744.
Patterson, A.G. et al. (2017, e-pub. Mar. 27, 2017). "Regulation of CRISPR-Cas Adaptive Immune Systems," Current Opinion in Microbiology 37:1-7.
Patterson, A.G. et al. (Dec. 15, 2016). "Quorum Sensing Controls Adaptive Immunity Through The Regulation Of Multiple CRISPR-Cas Systems," Mol. Cell 64(6):1102-1108.
Pawluk, A. et al. (Apr. 15, 2014). "A New Group Of Phage Anti-CRISPR Genes Inhibits The Type I-E CRISPR-Cas System Of Pseudomonas aeruginosa," mBio. 5(2):e00896.
Perez-Chanona, E. et al. (2016, e-pub. Jan. 26, 2016). "The Role of Microbiota in Cancer Therapy," Current Opinion in Immunology 39:75-81.
Pires, D.P. et al. (Sep. 2016, e-pub. Jun. 1, 2016). "Genetically Engineered Phages: A Review of Advances Over the Last Decade," Microbiology and Molecular Biology Reviews 80(3):523-543.
Pul, Ü. et al. (2010, e-pub. Feb. 17, 2010). "Identification and Characterization of *E. coli* CRISPR-cas Promoters and Their Silencing by H-NS," Molecular Microbiology 75(6):1495-1512.
Purdy, D. et al. (2002). "Conjugative Transfer Of Clostridial Shuttle Vectors From *Escherichia coli* To Clostridium difficile Through Circumvention Of The Restriction Barrier," Molec. Microbiology 46(2):439-452.
Ramalingam, S.S. et al. (2014). "LB2-Metastatic Non-Small Cell Lung Cancer: Phase II Study Of Nivolumab (Anti-PD-1, BMS-936558, ONO-4538) In Patients With Advanced, Refractory Squamous Non-Small Cell Lung Cancer," International Journal Of Radiation Oncology Biology Physics Late Breaking Abstract (LB2).
Ran, F.A. et al. (Apr. 9, 2015). "In vivo Genome Editing Using Staphylococcus aureus Cas9," Nature 520(7546):186-191, 28 pages.
Rashid, T. et al. (2013). "The Role of Klebsiella in Crohn's Disease With a Potential for the Use of Antimicrobial Measures," International Journal of Rheumatology 2013(Article ID 610393):1-9.
Ray, K. (Jan. 2020). "Manipulating the Gut Microbiota to Combat Alcoholic Hepatitis," Nature Reviews Gastroenterology & Hepatology 17:3, 1 page.
Rea, K. et al. (2020, e-pub. Nov. 14, 2019). "Gut Microbiota: A Perspective for Psychiatrists," Neuropsychobiology 79:50-62.
Request for Ex Parte Re-Exam Under 35 U.S.C. § 302 and 37 C.F.R. § 1.510 dated Jun. 7, 2022, for U.S. Pat. No. 11,291,723, 328 pages.
Request for Ex Parte Re-Exam Under 35 U.S.C. § 302 and 37 C.F.R. § 1.510 dated Jun. 7, 2022, for U.S. Pat. No. 11,351,252, 219 pages.
Request for Ex Parte Reexamination mailed Aug. 10, 2018, for U.S. Appl. No. 15/160,405, U.S. Pat 9,701,964, 42 pages.
Request for Ex Parte Reexamination mailed Nov. 1, 2018, for U.S. Appl. No. 15/160,405, U.S. Pat. No. 9,701,964, 35 pages.
Request for Ex Parte Reexamination under 35 U.S. C. § 302 and 37 C.F.R. § 1.510, dated Feb. 16, 2021, 72 pages.
Richter, C. et al. (2012, e-pub. Oct. 19, 2012). "Function and Regulation of Clustered Regularly Interspaced Short Palindromic Repeats (CRISPR) / CRISPR Associated (Cas) Systems," Viruses 4(12):2291-2311.
Ridaura, V.K. et al. (Sep. 6, 2013). "Cultured Gut Microbiota From Twins Discordant For Obesity Modulate Adiposity and Metabolic Phenotypes In Mice," Science 341(6150):1241214, 22 pages.
Roberts, A.P. et al. (Dec. 1, 2003). "Development of An Integrative Vector For the Expression of Antisense RNA in Clostridium difficile," Journal of Microbiological Methods 55(3):617-624.
Roberts, A.P. et al. (Jun. 2009, e-pub. May 20, 2009). "A Modular Master On The Move: The Tn916 Family Of Mobile Genetic Elements," Trends Microbiol. 17(6):251-258. Abstract Only.
Rogers, L. et al. (2016). "*Escherichia coli* and Other Enterobacteriaceae: Occurrence and Detection," Encyclopedia of Food and Health pp. 545-551.
Rong, Z. et al. (Mar. 14, 2014). "Homologous Recombination in Human Embryonic Stem Cells Using CRISPR/Cas9 Nickase and a Long DNA Donor Template," Protein & Cell 5(4):258-260.
Routy, B. et al. (Jan. 5, 2018, e-pub. Nov. 2, 2017). "Gut Microbiome Influences Efficacy Of PD-1-Based Immunotherapy Against Epithelial Tumors," Science 359(6371):91-97.
Roy, S. et al. (May 2017, e-pub. Mar. 17, 2017). "Microbiota: A Key Orchestrator Of Cancer Therapy," Nat. Rev. Cancer 17(5):271-285.
Safdar, N. et al. (Jun. 4, 2002). "The Commonality Of Risk Factors For Nosocomial Colonization and infection With Antimicrobial-Resistant *Staphylococcus Aureus*, Enterococcus, Gram-Negative Bacilli, Clostridium difficile, and Candida," Ann. Intern. Med. 136(11):834-844.
Saito, H. et al. (Jun. 15, 2016, e-pub. Apr. 12, 2016). "Adoptive Transfer of CD8+ T Cells Generated From Inducted Pluripotent Stem Cells Triggers Regressions of Large Tumors Along With Immunological Memory," Cancer Research 76(12):3473-3483.
Samaržija, D. et al. (2001). "Taxonomy, Physiology and Growth Of Lactococcus Lactis: A Review," Mljekarstvo 51(1):35-48.
Samonis, G. et al. (Sep. 2013, e-pub. Apr. 27, 2013). "A Prospective Study Of Characteristics And Outcomes of Bacteremia In Patients With Solid Organ Or Hematologic Malignancies," Support Care Cancer 21(9):2521-2526.
Sapranauskas, R. et al. (Nov. 1, 2011, e-pub. Aug. 3, 2011). "The *Streptococcus thermophilus* CRISPR/Cas System Provides Immunity In *Escherichia coli*," Nucleic Acids Research 39(21):9275-9282.
Schnabi, B.G. (2020), "The Role of Enterococcus Faecalis in Alcoholic Liver Disease," retrieved from https://grantome.com/grant/NIH/O01-BX004594-01A2, last visited Oct. 20, 2020, 2 pages.
Seed, K.D. et al. (Feb. 27, 2013). "A Bacteriophage Encodes Its Own CRISPR/Cas Adaptive Response To Evade Host Innate Immunity," Nature 494(7438):489-491.
Selle, K. et al. (Apr. 1, 2015). "Harnessing CRISPR-Cas Systems For Bacterial Genome Editing," Trends in Microbiology 23(4):225-232.
Sepsis Alliance. (Dec. 14, 2017). "What Are Vaccines," Retrieved from https://www.sepsis.org/sepsisand/prevention-vaccinations/; last visited Jul. 8, 2019, 3 pages.
Sepsis Alliance. (Jul. 8, 2019). "Prevention," Retrieved from https://www.sepsis.org/sepsisand/prevention/; accessed last visited Jul. 8, 2019, 5 pages.
Sharan, S.K. et al. (2009). "Recombineering: A Homologous Recombination-Based Method Of Genetic Engineering," Nat. Protoc. 4(2):206-223, 37 pages.
Shoemaker, N.B. et al. (Feb. 2001). "Evidence For Extensive Resistance Gene Transfer Among *Bacteroides* spp. And Among Bacteroides and Other Genera In The Human Colon," Appl. Environ. Microbiol. 67(2):561-68.
Sivan, A. et al. (Nov. 27, 2015, e-pub Nov. 5, 2015). "Commensal Bifidobacterium Promotes Antitumor Immunity and Facilitates Anti-PD-L1 Efficacy," Science 350(6264):1084-1089, 13 pages.
Sivan, A. et al. (Nov. 6, 2014). "Evidence Implicating the Commensal Microbiota in Shaping Anti-Tumor Immunity in Melanoma," Journal for ImmunoTherapy of Cancer 2(Suppl. 3):O11, 1 page.

(56) References Cited

OTHER PUBLICATIONS

Skennerton, C.T. et al. (May 2011). "Phage Encoded H-NS: A Potential Achilles Heel in the Bacterial Defence System," PLoS ONE 6(5):e20095.
Slutsker, L. et al. (Apr. 1998). "A Nationwide Case-Control Study Of *Escherichia coli* O157:H7 Infection In The United States," J. Infect. Dis. 177(4):962-966.
Somkuti, G. A. et al. (Apr. 1988). "Genetic Transformation Of *Streptococcus thermophilus* By Electroporation," Biochimie 70(4):579-585. Abstract Only.
Sorek, R. et al. (2013, e-pub. Mar. 11, 2013). "CRISPR-Mediated Adaptive Immune Systems in Bacteria and Archaea," Annual Review of Biochemistry 82:237-266.
Sorg, R.A. et al. (Mar. 20, 2014, e-pub. Jun. 4, 2014). "Gene Expression Platform For Synthetic Biology In The Human Pathogen *Streptococcus pneumonia*," ACS Synthetic Biology 4(3):228-239, 38 pages.
Soutourina, O.A. et al. (May 9, 2013). "Genome-Wide Identification of Regulatory RNAs in the Human Pathogen Clostridium difficile," PLos Genet. 9(5):e1003493, 20 pages.
Stern, A. et al. (2012). "CRISPR Targeting Reveals a Reservoir Of Common Phages Associated With The Human Gut Microbiome," Genome Research 22(10):1985-1994.
Stern, A. et al. (Aug. 2010), Self-Targeting By CRISPR: Gene Regulation Or Autoimmunity? Trends Genet. 26(8):335-340, 10 pages.
Stiefel, U. et al. (Aug. 2014, e-pub. May 27, 2014). "Gastrointestinal Colonization With a Cephalosporinase-Producing Bacteroides Species Preserves Colonization Resistance Against Vancomycin-Resistant Enterococcus and Clostridium Difficile In Cephalosporin-Treated Mice," Antimicrob. Agents Chemother. 58(8):4535-4542.
Stoebel, D.M. et al. (2008). "Anti-Silencing: Overcoming H-NS-Mediated Repression Of Transcription In Gramnegative Enteric Bacteria," Microbiology 154:2533-2545.
Suvorov, A. (1988). "Transformation Of Group A Streptococci By Electroporation," FEMS Microbiology Letters 56(1):95-100.
Svenningsen, S.L. et al. (Mar. 22, 2005). "On the Role of Cro in λ Prophage Induction," PNAS 102(12):4465-4469.
Takaishi, H. et al. (2008). "Imbalance In Intestinal Microflora Constitution Could Be Involved In The Pathogenesis of Inflammatory Bowel Disease," Int. J. Med. Microbiol.298:463-472.
Takeda, T. et al. (2011). "Distribution of Genes Encoding Nucleoid-Associated Protein Homologs in Plasmids," International Journal of Evolutionary Biology 2001:685015, 31 pages.
Tan, J. (Dec. 17, 2015). "Immunotherapy Meets Microbiota," Cell 163:1561.
Tarr, P.I. et al. (Mar. 19-25, 2005). "Shiga-Toxin-Producing *Escherichia coli* and Haemolytic Uraemic Syndrome," Lancet 365(9464):1073-1086.
Tlaskalová-Hogenová, H. et al. (2011, e-pub. Jan. 31, 2011). "The Role of Gut Microbiota (Commensal Bacteria) and the Mucosal Barrier in the Pathogenesis of Inflammatory and Autoimmune Diseases and Cancer Contribution of Germ-Free and Gnotobiotic Animal Models of Human Diseases," Cellular & Molecular Immunology 8:110-120.
Todar, K. (2012). "The Normal Bacterial Flora of Humans," Todar's Online Textbook of Bacteriology, 8 pages.
Topalian, S.L. et al. (Jun. 28, 2012). "Safety, Activity, and Immune Correlates Of Anti-PD-1 Antibody In Cancer," N. Engl. J Med 366(26):2443-2454, 19 pages.
Turnbaugh, P.J. et al. (Dec. 2006). "An Obesity-Associated Gut Microbiome With Increased Capacity For Energy Harvest," Nature 444:1027 1131.
U.S. Appl. No. 62/168,355, filed May 29, 2015, Barrangou, R. et al.(submitted herewith pursuant to the waiver of 37 C.F.R. 1 98(a)(2)(iii) issued by the Office on Sep. 21, 2004).
U.S. Appl. No. 62/296,853, filed Feb. 18, 2016, Barrangou, R. et al.(submitted herewith pursuant to the waiver of 37 C.F.R. 1 98(a)(2)(iii) issued by the Office on Sep. 21, 2004).
Uchiyama, J. et al. (2013, e-pub. Mar. 8, 2013). "Characterization of Helicobacter pylori Bacteriophage KHP30," Applied and Environmental Microbiology 79(10):3176-3184.
USPTO Interference 106,123—Declaration to Declare Interference Jun. 11, 2020, 11 pages.
USPTO Interference 106,123—Junior Party Annotated Claims Jul. 9, 2020, 31 pages.
UUSPTO Interference 106,123—Junior Party List of Motions Jul. 16, 2020, 6 pages.
USPTO Interference 106,123—Redeclaration Jul. 21, 2020, 6 pages.
USPTO Interference 106,123—Rockefeller Clean Claims Jun. 25, 2020, 7 pages.
USPTO Interference 106,123—Rockefeller Motion 2 (Indefiniteness), Oct. 16, 2020, 24 pages.
USPTO Interference 106,123—Rockefeller Notice of Lead and Backup Counsel Jun. 25, 2020, 3 pages.
USPTO Interference 106,123—Rockefeller Notice of Real Party in Interest Jun. 25, 2020, 3 pages.
USPTO Interference 106,123—Rockefeller Notice of Related Proceedings Jun. 25, 2020, 3 pages.
USPTO Interference 106,123—Rockefeller Power of Attorney Jun. 25, 2020, 3 pages.
USPTO Interference 106,123—Rockefeller Request for File Jun. 25, 2020, 10 pages.
USPTO Interference 106,123—Rockefeller Revised List of Proposed Motions Aug. 13, 2020, 4 pages.
USPTO Interference 106,123—Senior Party List of Proposed Motions Jul. 16, 2020, 5 pages.
USPTO Interference 106,123—SNIPR Clean Jun. 25, Claims 2020, 27 pages.
USPTO Interference 106,123—SNIPR Motion 2 (Lack of Enablement and Written Description), Oct. 16, 2020, 32 pages.
USPTO Interference 106,123—SNIPR Motion 4 (Deny Benefit to Count 1), Oct. 16, 2020, 16 pages.
USPTO Interference 106,123—SNIPR Motion 5 (Substitute Count), Oct. 16, 2020, 41 pages.
USPTO Interference 106,123—SNIPR Motion 6 (Motion to Designate Claims as Not Corresponding to Count 1 or Proposed Count 2), Oct. 16, 2020, 24 pages.
USPTO Interference 106,123—SNIPR Notice of Lead and Backup Counsel Jun. 25, 2020, 4 pages.
USPTO Interference 106,123—SNIPR Notice of Related Proceedings Jun. 25, 2020, 4 pages.
USPTO Interference 106,123—SNIPR Real Party in Interest Jun. 25, 2020, 3 pages.
USPTO Interference 106,123—SNIPR Request for File Jun. 25, 2020, 10 pages.
USPTO Interference 106,123—Standing Order Jun. 11, 2020, 81 pages.
USPTO Interference 106,123—Decision on Motions, Sep. 7, 2021, 18 pages.
USPTO Interference 106,123—Joint Stipulated Extension of Time, Sep. 4, 2020, 4 pages.
USPTO Interference 106,123—Judgement, Nov. 19, 2021, 3 pages.
USPTO Interference 106,123—Junior Party Revised List of Motions Aug. 13, 2020, 6 pages.
USPTO Interference 106,123—Memorandum, Jan. 19, 2021, 6 pages.
USPTO Interference 106,123—Notice of Cross Examination—van der Oost, Dec. 1, 2020, 3 pages.
USPTO Interference 106,123—Order Additional Applications 37 C.F.R. § 41.104(a), Sep. 3, 2020, 6 pages.
USPTO Interference 106,123—Order Authorizing Motions and Setting Times 37 C.F.R. 11.104(c) and 121 Aug. 24, 2020, 10 pages.
USPTO Interference 106,123—Order—Additional Applications, Jan. 13, 2021, 6 pages.
USPTO Interference 106,123—Order—Bd.R. 109(b)—Authorizing Copies of Office Records Jul. 21, 2020, 3 pages.
USPTO Interference 106,123—Order-Video Dispositions 37 C.F.R. § 41.104(a), Sep. 25, 2020, 3 pages.
USPTO Interference 106,123—Rockefeller List of Exhibits, Oct. 16, 2020, 4 pages.

(56) References Cited

OTHER PUBLICATIONS

USPTO Interference 106,123—Rockefeller List Of Exhibits, Nov. 13, 2020, 4 pages.
USPTO Interference 106,123—Rockefeller List Of Exhibits, Feb. 19, 2021, 5 pages.
USPTO Interference 106,123—Rockefeller Motion 1 (Lack of Written Description), Oct. 16, 2020, 30 pages.
USPTO Interference 106,123—Rockefeller Motion 3 (To Add A Claim), Nov. 13, 2020, 36 pages.
USPTO Interference 106,123—Rockefeller Notice of Settlement Discussions, Oct. 21, 2020, 3 pages.
USPTO Interference 106,123—Rockefeller Order—Responsive Motion 37 C.F.R. § 41.121(a)(2), Nov. 2, 2020, 2 pages.
USPTO Interference 106,123—Rockefeller Reply 1, Feb. 19, 2021, 51 pages.
USPTO Interference 106,123—Rockefeller Reply 2, Feb. 19, 2021, 37 pages.
USPTO Interference 106,123—Rockefeller Reply 3, Feb. 19, 2021, 48 pages.
USPTO Interference 106,123—Rockefeller Updated Notice Of Related Proceedings, Nov. 13, 2020, 3 pages.
USPTO Interference 106,123—SNIPR Exhibit List, Oct. 16, 2020, 7 pages.
USPTO Interference 106,123—SNIPR Exhibit List, Oct. 19, 2021, 8 pages.
USPTO Interference 106,123—SNIPR Motion 1 (Terminate Interference As Contrary to AIA), Oct. 16, 2020, 20 pages.
USPTO Interference 106,123—SNIPR Notice of Appeal, Dec. 14, 2021, 28 pages.
USPTO Interference 106,123—SNIPR Request for Oral Argument, Mar. 12, 2021, 4 pages.
USPTO Interference 106,123—Order—Show Cause, Aug. 19, 2021, 4 pages.
USPTO Interference 106,123—Rockefeller Notice, Aug. 13, 2021, 3 pages.
USPTO Interference 106,123—Rockefeller Request for Oral Argument, Mar. 12, 2021, 3 pages.
USPTO Interference 106,123—Rockefeller Response To Show Cause, Sep. 7, 2021, 7 pages.
USPTO Interference 106,123—Rockefeller Updated Notice of Related Proceedings, Jul. 15, 2021, 3 pages.
USPTO Interference 106,123—SNIPR Reply 1, Feb. 19, 2021, 19 pages.
USPTO Interference 106,123—SNIPR Reply 2, Feb. 19, 2021, 42 pages.
USPTO Interference 106,123—SNIPR Reply 4, Feb. 19, 2021, 28 pages.
USPTO Interference 106,123—SNIPR Reply 5, Feb. 19, 2021, 44 pages.
USPTO Interference 106,123—SNIPR Reply 6, Feb. 19, 2021, 27 pages.
Veeranagouda, Y. et al. (Jun. 4, 2014). "Identification Of Genes Required For The Survival Of B. fragilis Using Massive Parallel Sequencing Of a Saturated Transposon Mutant Library," BMC Genomics 15:429, 11 pages.
Vega, N.M. et al. (Oct. 2014). "Collective Antibiotic Resistence: Mechanisms and Implications," Curr. Opin. Microbiol. 21:28-34, 14 pages.
Velasco, E. et al. (2006). "Comparative Study Of Clinical Characteristics Of Neutropenic and Non-Neutropenic Adult Cancer Patients With Bloodstream Infections," Eur. J. Clin. Microbiol. Infect. Dis. 25:1-7.
Vercoe, R.B. et al. (Apr. 18, 2013). "Cytotoxic Chromosomal Targeting by CRISPR/Cas Systems Can Reshape Bacterial Genomes and Expel Or Remodel Pathogenicity Islands," PLOS Genetics 9(4):e1003454, 13 pages.
Villarino, N.F. et al. (Feb. 23, 2016, e-pub. Feb. 8, 2016). "Composition Of The Gut Microbiota Modulates The Severity Of Malaria," Proc. Natl. Acad. Sci. USA 113(8):2235-2240.

Vétizou, M. et al. (Nov. 27, 2015, e-pub Nov. 5, 2015). "Anticancer Immunotherapy By CTLA-4 Blockade Relies On The Gut Microbiota," Science 350(6264):1079-1084, 13 pages.
Wagner, P.L. (2002). "Bacteriophage Control Of Shiga Toxin 1 Production and Release By *Escherichia coli*," Molecular Microbiology 44(4):957-970.
Walters, W.A. et al. (Nov. 17, 2014). "Meta-Analyses Of Human Gut Microbes Associated With Obesity and IBD," FEBS Letters 588(22):4223-4233, 34 pages.
Wang, I.-N. et al. (2000). "HOLINS: The Protein Clocks of Bacteriophage Infections," Annu. Rev. Microbiol. 54:799-825.
Wang, J. et al. (2019). "Core Gut Microbiota Analysis of Feces in Healthy Mouse Model," Supplementary Information, 12 pages.
Wang, J. et al. (Apr. 24, 2019). "Core Gut Bacteria Analysis of Healthy Mice," Frontiers in Microbiology 10(887):1-14.
Waters, J. L. et al. (Nov./Dec. 2013). "Regulation of CTnDOT Conjugative Transfer is a Complex and Highly Coordinated Series of Events," MBIO 4(6):e00569-13, 8 pages.
Wegmann, U. et al. (Apr. 2007). "Complete Genome Sequence Of The Prototype Lactic Acid Bacterium *Lactococcus lactis* Subsp. *Cremoris* MG 1363," Journal Of Bacteriology 189(8):3256-3270.
Wei, Y. et al. (2015, e-pub. Jan. 14, 2015). "Sequences Spanning The Leader-Repeat Junction Mediate CRISPR Adaptation To Phage In *Streptococcus thermophiles*," Nucleic Acids Research 43(3):1749-1758.
Weir, T.L. et al. (Aug. 6, 2013). "Stool Microbiome and Metabolome Differences Between Colorectal Cancer Patients and Healthy Adults," PLOS ONE 8(8):e70803, 10 pages.
West, N.R. et al. (Dec. 14, 2015). "Immunotherapy Not Working? Check Your Microbiota," Cancer cell 28:687-689.
Westra, E.R. et al. (Jun. 8, 2012). "CRISPR Immunity Relies on the Consecutive Binding and Degradation of Negatively Supercoiled Invader DNA by Cascade and Cas3," Molecular Cell 46:595-605.
Westra, E.R. et al. (Sep. 1, 2010, e-pub. Aug. 18, 2010). "H-NS—Mediated Repression of CRISPR-Based Immunity in *Escherichia coli* K12 Can Be Relieved By The Transcription Activator LeuO," Molecular Microbiology 77(6):1380-1393.
Westwater, C. et al. (2002). "Development of a P1 Phagemid System for the Delivery of DNA Into Gram-Negative Bacteria," Microbiology 148:943-950.
Westwater, C. et al. (Apr. 2003). "Use of Genetically Engineered Phage To Deliver Antimicrobial Agents To Bacteria: An Alternative Therapy For Treatment of Bacterial Infections," Antimicrobial Agents and Chemotherapy 47(4):1301-1307.
Wexler, H.M. (Oct. 2007). "Bacteroides: the Good, the Bad, and the Nitty-Gritty," Clinical Microbiology Reviews 20(4):593-621.
Wong, C.S. et al. (Jun. 29, 2000). "The Risk Of The Hemolytic-Uremic Syndrome After Antibiotic Treatment Of *Escherichia coli* O157:H7 Infections," N. Engl. J. Med. 342(26):1930-1936, 13 pages.
Written Opinion for PCT Application No. PCT/EP2016/059803, dated Jun. 30, 2016, filed May 3, 2016, 6 pages.
Written Opinion for PCT/EP2018/082053, dated Mar. 14, 2019, filed Nov. 21, 2018, 6 pages.
Wu, J. et al. (Jun. 2019). "Fusobacterium nucleatum Contributes to the Carcinogenesis of Colorectal Cancer by Inducting Inflammation and Suppressing Host Immunity," Translational Oncology 12(6):846-851.
Xie, Z. et al. (2013, e-pub. Aug. 9, 2013). "Development Of a Tunable Wide-Range Gene Induction System Useful For The Study Of Streptococcal Toxin-Antitoxin Systems," Applied And Environmental Microbiology 79(20):6375-6384.
Xu, T. et al. (Jul. 2015). "Efficient Genome Editing in Clostridium cellulolyticum via CRISPR-Cas9 Nickase," Applied and Environmental Microbiology 81(13):4423-4431.
Yang, Y. et al. (Jun. 5, 2014, e-pub. Apr. 13, 2014). "Focused Specificity Of Intestinal Th17 Cells Towards Commensal Bacterial Antigens," Nature 510(7503):152-156, 29 pages.
Yao, J. et al. (2016, e-pub. May 9, 2016). "A Pathogen-Selective Antibiotic Minimizes Disturbance to the Microbiome," Antimicrob. Agents Chemother., 24 pages.

(56) References Cited

OTHER PUBLICATIONS

Yosef, I. et al. (2011). "High-Temperature Protein G Is Essential For Activity Of The *Escherichia coli* Clustered Regularly Interspaced Palindromic Repeats (CRISPR)/Cas System," Proc. Natl. Acad. Sci. USA 108(50):20136-20141.

Yosef, I. et al. (Jun. 9, 2015). "Temperate and Lytic Bacteriophages Programmed To Sensitize and Kill Antibiotic-Resistant Bacteria," Proc. Natl. Acad. Sci. USA 112(23):7267-7272.

Young, R. et al. (1995). "Holins: Form and Function in Bacteriophage Lysis," FEMS Microbiology Reviews 17:191-205.

YourGenome: CRISPR/CAS9, retrieved from https://www.yourgenonne.org/facts/what-is-crispr-cas9, last visited Jan. 6, 2020, 8 pages.

Yu, Z. et al. (Mar. 21, 2014). "Various Applications of TALEN- and CRISPR/Cas9-Mediated Homologous Recombination to Modify the *Drosophila Genome*," Biology Open 3(4):271-280.

Zembower, T.R. (2004). "Epidemiology of Infections in Cancer Patients," in Infectious Complications in Cancer Patients, Springer International Publishing Switzerland, 48 pages.

Zhang, R. et al. (2009, e-pub. Oct. 30, 2008). "DEG 5.0, A Database of Essential Genes in Both Prokaryotes and Eukaryotes," Nucleic Acids Research 37:D455-D458.

Zhang, T. et al. (Sep. 24, 2016). "The Efficacy and Safety Of Anti-PD-1/PD-L1 Antibodies For Treatment Of Advanced Or Refractory Cancers: A Meta-Analysis," Oncotarget 7(45):73068-73079.

Zhang, X.Z. (2011). "Simple, Fast and High-Efficiency Transformation System For Directed Evolution Of Cellulase In Bacillus Subtilis," Microbial Biotechnology 4(1):98-105.

Zimmerhackl, L.B. (Jun. 29, 2000). "*E. coli*, Antibiotics, and The Hemolytic-Uremic Syndrome," N. Engl. J. Med. 342(26):1990-1991.

Zitvogel, L. et al. (Jan. 2015), "Cancer and The Gut Microbiota: An Unexpected Link," Sci. Transl. Med. 7(271):271ps1, 10 pages.

Zitvogel, L. et al. (Mar. 2018). "The Microbiome In Cancer Immunotherapy: Diagnostic Tools and Therapeutic Strategies," Science 359(6382):1366-1370.

Ex Parte Re-Exam Communication Transmittal Form, dated Sep. 2, 2022, for Control No. 90/015,048, for Reexamination of U.S. Pat. No. 11,291,723, 17 pages.

Extended European Search Report, dated Aug. 12, 2022, for European Patent Application No. 22166966.6, 12 pages.

Extended European Search Report, dated Oct. 10, 2022, for European Patent Application No. 22171899.2, 13 pages.

Gao, X. et al. (2010, e-pub Sep. 19, 2010). "Engineered Polyketide Biosynthesis and Biocatalysis in *Escherichia coli*," Appl. Microbiol. Biotechnol. 88:1233-1242.

Allaker, R.P. (2019). "Chapter 36—Non-Sporing Anaerobes: Wound Infection; Periodontal Disease; Abscess; Normal Flora," in Bacterial Pathogens and Associated Diseases, pp. 359-364.

Bashir, A. et al. (2016, E-PUB. Dec. 30, 2014). "Fusobacterium nucleatum, Inflammation, and Immunity: The Fire Within Human Gut," Tumor Biol. 37:2805-2810.

Ex Parte Re-Exam Communication Transmittal Form, dated Dec. 29, 2022, for Control No. 90/015,047, for Reexamination of U.S. Pat. No. 11,351,252, 19 pages.

Ex Parte Re-Exam Communication Transmittal Form, dated Feb. 1, 2023, for Control No. 90/015,048, for Reexamination of U.S. Pat. No. 11,291,723, 30 pages.

Ex Parte Re-Exam Communication Transmittal Form, dated Mar. 15, 2023, for Control No. U.S. 90/015,047, for Reexamination of U.S. Pat. No. 11,351,252, 11 pages.

Garcia-Carretero, R. et al. (2017). "Clinical Features and Outcomes of *Fusobacterium* Species Infections in a Ten-Year Follow-Up," The Journal of Critical Care Medicine 3(4):141-147.

Mahanonda Ishii, T. et al. (1992). "The Establishment of Human T-Cell Lines Reactive With Specific Periodontal Bacteria," Oral Microbiol. Immunol. 7:225-229.

Kamada, N. et al. (May 1, 2013). "Role of the Gut Microbiota in Immunity and Inflammatory Disease," The Journal of Immunology 13(5):321-335.

Kim, H. et al. (2014, e-pub. Apr. 2, 2014). "A Guide to Genome Engineering with Programmable Nucleases," Nature Reviews Genetics 15(5):321-334.

Li, K. et al. (Jun. 13, 2012). "Analyses of the Microbial Diversity Across the Human Microbiome," PloS ONE 7(6): e32118, 18 pages.

Mazmanian, S.K. et al. (May 29, 2008). "A Microbial Symbiosis Factor Prevents Intestinal Inflammatory Disease," Nature 453:620-625.

Moubareck, C. et al. (2005, e-pub. Dec. 1, 2004). "Antimicrobial Susceptibility of Bifidobacteria," Journal of Antimicrobial Chemotherapy 55:38-44.

Pongnarisorn, N.J. et al. (2007). "Inflammation Associated With Implants With Different Surface Types," Clinical Oral Impl. Res. 18:114-125.

Qin, J. et al. (Mar. 4, 2010). "A Human Gut Microbial Gene Catalogue Established by Metagenomic Sequencing," Nature 464:59-65, 9 pages.

Rajilić-Stojanović, M. et al. (2014, e-pub Jun. 27, 2014). "The First 1000 Cultured Species of the Human Gastrointestinal Microbiota," FEMS Microbiol. Rev 38(5):996-1047.

Round, J.L. et al. (May 1, 2009, e-pub. Jul. 14, 2014). "The Gut Microbiome Shapes Intestinal Immune Responses During Health and Disease," The Journal of Immunology 9(5):313-323, 25 pages.

Sears, C.L. et al. (Oct. 2014). "Bacteroides fragilis Subverts Mucosal Bilogy: From Symbiont to Colon Carcinogenesis," The Journal of Clinical Investigation 124(10):4166-4172.

Sharma, P. et al. (Apr. 3, 2015). "The Future of Immune Checkpoint Therapy," Science 348(6230):56-61.

Takahashi, K. et al. (Apr. 2001). "Heterogeneity of Host Immunological Risk Factors in Patients With Aggressive Periodontitis," J. Periodontol 72(4):425-437, 17 pages.

The Human Microbiome Project Consortium (Jun. 14, 2012). "Structure, Function and Diversity of the Healthy Human Microbiome," Nature 486:207-214.

Van Erp, P.B.G. et al. (Jun. 1, 2015, e-pub. Apr. 26, 2015). "The History and Market Impact of CRISPR RNA-Guided Nucleases," Current Opinion in Virology 12:85-90.

Wang, F. et al. (Jan. 2, 2018). "Bifidobacterium Can Mitigate Intestinal Immunopathology in the Context of CTLA-4 Blockade," PNAS 115(1):57-161.

Bikard, D. et al. (Nov. 2014, e-pub. Oct. 5, 2014). "Exploiting CRISPR-Cas Nucleases to Produce Sequence-Specific Antimicrobials," Nature Biotechnology 32(11):1146-1150, 6 pages.

Galmbacher, K. et al. (Mar. 8, 2010). "Shigella Mediated Depletion of Macrophages in a Murine Breast Cancer Model is Associated with Tumor Regression," PLoS One 5(3):e9572, 11 pages.

Stackebrandt, E. (2014). "Chapter 15—The Family Lachnospiraceae," in The Prokaryotes—Firmicutes and Tenericutes, 5 pages.

\* cited by examiner

TREATING AND PREVENTING MICROBIAL INFECTIONS

CROSS REFERENCE TO RELATED APPLICATIONS

This application is a continuation of U.S. patent application Ser. No. 17/029,860, filed Sep. 23, 2020, which is a continuation of Ser. No. 16/700,856, filed Dec. 2, 2019, which is a continuation of U.S. patent application Ser. No. 15/967,484, filed Apr. 30, 2018, the contents of which are incorporated herein by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 786212000305SEQLIST.TXT, date recorded: May 17, 2022, size: 21,079 bytes).

TECHNICAL FIELD

The invention provides methods for treating or preventing microbial (eg, bacterial) infections and means for performing these methods. In particular, treatment of infections requiring rapid or durable therapy is made possible, such as for treating acute conditions such as septicemia, sepsis, SIRS or septic shock. The invention is also particularly useful, for example, for treatment of microbes for environmental, food and beverage use. The invention relates inter alia to methods of controlling microbiologically influenced corrosion (MIC) or biofouling of a substrate or fluid in an industrial or domestic system.

The invention also useful for the treatment of pathogenic bacterial infections in subjects receiving a treatment for a disease or condition, such as a transplant or a treatment for cancer, a viral infection or an autoimmune disease.

BACKGROUND

Septicaemia is an acute and serious bloodstream infection. It is also known as bacteraemia, or blood poisoning. Septicaemia occurs when a bacterial infection elsewhere in the body, such as in the lungs or skin, enters the bloodstream. This is dangerous because the bacteria and their toxins can be carried through the bloodstream to a subject's entire body. Septicaemia can quickly become life-threatening. It must be rapidly treated, such as in a hospital. If it is left untreated, septicaemia can progress to sepsis.

Septicaemia and sepsis aren't the same. Sepsis is a serious complication of septicaemia. Sepsis is when inflammation throughout the body occurs. This inflammation can cause blood clots and block oxygen from reaching vital organs, resulting in organ failure. The US National Institutes of Health (NIH) estimates that over 1 million Americans get severe sepsis each year. Between 28 and 50 percent of these patients may die from the condition. When the inflammation occurs with extremely low blood pressure, it's called septic shock. Septic shock is fatal in many cases.

The increase in average age of the population, more people with chronic diseases, on immunosuppressive drugs, and increase in the number of invasive procedures being performed has led to an increased rate of sepsis. People over 65 years old, particularly those who have health issues, are even more susceptible to sepsis than any other group. According to a study published in 2006, while people aged 65 years and older make up about 12% of the American population, they make up 65% of sepsis cases in the hospitals.

Septicaemia is caused by an infection in a part of the body. This infection is typically acute. Many types of bacteria can lead to septicaemia. The exact source of the infection often can't be determined. The most common infections that lead to septicaemia are:
 urinary tract infections
 lung infections, such as pneumonia
 kidney infections
 infections in the abdominal area Bacteria from these infections enter the bloodstream and multiply rapidly, causing acute infection and immediate symptoms.

People who are already in the hospital for something else, such as a surgery, are at a higher risk of developing septicaemia. Secondary infections can occur while in the hospital. These infections are often more dangerous because the bacteria may already be resistant to antibiotics. There is a higher risk of developing septicaemia if the subject:
 has severe wounds or burns
 is very young or very old
 has a compromised immune system, which can occur from diseases such as HIV or leukaemia
 has a urinary or intravenous catheter
 is on mechanical ventilation
 is receiving medical treatments that weakens the immune system, such as chemotherapy or steroid injections The symptoms of septicaemia usually start very quickly. Even in the first stages of the illness, a person can look very sick. They may follow an injury, surgery, or another localized (eg, confined to one location) infection, like pneumonia. The most common initial symptoms are:
 chills
 elevated body temperature (fever)
 very fast respiration
 rapid heart rate More severe symptoms will begin to emerge as the septicaemia progresses without proper treatment. These include the following:
 confusion or inability to think clearly
 nausea and vomiting
 red dots that appear on the skin
 reduced urine volume
 inadequate blood flow (shock)

Septicaemia that has started to affect the organs or tissue function is an acute medical emergency. It must be rapidly treated at a hospital. Many people with septicaemia are admitted to a hospital's ICU for treatment and recovery. It is recommended to never take a "wait and see" approach or try to treat the problem at home. It is crucial to get to the hospital right away if the subject is showing signs of septicaemia.

Septicaemia has a number of serious complications. These complications may be fatal if left untreated or if treatment is delayed for too long.

Septic Shock

One complication of septicaemia is a serious drop in blood pressure. This is called septic shock. Toxins released by the bacteria in the bloodstream can cause extremely low blood flow, which may result in organ or tissue damage. Septic shock is an acute medical emergency. People with septic shock are usually cared for in a hospital's intensive care unit (ICU). The patient may need to be put on a ventilator, or breathing machine, if in septic shock.

Acute Respiratory Distress Syndrome (ARDS)

Another complication of septicaemia is acute respiratory distress syndrome (ARDS). This is a life-threatening condition that prevents enough oxygen from reaching your lungs and blood. According to the National Heart, Lung, and Blood Institute (NHLBI), ARDS is fatal in about one-third of cases. It often results in some level of permanent lung damage. It can also damage the brain, which can lead to memory problems.

Sepsis

Sepsis occurs when the body has a strong immune response to the infection. This leads to widespread inflammation throughout the body. It is called severe sepsis if it leads to organ failure. People with chronic diseases, such as HIV or cancer, are at a higher risk of sepsis. This is because they have a weakened immune system and cannot fight off the infection on their own. Sepsis causes millions of deaths globally each year and is the most common cause of death in people who have been hospitalized. The worldwide incidence of sepsis is estimated to be 18 million cases per year. In the United States sepsis affects approximately 3 in 1,000 people, and severe sepsis contributes to more than 200,000 deaths per year. Sepsis occurs in 1-2% of all hospitalizations and accounts for as much as 25% of ICU bed utilization.

Early diagnosis is necessary to properly manage sepsis, as initiation of rapid therapy is key to reducing deaths from severe sepsis. Within the first three hours of suspected sepsis, diagnostic studies should include white blood cell counts, measuring serum lactate, and obtaining appropriate cultures before starting antibiotics, so long as this does not delay their use by more than 45 minutes The most common primary sources of infection resulting in sepsis are the lungs, the abdomen, and the urinary tract. Typically, 50% of all sepsis cases start as an infection in the lungs.

Speed of treatment is essential. Two sets of blood cultures (aerobic and anaerobic) should be taken without delaying the initiation of antibiotics. Cultures from other sites such as respiratory secretions, urine, wounds, cerebrospinal fluid, and catheter insertion sites (in-situ more than 48 hours) can be taken if infections from these sites are suspected. In severe sepsis and septic shock, broad-spectrum antibiotics (usually two, a β-lactam antibiotic with broad coverage, or broad-spectrum carbapenem combined with fluoroquinolones, macrolides, or aminoglycosides) are conventional. However, combination of antibiotics is not recommended for the treatment of sepsis without shock and in immunocompromised persons unless the combination is used to broaden the anti-bacterial activity. The administration of antibiotics is important in determining the survival of the person. Some recommend they be given within one hour of making the diagnosis, stating that for every hour of delay in the administration of antibiotics, there is an associated 6% rise in mortality.

Early goal directed therapy (EGDT) is an approach to the management of severe sepsis during the initial 6 hours after diagnosis. It is a step-wise approach, with the physiologic goal of optimizing cardiac preload, afterload, and contractility. It includes giving early antibiotics.

Neonatal sepsis can be difficult to diagnose as newborns may be asymptomatic. If a newborn shows signs and symptoms suggestive of sepsis, antibiotics are immediately started and are either changed to target a specific organism identified by diagnostic testing or discontinued after an infectious cause for the symptoms has been ruled out.

Approximately 20-35% of people with severe sepsis and 30-70% of people with septic shock die. The Surviving Sepsis Campaign (SSC) is a global initiative to bring together professional organizations in reducing mortality from sepsis. Antibiotics are administered within two hours of admission/diagnosis. For every hour a patient is denied antibiotic therapy after the onset of septic shock, the patient's chance of survival is reduced by 7.9% (Survivesepsis.org 2005)

There is, therefore, a need for a rapid treatment of acute microbial infections, such as bacterial infections associated with septicaemia, sepsis or septic shock. It would also be advantageous if the treatment is durable for many hours. Rapid and durable treatment of microbes is also desirable for is for controlling microbiologically influenced corrosion (MIC) or biofouling of a substrate in industrial and domestic systems.

Acute bacterial infections can, in certain circumstances, be health-threatening or even life-threatening. This may be the case, for example, in cancer patients, transplant patients or other subjects. The need for the treatment of the bacterial infection can become urgent and indeed an immediate focus of attention in the medical care. It would be useful to provide methods of treating such pathogenic bacterial infections in a way that does not adversely undermine the efficacy of the cancer or other separate therapy to which the patient also needs to respond.

SUMMARY OF THE INVENTION

The invention provides a solution by using the action of programmable nuclease cutting of microbe genomes; this is different from the metabolic inhibitor and other mechanisms of action used by beta-lactams and other conventional antibiotics for treating infections. The targeted cutting provides selective microbe killing or reduction of growth or proliferation to treat or prevent infection. Moreover, the inventors have surprisingy found a substantial killing (by several logs) can be achieved very rapidly (eg, within 15 minutes) and sustainable effects can be achieved (eg, for more than 1 hour, and even around 3 hours after treatment commenced) in some embodiments. Thus, the invention provides the following configurations.

In a First Configuration

A programmable nuclease for use in a method of treating a microbial infection of a subject, wherein the microbial infection is caused by microbes of a first species or strain and the nuclease is programmable to cut a target site comprised by the genomes of microbes that have infected the subject, whereby microbes of the first species or strain are killed, or growth or proliferation of the microbes is reduced, the treatment method comprising exposing the subject to the nuclease wherein the nuclease is programmed to cut the target site, whereby genomes of the microbes comprised by the subject are cut and microbial infection of the subject is treated.

In a Second Configuration

A plurality of viruses (eg, phage or phagemids for producing phage) for use with a programmable nuclease in a method of treating a microbial infection of a subject, wherein the microbial infection is caused by microbes of a first species or strain and the nuclease is programmable to cut a target site comprised by the genomes of microbes that have infected the subject, whereby microbes of the first species or strain are killed, or growth or proliferation of the microbes is reduced, the treatment method comprising exposing the subject to the nuclease and viruses wherein the nuclease is programmed to cut the target site, whereby genomes of the microbes comprised by the subject are cut and microbial infection of the subject is treated; wherein each virus comprises a copy of a nucleic acid that encodes an RNA for expression of the RNA in the subject, wherein the RNA complexes with the nuclease to program the nuclease to cut the target site in microbes comprised by the subject; wherein the viruses are capable of infecting microbes comprised by the subject to deliver thereto the nucleic acid.

In a Third Configuration

A composition comprising a plurality of nucleic acids for programming a programmable nuclease in a method of treating a microbial infection of a subject, wherein the microbial infection is caused by microbes of a first species or strain and the nuclease is programmable to cut a target site comprised by the genomes of microbes that have infected the subject, whereby microbes of the first species or strain are killed, or growth or proliferation of the microbes is reduced, the treatment method comprising exposing the subject to the nuclease and the nucleic acids wherein the nuclease is programmed to cut the target site, whereby genomes of the microbes comprised by the subject are cut and microbial infection of the subject is treated; wherein each nucleic acid encodes an RNA for expression of the RNA in the subject, wherein the RNA complexes with the nuclease to program the nuclease to cut the target site in microbes comprised by the subject.

In a Fourth Configuration

A CRISPR/Cas system comprising a nuclease according to the invention for use in the method of treatment, wherein the nuclease is a Cas nuclease (eg, a Cas 3 or 9) and the system comprises one or more guide RNAs or DNA encoding one or more guide RNAs, wherein each guide RNA is capable of programming the Cas nuclease to cut a target site comprised by the genomes of the microbes.

In a Fifth Configuration

A method of treating a microbial infection of a subject, wherein the microbial infection is caused by microbes of a first species or strain and the nuclease is programmable to cut a target site comprised by the genomes of microbes that have infected the subject, whereby microbes of the first species or strain are killed, or growth or proliferation of the microbes is reduced, the treatment method comprising exposing the subject to the nuclease wherein the nuclease is programmed to cut the target site, whereby genomes of the microbes comprised by the subject are cut and microbial infection of the subject is treated.

In a Sixth Configuration

A method of treating a microbial infection of a subject, wherein the microbial infection is caused by microbes of a first species or strain and the nuclease is programmable to cut a target site comprised by the genomes of microbes that have infected the subject, whereby microbes of the first species or strain are killed, or growth or proliferation of the microbes is reduced, the treatment method comprising exposing the subject to the nuclease and a plurality of viruses wherein the nuclease is programmed to cut the target site, whereby genomes of the microbes comprised by the subject are cut and microbial infection of the subject is treated; wherein each virus comprises a copy of a nucleic acid that encodes an RNA for expression of the RNA in the subject, wherein the RNA complexes with the nuclease to program the nuclease to cut the target site in microbes comprised by the subject; wherein the viruses are capable of infecting microbes comprised by the subject to deliver thereto the nucleic acid.

In a Seventh Configuration

A method of treating a microbial infection of a subject, wherein the microbial infection is caused by microbes of a first species or strain and the nuclease is programmable to cut a target site comprised by the genomes of microbes that have infected the subject, whereby microbes of the first species or strain are killed, or growth or proliferation of the microbes is reduced, the treatment method comprising exposing the subject to the nuclease and a plurality of nucleic acids wherein the nuclease is programmed to cut the target site, whereby genomes of the microbes comprised by the subject are cut and microbial infection of the subject is treated; wherein each virus comprises a copy of a nucleic acid that encodes an RNA for expression of the RNA in the subject, wherein the RNA complexes with the nuclease to program the nuclease to cut the target site in microbes comprised by the subject; wherein each nucleic acid encodes an RNA for expression of the RNA in the subject, wherein the RNA complexes with the nuclease to program the nuclease to cut the target site in microbes comprised by the subject.

In a Eighth Configuration

Use of a nuclease, plurality of viruses, system, guide RNA, DNA or vector of the invention, in the manufacture of a composition for carrying out a method of treatment as defined herein, wherein the subject is an organism other than a human or animal.

In a Ninth Configuration

Use of a nuclease, plurality of viruses, system, guide RNA, DNA or vector of the invention, in the manufacture of a composition for carrying out an ex vivo or in vitro a method of treatment of a microbial infection of a substrate, wherein the microbial infection is caused by microbes of a first species or strain and the nuclease is programmable to cut a target site comprised by the genomes of microbes that have infected the substrate, whereby microbes of the first species or strain are killed, or growth or proliferation of the microbes is reduced, the treatment method comprising exposing the subject to the nuclease wherein the nuclease is programmed to cut the target site, whereby genomes of the microbes comprised by the subject are cut and acute microbial infection of the substrate is treated.

In a Tenth Configuration

Use of a programmable nuclease in the manufacture of a composition for carrying out an ex vivo method of treatment of a microbial infection of a substrate, wherein the microbial infection is caused by microbes of a first species or strain and the nuclease is programmable to cut a target site comprised by the genomes of microbes that have infected the substrate, whereby microbes of the first species or strain are killed, or growth or proliferation of the microbes is reduced, the treatment method comprising exposing the subject to the nuclease wherein the nuclease is programmed to cut the target site, whereby genomes of the microbes comprised by the subject are cut and acute microbial infection of the substrate is treated.

In any Configuration: For example, the infection is an acute infection. For example, the infection is an acute infection that is rapidly treated. For example, the infection is treated rapidly—for example, the method comprises reducing the infection at least 100-fold by the first 30 minutes (eg, by the first 15 minutes) of the treatment. For example, the treatment is durable—for example, the reduction in infection persists for at least 30 minutes immediately after the first 30 minutes of the treatment. Also, optionally a reduction of the infection by at least 100-fold or 1000-fold is maintained for at least 60 minutes (eg, at least 120 minutes) after commencement of the treatment. Exemplification is provided below which surprisingly demonstrates these, such as a rapid killing that was durable around 3 hours after treatment commenced. For example, the method improves survival of the subject, or improves survival rates in humans or human patients suffering from infection by the microbes of the first species or strain.

The invention also provides a solution to the need for effective treatment of pathogenic bacterial infections in subjects undergoing a cancer or other, separate therapy which must also be efficacious. Thus, the invention further provides:—

In an Eleventh Configuration

A method for treating a pathogenic bacterial infection in a human or animal subject caused by bacteria (first bacteria) of a first species or strain, the method comprising selectively killing first bacteria comprised by the subject by cutting a target site comprised by the genomes of the first bacteria, wherein the cutting is carried out using a programmable nuclease that is programmed to cut the target site, wherein the subject is suffering from a further disease or condition other than the pathogenic bacterial infection and the method comprises administering a therapy to the subject for treating or preventing the further disease or condition, wherein the nuclease treats the infection and the therapy is efficacious in the presence of the programmed nuclease to treat or prevent the disease or condition.

A method for treating a pathogenic bacterial infection in a cancer patient caused by bacteria (first bacteria) that are *E. coli, Pseudomonas aeruginosa* or *Klebsiella* bacteria, the method comprising selectively killing first bacteria comprised by the subject by cutting a target site comprised by the genomes of the first bacteria, wherein the cutting is carried out using a Cas nuclease that is programmed by guide RNA to cut the target site, wherein the method comprises administering an immunotherapy to the subject for treating cancer in the patient, wherein the nuclease treats the infection and the immunotherapy is efficacious in the presence of the programmed nuclease to treat the cancer;

Wherein
(a) The immunotherapy comprises administering to the patient an anti-PD-1/PD-L1 axis antibody optionally selected from pembrolizumab, nivolumab, atezolimumab, avelumab and durvalumab; and
(b) The cancer is selected from melanoma; renal cell carcinoma; bladder cancer; a solid tumour; non-small cell lung cancer (NSCLC); forehead and neck squamous cell carcinoma (HNSCC); Hodgkin's lymphoma; a cancer that overexpresses PD-L1 and no mutations in EGFR or in ALK; colorectal cancer and hepatocellular carcinoma.

A method for treating a pathogenic bacterial infection in a cancer patient caused by bacteria (first bacteria) of a first species or strain, the method comprising selectively killing first bacteria comprised by the subject by cutting a target site comprised by the genomes of the first bacteria, wherein the cutting is carried out using a programmable nuclease that is programmed to cut the target site, wherein the subject is suffering from a cancer and the method comprises administering a cancer therapy to the subject for treating the cancer, wherein the nuclease treats the infection and the cancer therapy is efficacious in the presence of the programmed nuclease to treat the cancer.

In a Twelfth Configuration

A method for treating a pathogenic bacterial infection in a cancer patient caused by bacteria (first bacteria) of a first species or strain, the method comprising selectively killing first bacteria comprised by the subject by cutting a target site comprised by the genomes of the first bacteria, wherein the cutting is carried out using a Cas nuclease that is programmed by guide RNA to cut the target site, wherein the method comprises administering an immunotherapy to the subject for treating cancer in the patient, wherein the nuclease treats the infection and the immunotherapy is efficacious in the presence of the programmed nuclease to treat the cancer.

In a Thirteenth Configuration

A programmable nuclease for use in the method of the invention.

In a Fourteenth Configuration

A CRISPR/Cas system comprising a nuclease according to the 13$^{th}$ Configuration for use in the method of the 11$^{th}$ or 12$^{th}$ Configuration, wherein the nuclease is a Cas nuclease (eg, a Cas 3 or 9) and the system comprises one or more guide RNAs (gRNAs) or DNA encoding one or more guide RNAs, wherein each guide RNA is capable of programming the Cas nuclease to cut a target site comprised by the genomes of first bacteria.

In a Fifteenth Configuration

A guide RNA or a DNA encoding a guide RNA for use in the system or method of treating a pathogenic bacterial infection.

In a Sixteenth Configuration

A nucleic acid vector comprising the guide RNA or DNA.

In a Seventeenth Configuration

A pharmaceutical composition comprising a first nucleic acid vector (or a plurality thereof) encoding the nuclease and a second nucleic acid vector (or a plurality thereof) encoding the guide RNA.

BRIEF DESCRIPTION OF THE DRAWINGS

FIG. 1A shows that CRISPR induction killed 99.98% of the population in 30 minutes (black line). Growth in absence of induction is shown in dashed lines. CRISPR was induced at time-point 0 and monitored until 60 minutes. FIG. 1B shows dilution series ($10^1$-$10^6$) of drop spots (5 µl) on LB agar plates of *E. coli* ATCC43888 harboring the CGV system after 30 minutes of induction.

FIG. 5A shows that CRISPR induction killed 99.98% of the population in 15 minutes (black line). Growth in absence of induction is shown in dashed lines. CRISPR was induced at time-point 0 and monitored over 3 h. FIG. 5B shows dilution series ($10^1$-$10^6$) of drop spots (5 µl) on LB agar plates of *E. coli* Nissle 1917 harboring the CCV system after 15 minutes of induction.

FIG. 6A shows that CRISPR induction killed 99.98% of the population in 15 minutes (black line). Growth in absence of induction is shown in dashed lines. CRISPR was induced at time-point 0 and monitored over 3 h. FIG. 6B shows dilution series ($10^1$-$10^6$) of drop spots (5 µl) on LB agar plates of *E. coli* Nissle 1917 harboring the CGV system after 15 minutes of induction.

DETAILED DESCRIPTION

Figure 1A:
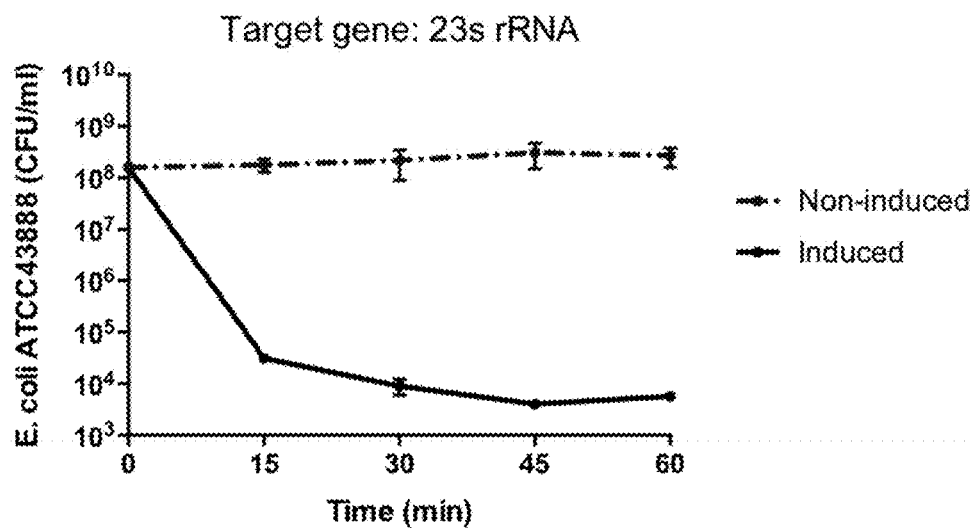
FIGS. 1A-1B show time-kill curves for *Escherichia coli* (EHEC) ATCC43888 strain harboring the CGV system.

The approach of the present invention is different from conventional antibiotic approaches. The present invention utilizes targeted cutting of microbial genomes using programmed nucleases, whereas conventional antibiotics rely upon metabolic processes and cell replication cycles—and the inhibition of these—for their activity. By focusing instead on nuclease cutting, the invention surprisingly achieves very quick and efficient microbial killing that also is remarkably durable. This is demonstrated in experiments below with different microbes, different nucleases and different delivery approaches. Typically, 99-100% killing was surprisingly observed many times and killing of 3-4 logs was very quickly achieved and with lasting duration.

The invention provides methods for treating or preventing microbial (eg, bacterial) infections and means for performing these methods. In particular, treatment of infections requiring rapid therapy is made possible, such as for treating acute conditions such as septicemia, sepsis, SIRS or septic shock. As explained herein, a rapid response is vital to address microbial infection in many settings. Speed is of the essence for many infection scenarios, such as acute infections requiring hospital admission. Benefits of the invention can be one or more of: the reduction in the spread, severity or progression of the infection in the subject; reduction in the development, severity or progression of symptoms of the infection (eg, sepsis or septic shock); and an increase in the likelihood of survival in human or animal patients.

The invention uses programmable nuclease cutting of microbe genomes. The targeted cutting provides selective microbe killing or reduction of growth or proliferation to treat or prevent infection, as opposed to more broad-spectrum microbial killing of several different species as seen with conventional antibiotics. Selective killing is advantageous to leave beneficial microbes untargeted by the treatment, which may be beneficial to the patient. Moreover, the inventors have surprisingy found a substantial (by several logs) killing can be achieved very rapidly (eg, within 15 minutes) and sustainable effects can be achieved (eg, for more than 1 hour) in some embodiments. As exemplified below, the inventors surprisingly could remarkably achieve a fast and durable killing for around 2-3 hours.

Thus, the invention provides the following aspects:—

A programmable nuclease for use in a method of treating a microbial infection (eg, an acute bacterial infection) of a subject, wherein the microbial infection is caused by microbes of a first species or strain and the nuclease is programmable to cut a target site comprised by the genomes of microbes that have infected the subject, whereby microbes of the first species or strain are killed, or growth or proliferation of the microbes is reduced, the treatment method comprising exposing the subject to the nuclease wherein the nuclease is programmed to cut the target site, whereby genomes of the microbes comprised by the subject are cut and microbial infection of the subject is treated.

Another aspect provides: A programmable nuclease for use in a method of rapidly treating an acute microbial (eg, bacterial) infection of a subject, wherein the microbial infection is caused by microbes of a first species or strain and the nuclease is programmable to cut a target site comprised by the genomes of microbes that have infected the subject, whereby microbes of the first species or strain are killed, or growth or proliferation of the microbes is reduced, the treatment method comprising exposing the subject to the nuclease wherein the nuclease is programmed to cut the target site, whereby genomes of the microbes comprised by the subject are cut and acute microbial infection of the subject is rapidly treated.

Another aspect provides: A programmable nuclease for use in a method of treating a microbial (eg, bacterial) infection of a subject, wherein the microbial infection is caused by microbes of a first species or strain and the nuclease is programmable to cut a target site comprised by the genomes of microbes that have infected the subject, whereby microbes of the first species or strain are killed, or growth or proliferation of the microbes is reduced, the treatment method comprising exposing the subject to the nuclease and a nucleic acid that programs the nuclease to recognise and cut the target site, whereby genomes of the microbes comprised by the subject are cut and microbial infection of the subject is treated.

Another aspect provides: A programmable nuclease for use in a method of rapidly treating an acute microbial (eg, bacterial) infection of a subject, wherein the microbial infection is caused by microbes of a first species or strain and the nuclease is programmable to cut a target site comprised by the genomes of microbes that have infected the subject, whereby microbes of the first species or strain are killed, or growth or proliferation of the microbes is reduced, the treatment method comprising exposing the subject to the nuclease and a nucleic acid that programs the nuclease to recognise and cut the target site, whereby genomes of the microbes comprised by the subject are cut and acute microbial infection of the subject is rapidly treated.

Another aspect provides: A programmable nuclease for use in a method of durably treating a microbial (eg, bacterial) infection of a subject, wherein the microbial infection is caused by microbes of a first species or strain and the nuclease is programmable to cut a target site comprised by the genomes of microbes that have infected the subject, whereby microbes of the first species or strain are durably killed, or growth or proliferation of the microbes is reduced, the treatment method comprising exposing the subject to the nuclease wherein the nuclease is programmed to cut the target site, whereby genomes of the microbes comprised by the subject are cut and microbial infection of the subject is treated.

Another aspect provides: A programmable nuclease for use in a method of durably treating a microbial (eg, bacterial) infection of a subject, wherein the microbial infection is caused by microbes of a first species or strain and the nuclease is programmable to cut a target site comprised by the genomes of microbes that have infected the subject, whereby microbes of the first species or strain are durably killed, or growth or proliferation of the microbes is reduced, the treatment method comprising exposing the subject to the nuclease and a nucleic acid that programs the nuclease to recognise and cut the target site, whereby genomes of the microbes comprised by the subject are cut and microbial infection of the subject is treated.

Another aspect provides: A programmable nuclease for use in a method of durably treating an acute microbial (eg, bacterial) infection of a subject, wherein the microbial infection is caused by microbes of a first species or strain and the nuclease is programmable to cut a target site comprised by the genomes of microbes that have infected the subject, whereby microbes of the first species or strain are durably killed, or growth or proliferation of the microbes is reduced, the treatment method comprising exposing the subject to the nuclease and a nucleic acid that programs the nuclease to recognise and cut the target site, whereby genomes of the microbes comprised by the subject are cut and acute microbial infection of the subject is treated.

Surprisingly, as exemplified below, a durable effect of several logs (eg, 3 or 4 logs) using a nuclease (as opposed to conventional means for conventional antibiotic killing) was observed around 3 hours after the first exposure of bacteria with a programmed nuclease. This aspect of the invention, therefore, makes possible dosing regimens for less frequent exposure to a programmed nuclsase (ie, less frequent administration of a programmed nuclease, programmable nuclease and/or nucleic acid for programming the nuclease). For example, a Cas and gRNA (or DNA encoding a gRNA) for programming the nuclease are administered with a programmable nuclease (eg, a Cas 9 or Cas3) to the subject at a first time (T1) and at a second time (T2); or gRNA (or DNA encoding a gRNA) is administered on T1 and T2 for programming an endogenous Cas nuclease (eg, a Cas9 or Cas3) of bacteria of said first species or strain, wherein the programmed endogenous Cas cuts the genomes of the bacteria to kill the bacteria or to reduce growth or proliferation, thus treating the infection. Such less frequent dosing is convenient for the healthcare practitioner and patient, as well as provides for economical therapy. Thus, optionally, the nuclease and/or nucleic acid is administered to the subject on T1 and T2, wherein T2 is at least 2, 3, 4, 5, 6, 7, 8, 9, 10, 11, 12, 13, 14 or 24 hours after T1. For example, T2 is 2, 3, 4, 5, 6, 7, 8, 9, 10, 11, 12, 13, 14 or 24 hours after T1. For example, T2 is 2-7 hours after T1. For example, T2 is 1 hour after T1. For example, T2 is 2 hours after T1. For example, T2 is 3 hours after T1. For example, T2 is 4 hours after T1. For example, T2 is 5 hours after T1.

Optionally, the nuclease (eg, programmed nuclease) and/or a nucleic acid that programs the nuclease to recognise and cut the target site is administered to the subject on T1 and T2, wherein T2 is at least 1 hour (eg, 1, 1.5, 2, 2.5 or 3 hours) after T1.

Another aspect provides: A Cas nuclease for use in a method of treating a microbial (eg, bacterial) infection of a subject, wherein the microbial infection is caused by microbes of a first species or strain and the nuclease is programmable with a guide RNA (gRNA) to cut a target site comprised by the genomes of microbes that have infected the subject, whereby microbes of the first species or strain are killed, or growth or proliferation of the microbes is reduced, the treatment method comprising administering to the subject said a nucleic acid, wherein the nucleic acid is the gRNA or a DNA encoding the gRNA, thereby programming the nuclease to recognise and cut the target site of the microbes comprised by the subject, whereby genomes of the microbes are cut and microbial infection of the subject is treated, wherein the method comprises administering the nucleic acid to the subject on at a first time (T1) and at a second time (T2), whereby the subject is exposed to programmed nuclease on T1 and T2, and wherein T2 is no less than 1 hour after T1.

Optionally, T2 is no less than 2 hours after T1; optionally, T2 is no less than 3 hours after T1; optionally, T2 is no less than 4 hours after T1; optionally, T2 is no less than 5 hours after T1; optionally, T2 is no less than 6 hours after T1; optionally, T2 is no less than 7 hours after T1; optionally, T2 is no less than 8 hours after T1; optionally, T2 is no less than 9 hours after T1; optionally, T2 is no less than 10 hours after T1; optionally, T2 is no less than 11 hours after T1; optionally, T2 is no less than 12 hours after T1; optionally, T2 is no less than 13 hours after T1; optionally, T2 is no less than 14 hours after T1; or optionally, T2 is no less than 24 hours after T1. Additionally or alternatively: Optionally, T2 is no more than 7 hours after T1; optionally, T2 is no more than 12 hours after T1; optionally, T2 is no more than 24 hours after T1; optionally, T2 is 2-7 hours after T1; optionally, T2 is 24 hours after T1; optionally, T2 is 7 hours after T1; optionally, T2 is 6 hours after T1; optionally, T2 is 5 hours after T1; optionally, T2 is 4 hours after T1; optionally, T2 is 3 hours after T1; optionally, T2 is 2 hours after T1; optionally, T2 is 1 hour after T1. For example, T2 is 2, 3, 4, 5, 6, 7, 8, 9, 10, 11, 12, 13, 14 or 24 hours after T1. For example, T2 is 1-7 hours after T1; or T2 is 2-7 hours after T1; or T2 is 3-7 hours after T1; or T2 is 4-7 hours after T1; or T2 is 5-7 hours after T1; or T2 is 6-7 hours after T1.

Optionally, the method comprises reducing the infection at least 100-fold by the first 30 minutes (eg, by the first 15 minutes) of the treatment. Optionally, the method comprises reducing the infection at least 1000-fold by the first 30 minutes (eg, by the first 15 minutes) of the treatment. Optionally, the method comprises reducing the infection at least 10000-fold by the first 30 minutes (eg, by the first 15 minutes) of the treatment.

Optionally, the method comprises reducing the infection such that the reduction in infection persists for 30 minutes immediately after the first 30 minutes of the treatment. Optionally, the method comprises reducing the infection such that a reduction in infection by at least 100-fold persists for 30 minutes immediately after the first 30 minutes of the treatment. Optionally, the method comprises reducing the infection such that a reduction in infection by at least 1000-fold persists for 30 minutes immediately after the first 30 minutes of the treatment. Optionally, the method comprises reducing the infection such that a reduction in infection by at least 10000-fold persists for 30 minutes immediately after the first 30 minutes of the treatment.

Optionally, the method comprises reducing the infection at least 100-fold by the first 30 minutes (eg, by the first 15 minutes) of the treatment; and wherein a reduction in infection by at least 100-fold persists for 30 minutes immediately after the first 30 minutes of the treatment. Optionally, the method comprises reducing the infection at least 1000-fold by the first 30 minutes (eg, by the first 15 minutes) of the treatment; and wherein a reduction in infection by at least 1000-fold persists for 30 minutes immediately after the first 30 minutes of the treatment. Optionally, the method comprises reducing the infection at least 10000-fold by the first 30 minutes (eg, by the first 15 minutes) of the treatment; and wherein a reduction in infection by at least 10000-fold persists for 30 minutes immediately after the first 30 minutes of the treatment.

Optionally, the method comprises maintaining reduction of the infection by at least 100-fold for at least 60 minutes (eg, at least 120, 145 or 180 minutes) after exposing the subject to the programmed nuclease. Optionally, a reduction of the infection by at least 100-fold is maintained for at least 60 minutes (eg, at least 120, 145 or 180 minutes) after exposing the subject to the programmed nuclease. Optionally, the method comprises maintaining reduction of the infection by at least 1000-fold for at least 60 minutes (eg, at least 120, 145 or 180 minutes) after exposing the subject to the programmed nuclease. Optionally, a reduction of the infection by at least 1000-fold is maintained for at least 60 minutes (eg, at least 120, 145 or 180 minutes) after exposing the subject to the programmed nuclease. Optionally, the method comprises maintaining reduction of the infection by at least 10000-fold for at least 60 minutes (eg, at least 120, 145 or 180 minutes) after exposing the subject to the programmed nuclease. Optionally, a reduction of the infection by at least 10000-fold is maintained for at least 60 minutes (eg, at least 120, 145 or 180 minutes) after exposing the subject to the programmed nuclease.

Optionally, the method comprises reducing the infection at least 100-fold by the first 30 minutes (eg, by the first 15 minutes) of the treatment; and wherein reduction of the infection by at least 100-fold is maintained for at least 60 minutes (eg, at least 120, 145 or 180 minutes) after exposing the subject to the programmed nuclease. Optionally, the method comprises reducing the infection at least 1000-fold by the first 30 minutes (eg, by the first 15 minutes) of the treatment; and wherein reduction of the infection by at least 1000-fold is maintained for at least 60 minutes (eg, at least 120, 145 or 180 minutes) after exposing the subject to the programmed nuclease. Optionally, the method comprises reducing the infection at least 10000-fold by the first 30 minutes (eg, by the first 15 minutes) of the treatment; and wherein reduction of the infection by at least 10000-fold is maintained for at least 60 minutes (eg, at least 120, 145 or 180 minutes) after exposing the subject to the programmed nuclease.

Optionally, the method comprises reducing the infection at least 10000-fold by the first 15 minutes of the treatment; and wherein reduction of the infection by at least 10000-fold is maintained for at least 45 minutes after exposing the subject to the programmed nuclease. This is exemplified below.

In an example, the infection is durably treated, wherein a reduction of the infection by at least 100-fold is maintained for at least 60 minutes (eg, at least 120, 145 or 180 minutes) after commencement of the treatment. In an example, the infection is durably treated, wherein a reduction of the infection by at least 1000-fold is maintained for at least 60 minutes (eg, at least 120, 145 or 180 minutes) after commencement of the treatment. In an example, the infection is durably treated, wherein a reduction of the infection by at least 10000-fold is maintained for at least 60 minutes (eg, at least 120, 145 or 180 minutes) after commencement of the treatment.

Optionally, the infection is reduced at least 100,000-fold by the first 30 or 45 minutes of the treatment. Optionally, the infection is reduced at least 100,000-fold by the first 30 or 45 minutes of the treatment and the reduction is maintained until the $60^{th}$ minute of the treatment.

Optionally, the infection is reduced at least 1000,000-fold by the first 30 or 45 minutes of the treatment. Optionally, the infection is reduced at least 1000,000-fold by the first 30 or 45 minutes of the treatment and the reduction is maintained until the $60^{th}$ minute of the treatment.

Optionally, the infection is reduced at least 100-fold by the first 15 minutes of the treatment. Optionally, the infection is reduced at least 1000-fold by the first 15 minutes of the treatment. Optionally, the infection is reduced at least 100-fold by the first 15 minutes of the treatment and at least 1000-fold by the first 30 minutes of the treatment.

For example, the reduction is maintained for at least 15 further minutes, eg, the infection is reduced at least 100-fold or at least 1000-fold by the first 15 minutes of the treatment and the reduction is maintained from the 15-$30^{th}$ minute or 15-$45^{th}$ minute of the treatment or 15-$60^{th}$ minute of the treatment.

For example, the infection is reduced at least 100-fold or at least 1000-fold or at least 10000-fold by the first 15 minutes of the treatment in the first 15 minutes and the reduction is maintained for from the 15-$30^{th}$ minute or 15-$45^{th}$ minute of the treatment.

Optionally, the method comprises reducing the infection at least 100-fold by the first 30 minutes (eg, by the first 15 minutes) of the treatment.

Optionally the method comprises reducing the infection at least 1000-fold by the first 30 minutes (eg, by the first 15 minutes) of the treatment.

Optionally the method comprises reducing the infection at least 10000-fold by the first 30 minutes (eg, by the first 15 minutes) of the treatment.

Figure 5A:
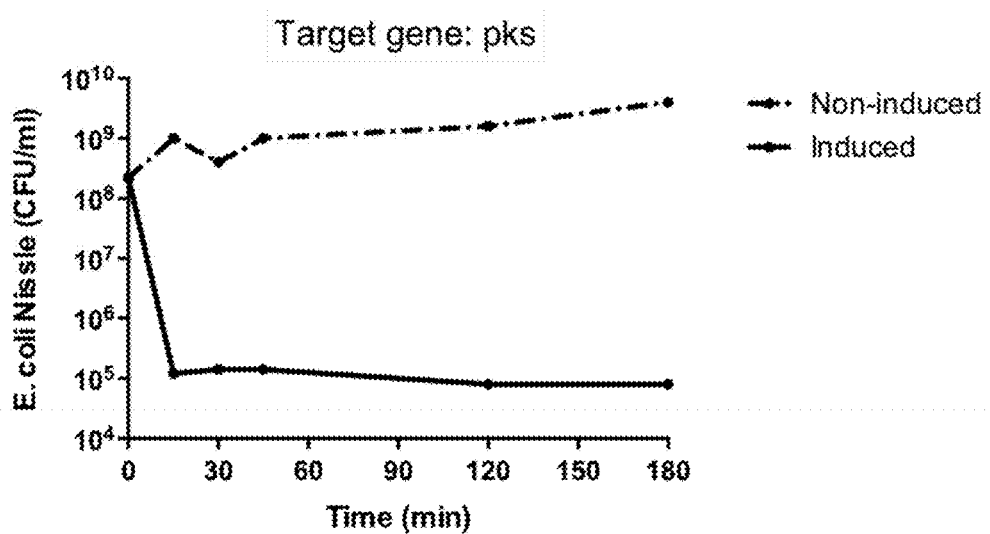
FIGS. 5A-5B show time-kill curves for *Escherichia coli* Nissle 1917 harboring the CGV system targeting pks.
Figure 6A:
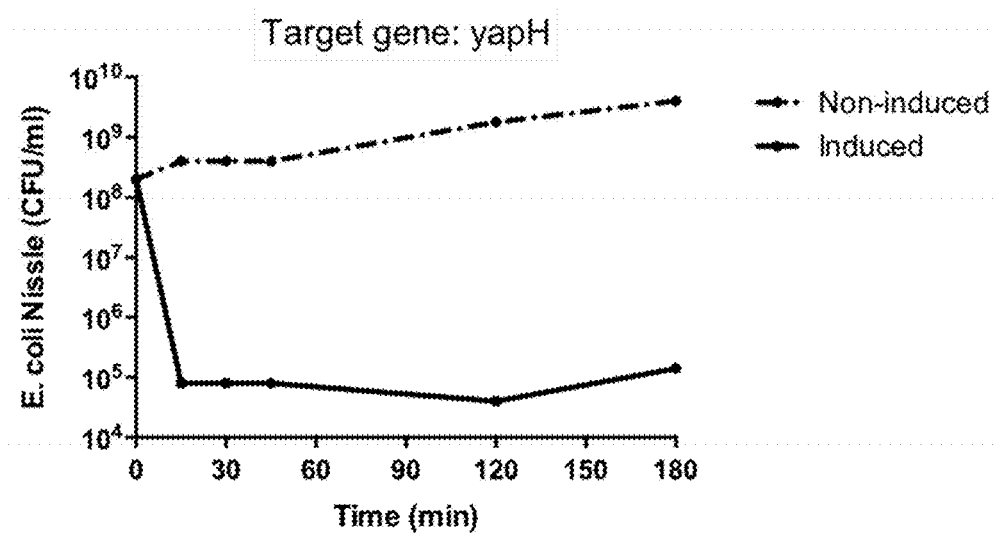
FIGS. 6A-6B show time-kill curves for *Escherichia coli* Nissle 1917 harboring the CCV system targeting yapH.

Optionally, the method comprises reducing the infection such that the reduction in infection persists for 30 minutes immediately after the first 30 minutes of the treatment, eg, the reduction may persist for at least 60 minutes after the first 30 minutes of the treatment. If the treatment is administered at time zero (T0), then the reduction in infection may be present at 60 minutes counted after T0, and indeed may persist after that 60 minutes. In FIGS. 1A, 5A and 6A, for example, reduction is seen at 60-180 minutes after T0. Optionally, the reduction in infection persists for at least 30 minutes after the first 30 minutes of the treatment.

In an example, the infection is reduced by at least 10, 20, 30, 40, 50, 60, 70, 80, 90, 91, 92, 93, 94, 95, 96, 97, 98 or 99%, eg, in the first 15 minutes of treatment. In an example, the infection is reduced by at least 10, 20, 30, 40, 50, 60, 70, 80, 90, 91, 92, 93, 94, 95, 96, 97, 98 or 99%, eg, in the first 30 minutes of treatment.

For determining killing or reduction in growth or proliferation of the target microbes, one can, for example, determine the difference in the number of microbes of the first species or strain in (i) a sample taken from the subject (eg, a blood, gut or leaf sample) immediately before commencement of the treatment and (ii) a sample (of the same type as the sample of (i), eg, a blood, gut or leaf sample respectively) taken from the subject at 30 minutes of the treatment. For example, if the microbes are bacteria, the samples may be assessed for the difference in colony forming units (CFU)/ml sample, eg, when the samples have been plated on agar in respective petri dishes and incubated under identical conditions. Another example may use microscopic counting of microbes in samples, or other routine methods know to the skilled addressee.

In an example, at least 60, 70, 80, 90, 91, 92, 93, 94, 95, 96, 97, 98 or 99% killing of the microbes is achieved by the first 30, 60, 90 or 120 minutes (eg, by the first 30 minutes; or by the first 120 minutes) of the treatment. For example, wherein the subject is a human or animal, the killing is determined comparing the prevalence (eg, by standard colony counting on an agar plate) of the microbes (eg, bacteria) in a blood sample taken immediately before commencement of the treatment versus a sample taken after the first 15 or 30 minutes of the treatment. In an example, at least 80, 90, 91, 92, 93, 94, 95, 96, 97, 98 or 99% killing of the microbes is achieved by the first 0.5, 1 or 2 hours of the treatment. In an example, at least 99% killing of the microbes is achieved by the first 30 minutes of the treatment. In an example, at least 99% killing of the microbes is achieved by the first 2 hours of the treatment. In an example, 100% killing is achieved. These are exemplified below. In an embodiment, less than 100% of the microbes are killed.

Worked examples of killing in bacteria are shown below. Surprisingly, using a programmed nuclease to target the bacteria of choice, specific cutting resulted in rapid killing of the target bacteria—at least 3 or 4 logs of killing (ie, 1000- or 10,000 fold killing) could be observed in very short spaces of time and surprisingly these were sustained for at least to an hour. Optionally, the infection is reduced at least 1000-fold by the first 15, 30 or 45 minutes of the treatment. Optionally, the infection is reduced at least 1000-fold by the first 15, 30 or 45 minutes of the treatment and the reduction is maintained until the $60^{th}$, $120^{th}$ or $180^{th}$ minute of the treatment. Optionally, the infection is reduced at least 10,000-fold by the first 15, 30 or 45 minutes of the treatment. Optionally, the infection is reduced at least 10,000-fold by the first 15, 30 or 45 minutes of the treatment and the reduction is maintained until the $60^{th}$, $120^{th}$ or $180^{th}$ minute of the treatment. See, for example, exemplification in FIG. 5A.

In an example, 100% killing is achieved by 24 hours after commencement of the treatment.

In an example, the infection is reduced at least 1000-fold for 2 hours or more (eg, for 2-3 hours). Optionally also the infection is reduced by at least 1000-fold by the first 15 or 13 minutes of the treatment.

In an example, the infection is reduced at least 10,000-fold for 2 hours or more (eg, for 2-3 hours). Optionally also the infection is reduced by at least 10,000-fold by the first 15 or 13 minutes of the treatment.

In an example, the infection is reduced by at least 90, 91, 92, 93, 94, 95, 96, 97, 98 or 99% for 1 hour; or for 1 hour or more; or for 2 hours or more (eg, for 2-3 hours). Optionally, the infection is reduced by at least 90% for 1 hour; or for 1 hour or more; or for 2 hours or more (eg, for 2-3 hours), and optionally by the first 30 minutes (eg, by the first 15 minutes) of the treatment. Optionally, the infection is reduced by at least 90% for 1 hour or more, and by the first 30 minutes (eg, by the first 15 minutes) of the treatment. Optionally, the infection is reduced by at least 90, 91, 92, 93, 94, 95, 96, 97, 98 or 99% by the first 15 or 13 minutes of the treatment. Optionally, the infection is reduced by at least 90, 91, 92, 93, 94, 95, 96, 97, 98 or 99% by the first 15 or 13 minutes of the treatment; and wherein the reduction is maintained for 1 hour or more (eg, for 2 hours or more; or for 3 hours or more; or for about 2 hours; or for 2 hours; or for about 3 hours; or for 3 hours). Exemplification below is provided, wherein the bacteria are *E. coli*.

Optionally, the subject is a human or animal and the microbes are bacteria (eg, *E. coli* or *C. difficile*), wherein blood infection of the subject by the bacteria is reduced at least 100-fold by the first 30 minutes (eg, by the first 15 minutes) of the treatment. Optionally, the subject is a human or animal and the microbes are bacteria (eg, *E. coli* or *C. difficile*), wherein blood infection of the subject by the bacteria is reduced at least 1000-fold by the first 30 minutes (eg, by the first 15 minutes) of the treatment. Optionally, the subject is a human or animal and the microbes are bacteria (eg, *E. coli* or *C. difficile*), wherein blood infection of the subject by the bacteria is reduced at least 10,00-fold by the first 30 minutes (eg, by the first 15 minutes) of the treatment. Optionally, the *E. coli* are EHEC *E. coli*.

Optionally, the programmed nuclease (eg, a Cas9 or Cas3) is capable of cutting a target site comprised by *E. coli* (EHEC) ATCC43888. Optionally, the programmed nuclease (eg, a Cas9 or Cas3) is capable of cutting a target site comprised by *E. coli* Nissle.

Optionally, the blood of the subject is infected with from $10^7$ to $10^{12}$ CFU/ml (eg, from $10^7$ to $10^{11}$, from $10^7$ to $10^{10}$, from $10^7$ to $10^9$ or from $10^7$ to $10^8$ CFU/ml) of the bacteria immediately before the treatment.

The worked example below shows improved survival using the method of the invention in an in vivo model. In an example, therefore, the method of the invention is for improving survival of the subject by treating acute microbial infection of a subject. In an example, the programmed nuclease herein is capable of carrying out the killing of bacteria of the first species or strain in *Galleria mellonella* larvae in vivo infection model.

The nuclease may be, for example, a DNase (eg, a Cpf1, Cas9 or Cas3) or a RNase (eg, Cas13b).

In an example, the nuclease is an isolated or recombinant nuclease. For example, the nuclease is a synthetic or non-naturally occurring nuclease.

In an example, the nuclease is ex vivo, eg, in vitro. In an example, the nucleic acid is ex vivo. In an example, the guide RNA or DNA encoding guide RNA(s) herein is ex vivo, eg, in vitro.

Optionally, the nuclease is a Cas nuclease (eg, a Cpf1, CasX, CasY, Cas13b, Cas 3 or 9), a meganuclease, a TALEN (Transcription activator-like effector nuclease) or zinc finger nuclease. In an example, the Cas is a *Streptococcus* (eg, pyo genes or *aureus*) Cas9, *Clostridium* (eg, *dificile*), *Salmonella* (eg, *typhimurium*) or *E. coli* Cas3. For example, the Cas is a spCas. In an example, the Cas9 is in combination with a tracrRNA or a DNA encoding a tracrRNA which is operable with the Cas. For example, the tracrRNA is of the same species as the Cas, eg, a *S. pyogenes* tracrRNA or DNA encoding this.

In an example, the nuclease is a Cas 3 encoded by a nucleic acid comprising SEQ ID NO: 9 or a sequence that is at least 80, 85, 90, 95, 96, 97, 98 or 99% identical thereto. Optionally, also the bacteria are *Clostridium* (eg, *C. dificile*) bacteria; or any *Clostridium* shown in Table 1. This is exemplified below.

In an example, the nuclease is a Cas 9 encoded by a nucleic acid comprising SEQ ID NO: 10 or a sequence that is at least 80, 85, 90, 95, 96, 97, 98 or 99% identical thereto. In an example, the nuclease is a Cas 9 comprising SEQ ID NO: 11 or a sequence that is at least 80, 85, 90, 95, 96, 97, 98 or 99% identical thereto. Optionally, also the bacteria are *Clostridium* (eg, *C. dificile*) bacteria; or any *Clostridium* shown in Table 1. Optionally, also the bacteria are *E. coli* (eg, EHEC). This is exemplified below.

Optionally, the method comprises administering to the subject a RNA or a nucleic acid (eg, DNA) that encodes an RNA for expression of the RNA in the subject, wherein the RNA complexes with the nuclease to program the nuclease to cut the target site in microbes comprised by the subject.

Optionally, the nuclease is administered simultaneously or sequentially with the RNA or nucleic acid to the subject.

Optionally, subject comprises the nuclease prior to administration of the RNA or nucleic acid to the subject. For example, the nuclease is a Cas nuclease that is an endogenous Cas nuclease of bacterial cells of the first species or strain that are comprised by the subject. Thus, in this example, the RNA or nucleic acid may be administered to the subject and introduced into the bacteria for programming endogenous Cas comprised by the bacteria, thereby forming programmed Cas nuclease that cuts the target site in the genomes of the bacteria, whereby bacteria are killed or growth or proliferation of bacteria is reduced, thus treating or preventing the infection.

Optionally, a plurality of viruses (eg, phage or phagemids) are administered to the subject, wherein each virus comprises a copy (eg, one or more, eg, a plurality of copies) of the nucleic acid, wherein the viruses infect the microbes comprised by the subject to deliver thereto the nucleic acid. For example, viruses herein are phage or phagemids that infect (or are capable of infecting) the bacteria of the first species or strain.

Optionally, the ratio of administered viruses:microbes comprised by the subject is from 10 to 150. For example, the microbes are bacteria and the ratio is from 10 to 100, ie, a multiplicity of infection (MOI) of from 1 to 100 (eg, wherein the viruses are capable of replication, eg, are phage and not phagemid), eg, from 10 to 100. The ratio can be determined, for example, using a sample (eg, a blood or gut sample) from a human or animal subject immediately before the treatment and determining the number of microbes (eg, bacteria per ml of blood or gut sample). The amount of viruses to be administered can then be worked out according to the determination using the sample.

Optionally, the microbes are bacteria. Alternatively, the microbes are archaea. Alternatively, the microbes are viruses. Alternatively, the microbes are fungi. Alternatively, the microbes are algae. Alternatively, the microbes are protozoa.

In an example, the subject is a human and the infection is a nosocomial infection. In an example, the subject is a plant, yeast, protist or amoeba.

Optionally, the subject is a human (eg, an adult, child, neonate, toddler, teenager, male or female) or animal (eg, a dog, cat, horse, cow, sheep, goat, salmon, chicken, turkey, pig, companion animal or livestock animal).

In an example, the subject is a human or animal and: Optionally, the infection is an infection of the lungs, abdomen or urinary tract. In an example, the subject is suffering from a urinary tract infection, lung infections, such as pneumonia, a kidney infection or an abdominal infection. In an example, the subject is a surgery patient. In an example, the subject is a burns patient. In an example, the subject has an infected wound (eg, a bacterially infected wound). In an example, the patient is suffering from AIDS or is infected by HIV. In an example, the subject is suffering from a cancer, such as a blood cancer, eg, leukaemia, eg, AML or CML or CLL or a lymphoma. In an example, the subject is a tissue or organ transplant patient, eg, a haematopoietic stem cell transplant or bone marrow transplant patient. In an example, the subject has a urinary or intravenous catheter. In an example, the subject is on mechanical ventilation. In an example, the subject has been receiving an immunosuppressant. In an example, the subject is suffering from pneumonia. In an example, the subject is an intensive care unit (ICU) patient. In an example, the subject is an Acute respiratory distress syndrome (ARDS) patient. In an example, the subject is suffering from meningitis, an infection in pregnancy, a ruptured gallbladder (a gallbladder rupture is a medical condition where the gallbladder leaks or bursts. Ruptures are commonly caused by inflammation of the gallbladder), abortion with septic shock (abortion with septic shock can be an acute life-threatening illness), endometritis (endometritis is an inflammatory condition of the lining of the uterus, usually due to an infection), Acute Respiratory Distress Syndrome (Acute respiratory distress syndrome is a lung condition; it occurs when fluid fills up the air sacs in the lungs) or cellulitis.

The increase in average age of the population, more people with chronic diseases, on immunosuppressive drugs, and increase in the number of invasive procedures being performed has led to an increased rate of sepsis. Optionally, the subject has undergone surgery, is on an immunosuppressant medication and/or is suffering from a chronic disease.

Optionally, the subject is a human over 60, 65, 70, 75 or 80 years of age or is a paediatric patient. In an alternative, the subject is a paediatric patient (eg, a human baby or child) or adolescent. In an example, the method treats or prevents neonatal sepsis in the subject. In an example the subject is an immune-compromised human or animal, eg, suffering from an acute viral infection, such as HIV infection; or the subject is suffering from a cancer, eg, a blood cancer, such as a leukaemia; or the patient is a transplant patient, eg, that has received an organ, tissue or bone marrow transplant. In an example, the subject is a human or animal that is positive for gram negative bacterial lipopolysaccharide or lipid A. In an example, the subject is a human or animal that is positive for gram positive bacterial cell wall lipoteichoic acid.

Optionally, the method treats or prevents septicaemia and/or sepsis (eg, septic shock) in the subject.

SIRS (Systemic Inflammatory Response Syndrome) criteria has been used to define sepsis.

SIRS is the presence of two or more of the following: abnormal body temperature, heart rate, respiratory rate, or blood gas, and white blood cell count. Sepsis is, for example, SIRS in response to an infectious process. Severe sepsis is, for example, sepsis with sepsis-induced organ dysfunction or tissue hypoperfusion (manifesting as hypotension, elevated lactate, or decreased urine output). Septic shock is, for example, severe sepsis plus persistently low blood pressure, despite the administration of intravenous fluids.

In an embodiment, the method prevents or delays progression of end-organ dysfunction in the subject (when the subject is a human or animal).

Examples of end-organ dysfunction include the following:
  Lungs: acute respiratory distress syndrome (ARDS) ($PaO_2/FiO_2<300$)
  Brain: encephalopathy symptoms including agitation, confusion, coma; causes may include ischemia, bleeding, formation of blood clots in small blood vessels, microabscesses, multifocal necrotizing leukoencephalopathy Liver: disruption of protein synthetic function manifests acutely as progressive disruption of blood clotting due to an inability to synthesize clotting factors and disruption of metabolic functions leads to impaired bilirubin metabolism, resulting in elevated unconjugated serum bilirubin levels Kidney: low urine output or no urine output, electrolyte abnormalities, or volume overload Heart: systolic and diastolic heart failure, likely due to chemical signals that depress myocyte function, cellular damage, manifest as a troponin leak (although not necessarily ischemic in nature)

More specific definitions of end-organ dysfunction exist for SIRS in pediatrics.

Cardiovascular dysfunction (after fluid resuscitation with at least 40 ml/kg of crystalloid)
hypotension with blood pressure<5th percentile for age or systolic blood pressure<2 standard deviations below normal for age, or
vasopressor requirement, or
two of the following criteria:
unexplained metabolic acidosis with base deficit>5 mEq/l
lactic acidosis: serum lactate 2 times the upper limit of normal
oliguria (urine output<0.5 ml/kg/h)
prolonged capillary refill>5 seconds
core to peripheral temperature difference>3° C.
Respiratory dysfunction (in the absence of cyanotic heart disease or known chronic lung disease)
the ratio of the arterial partial-pressure of oxygen to the fraction of oxygen in the gases inspired ($PaO_2/FiO_2$) <300 (the definition of acute lung injury), or
arterial partial-pressure of carbon dioxide ($PaCO_2$)>65 torr (20 mmHg) over baseline $PaCO_2$ (evidence of hypercapnic respiratory failure), or
supplemental oxygen requirement of greater than $FiO_2$ 0.5 to maintain oxygen saturation>92%
Neurologic dysfunction
Glasgow Coma Score (GCS)≤11, or
altered mental status with drop in GCS of 3 or more points in a person with developmental delay/intellectual disability
Hematologic dysfunction
platelet count<80,000/mm$^3$ or 50% drop from maximum in chronically thrombocytopenic, or
international normalized ratio (INR)>2
Disseminated intravascular coagulation
Kidney dysfunction
serum creatinine>2 times the upper limit of normal for age or 2-fold increase in baseline creatinine in people with chronic kidney disease
Liver dysfunction (only applicable to infants>1 month)
total serum bilirubin>4 mg/dl, or
alanine aminotransferase (ALT)>2 times the upper limit of normal Table 2 sets out the criteria for a positive diagnosis of sepsis.

Optionally, the method reduces one or more symptoms in the patient selected from fever, low body temperature, rapid breathing, elevated heart rate, confusion, confusion, metabolic acidosis, respiratory alkalosis, low blood pressure, dysfunction of blood coagulation (such as blood clotting in one or more organs, or bruising) and oedema. Optionally, the method reduces septic shock. Optionally, the sepsis is severe sepsis.

Optionally, at the start of the treatment, the subject (eg, a human) has a temperature of <36° C. or >38° C.; a heart rate of >90/min, a respiratory rate of >20 breaths/min or $PaCO_2$<43 kPa; and white blood cell count of <4000/mm$^3$ or >12,000/mm$^3$.

Optionally, at the start of the treatment, the subject (eg, a human) has presence of two or more of the following: abnormal body temperature, abnormal heart rate, abnormal respiratory rate, abnormal blood gas and abnormal white blood cell count.

Optionally, the subject is a plant. In an example, the subject is a protist, eg, amoeba. Optionally in this example, the microbes are viruses (eg, large or gian viruses, eg, Mimiviruses). The nuclease, for example, is a Cas and is programmable using a guide RNA delivered by a virophage that infects the virus microbes In an example the microbes are yeast, eg, Candida.

Preferably, the microbes are bacteria. Optionally, the bacteria are gram positive bacteria. Optionally, the bacteria are Staphylococcus, Streptococcus, Enterococcus, Legionella, Heamophilus, Ghonnorhea, Acinetobacter, Escherichia, Klebsiella, Pseudomonas or Stenotrophomonas bacteria (eg, E. coli (eg, EHEC E. coli), C. dificile, V. cholera, Staphylococcus (eg, S. aureus or MRSA), Streptococcus pyogenes, Acinetobacter baumannii, Legionella, Pseudomonas aeruginosa, Klebsiella pneumoniae bacteria).

Optionally, the first species is selected from the species in Table 1.

Optionally, the first species is enterohemorrhagic E. coli (EHEC), E. coli Serotype O157:H7 or Shiga-toxin producing E. coli (STEC)). In an example, the bacteria are selected from
Shiga toxin-producing E. coli (STEC) (STEC may also be referred to as Verocytotoxin-producing E. coli (VTEC);
Enterohemorrhagic E. coli (EHEC) (this pathotype is the one most commonly heard about in the news in association with foodborne outbreaks);
Enterotoxigenic E. coli (ETEC);
Enteropathogenic E. coli (EPEC);
Enteroaggregative E. coli (EAEC);
Enteroinvasive E. coli (EIEC); and
Diffusely adherent E. coli (DAEC).

Enterohemorrhagic Escherichia coli (EHEC) serotype O157:H7 is a human pathogen responsible for outbreaks of bloody diarrhoea and haemolytic uremic syndrome (HUS) worldwide. Conventional antimicrobials trigger an SOS response in EHEC that promotes the release of the potent Shiga toxin that is responsible for much of the morbidity and mortality associated with EHEC infection. Cattle are a natural reservoir of EHEC, and approximately 75% of EHEC outbreaks are linked to the consumption of contaminated bovine-derived products. EHEC causes disease in humans but is asymptomatic in adult ruminants. Characteristics of E. coli serotype O157:H7 (EHEC) infection includes abdominal cramps and bloody diarrhoea, as well as the life-threatening complication haemolytic uremic syndrome (HUS). Currently there is a need for a treatment for EHEC infections (Goldwater and Bettelheim, 2012). The use of conventional antibiotics exacerbates Shiga toxin-mediated cytotoxicity. In an epidemiology study conducted by the Centers for Disease Control and Prevention, patients treated with antibiotics for EHEC enteritis had a higher risk of developing HUS (Slutsker et al., 1998). Additional studies support the contraindication of antibiotics in EHEC infection; children on antibiotic therapy for hemorrhagic colitis associated with EHEC had an increased chance of developing HUS (Wong et al., 2000; Zimmerhackl, 2000; Safdar et al., 2002; Tarr et al., 2005). Conventional antibiotics promote Shiga toxin production by enhancing the replication and expression of stx genes that are encoded within a chromosomally integrated lambdoid prophage genome. The approach of the present invention relies on nuclease cutting. Stx induction also promotes phage-mediated lysis of the EHEC cell envelope, allowing for the release and dissemination of Shiga toxin into the environment (Karch et al., 1999; Matsushiro et al., 1999; Wagner et al., 2002). Thus, advantageously, the invention provides alternative means for treating EHEC in human and animal subjects. This is exemplified below with surprising results on the speed and duration of anti-EHEC action produced by nuclease action (as opposed to conventional antibiotic action).

In an example, the subject (eg, a human) is suffering from or at risk of haemolytic uremic syndrome (HUS), eg, the subject is suffering from an *E. coli* infection, such as an EHEC *E. coli* infection.

An aspect of the invention provides: A plurality of viruses (eg, phage or phagemids for producing phage) for use with the nuclease of the invention in the method of treatment, wherein each virus comprises a copy of a nucleic acid described herein, wherein the viruses are capable of infecting microbes comprised by the subject to deliver thereto the nucleic acid.

A aspect of the invention provides: A plurality of viruses (eg, phage or phagemids for producing phage) for use with a programmable nuclease in a method of treating a microbial infection of a subject, wherein the microbial infection is caused by microbes of a first species or strain and the nuclease is programmable to cut a target site comprised by the genomes of microbes that have infected the subject, whereby microbes of the first species or strain are killed, or growth or proliferation of the microbes is reduced, the treatment method comprising exposing the subject to the nuclease wherein the nuclease is programmed to cut the target site, whereby genomes of the microbes comprised by the subject are cut and microbial infection of the subject is treated;

wherein each virus comprises a copy of a nucleic acid that encodes an RNA for expression of the RNA in the subject, wherein the RNA complexes with the nuclease to program the nuclease to cut the target site in microbes comprised by the subject;

wherein the viruses are capable of infecting microbes comprised by the subject to deliver thereto the nucleic acid.

Optionally, the method is for durable treatment, eg, as described herein; and/or optionally, the infection is acute infection.

Optionally, the method is for rapid treatment, eg, as described herein; and/or optionally, the infection is acute infection.

Optionally, the nuclease is according to any nuclease of the invention herein. Optionally, the nucleic acid is according to any nucleic acid of the invention herein.

Optionally, the nuclease is according to any nuclease of the invention herein. Optionally, the nucleic acid is according to any nucleic acid of the invention herein.

In an alternative, when the microbes are viruses, the plurality of viruses are phage that are capable of infecting host cells harbouring the microbes, wherein the nucleic acids are introduced into the host cells for expression therein of the RNA. The RNA complexes with the nuclease in the host cells to guide the nuclease to cut a target site of the microbes (ie, to cut viral RNA or DNA), thereby inactivating the viral microbes. For example, the microbes are viruses (eg, in amoeba; or in human or animal or plant cells) and the viruses of said plurality of viruses are capable of targeting the microbes, whereby the nuclease is programmed to cut the microbes (eg, in the amoeba or in said cells).

An aspect of the invention provides: A composition comprising a plurality of nucleic acids for programming the nuclease of the invention in the method of treatment, wherein each nucleic acid is a nucleic acid as defined herein.

An aspect of the invention provides: A composition comprising a plurality of nucleic acids for programming a programmable nuclease in a method of treating a microbial infection of a subject, wherein the microbial infection is caused by microbes of a first species or strain and the nuclease is programmable to cut a target site comprised by the genomes of microbes that have infected the subject, whereby microbes of the first species or strain are killed, or growth or proliferation of the microbes is reduced, the treatment method comprising exposing the subject to the nuclease and the nucleic acids wherein the nuclease is programmed to cut the target site, whereby genomes of the microbes comprised by the subject are cut and microbial infection of the subject is treated; wherein each nucleic acid encodes an RNA for expression of the RNA in the subject, wherein the RNA complexes with the nuclease to program the nuclease to cut the target site in microbes comprised by the subject.

Optionally, the method is for durable treatment, eg, as described herein; and/or optionally, the infection is acute infection.

Optionally, the method is for rapid treatment, eg, as described herein; and/or optionally, the infection is acute infection.

Optionally, the nuclease is according to any nuclease of the invention herein. Optionally, each nucleic acid is according to any nucleic acid of the invention herein.

Optionally, the composition is a pharmaceutical composition comprising the nucleic acids and a pharmaceutically acceptable diluent, carrier or excipient. Optionally, the composition is for oral, intravenous, pulmonary, rectal, topical, buccal, ocular, intranasal, or subcutaneous administration to a human or animal subject. Optionally, the composition is a herbicide or pesticide or insecticide or nematodicide or aracnicide. Optionally, the composition is toxic to yeast. Optionally, the composition is toxic to giant viruses.

An aspect of the invention provides: A CRISPR/Cas system comprising a nuclease according to the invention for use in the method of treatment, wherein the nuclease is a Cas nuclease (eg, a Cas 3 or 9 or any other Cas mentioned herein) and the system comprises one or more guide RNAs or DNA encoding one or more guide RNAs, wherein each guide RNA is capable of programming the Cas nuclease to cut a target site comprised by the genomes of the microbes.

In an example, each guide RNA mentioned herein is a single guide RNA (ie, a chimaeric guide RNA). In another example, each guide RNA comprises a crRNA that is hybridised to a tracrRNA.

In an example, a target site mentioned herein is comprised by an essential gene, virulence gene or antibiotic resistance gene of the bacteria. In an example, a target site mentioned herein is comprised by a multi-copy sequence (ie, a sequence that is present in more than one (eg, 2, 3, 4, 5, 6, 7, 8 or 9, or more) copies in each bacterial genome). For example, the target site is comprised by a ribosomal RNA gene. In an example, a target site mentioned herein is comprised by a ribosomal RNA gene (eg, a 23S ribosomal RNA gene), a yapH gene; or a pks gene; or homologue or orthologue thereof.

Optionally, each guide RNA herein is capable of hybridizing to a protospacer sequence comprising the target site, wherein the protospacer sequence is 15-45 nucleotides in length, eg, 15-25; 18-21; 20; or about 20 nucleotides in length. Optionally, each guide RNA herein comprises a spacer sequence that is 15-45 nucleotides in length, eg, 15-25; 18-21; 20; or about 20 nucleotides in length.

Optionally, each guide RNA herein is cognate to a 5'-NGG protospacer adjacent motif (PAM), eg, wherein the bacteria are *E. coli*. Optionally, each guide RNA herein is cognate to a 5'-CCA or 5'-CCT protospacer adjacent motif (PAM), eg, wherein the bacteria are *C. dificile*.

An aspect of the invention provides: A guide RNA or a DNA encoding a guide RNA for use in the system of the invention for use in the method of treating an acute microbial infection in the subject, eg, septicaemia or sepsis.

An aspect of the invention provides: A nucleic acid vector comprising the guide RNA or DNA.

Optionally, the vector is a phage, phagemid, viriophage, virus, plasmid (eg, conjugative plasmid) or transposon. The example below shows almost complete killing can be achieved using a conjugative plasmid as the vector. Thus, in an embodiment, each vector is a conjugative plasmid that is delivered from carrier bacteria eg, probiotic carrier bacteria for administration to the human or animal subject. In an example, the carrier bacteria are *Lactobacillus* (eg, *L. reuteri*) or *E. coli*. This is exemplified below and achieved complete (100%) killing An aspect of the invention provides: An anti-sepsis or anti-septicaemia composition for administration to a human or animal for treating sepsis or septicaemia, the composition comprising a plurality of vectors, wherein each vector a vector of the invention.

An aspect of the invention provides: A method of treating (eg, rapidly and/or durably treating) an acute microbial infection of a subject, wherein the method is as defined herein.

An aspect of the invention provides: A method of treating (eg, rapidly and/or durably treating) an acute microbial infection of a subject, wherein the microbial infection is caused by microbes of a first species or strain and the nuclease is programmable to cut a target site comprised by the genomes of microbes that have infected the subject, whereby microbes of the first species or strain are killed, or growth or proliferation of the microbes is reduced, the treatment method comprising exposing the subject to the nuclease wherein the nuclease is programmed to cut the target site, whereby genomes of the microbes comprised by the subject are cut and acute microbial infection of the subject is treated (eg, rapidly and/or durably treated).

An aspect of the invention provides: A method of treating (eg, rapidly and/or durably treating) an acute microbial infection of a subject, wherein the microbial infection is caused by microbes of a first species or strain and the nuclease is programmable to cut a target site comprised by the genomes of microbes that have infected the subject, whereby microbes of the first species or strain are killed, or growth or proliferation of the microbes is reduced, the treatment method comprising exposing the subject to the nuclease and a plurality of viruses wherein the nuclease is programmed to cut the target site, whereby genomes of the microbes comprised by the subject are cut and acute microbial infection of the subject is treated (eg, rapidly and/or durably treated); wherein each virus comprises a copy of a nucleic acid that encodes an RNA for expression of the RNA in the subject, wherein the RNA complexes with the nuclease to program the nuclease to cut the target site in microbes comprised by the subject; wherein the viruses are capable of infecting microbes comprised by the subject to deliver thereto the nucleic acid.

Optionally, the nuclease is according to any nuclease of the invention herein. Optionally, the nucleic acid is according to any nucleic acid of the invention herein.

An aspect of the invention provides: A method of treating (eg, rapidly and/or durably treating) an acute microbial infection of a subject, wherein the microbial infection is caused by microbes of a first species or strain and the nuclease is programmable to cut a target site comprised by the genomes of microbes that have infected the subject, whereby microbes of the first species or strain are killed, or growth or proliferation of the microbes is reduced, the treatment method comprising exposing the subject to the nuclease and a plurality of nucleic acids wherein the nuclease is programmed to cut the target site, whereby genomes of the microbes comprised by the subject are cut and acute microbial infection of the subject is treated (eg, rapidly and/or durably treated); wherein each virus comprises a copy of a nucleic acid that encodes an RNA for expression of the RNA in the subject, wherein the RNA complexes with the nuclease to program the nuclease to cut the target site in microbes comprised by the subject; wherein each nucleic acid encodes an RNA for expression of the RNA in the subject, wherein the RNA complexes with the nuclease to program the nuclease to cut the target site in microbes comprised by the subject.

Optionally, the nuclease is according to any nuclease of the invention herein. Optionally, each nucleic acid is according to any nucleic acid of the invention herein.

In an example, the invention is for medical or dental or ophthalmic use (eg, for treating or preventing an infection in an organism or limiting spread of the infection in an organism).

In an example, the invention is for cosmetic use (eg, use in a cosmetic product, eg, make-up), or for hygiene use (eg, use in a hygiene product, eg, soap).

In an example, the vectors and/or nuclease prior to administration to the subject are comprised by a composition which is as any of the following (host here refers to the microbes of the first species or strain): In an example, the composition is a medical, ophthalmic, dental or pharmaceutical composition (eg, comprised by an anti-host vaccine). In an example, the composition is an antimicrobial composition, eg, an antibiotic or antiviral, eg, a medicine, disinfectant or mouthwash. In an example, the composition is a cosmetic composition (eg, face or body make-up composition). In an example, the composition is a herbicide. In an example, the composition is a pesticide (eg, when the host is a *Bacillus* (eg, *thuringiensis*) host). In an example, the composition is a beverage (eg, beer, wine or alcoholic beverage) additive. In an example, the composition is a food additive (eg, where the host is an *E. coli, Salmonella, Listeria* or *Clostridium* (eg, *botulinum*) host). In an example, the composition is a water additive. In an example, the composition is a additive for aquatic animal environments (eg, in a fish tank). In an example, the composition is an oil or petrochemical industry composition or comprised in such a composition (eg, when the host is a sulphate-reducing bacterium, eg, a *Desulfovibrio* host). In an example, the composition is a oil or petrochemical additive. In an example, the composition is a chemical additive. In an example, the composition is a disinfectant (eg, for sterilizing equipment for human or animal use, eg, for surgical or medical use, or for baby feeding). In an example, the composition is a personal hygiene composition for human or animal use. In an example, the composition is a composition for environmental use, eg, for soil treatment or environmental decontamination (eg, from sewage, or from oil, a petrochemical or a chemical, eg, when the host is a sulphate-reducing bacterium, eg, a *Desulfovibrio* host). In an example, the composition is a plant growth stimulator. In an example, the composition is a composition for use in oil, petrochemical, metal or mineral extraction. In an example, the composition is a fabric treatment or additive. In an example, the composition is an animal hide, leather or suede treatment or additive. In an example, the composition is a dye additive. In an example, the composition is a beverage (eg, beer or wine) brewing or fermentation additive (eg, when the host is a *Lactobacillus* host). In an example, the composition is a paper additive. In an example, the composition is an ink additive. In an example, the composition is a glue additive. In an example, the composition is an anti-human or animal or plant parasitic composition. In an example, the composition is an air additive (eg, for air in or produced by air conditioning equipment, eg, where the host is a *Legionella* host). In an example, the composition is an anti-freeze additive (eg, where the host is a *Legionella* host). In an example, the composition is an eyewash or ophthalmic composition (eg, a contact lens fluid). In an example, the composition is comprised by a dairy food (eg, the composition is in or is a milk or milk product; eg, wherein the host is a *Lactobacillus, Streptococcus, Lactococcus* or *Listeria* host). In an example, the composition is or is comprised by a domestic or industrial cleaning product (eg, where the host is an *E. coli, Salmonella, Listeria* or *Clostridium* (eg, *botulinum*) host). In an example, the composition is comprised by a fuel. In an example, the composition is comprised by a solvent (eg, other than water). In an example, the composition is a baking additive (eg, a food baking additive). In an example, the composition is a laboratory reagent (eg, for use in biotechnology or recombinant DNA or RNA technology). In an example, the composition is comprised by a fibre retting agent. In an example, the composition is for use in a vitamin synthesis process. In an example, the composition is an anti-crop or plant spoiling composition (eg, when the host is a saprotrophic bacterium). In an example, the composition is an anti-corrosion compound, eg, for preventing or reducing metal corrosion (eg, when the host is a sulphate-reducing bacterium, eg, a *Desulfovibrio* host, eg for use in reducing or preventing corrosion of oil extraction, treatment or containment equipment; metal extraction, treatment or containment equipment; or mineral extraction, treatment or containment equipment). In an example, the composition is an agricultural or farming composition or comprised in such a composition. In an example, the composition is a silage additive. The invention provides a CRISPR array, gRNA-encoding nucleotide sequence, vector or plurality of vectors described herein for use in any of the compositions described in this paragraph or for use in any application described in this paragraph, eg, wherein the host cell is a bacterial or archaeal cell. The invention provides a method for any application described in this paragraph, wherein the method comprises combining a CRISPR array, gRNA-encoding nucleotide sequence, vector or plurality of the invention with a host cell (eg, bacterial or archaeal cell). In an embodiment, the host cell is not present in or on a human (or human embryo) or animal.

Any aspect of the present invention is, for example, for an industrial or domestic use, or is used in a method for such use. For example, it is for or used in agriculture, oil or petroleum industry, food or drink industry, clothing industry, packaging industry, electronics industry, computer industry, environmental industry, chemical industry, aerospace industry, automotive industry, biotechnology industry, medical industry, healthcare industry, dentistry industry, energy industry, consumer products industry, pharmaceutical industry, mining industry, cleaning industry, forestry industry, fishing industry, leisure industry, recycling industry, cosmetics industry, plastics industry, pulp or paper industry, textile industry, clothing industry, leather or suede or animal hide industry, tobacco industry or steel industry.

Host cells herein refers to the microbes of the first species or strain. Optionally, any host cell(s) herein is/are bacterial or archaeal cells. In an example, the cell(s) is/are in stationary phase. In an example, the cell(s) is/are in exponential phase. In an example, the cell(s) is/are in lag phase. In an example, the cell(s) is/are wild-type cells or naturally-occurring cells, eg, comprised by a naturally-occurring microbiome, eg, of a human, animal, plant, soil, water, sea, waterway or environment. In an example, the cell(s) is/are artificially genetically modified.

In an example, a plurality of vectors of the invention are introduced into a plurality of said host cells, wherein the host cells are comprised by a bacterial population, eg, ex vivo, in vivo or in vitro. In an example, the host cells are comprised by a microbiota population comprised by an organism or environment (eg, a waterway microbiota, water microbiota, human or animal gut microbiota, human or animal oral cavity microbiota, human or animal vaginal microbiota, human or animal skin or hair microbiota or human or animal armpit microbiota), the population comprising first bacteria that are symbiotic or commensal with the organism or environment and second bacteria comprising said host cells, wherein the host cells are detrimental (eg, pathogenic) to the organism or environment. In an embodiment, the population is ex vivo. In an example, the ratio of the first bacteria sub-population to the second bacteria sub-population is increased. In an example, the first bacteria are *Bacteroides* (eg, *B. fragalis* and/or *B. thetaiotamicron*) bacteria. Optionally, the *Bacteroides* comprises one, two, three or more *Bacteroides* species selected from *caccae, capillosus, cellulosilyticus, coprocola, coprophilus, coprosuis, distasonis, dorei, eggerthii, faecis, finegoldii, fluxus, fragalis, intestinalis, melaninogenicus, nordii, oleiciplenus, oralis, ovatus, pectinophilus, plebeius, stercoris, thetaiotaomicron, uniformis, vulgatus* and *xylanisolvens*. For example, the *Bacteroides* is or comprises *B. thetaiotaomicron*. For example, the *Bacteroides* is or comprises *B. fragalis*.

In an example, the host, first or second cells are any bacterial species disclosed in US20160333348, GB1609811.3, PCT/EP2017/063593 and all US equivalent applications. The disclosures of these species (including specifically, Table 1 of PCT/EP2017/063593), are incorporated herein in their entirety and for potential inclusion of one or more disclosures therein in one or more claims herein.

In an example, the host cell(s) or bacterial population is harboured by a beverage or water (eg, a waterway or drinking water) for human consumption. In an example, the host cell(s) or said population is comprised by a composition (eg, a medicament (eg, bacterial gut transplant), beverage, mouthwash or foodstuff) for administration to a human or non-human animal for populating and rebalancing the gut or oral microbiota thereof (eg, wherein said use of the medicament is to treat or prevent a disease or condition in the human or animal). In an example, the host cell(s) or said population are on a solid surface or comprised by a biofilm (eg, a gut biofilm or a biofilm on an industrial apparatus). In an example of the invention for in vitro treating an industrial or medical fluid, solid surface, apparatus or container (eg, for food, consumer goods, cosmetics, personal healthcare product, petroleum or oil production); or for treating a waterway, water, a beverage, a foodstuff or a cosmetic, wherein the host cell(s) are comprised by or on the fluid, surface, apparatus, container, waterway, water, beverage, foodstuff or cosmetic.

In an example, the invention provides a container for medical or nutritional use, wherein the container comprises the vectors for use in the method. For example, the container is a sterilised container, eg, an inhaler or connected to a syringe or IV needle.

In an example, the vectors or composition is for administration (or is administered) to the human or non-human animal subject by mucosal, gut, oral, intranasal, intrarectal, intravaginal, ocular or buccal administration.

Optionally, each host cell is of a strain or species found in human microbiota, optionally wherein the host cells are mixed with cells of a different strain or species, wherein the different cells are Enterobacteriaceae or bacteria that are probiotic, commensal or symbiotic with humans (eg, in the human gut. In an example, the host cell is an *E. coli* or *Salmonella* cell.

The invention is optionally for altering the relative ratio of sub-populations of first and second bacteria in a mixed population of bacteria, eg, for altering human or animal microbiomes, such as for the alteration of the proportion of Bacteroidetes (eg, *Bacteroides*, eg, *fragalis* and/or *thetaiotamicron*), Firmicutes and/or gram positive or negative bacteria in microbiota of a human.

In an example, the vectors or composition of the invention comprises a nucleotide sequence for expressing in the host cell an endolysin for host cell lysis, optionally wherein the endolysin is a phage phi11, phage Twort, phage P68, phage phiWMY or phage K endolysin (eg, MV-L endolysin or P-27/HP endolysin).

In an example, the target site is comprised by a chromosome of each microbe host cell, eg, wherein the sequence is comprised by an antibiotic resistance gene, virulence gene or essential gene of the host cell. An example, provides the vectors of the invention in combination with an antibiotic agent (eg, a beta-lactam antibiotic), eg, wherein the vectors target a protospacer sequence comprised by an antibiotic resistance gene comprised by host cell genome or episome (eg, a plasmid comprised by the host cells). In an example, the episome is a plasmid, transposon, mobile genetic element or viral sequence (eg, phage or prophage sequence).

In an example, the target is a chromosomal sequence, an endogenous host cell sequence, a wild-type host cell sequence, a non-viral chromosomal host cell sequence, not an exogenous sequence and/or a non-phage sequence (ie, one more or all of these), eg, the sequence is a wild-type host chromosomal cell sequence such as antibiotic resistance gene or essential gene sequence comprised by a host cell chromosome. In an example, the sequence is a host cell plasmid sequence, eg, an antibiotic resistance gene sequence.

Optionally, the nuclease is a Cas and the target site is comprised by a protospacer sequence that is a adjacent a NGG, NAG, NGA, NGC, NGGNG, NNGRRT or NNAGAAW protospacer adjacent motif (PAM), eg, a AAAGAAA or TAAGAAA PAM (these sequences are written 5' to 3'). In an embodiment, the PAM is immediately adjacent the 3' end of the protospacer sequence. In an example, the Cas is a *S. aureus, S. thermophilus* or *S. pyogenes* Cas. In an example, the Cas is Cpf1 and/or the PAM is TTN or CTA. Optionally, the Cas is a Type I (eg, Type I-A, I-B, I-C, I-D, I-E, or I-F) CRISPR system Cas. Optionally, the Cas is a Type II CRISPR system Cas. Optionally, the Cas is a Type IIII CRISPR system Cas. Optionally, the Cas is a Type IV CRISPR system Cas. Optionally, the Cas is a Type V CRISPR system Cas. Optionally, the Cas is a Type VI CRISPR system Cas.

Optionally, the nuclease is a Cas and each vector comprises a cognate CRISPR array that comprises multiple copies of the same spacer for targeting the target site. Optionally, there is provide a vector or plurality of vectors of the invention, wherein the vector(s) comprises a plurality of CRISPR arrays of said gRNA-encoding sequences for host cell protospacer sequence targeting, wherein the protospacers comprise the target site. Optionally, the or each vector comprises two, three or more of copies of nucleic acid sequences encoding crRNAs (eg, gRNAs), wherein the copies comprise the same spacer sequence for targeting a host cell target site (eg, a site comprised by a virulence, resistance or essential gene sequence).

In an example, at least two target sequences are modified by Cas, for example an antibiotic resistance gene and an essential gene. Multiple targeting in this way may be useful to reduce evolution of escape mutant host cells.

In an example, the Cas is a wild-type endogenous host cell Cas nuclease. In an example, target site cutting is carried out by a dsDNA Cas nuclease (eg, a Cas9, eg, a spCas9 or saCas9), whereby repair of the cut is by non-homologous end joining (NHEJ); alternatively the Cas is an exonuclease or Cas3

In an example, the array, gRNA-encoding sequence or vector is not in combination with a Cas endonuclease-encoding sequence that is naturally found in a cell together with repeat sequences of the array or gRNA-encoding sequence.

A tracrRNA sequence may be omitted from an array or vector of the invention, for example for Cas systems of a Type that does not use tracrRNA, or an endogenous tracrRNA may be used with the cRNA encoded by the vector.

In an example, the host target site is comprised by at least 5, 6, 7, 8, 9, 10, 20, 30 or 40 contiguous nucleotides.

In an example, the or each vector comprises an exogenous promoter functional for transcription of the crRNA or gRNA in the microbes.

Optionally, each vector is a plasmid, cosmid, virus, a virion, phage, phagemid or prophage. For example, the invention provides a plurality of bacteriophage comprising a plurality of vectors of the invention, eg, wherein the vectors are identical. In an example, the vector is a viral vector. Viral vectors have a particularly limited capacity for exogenous DNA insertion, thus virus packaging capacity needs to be considered. Room needs to be left for sequences encoding vital viral functions, such as for expressing coat proteins and polymerase. In an example, the vector is a phage vector or an AAV or lentiviral vector. Phage vectors are useful where the host is a bacterial cell. In an example, the vector is a virus capable of infecting an archaea host cell.

Optionally, vector components are comprised by a transposon that is capable of transfer into and/or between host cells. The transposon can be a transposon as described in US20160333348, GB1609811.3 and all US equivalent applications; the disclosures of these, including these specific transposon disclosures, are incorporated herein in its entirety and for potential inclusion of one or more disclosures therein in one or more claims herein.

In an example, the or each vector is provided by a nanoparticle or in liposomes.

In an example, the or each host cell (or first and/or second bacteria) is a gram positive cell. In an example, the or each host cell is an Enterobacteriaceae, eg, *Salmonella, Yersinia pestis, Klebsiella, Shigella, Proteus, Enterobacter, Serratia*, or *Citrobacter* cells. Optionally, the or each cell is an *E. coli* (eg, *E. coli* K12) or *Salmonella* (eg, S enteric serovar *typhimurium*) cell. Optionally, the or each host cell (or first and/or second bacteria) is a gram negative cell.

Optionally, the host (or first and/or second bacteria) is a *mycoplasma*, chlamydiae, spirochete or *mycobacterium*. Optionally, the host (or first and/or second bacteria) is a *Streptococcus* (eg, *pyogenes* or *thermophilus*) host. Optionally, the host (or first and/or second bacteria) is a *Staphylococcus* (eg, *aureus*, eg, MRSA) host. Optionally, the host (or first and/or second bacteria) is an *E. coli* (eg, O157:H7) host. Optionally, the host (or first and/or second bacteria) is a *Pseudomonas* (eg, *aeruginosa*) host. Optionally, the host (or first and/or second bacteria) is a Vibro (eg, *cholerae* (eg, 0139) or *vulnificus*) host. Optionally, the host (or first and/or second bacteria) is a *Neisseria* (eg, gonnorrhoeae or *meningitidis*) host. Optionally, the host (or first and/or second bacteria) is a *Bordetella* (eg, pertussis) host. Optionally, the host (or first and/or second bacteria) is a *Haemophilus* (eg, *influenzae*) host. Optionally, the host (or first and/or second bacteria) is a *Shigella* (eg, *dysenteriae*) host. Optionally, the host (or first and/or second bacteria) is a *Brucella* (eg, *abortus*) host. Optionally, the host (or first and/or second bacteria) is a *Francisella* host. Optionally, the host (or first and/or second bacteria) is a *Xanthomonas* host. Optionally, the host (or first and/or second bacteria) is a *Agrobacterium* host. Optionally, the host (or first and/or second bacteria) is a *Erwinia* host. Optionally, the host (or first and/or second bacteria) is a *Legionella* (eg, *pneumophila*) host. Optionally, the host (or first and/or second bacteria) is a *Listeria* (eg, *monocytogenes*) host. Optionally, the host (or first and/or second bacteria) is a *Campylobacter* (eg, *jejuni*) host. Optionally, the host (or first and/or second bacteria) is a *Yersinia* (eg, *pestis*) host. Optionally, the host (or first and/or second bacteria) is a *Borelia* (eg, *burgdorferi*) host. Optionally, the host (or first and/or second bacteria) is a *Helicobacter* (eg, *pylori*) host. Optionally, the host (or first and/or second bacteria) is a *Clostridium* (eg, *dificile* or *botulinum*) host. Optionally, the host (or first and/or second bacteria) is a *Erlichia* (eg, *chaffeensis*) host. Optionally, the host (or first and/or second bacteria) is a *Salmonella* (eg, *typhi* or *enterica*, eg, serotype *typhimurium*, eg, DT 104) host. Optionally, the host (or first and/or second bacteria) is a *Chlamydia* (eg, *pneumoniae*) host. Optionally, the host (or first and/or second bacteria) is a *Parachlamydia* host. Optionally, the host (or first and/or second bacteria) is a *Corynebacterium* (eg, *amycolatum*) host. Optionally, the host (or first and/or second bacteria) is a *Klebsiella* (eg, *pneumoniae*) host. Optionally, the host (or first and/or second bacteria) is a *Enterococcus* (eg, *faecalis* or faecim, eg, linezolid-resistant) host. Optionally, the host (or first and/or second bacteria) is a *Acinetobacter* (eg, *baumannii*, eg, multiple drug resistant) host.

Optionally, the invention is for reducing the growth or proliferation of host cell(s) in an environment (eg, soil, a composition comprising said host cells and yeast cells), human, animal or plant microbiome. This is useful, for example, when the microbiome is naturally-occurring.

Optionally, the nuclease is a Cas and the target is comprised by a protospacer sequence comprising at least 5, 6, 7, 8, 9 or 10 contiguous nucleotides immediately 3' of a cognate PAM in the genome of the host cell, wherein the PAM is selected from AWG, AAG, AGG, GAG and ATG.

Non-Medical, Ex vivo & In Vitro Uses Etc

In certain configurations, the inventive observation of rapid and durable microbial killing and growth or proliferation inhibition using nuclease cutting finds application in subjects other than humans and animals (eg, to treat plants or yeast cultures), or for ex vivo or in vitro treatment of substrates, such as industrial surfaces, fluids and apparatus. Thus, the invention further provides the following Concepts. Any other feature herein of the invention, its configurations, aspects, embodiments, options and examples above and elsewhere herein are combinable mutatis mutandis with these Concepts (including for providing combinations of features in the claims herein).

A Concept provides: Use of a nuclease, plurality of viruses, system, guide RNA, DNA or vector of the invention, in the manufacture of a composition for carrying out a method of treatment as defined herein, wherein the subject is an organism other than a human or animal.

A Concept provides: Use of a nuclease, plurality of viruses, system, guide RNA, DNA or vector of the invention, in the manufacture of a composition for carrying out an ex vivo or in vitro a method of treatment of a microbial infection of a substrate, wherein the microbial infection is caused by microbes of a first species or strain and the nuclease is programmable to cut a target site comprised by the genomes of microbes that have infected the substrate, whereby microbes of the first species or strain are killed, or growth or proliferation of the microbes is reduced, the treatment method comprising exposing the subject to the nuclease wherein the nuclease is programmed to cut the target site, whereby genomes of the microbes comprised by the subject are cut and acute microbial infection of the substrate is treated.

Herein, treatment of an infection of a substrate may mean the treatment of a bacterial population (eg, one or more colonies) on a surface of the substrate and/or incorporated in the material of the substrate. For example, the treatment may be the treatment to kill bacteria on the surface of an industrial apparatus or equipment (eg, medical equipment, such as a scalpel or medical device or tubing). In another example, the substrate is a fluid (eg, a liquid or a gas), such as a medical fluid or petroleum product in fluid form (eg, an oil or hydrocarbon fluid or liquid).

A Concept provides: Use of a programmable nuclease in the manufacture of a composition for carrying out an ex vivo method of treatment of a microbial infection of a substrate, wherein the microbial infection is caused by microbes of a first species or strain and the nuclease is programmable to cut a target site comprised by the genomes of microbes that have infected the substrate, whereby microbes of the first species or strain are killed, or growth or proliferation of the microbes is reduced, the treatment method comprising exposing the subject to the nuclease wherein the nuclease is programmed to cut the target site, whereby genomes of the microbes comprised by the subject are cut and acute microbial infection of the substrate is treated.

Optionally the nuclease (eg, programmed nuclease) and/or a nucleic acid that programs the nuclease to recognise and cut the target site is administered to the subject or substrate at a first time (T1) and at a second time (T2) wherein T2 is at least 1 hour after T1. T1 and T2 may be as defined herein.

Optionally, the infection is reduced at least 100-fold by the first 30 minutes (eg, by the first 15 minutes) of the treatment. Optionally, the infection is maintained by at least 100-fold for at least 60 minutes (eg, at least 120 minutes) after exposing the subject to the programmed nuclease.

Optionally, the reduction in infection persists for 30 minutes immediately after the first 30 minutes of the treatment.

Optionally, the method comprises administering to the subject or substrate a RNA or a nucleic acid that encodes an RNA for expression of the RNA in or on the subject or substrate, wherein the RNA complexes with the nuclease to program the nuclease to cut the target site in microbes comprised by the subject or substrate.

Optionally, the nuclease is administered simultaneously or sequentially with the RNA or nucleic acid to the subject or substrate.

Optionally, the subject or substrate comprises the nuclease prior to administration of the RNA or nucleic acid.

Optionally, a plurality of viruses (eg, phage) are administered to the subject or substrate, wherein each virus comprises a copy of the nucleic acid, wherein the viruses infect the microbes comprised by the subject or substrate to deliver thereto the nucleic acid.

Optionally, the ratio of administered viruses:microbes is from 10 to 150.

Optionally, the infection is reduced by at least 90% for 1 hour or more, optionally by the first 30 minutes (eg, by the first 15 minutes) of the treatment.

Optionally, the infection is reduced at least 100-fold by the first 30 minutes (eg, by the first 15 minutes) of the treatment; and wherein reduction of the infection by at least 100-fold is maintained for at least 60 minutes (eg, at least 120, 145 or 180 minutes) after exposing the subject or substrate to the programmed nuclease.

Optionally, the subject is a plant; or wherein the substrate is a metallic, plastic, concrete, stone, wood, glass or ceramic substrate. Optionally, the subject is a fluid (eg, a liquid or a gas).

Optionally, the microbes are bacteria or archaea. Optionally, the bacteria are gram positive bacteria. Optionally, the bacteria are *Staphylococcus, Streptococcus, Enterococcus, Legionella, Heamophilus, Ghonnorhea, Acinetobacter, Escherichia, Klebsiella, Pseudomonas* or *Stenotrophomonas* bacteria (eg, *E. coli* (eg, EHEC *E. coli*), *C. dificile, V. cholera, Staphylococcus* (eg, *S. aureus* or MRSA), *Streptococcus pyogenes, Acinetobacter baumannii, Legionella, Pseudomonas aeruginosa, Klebsiella pneumoniae* bacteria).

Optionally, the nuclease is a Cas nuclease (eg, a Cas 3 or 9), a meganuclease, a TALEN (Transcription activator-like effector nuclease) or zinc finger nuclease.

Reference is made to WO2016177682, which discusses aspects of microbiologically influenced corrosion (MIC) or biofouling of substrates and discloses methods for controlling MIC or biofouling of a substrate. The methods, nucleases, arrays, RNAs, vectors and viruses disclosed in that document can be employed in the present invention, for example for carrying out the method or use of the present invention and the disclosures of these parts and the substrates and bacteria disclosed in WO2016177682 are incorporated herein by reference for potentially providing disclosure of features possible to be used in one or more claims herein.

Optionally, the use of the present invention is for controlling microbiologically influenced corrosion (MIC) or biofouling of a substrate in an industrial or domestic system (eg, a system disclosed in WO2016177682, which disclosure is incorporated herein by reference). In an example, the system comprises equipment (eg, for use in an industrial process) and the surface is a surface of said equipment. In an example, the biofouling comprises microbial biofilm and/or sludge formation, proliferation or maintenance. In an example, the microbes are sessile. In an example "controlling" comprises preventing, reducing or eliminating said MIC or biofouling, or reducing spread of said MIC or biofouling in the system. Cell growth or proliferation or maintenance is, for example, a characteristic of cell viability. Thus, in an example, the method reduces microbe proliferation and/or maintenance.

Optionally, the microbes are comprised by a microbial biofilm that is in contact with said substrate. Optionally, said surface and host cells are in contact with a fluid, such as an aqueous liquid (eg, sea water, fresh water, stored water or potable water).

Fresh water is naturally occurring water on the Earth's surface in ice sheets, ice caps, glaciers, icebergs, bogs, ponds, lakes, rivers and streams, and underground as groundwater in aquifers and underground streams. Fresh water is generally characterized by having low concentrations of dissolved salts and other total dissolved solids. The term specifically excludes sea water and brackish water, although it does include mineral-rich waters such as chalybeate springs. In an example said fresh water is any of these fresh water types. Potable water is water for human or animal (eg, livestock) consumption. In an example, the fluid is selected from industrial cooling water wherein the system is a cooling system; sewage water wherein the system is a sewage treatment or storage system; drinking water wherein the system is a drinking water processing, storage, transportation or delivery system; paper making water wherein the system is a paper manufacture or processing system; swimming pool water wherein the system is a swimming pool or swimming pool water treatment or storage system; fire extinguisher water wherein the system is a fire extinguishing system; or industrial process water in any pipe, tank, pit, pond or channel.

Optionally, the use is for controlling bacterial souring of a liquid in a reservoir or container), wherein the fluid comprises a population of first host cells of a first microbial species that mediates said biofouling, the method comprising (i) contacting the population with a plurality of vectors that are capable of transforming or transducing the cells, each vector comprising a CRISPR array whereby CRISPR arrays are introduced into the host cells, wherein
  (a) each CRISPR array comprises one or more sequences for expression of a crRNA and a promoter for transcription of the sequence(s) in a host cell; and
  (b) each crRNA is capable of hybridising to a target sequence of a host cell to guide Cas (eg, a Cas nuclease) in the host cell to modify the target sequence (eg, to cut the target sequence); the target sequence being a gene sequence for mediating host cell viability; and wherein the method comprises allowing expression of said cRNAs in the presence of Cas in host cells, thereby modifying target sequences in host cells, resulting in reduction of host cell viability and control of said biofouling.

In an example, the fluid is a liquid. In an example, the fluid is a gaseous fluid.

Systems:

An example system is selected from the group consisting of a: —
Petrochemical recovery, processing, storage or transportation system; hydrocarbon recovery, processing, storage or transportation system; crude oil recovery, processing, storage or transportation system; natural gas recovery, processing, storage or transportation system, (eg, an oil well, oil rig, oil drilling equipment, oil pumping system, oil pipeline, gas rig, gas extraction equipment, gas pumping equipment, gas pipeline, oil tanker, gas tanker, oil storage equipment or gas storage equipment); Water processing or storage equipment; water reservoir (eg, potable water reservoir); Air or water conditioning (eg, cooling or heating) equipment, eg, a coolant tube, condenser or heat exchanger; Medical or surgical equipment; Environmental (eg, soil, waterway or air) treatment equipment; Paper manufacturing or recycling equipment; Power plant, eg, a thermal or nuclear power plant; Fuel (eg, hydrocarbon fuel, eg, petroleum, diesel or LPG) storage equipment; Mining or metallurgical, mineral or fuel recovery system, eg, a mine or mining equipment; Engineering system; Shipping equipment; Cargo or goods storage equipment (eg, a freight container); Food or beverage manufacturing, processing or packaging equipment; Cleaning equipment (eg, laundry equipment, eg, a washing machine or dishwasher); Catering (eg, domestic or commercial catering) equipment; Farming equipment; Construction (eg, building, utilities infrastructure or road construction) equipment; Aviation equipment; Aerospace equipment; Transportation equipment (eg, a motor vehicle (eg, a car, lorry or van); a railcar; an aircraft (eg, an aeroplane) or a marine or waterway vehicle (eg, a boat or ship, submarine or hovercraft)); Packaging equipment, eg, consumer goods packaging equipment; or food or beverage packaging equipment; Electronics (eg, a computer or mobile phone or an electronics component thereof); or electronics manufacture or packaging equipment; Dentistry equipment; Industrial or domestic piping (eg, a sub-sea pipe) or storage vessel (eg, a water tank or a fuel tank (eg, gasoline tank, eg, a gasoline tank of a vehicle)); Underground equipment; Building (eg, a dwelling or office or commercial premises or factory or power station); Roadway; Bridge; Agricultural equipment; Factory system; Crude oil or natural gas exploration equipment; Office system; and a Household system.

In an example, the system is used in an industry or business selected from the group consisting of agriculture, oil or petroleum industry, food or drink industry, clothing industry, packaging industry, electronics industry, computer industry, environmental industry, chemical industry, aerospace industry, automotive industry, biotechnology industry, medical industry, healthcare industry, dentistry industry, energy industry, consumer products industry, pharmaceutical industry, mining industry, cleaning industry, forestry industry, fishing industry, leisure industry, recycling industry, cosmetics industry, plastics industry, pulp or paper industry, textile industry, clothing industry, leather or suede or animal hide industry, tobacco industry and steel industry. In an example, the surface or fluid to be treated is a surface or fluid of equipment used in said selected industry. In an example, the system is used in the crude oil industry. In an example, the system is used in the natural gas industry. In an example, the system is used in the petroleum industry. In an example, the system is a sea container, platform or rig (eg, oil or gas platform or rig for use at sea or at sea), ship or boat. In an embodiment, such a system is anchored at sea; eg, non-temporarily anchored at sea, eg, has been anchored at sea for 1, 2, 3, 4, 5, 6, 7, 8, 9, 10, 11, 12, 13, 14, 15, 16, 17, 18, 19, 20, 21, 22, 23, 24 or more months (eg, contiguous months). In an embodiment, such a system is in the waters of a country or state; eg, non-temporarily at sea in such waters, eg, has been in waters of said country for 1, 2, 3, 4, 5, 6, 7, 8, 9, 10, 11, 12, 13, 14, 15, 16, 17, 18, 19, 20, 21, 22, 23, 24 or more months (eg, contiguous months).

In an example, the substrate surface to be treated comprises stainless steel, carbon steel, copper, nickel, brass, aluminium, concrete, a plastic or wood. In an example, the substrate is a metal weld or join. In an example, the surface is a metallic (eg, steel or iron) or non-metallic (eg, plastic, concrete, asphalt, wood, rubber or stone) surface. In an example, the metal is an alloy (eg, stainless steel, brass or a nickel-, zinc-, copper-, nickel- or aluminium-alloy). In an example, the surface is a man-made polymer surface. In an example, the surface is a substrate coating. In an example, the substrate is in contact with soil, fresh water or sea water.

In an example, the fluid is potable water; a waterway; brackish water; or a liquid fuel, eg, gasoline or diesel (eg, for a car or motorised vehicle), LPG, kerosine, an alcohol (eg, ethanol, methanol or butanol), liquid hydrogen or liquid ammonia), in an example, the fuel is stored liquid fuel. In an example the fluid is an oil or non-aqueous liquid. In an example, the fluid is a liquid comprised by a waterway or body of water, eg, sea water, fresh water, potable water, a river, a stream, a pond, a lake, a reservoir, stored water (eg, in a water storage tank or cooling equipment), groundwater, well water, water in a rock formation, soil water or rainwater. In an example, the liquid is sea water. In an example, the substrate is in contact with a liquid mentioned in this paragraph. In an example, the fluid or liquid is selected from the group consisting of an oil, an aqueous solution, a hydraulic fracturing fluid, a fuel, carbon dioxide, a natural gas, an oil/water mixture, a fuel/water mixture, water containing salts, ocean or sea water, brackish water, sources of fresh water, lakes, rivers, stream, bogs, ponds, marshes, runoff from the thawing of snow or ice, springs, groundwater, aquifers, precipitation, any substance that is a liquid at ambient temperature (eg, at rtp) and is hydrophobic but soluble in organic solvents, hexanes, benzene, toluene, chloroform, diethyl ether, vegetable oils, petrochemical oils, crude oil, refined petrochemical products, volatile essential oils, fossil fuels, gasoline, mixtures of hydrocarbons, jet fuel, rocket fuel, biofuels. In an example the fluid is an oil/water mixture.

The terms "microbiologically influenced corrosion" or "MIC" as used herein, unless otherwise specified, refer to processes in which any element (substrate) of a system is structurally compromised due to the action of at least one member of a microbial population, eg, bacterial or archaeal population. The term "biofouling" as used herein, unless otherwise specified, refers to processes in which microorganisms (such as bacteria and/or archaea) accumulate on a substrate surface in contact with a fluid (eg, water or an aqueous liquid, or a hydrocarbon, or a petrochemical). Also included is the undesirable accumulation and proliferation of microorganisms (such as bacteria and/or archaea) in a fluid (eg, water or an aqueous liquid, or a hydrocarbon, or a petrochemical), ie, "souring" of the fluid. In an example, the bacteria are comprised by ship or boat ballast water and the bacteria are environmentally undesirable. The term "substrate" as used herein refers to any type of surface on which cells can attach and a biofilm can form and grow or on which biofouling (eg slime or sludge formation) can occur. The substrate may be an "industrial" substrate such as the surface of equipment in an petrochemical, fuel, crude oil or gas piping system, or a "non-industrial" (eg, domestic, eg, household or office) substrate such as a kitchen counter or a shower substrate or a garden substrate.

In an alternative, instead of a population of host bacterial cells, the population is a population of archaeal cells of a first species.

Optionally, said fluid is an aqueous liquid (eg, sea water, fresh water, stored water or potable water).

In an alternative, instead the microbes are algal cells.

Optionally, the microbes are sulphate reducing bacteria (SRB) cells (eg, *Desulfovibrio* or *Desulfotomaculum* cells). In an example, the cells are selected from the group consisting of *Desulfotomaculum nigrificans, Desulfacinum infenum, Thermodesulfobacterium mobile, Thermodesulforhabdus norvegicus, Archaeoglobus fulgidus, Desulfomicrobium apsheronum, Desulfovibrio gabonensis, Desulfovibrio longus, Desulfovibrio vietnamensis, Desulfobacterium cetonicum, Desulphomaculum halophilum, Desulfobacter vibrioformis* and *Desulfotomaculum thermocisternum* cells. In an example, the population comprises a mixture of two or more of these cell species.

Optionally, the surface or fluid is comprised by a crude oil, gas or petrochemicals recovery, processing, storage or transportation equipment. Crude oil is one of the most important energetic resources in the world. It is used as raw material in numerous industries, including the refinery-petrochemical industry, where crude oil is refined through various technological processes into consumer products such as gasoline, oils, paraffin oils, lubricants, asphalt, domestic fuel oil, vaseline, and polymers. Oil-derived products are also commonly used in many other chemical processes. In an alternative, the fluid is a said consumer product or the surface is in contact with such a consumer product.

Optionally, the surface is in contact with sea water, a fracking liquid or liquid in a well; or wherein the fluid is sea water, a fracking liquid or liquid in a well.

Optionally, step (i) of the method comprises providing a population of microbial cells of a second species (second host cells), the second cells comprising said vectors, wherein the vectors are capable of transfer from the second host cells to the first host cells; and combining the second host cells with the first host cells, whereby vectors are introduced into the first host cells. In an example, the second cell(s) are environmentally-, industrially-, or domestically-acceptable in an environment (eg, in a water or soil environment) and the first host cell(s) are not acceptable in the environment.

Optionally, the first host cells are comprised by a mixture of microbial cells (eg, comprised by a microbial biofilm) before contact with said vectors, wherein the mixture comprises cells of said second species.

Optionally, said second species is a species of *Bacillus* or nitrate-reducing bacteria or nitrate reducing sulfide oxidizing bacteria (NRB)

Optionally, the NRB is selected from the group consisting of *Campylobacter* sp., *Nitrobacter* sp., *Nitrosomonas* sp., *Thiomicrospira* sp., *Sulfurospirillum* sp., *Thauera* sp., *Paracoccus* sp., *Pseudomonas* sp., *Rhodobacter* sp. and *Desulfovibrio* sp; or comprises at least 2 of said species.

Optionally, the NRB is selected from the group consisting of *Nitrobacter vulgaris, Nitrosomonas europea, Pseudomonas stutzeri, Pseudomonas aeruginosa, Paracoccus denitrificans, Sulfurospirillum deleyianum*, and *Rhodobacter spheroides*.

Optionally, the method comprises contacting the host cells of said first species with a biocide simultaneously or sequentially with said vectors. In an example, the vectors and biocide are provided pre-mixed in a composition that is contacted with the host cells.

Optionally, the biocide is selected from the group consisting of tetrakis hydroxymethyl phosphonium sulfate (THPS), glutaraldehyde, chlorine monoxide, chlorine dioxide, calcium hypochlorite, potassium hypochlorite, sodium hypochlorite, dibromonitriloproprionamide (DBNPA), methylene bis(thiocyanate) (MBT), 2-(thiocyanomethylthio) benzothiazole (TCMTB), bronopol, 2-bromo-2-nitro-1,3-propanediol (BNPD), tributyl tetradecyl phosphonium chloride (TTPC), taurinamide and derivatives thereof, phenols, quaternary ammonium salts, chlorine-containing agents, quinaldinium salts, lactones, organic dyes, thiosemicarbazones, quinones, carbamates, urea, salicylamide, carbanilide, guanide, amidines, imidazolines, acetic acid, benzoic acid, sorbic acid, propionic acid, boric acid, dehydroacetic acid, sulfurous acid, vanillic acid, p-hydroxybenzoate esters, isopropanol, propylene glycol, benzyl alcohol, chlorobutanol, phenylethyl alcohol, formaldehyde, iodine and solutions thereof, povidone-iodine, hexamethylenetetramine, noxythiolin, 1-(3-chloroallyl)-3,5,7-triazo-1-azoniaadamantane chloride, taurolidine, taurultam, N-(5-nitro-2-furfurylidene)-1-amino-hydantoin, 5-nitro-2-furaldehyde semicarbazone, 3,4,4'-trichlorocarbanilide, 3,4', 5-tribromosalicylanilide, 3-trifluoromethyl-4,4'-dichlorocarbanilide, 8-hydroxyquinoline, 1-cyclopropyl-6-fluoro-1,4-dihydro-4-oxo-7-(1-piperazinyl)-3-quinolinecarboxylic acid, 1,4-dihydro-1-ethyl-6-fluoro-4-oxo-7-(1-piperazinyl)-3-quinolinecarboxylic acid, hydrogen peroxide, peracetic acid, sodium oxychlorosene, parachlorometaxylenol, 2,4,4'-trichloro-2'-hydroxydiphenol, thymol, chlorhexidine, benzalkonium chloride, cetylpyridinium chloride, silver sulfadiazine, silver nitrate, bromine, ozone, isothiazolones, polyoxyethylene (dimethylimino) ethylene (dimethylimino) ethylene dichloride, 2-(tert-butylamino)-4-chloro-6-ethylamino-5'-triazine (terbutylazine), and combinations thereof. In an example the biocide is tetrakis hydroxymethyl phosphonium sulfate (THPS). In an example, the biocide is a quaternary ammonium compound.

Optionally, the system is used in an industry operation selected from the group consisting of mining; shipping; crude oil, gas or petrochemicals recovery or processing; hydraulic fracturing; air or water heating or cooling; potable water production, storage or delivery; transportation of hydrocarbons; and wastewater treatment.

Optionally, the surface is a surface of equipment used in said selected industry; or wherein the fluid is a fluid comprised by equipment used in said selected industry.

Optionally, the surface is a surface of kitchen, bathing or gardening equipment; or wherein the fluid is comprised by kitchen, bathing or gardening equipment. For example, the equipment is used in a domestic setting.

Optionally, the fluid is a potable liquid contained in a container (eg, water tank or bottle) and the surface is a surface of the container in contact with the liquid.

Optionally, each vector comprises a mobile genetic element (MGE), wherein the MGE comprises an origin of transfer (oriT) and a said CRISPR array; wherein the MGE is capable of transfer between a host cell of said first species and a further microbial host cell in said industrial or domestic system. For example, the further cell(s) are environmentally-, industrially-, or domestically-acceptable in an environment (eg, in a water or soil environment) and the first host cell(s) are not acceptable in the environment. Optionally, the oriT is functional in the first and further host cells.

Optionally, the first and further host cells are comprised by a biofilm of fluid in contact with said surface; or wherein said cells are comprised by said fluid.

Optionally, each MGE is or comprises an integrative and conjugative element (ICE); or wherein each vector is a phage that is capable of infecting host cells of said first species and each MGE is a phage nucleic acid that is capable of said transfer between the cells. Optionally, each ICE is a transposon, eg, a conjugative transposon. Optionally, each vector is a plasmid, optionally comprising an MGE as described herein. Optionally, the sequences are comprised by a conjugative transposon of the first cell and/or further cell.

In an example, the method is a method of controlling microbiologically influenced corrosion (MIC) or biofouling of a substrate comprised by a crude oil, gas or petrochemicals recovery, processing, storage or transportation equipment (eg, a crude oil tanker, oil rig or oil drilling equipment), wherein a surface of the substrate is in contact with a population of first host cells, wherein the first host cells are sulphur- or sulphate-reducing bacteria (SRB), extracellular polymeric substance-producing bacteria (EPSB), acid-producing bacteria (APB), sulphur- or sulphide-oxidizing bacteria (SOB), iron-oxidising bacteria (IOB), manganese-oxidising bacteria (MOB), ammonia producing bacteria (AmPB) or acetate producing bacteria (AcPB) of a first species that mediates MIC or biofouling of the substrate, wherein the surface and cell population are in contact with a liquid selected from sea water, fresh water, a fracking liquid or liquid in a well (eg, oil or natural gas well), the method comprising
  (i) contacting the cell population with vectors by mixing the liquid with a plurality of vectors that are capable of transforming or transducing first host cells, each vector comprising a CRISPR array whereby CRISPR arrays are introduced into the host cells, wherein
    (a) each CRISPR array comprises one or more sequences for expression of a crRNA and a promoter for transcription of the sequence(s) in a host cell;
    (b) each crRNA is capable of hybridising to a target sequence of a host cell to guide Cas (eg, a Cas nuclease, eg, a Cas9 or Cfp1) in the host cell to modify the target sequence (eg, to cut the target sequence); the target sequence being a gene sequence for mediating host cell viability;
    (c) wherein each sequence of (a) comprises a sequence R1-S1-R1' for expression and production of the respective crRNA in a first host cell, wherein R1 is a first CRISPR repeat, R1' is a second CRISPR repeat, and R1 or RP is optional; and S1 is a first CRISPR spacer that comprises or consists of a nucleotide sequence that is 70, 75, 80, 85, 90 or 95% or more identical to a target sequence of a said first host cell and
  (ii) allowing expression of said cRNAs in the presence of Cas in host cells, thereby modifying target sequences in host cells, resulting in reduction of host cell viability and control of MIC or biofouling of said substrate. In an embodiment, both R1 and R1' are present.

In an example, the method is a method of controlling bacterial biofouling in ballast water of a ship or boat, wherein the water comprises a population of first host cells of a first microbial species that mediates said biofouling, the method comprising
  (i) contacting the population with a plurality of vectors that are capable of transforming or transducing the cells, each vector comprising a CRISPR array whereby CRISPR arrays are introduced into the host cells, wherein
    (a) each CRISPR array comprises one or more sequences for expression of a crRNA and a promoter for transcription of the sequence(s) in a host cell; and
    (b) each crRNA is capable of hybridising to a target sequence of a host cell to guide Cas (eg, a Cas nuclease) in the host cell to modify the target sequence (eg, to cut the target sequence); the target sequence being a gene sequence for mediating host cell viability; and
  (ii) allowing expression of said cRNAs in the presence of Cas in host cells, thereby modifying target sequences in host cells, resulting in reduction of host cell viability and control of said biofouling.

Optionally, the first host cells are *Vibrio cholerae*, *E. coli* or Enterococci sp cells.

Optionally, step (i) comprises mixing the ballast water with the vectors, eg, in the hull of a ship or boat. Optionally, the ship or boat is a marine vehicle and the water is sea water. Optionally, instead of a ship or boat, the ballast water is comprised by a container or a drilling platform at sea, eg, an oil platform or oil rig. In an example, the ship, boat, container, platform or rig is anchored at sea (ie, not temporarily in its location).

In an example, the method is a method of discharging ballast water from a ship or boat, wherein the discharged ballast water comprises water treated by the method. Optionally, the water is discharged into a body of water, eg, a sea, ocean or waterway (eg, a river, canal, lake or reservoir) or into a container.

Paragraphs:

The invention provides the following Paragraphs, which are supported by the Examples below:—
  1. A programmable Cas (eg, Cas3 or Cas9) nuclease for use in a method of treating *E. coli* or *C. dificile* infection of a subject, wherein the Cas nuclease is programmable with a guide RNA to cut a target site comprised by the genomes of *E. coli* or *C. dificile* bacteria that have infected the subject, whereby *E. coli* or *C. dificile* cells are killed, or growth or proliferation of the cells is reduced, the treatment method comprising exposing the subject to the Cas nuclease wherein the nuclease is programmed with guide RNA to cut the target site, whereby genomes of the *E. coli* or *C. dificile* bacteria comprised by the subject are cut and the infection of the subject is reduced by at least 100-fold by the first 30 minutes (eg, by the first 15 minutes) of the treatment.
  2. A programmable Cas (eg, Cas3 or Cas9) nuclease (optionally according to paragraph 1) for use in a method of treating *E. coli* or *C. dificile* infection of a subject, wherein the Cas nuclease is programmable with a guide RNA to cut a target site comprised by the genomes of *E. coli* or *C. dificile* bacteria that have infected the subject, whereby *E. coli* or *C. dificile* cells are killed, or growth or proliferation of the cells is reduced, the treatment method comprising exposing the subject to the Cas nuclease wherein the nuclease is programmed with guide RNA to cut the target site, whereby genomes of the *E. coli* or *C. dificile* bacteria comprised by the subject are cut and the infection of the subject is reduced, wherein a reduction of the infection by at least 100-fold is maintained for at least 60 minutes (eg, at least 120, 145 or 180 minutes) after exposing the subject to the programmed nuclease.

3. The nuclease of any preceding Paragraph, wherein at least 60% of the infection is reduced by 60 minutes after exposing the subject to the programmed nuclease.
4. The nuclease of any preceding Paragraph, wherein the nuclease (eg, programmed nuclease) and/or a nucleic acid encoding the guide RNA is administered to the subject at a first time (T1) and at a second time (T2) wherein T2 is at least 1 hour after T1.
5. The nuclease of any preceding Paragraph, wherein the method comprises reducing the infection such that the reduction in infection persists for 30 minutes immediately after the first 30 minutes of the treatment.
6. The nuclease of any preceding Paragraph, wherein the method comprises administering to the subject the RNA or a nucleic acid that encodes the RNA for expression of the RNA in the subject, wherein the RNA complexes with the nuclease to program the nuclease to cut the target site in microbes comprised by the subject.
7. The nuclease of any preceding Paragraph, wherein the nuclease is administered simultaneously or sequentially with the RNA or nucleic acid encoding the RNA to the subject.
8. The nuclease of Paragraph 7, wherein the subject comprises the nuclease prior to administration of the RNA or nucleic acid to the subject.
9. The nuclease of any preceding Paragraph, wherein a plurality of viruses (eg, phage) are administered to the subject, wherein each virus comprises a copy of a nucleic acid encoding the RNA, wherein the viruses infect the microbes comprised by the subject to deliver thereto the nucleic acid.
10. The nuclease of Paragraph 9, wherein the ratio of administered viruses:microbes comprised by the subject is from 10 to 150.
11. The nuclease according to any preceding Paragraph, wherein the subject is a human or animal, optionally wherein the subject is a human over 65 years of age or is a paediatric patient.
12. The nuclease according to Paragraph 11, wherein the infection is an infection of the lungs, abdomen or urinary tract; or wherein the subject has undergone surgery, is on an immunosuppressant medication and/or is suffering from a chronic disease.
13. The nuclease according to any preceding Paragraph, wherein the infection is reduced by at least 90% for 1 hour or more, optionally by the first 30 minutes (eg, by the first 15 minutes) of the treatment.
14. The nuclease according to any preceding Paragraph, wherein the method comprises reducing the infection at least 100-fold by the first 30 minutes (eg, by the first 15 minutes) of the treatment; and wherein reduction of the infection by at least 100-fold is maintained for at least 60 minutes (eg, at least 120, 145 or 180 minutes) after exposing the subject to the programmed nuclease.
15. The nuclease according to any one of Paragraphs 11 to 14, wherein the method treats or prevents septicaemia and/or sepsis (eg, septic shock) in the subject.
16. The nuclease of Paragraph 16, wherein at the start of the treatment, the subject (eg, a human) has a temperature of <36° C. or >38° C.; a heart rate of >90/min, a respiratory rate of >20 breaths/min or $PaCO_2$<4.3 kPa; and white blood cell count of <4000/mm$^3$ or >12,000/mm$^3$.
17. The nuclease of Paragraph 15 or 16, wherein at the start of the treatment, the subject (eg, a human) has presence of two or more of the following: abnormal body temperature, abnormal heart rate, abnormal respiratory rate, abnormal blood gas and abnormal white blood cell count.
18. The nuclease of any preceding Paragraph, wherein the subject is a human or animal and the microbes are bacteria (eg, *E. coli* or *C. dificile*), wherein blood infection of the subject by the bacteria is reduced at least 100- or 1000-fold by the first 30 minutes (eg, by the first 15 minutes) of the treatment.
19. The nuclease of any one of Paragraphs 11 to 18, wherein the blood of the subject is infected with from $10^7$ to $10^{12}$ CFU/ml of the bacteria immediately before the treatment.
20. The nuclease according to any one of Paragraphs 1 to 10, wherein the subject is a plant.
21. The nuclease according to any preceding Paragraph, wherein the bacteria are comprised by a microbiome.
22. The nuclease according to Paragraph 21, wherein the microbiome comprises *Lactobacillus* and/or *Streptococcus* bacteria.
23. The nuclease according to any preceding Paragraph, wherein the *E. coli* are EHEC *E. coli*.
24. The nuclease according to any preceding Paragraph, wherein the nuclease is a Cas nuclease (eg, a Cas 3 or 9), a meganuclease, a TALEN (Transcription activator-like effector nuclease) or zinc finger nuclease.
25. A plurality of viruses (eg, phage or phagemids for producing phage) for use with the nuclease of any preceding Paragraph in the method of treatment, wherein each virus comprises a copy of a nucleic acid encoding the RNA, wherein the viruses are capable of infecting microbes comprised by the subject to deliver thereto the nucleic acid.
26. A composition comprising a plurality of nucleic acids for programming the nuclease of any one of Paragraphs 1 to 24 in the method of treatment, wherein each nucleic acid is a nucleic acid as defined in any one of Paragraphs 6 to 9.
27. A CRISPR/Cas system comprising a nuclease according to any preceding Paragraph for use in the method of treatment, wherein the nuclease is a Cas nuclease (eg, a Cas 3 or 9) and the system comprises one or more guide RNAs or DNA encoding one or more guide RNAs, wherein each guide RNA is capable of programming the Cas nuclease to cut a target site comprised by the genomes of the microbes.
28. A guide RNA or a DNA encoding a guide RNA for use in the system of Paragraph 27 for use in the method of treating an acute microbial infection in the subject, eg, septicaemia or sepsis.
29. A nucleic acid vector comprising the guide RNA or DNA recited in Paragraph 27 or 28.
30. The vector of Paragraph 29 wherein the vector is a phage, phagemid, viriophage, virus, plasmid (eg, conjugative plasmid) or transposon.
31. An anti-sepsis or anti-septicaemia composition for administration to a human or animal for treating sepsis or septicaemia, the composition comprising a plurality of vectors, wherein each vector is according to Paragraph 29 or 30.
32. A method of treating an acute microbial infection of a subject, wherein the method is as defined by any preceding Paragraph.
33. Use of a nuclease, plurality of viruses, system, guide RNA, DNA or vector of any one of Paragraphs 1 to 25 and 27 to 30, in the manufacture of a composition for carrying out a method of treatment as defined by any preceding Paragraph, wherein the subject is an organism other than a human or animal.

34. Use of a nuclease, plurality of viruses, system, guide RNA, DNA or vector of any one of Paragraphs 1 to 25 and 27 to 30, in the manufacture of a composition for carrying out an ex vivo method of treatment of a microbial infection of a substrate, wherein the microbial infection is caused by microbes of a first species or strain and the nuclease is programmable to cut a target site comprised by the genomes of microbes that have infected the substrate, whereby microbes of the first species or strain are killed, or growth or proliferation of the microbes is reduced, the treatment method comprising exposing the subject to the nuclease wherein the nuclease is programmed to cut the target site, whereby genomes of the microbes comprised by the subject are cut and acute microbial infection of the substrate is treated.

35. Use of a programmable nuclease in the manufacture of a composition for carrying out an ex vivo method of treatment of a microbial infection of a substrate, wherein the microbial infection is caused by microbes of a first species or strain and the nuclease is programmable to cut a target site comprised by the genomes of microbes that have infected the substrate, whereby microbes of the first species or strain are killed, or growth or proliferation of the microbes is reduced, the treatment method comprising exposing the subject to the nuclease wherein the nuclease is programmed to cut the target site, whereby genomes of the microbes comprised by the subject are cut and acute microbial infection of the substrate is treated.

36. The use of Paragraph 33, 34, 35, wherein the nuclease (eg, programmed nuclease) and/or a nucleic acid that programs the nuclease to recognise and cut the target site is administered to the subject or substrate at a first time (T1) and at a second time (T2) wherein T2 is at least 1 hour after T1.

37. The use of any one of Paragraphs 33 to 36, wherein the infection is reduced at least 100-fold by the first 30 minutes (eg, by the first 15 minutes) of the treatment.

38. The use of any one of Paragraphs 33 to 37, wherein the reduction of the infection is maintained by at least 100-fold for at least 60 minutes (eg, at least 120 minutes) after exposing the subject to the programmed nuclease.

39. The use of any one of Paragraphs 33 to 38, wherein the reduction in infection persists for 30 minutes immediately after the first 30 minutes of the treatment.

40. The use of any one of Paragraphs 33 to 39, wherein the method comprises administering to the subject or substrate a RNA or a nucleic acid that encodes an RNA for expression of the RNA in or on the subject or substrate, wherein the RNA complexes with the nuclease to program the nuclease to cut the target site in microbes comprised by the subject or substrate.

41. The use of Paragraph 40, wherein the nuclease is administered simultaneously or sequentially with the RNA or nucleic acid to the subject or substrate.

42. The use of Paragraph 40, wherein the subject or substrate comprises the nuclease prior to administration of the RNA or nucleic acid.

43. The use of any one of Paragraphs 40 to 42, wherein a plurality of viruses (eg, phage) are administered to the subject or substrate, wherein each virus comprises a copy of the nucleic acid, wherein the viruses infect the microbes comprised by the subject or substrate to deliver thereto the nucleic acid.

44. The use of Paragraph 43, wherein the ratio of administered viruses:microbes is from 10 to 150.

45. The use of any one of Paragraphs 33 to 44, wherein the infection is reduced by at least 90% for 1 hour or more, optionally by the first 30 minutes (eg, by the first 15 minutes) of the treatment.

46. The use of any one of Paragraphs 44 to 45, wherein the infection is reduced at least 100-fold by the first 30 minutes (eg, by the first 15 minutes) of the treatment; and wherein reduction of the infection by at least 100-fold is maintained for at least 60 minutes (eg, at least 120, 145 or 180 minutes) after exposing the subject or substrate to the programmed nuclease.

47. The use of any one of Paragraphs 33 to 46, wherein the subject is a plant; or wherein the substrate is a metallic, plastic, concrete, stone, wood, glass or ceramic substrate.

48. The use of any one of Paragraphs 33 to 47, wherein the microbes are bacteria.

49. The use according to Paragraph 48, wherein the bacteria are gram positive bacteria.

50. The use according to Paragraph 48 or 49, wherein the bacteria are *Staphylococcus, Streptococcus, Enterococcus, Legionella, Heamophilus, Ghonnorhea, Acinetobacter, Escherichia, Klebsiella, Pseudomonas* or *Stenotrophomonas* bacteria (eg, *E. coli* (eg, EHEC *E. coli*), *C. dificile, V. cholera, Staphylococcus* (eg, *S. aureus* or MRSA), *Streptococcus pyogenes, Acinetobacter baumannii, Legionella, Pseudomonas aeruginosa, Klebsiella pneumoniae* bacteria).

51. The use of any one of Paragraphs 33 to 50, wherein the nuclease is a Cas nuclease (eg, a Cas 3 or 9), a meganuclease, a TALEN (Transcription activator-like effector nuclease) or zinc finger nuclease.

Treatment of Pathogenic Bacterial Infections

Infectious complications are a serious cause of morbidity and mortality in cancer patients, especially those with underlying haematological malignancies where autopsy studies demonstrate that approximately 60% of deaths are infection related. Although fewer data exist on infectious mortality in patients with solid organ tumours, approximately 50% of these patients are estimated to have an infection as either the primary or an associated cause of death ("Epidemiology of Infections in Cancer Patients", in "Infectious Complications in Cancer Patients", Springer International Publishing Switzerland (2014)). Bacterial infections dominate. These infectious complications remain a significant limitation of cancer treatment modalities.

Figure 8:
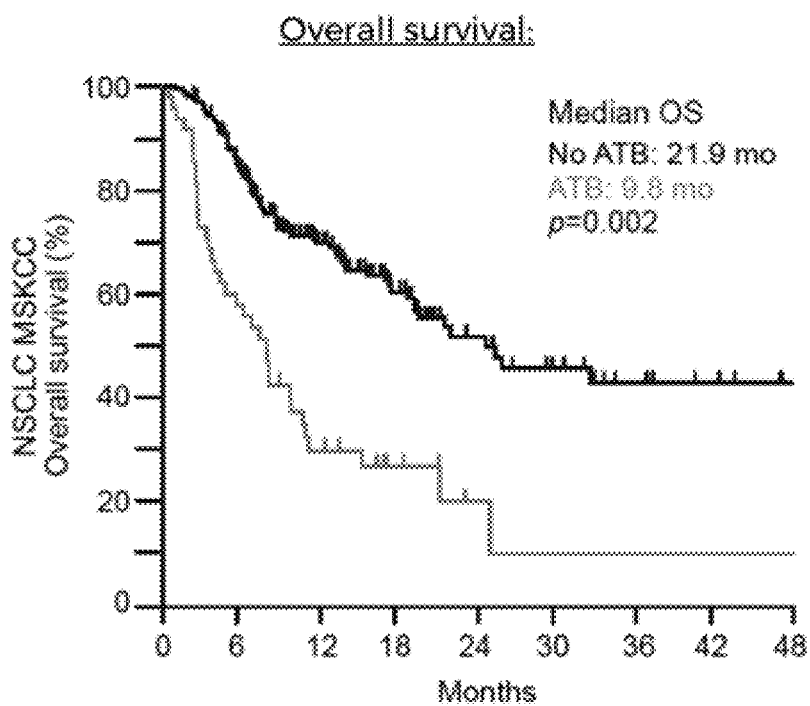
FIG. 8 shows the antibiotic treatment during ICI therapy has fatal outcomes. Kaplan Meier curve for overall survival of a validation cohort from the Memorial Sloan Ketterin Cancer Center including n=239 advanced NSCLC patients treated with anti-PD-L1/anti-PD-1 mAb who received (ATB, n=68) or not (no ATB, n=171) antibiotics (ATB) two months before the injection of immune checkpoint blockade. There was a medial overall survival of 21.9 months in the absence of antibiotic treatment, compared to an overall survival of 9.8 months with antibiotic treatment. So, the median overall survival in patients treated with classical antibiotics is <50% (or >12 months shorter) that of patients not receiving antibiotic treatment.

The detrimental effects of classic antibiotic treatment with broad-spectrum antibiotics have been demonstrated in immune checkpoint inhibitor (ICI)-treated cancer patients. Routy et al investigated how the gut microbiome influences efficacy of PD-1-based immunotherapy against epithelial tumours (Routy et al Science 2018, 359, 91-97). In this work, the authors also analyzed datasets for infections/antibiotic use in patients with advanced NSCLC (n=140), renal cell carcinoma (n=67), or urothelial carcinoma (n=42) who received antibody ICI against PD-1/PD-L1 interaction after one or several prior therapies. Among these patients, they were prescribed broad-spectrum antibiotics (beta-lactam+/−inhibitors, fluoroquinolones, or macrolides) within 2 months before, or 1 month after, the first administration of PD-1/PD-L1 mAb. Patients generally took antibiotic orally for common indications (dental, urinary, and pulmonary infections). The detrimental effect of treating infections in cancer patients undergoing ICI therapy with classical, broad-spectrum antibiotics was observed. See FIG. 8, which shows that the antibiotic treatment during ICI therapy has fatal outcomes: there was a medial overall survival of 21.9 months in the absence of antibiotic treatment, compared to an overall survival of 9.8 months with antibiotic treatment. So, the median overall survival in patients treated with classical antibiotics is <50% (or >12 months shorter) that of patients not receiving antibiotic treatment.

Figure 9A:
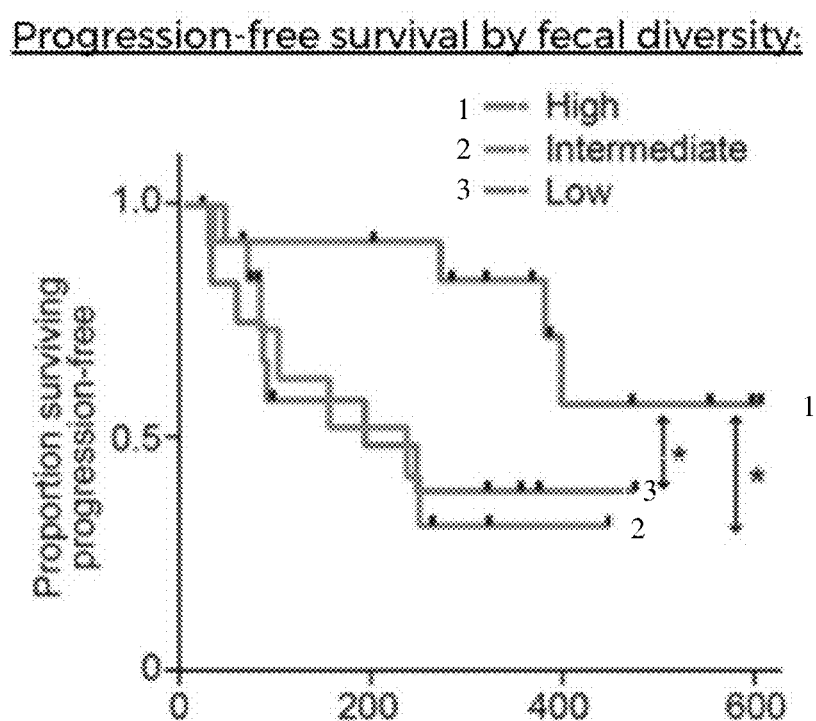
FIGS. 9A and 9B show that the gut microbiome modulates the efficacy of anti-PD-1 inhibition in melanoma patients (from Gopalakrishnan et al, *Science* 2018, 359, 97-103).
Figure 9B:
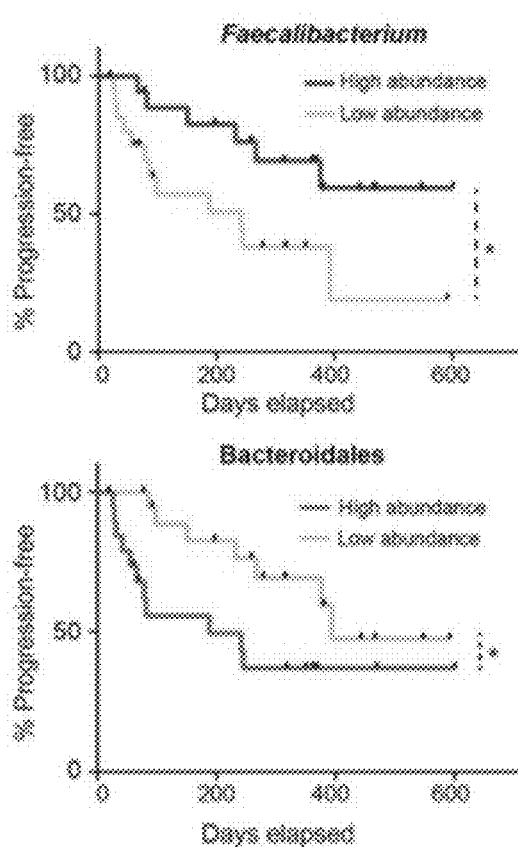

The work by Gopalakrishnan et al is another recent example lending support to the importance of a "healthy" microbiome in immuno-oncology therapy outcomes (Gopalakrishnan et al, Science 2018, 359, 97-103). See FIGS. 9A and 9B. It was observed that the gut microbiome modulates the efficacy of anti-PD-1 inhibition in melanoma patients.

Several other studies add to the expanding evidence base of the critical link between the microbiome and immuno-oncology outcomes:

"Microbiota: a key orchestrator of cancer therapy", Nat. Rev. Cancer 2017, 17, 271-285

Matson et al, Science 2018, 359, 104-108

L. Derosa et al Annals of Oncology 2018 (epub 30 Mar. 2018)

M. Vétizou et al Science. 2015, 350, 1079-84

Sivan et al Science 2015, 350, 1084-1089

Another report—claiming to be the first systematic review of infection among patients receiving immune checkpoint blockade for cancer therapy—investigated serious infections in melanoma patients treated with immune checkpoint inhibitors (against CTLA-4, PD-1, and/or PD-L1) (M. Del Castillo et al Clin. Infect. Dis. 2016, 63, 1490-1493). Serious infections were defined as infections requiring hospitalization or parenteral antimicrobials. Of 740 patients (898 courses of immune checkpoint blockade), serious infection developed in 54 patients (7.3%). Nine patients (17%) were deemed to have died of an infection. Total number of infections was 58, as some patients developed >1 infection. The majority of infections were bacterial in origin (~80%; i.e., bacterial infections: 80% of 7.3%: 5.8% of patients). Pneumonia and bloodstream infections were the two dominating bacterial infection types.

Immune checkpoint-blocking drugs are associated with immune-related adverse effects (irAEs) related to the upregulated immune system. The complications are managed with immunosuppressive drugs, such as steroids (immunosuppression is a risk factor for subsequent opportunistic infections). Of the 740 patients, 46% received steroids during the course of treatment. Risk of serious infections was 13.5% in the cohort receiving corticosteroids or infliximab (vs. 7.3% in the overall population).

In yet another report, the emerging concern of infectious diseases in lung cancer patients receiving ICI therapy was investigated. Of 84 NSCLC patients receiving nivolumab (a PD-1 inhibitor), 20 patients (23.8%) developed an infectious disease. Bacterial infections accounted for 75% of infections; i.e., bacterial infections in 18% of patients. Most common type of bacterial infection was pneumonia. See K. Fujita et al Eur. Resp. J. 2017, 50, OA1478.

The Gram-negative bacillus E. coli is one of the most common causes of bacteraemia in patients with cancer. The all-cause 30-day mortality rate for this pathogen is high (~15%) (Y. E. Ha et al Int. J. Antimicr. Agen. 2013, 42, 403-409). Published estimates of 30-day all-cause mortality among E. coli bacteraemia patients (cancer/non-cancer) vary from around 10 to 35% (J. K. Abernethy et al Clin. Microbiol. Infect. 2015, 21, 251.e1-251.e8), clearly highlighting the high burden associated with just this pathogen. Overall, causative pathogens in bacteraemia are primarily Gram-negative bacteria (65%), with E. coli (18.3%), P. aeruginosa (18.3%), and K pneumoniae (17.3%) being the most common organisms encountered; the three pathogens together account for 54% of the bacteraemia cases, or 85% of Gram-negative cases, according to a study investigating >100 bacteraemia cases in cancer patients (G. Samonis et al Support Care Cancer 2013, 21, 2521-2526). In-hospital mortality was 26.2% in this study. Comparable numbers can be found elsewhere. For example, a study of neutropenic and non-neutropenic adult cancer patients with bloodstream infections investigated 399 cases of bloodstream infections in 344 cancer patients: The largest causative pathogen group was Gram-negative bacilli (45%). Of the clinical isolates, E. coli (35%) accounted for the most cases within Gram-negatives, followed by K. pneumoniae (20%) and P. aeruginosa (19%) (E. Velasco et al Eur. J. Clin. Microbiol. Infect. Dis. 2006, 25, 1-7). The three pathogens collectively account for 33% of the bacteraemia cases (or 74% of Gram-negative cases). The overall 30-day mortality rate was 32% in this study. Two other reports looked at causative agents of bloodstream infection in patients with solid tumours and also found Gram-negative bacteria to be the dominating pathogen type (47-55% of the infections, across several hundred patients) (M. Marin et al Medicine 2014, 93, 143-149; M. Anatoliotaki et al Infection 2004, 32, 65-71; see also C. Gudiol et al Virulence 2016, 7, 298-308). In the larger of the two studies (with more robust numbers for individual pathogens), the three main pathogens within the Gram-negative group were again E. coli (55%), P. aeruginosa (18%), and Klebsiella spp. (11%)—corresponding to 92% of the Gram-negative cases, or 51% of the 528 total cases of bloodstream infections studied.

The above data on specific causative infectious pathogens in cancer patients are summarized in Table 5 below.

Thus, available data on bloodstream infections in cancer indicate that Gram-negative pathogens are involved in 45-65% of the infection cases, with three key pathogens—E. coli, K. pneumoniae, and P. aeruginosa—being the culprits in the vast majority of Gram-negative cases (73-92%).

The inventors, thus, formulated an oncologist's dilemma:

Reduction in efficacy of the cancer therapy is likely due to the reduced microbiome diversity resulting from antibiotic therapy At least ⅓ of patients on checkpoint inhibitors get serious and life-threatening infections Not treating these infections could result in death from the infection (1-2 weeks)

Treatment with classic antibiotics leads to reduction in progression free survival after 4 years from >40% to around 10%.

The choice is to treat the immediate need of a potentially fatal infection (which must be addressed) at the risk of seriously undermining the cancer therapy.

The inventors realised, therefore, that there is a need for methods that can treat a bacterial pathogenic infection in a different way that minimizes compromise to the cancer therapy. The inventors realised that this need would also be useful in other therapy settings where the microbiome composition can modulate therapy outcomes, eg, in transplant settings.

Whilst not wishing to be bound by any particular theory, the inventors believe that alleviating the detrimental effect of traditional antibiotic therapy on overall survival in ICI patients using the invention may, in some embodiments, translate to as much as a doubling of overall survival (or >12 months). Capturing a treatment effect of several months in terms of median overall survival is a very substantial achievement in this space. In fact, an effect size of this order of magnitude is comparable to the outcomes reported for ICI trials (i.e., where benefits usually are measured in months, not years). Additionally, PD-1/PD-L1 drugs are projected to dominate the ICI market. In 2023, PD-1/PD-L1 are projected to account for 94% of $46B USD global sales of ICIs (CTLA-4 blockers only account for 6%), source: "Landscape & Forecast: Immune Checkpoint Inhibitors", Decision Resources, December 2017. Thus, a need for improving treatment using immune checkpoint inhibitors of PD-1 or PD-L1 is particularly pressing in medicine, and we believe that the present invention finds particular benefit in this respect.

In an example, the method removes the need to administer a classic antibiotic, such as a broad-spectrum antibiotic (or any other one disclosed herein). In another example, the invention reduces the amount or dosing frequency of a classic antibiotic, such as a broad-spectrum antibiotic (or any other one disclosed herein) that is administered to the subject for treating the infection. For example, the subject can be administered a low-dose broad-spectrum antibiotic (eg, 50, 40, 30, 20, 10% or less of a conventional dose) whilst the guided nuclease cutting is used, and thus treatment of the infection in this setting. The invention may be particularly beneficial for patients on immunosuppressants, eg, for cancer patients, transplant patients or patients suffering from a viral infection (eg, HIV (human immunodeficiency virus), CMV (cytomegalovirus) or RSV (respiratory synctial virus) infection).

The term "broad-spectrum antibiotic" can refer to an antibiotic that acts on the two major bacterial groups, gram-positive and gram-negative, or any antibiotic that acts against a wide range of disease-causing bacteria. These medications are used when a bacterial infection is suspected but the group of bacteria is unknown (also called empiric therapy) or when infection with multiple groups of bacteria is suspected. Although powerful, broad-spectrum antibiotics pose specific risks, particularly the disruption of native, normal bacteria and the development of antimicrobial resistance. Examples of commonly used broad-spectrum antibiotics are Aminoglycosides (except for streptomycin), Ampicillin, Amoxicillin, Amoxicillin, clavulanic acid (Augmentin), Carbapenems (e.g. imipenem), Piperacillin, tazobactam, Quinolones (e.g. ciprofloxacin), Tetracyclines, Chloramphenicol, Ticarcillin, Trimethoprim and sulfamethoxazole (Bactrim). In veterinary medicine, examples are co-amoxiclav, (eg, in small animals), penicillin, streptomycin, oxytetracycline and potentiated sulfonamides.

Clauses:—

The invention, therefore, in one aspect provides the following Clauses that are directed to the treatment of a pathogenic bacterial infection using a programmed nuclease.

1. A method for treating a pathogenic bacterial infection in a human or animal subject caused by bacteria (first bacteria) of a first species or strain, the method comprising selectively killing first bacteria comprised by the subject by cutting a target site comprised by the genomes of the first bacteria, wherein the cutting is carried out using a programmable nuclease that is programmed to cut the target site, wherein the subject is suffering from a further disease or condition other than the pathogenic bacterial infection and the method comprises administering a therapy to the subject for treating or preventing the further disease or condition, wherein the nuclease treats the infection and the therapy is efficacious in the presence of the programmed nuclease to treat or prevent the disease or condition.

In an example, Clause 1 provides:—

A method for treating a pathogenic bacterial infection in a cancer patient caused by bacteria (first bacteria) of a first species or strain, the method comprising selectively killing first bacteria comprised by the subject by cutting a target site comprised by the genomes of the first bacteria, wherein the cutting is carried out using a Cas nuclease that is programmed by guide RNA to cut the target site, wherein the method comprises administering an immunotherapy to the subject for treating cancer in the patient, wherein the nuclease treats the infection and the immunotherapy is efficacious in the presence of the programmed nuclease to treat the cancer.

A method for treating a pathogenic bacterial infection in a cancer patient caused by bacteria (first bacteria) of a first species or strain, the method comprising selectively killing first bacteria comprised by the subject by cutting a target site comprised by the genomes of the first bacteria, wherein the cutting is carried out using a Cas nuclease that is programmed by guide RNA to cut the target site, wherein the method comprises administering an immunotherapy to the subject for treating cancer in the patient, wherein the nuclease treats the infection and the immunotherapy is efficacious in the presence of the programmed nuclease to treat the cancer;

Wherein
  (a) The immunotherapy comprises administering to the patient an anti-PD-1 antibody optionally selected from pembrolizumab (or KEYTRUDA™) and nivolumab (or OPDIVO™); and
  (b) The cancer is selected from metastatic melanoma; renal cell carcinoma; bladder cancer; a solid tumour; non-small cell lung cancer (NSCLC); forehead and neck squamous cell carcinoma (HNSCC); Hodgkin's lymphoma; a cancer that overexpresses PD-L1 and no mutations in EGFR or in ALK; colorectal cancer and hepatocellular carcinoma; and
  (c) The first bacteria are selected from *Pseudomonas aeruginosa, Klebsiella pneumoniae, E. coli, Salmonella* (eg, *S. typhimurium*), *Clostridium dificile, Staphylococcus* (eg, *S. aureus* or *S epidermis*), *Streptococcus* (eg, *S. viridans* or *S. thermophilus*), *Pneumococcus* and *Enterococcus* bacteria.

A method for treating a pathogenic bacterial infection in a cancer patient caused by bacteria (first bacteria) of a first species or strain, the method comprising selectively killing first bacteria comprised by the subject by cutting a target site comprised by the genomes of the first bacteria, wherein the cutting is carried out using a Cas nuclease that is programmed by guide RNA to cut the target site, wherein the method comprises administering an immunotherapy to the subject for treating cancer in the patient, wherein the nuclease treats the infection and the immunotherapy is efficacious in the presence of the programmed nuclease to treat the cancer;

Wherein
  (a) The immunotherapy comprises administering to the patient an anti-PD-L1 antibody optionally selected from atezolimumab (or TECENTRIQ™), avelumab (or BAVENCIO™) and durvalumab (or IMFINZI™); and
  (b) The cancer is selected from metastatic melanoma; renal cell carcinoma; a solid tumour; non-small cell lung cancer (NSCLC); forehead and neck squamous cell carcinoma (HNSCC); Merkel cell carcinoma; Hodgkin's lymphoma; a cancer that overexpresses PD-L1 and no mutations in EGFR or in ALK; colorectal cancer and hepatocellular carcinoma; and (c) The first bacteria are selected from *Pseudomonas aeruginosa*, *Klebsiella pneumoniae*, *E. coli*, *Salmonella* (eg, *S. typhimurium*), *Clostridium dificile*, *Staphylococcus* (eg, *S. aureus* or *S epidermis*), *Streptococcus* (eg, *S. viridans* or *S. thermophilus*), *Pneumococcus* and *Enterococcus* bacteria.

A method for treating a pathogenic bacterial infection in a cancer patient caused by bacteria (first bacteria) of a first species or strain, the method comprising selectively killing first bacteria comprised by the subject by cutting a target site comprised by the genomes of the first bacteria, wherein the cutting is carried out using a Cas nuclease that is programmed by guide RNA to cut the target site, wherein the method comprises administering an immunotherapy to the subject for treating cancer in the patient, wherein the nuclease treats the infection and the immunotherapy is efficacious in the presence of the programmed nuclease to treat the cancer;

Wherein (a) The immunotherapy comprises administering to the patient an anti-CD52, antibody optionally alemtuzumab (or CAMPATH™); and (b) The cancer is B-cell chronic lymphocytic leukemia (CLL); and (c) The first bacteria are selected from *Pseudomonas aeruginosa*, *Klebsiella pneumoniae*, *E. coli*, *Salmonella* (eg, *S. typhimurium*), *Clostridium dificile*, *Staphylococcus* (eg, *S. aureus* or *S epidermis*), *Streptococcus* (eg, *S. viridans* or *S. thermophilus*), *Pneumococcus* and *Enterococcus* bacteria.

A method for treating a pathogenic bacterial infection in a cancer patient caused by bacteria (first bacteria) of a first species or strain, the method comprising selectively killing first bacteria comprised by the subject by cutting a target site comprised by the genomes of the first bacteria, wherein the cutting is carried out using a Cas nuclease that is programmed by guide RNA to cut the target site, wherein the method comprises administering an immunotherapy to the subject for treating cancer in the patient, wherein the nuclease treats the infection and the immunotherapy is efficacious in the presence of the programmed nuclease to treat the cancer;

Wherein (a) The immunotherapy comprises administering to the patient an anti-CD20 antibody, optionally ofatumumab (or ARZERRA™) or rituximab (or RITUXAN™); and (b) The cancer is B-cell chronic lymphocytic leukemia (CLL) (eg, refractory CLL) or non-Hodgkin lymphoma; and (c) The first bacteria are selected from *Pseudomonas aeruginosa*, *Klebsiella pneumoniae*, *E. coli*, *Salmonella* (eg, *S. typhimurium*), *Clostridium dificile*, *Staphylococcus* (eg, *S. aureus* or *S epidermis*), *Streptococcus* (eg, *S. viridans* or *S. thermophilus*), *Pneumococcus* and *Enterococcus* bacteria.

A method for treating a pathogenic bacterial infection in a cancer patient caused by bacteria (first bacteria) of a first species or strain, the method comprising selectively killing first bacteria comprised by the subject by cutting a target site comprised by the genomes of the first bacteria, wherein the cutting is carried out using a Cas nuclease that is programmed by guide RNA to cut the target site, wherein the method comprises administering an immunotherapy to the subject for treating cancer in the patient, wherein the nuclease treats the infection and the immunotherapy is efficacious in the presence of the programmed nuclease to treat the cancer;

Wherein (a) The immunotherapy comprises administering to the patient an anti-KIR antibody, optionally lirilumab; and (b) The cancer is optionally acute myeloid leukaemia or squamous cell carcinoma of the head and neck (SCCHN); and (c) The first bacteria are selected from *Pseudomonas aeruginosa*, *Klebsiella pneumoniae*, *E. coli*, *Salmonella* (eg, *S. typhimurium*), *Clostridium dificile*, *Staphylococcus* (eg, *S. aureus* or *S. epidermis*), *Streptococcus* (eg, *S. viridans* or *S. thermophilus*), *Pneumococcus* and *Enterococcus* bacteria.

A method for treating a pathogenic bacterial infection in a cancer patient caused by bacteria (first bacteria) of a first species or strain, the method comprising selectively killing first bacteria comprised by the subject by cutting a target site comprised by the genomes of the first bacteria, wherein the cutting is carried out using a Cas nuclease that is programmed by guide RNA to cut the target site, wherein the method comprises administering an immunotherapy to the subject for treating cancer in the patient, wherein the nuclease treats the infection and the immunotherapy is efficacious in the presence of the programmed nuclease to treat the cancer;

Wherein (a) The immunotherapy comprises administering to the patient an anti-CD19 CAR-T optionally selected from axicabtagene ciloleucel (or YESCARTA™) and tisagenlecleucel (or KYMRIAH™); and (b) The cancer is selected from a B-cell lymphoma (eg, non-Hodgkin's lymphoma (NHL); diffuse large B-cell lymphoma (DLBCL); primary mediastinal large B-cell lymphoma; or high grade B-cell lymphoma); B-cell acute lymphoblastic leukaemia (ALL); or central nervous system lymphoma; and (c) The first bacteria are selected from *Pseudomonas aeruginosa*, *Klebsiella pneumoniae*, *E. coli*, *Salmonella* (eg, *S. typhimurium*), *Clostridium dificile*, *Staphylococcus* (eg, *S. aureus* or *S epidermis*), *Streptococcus* (eg, *S. viridans* or *S. thermophilus*), *Pneumococcus* and *Enterococcus* bacteria.

Alternatively, the CAR-T is an anti-CD30, CD38 or CD22 CAR-T. In an example the cancer is large B-cell lymphoma after at least two other kinds of treatment failed. In an example the cancer is high grade B-cell lymphoma and DLBCL arising from follicular lymphoma. In an example the cancer is relapsing/remitting B cell acute lymphoblastic leukaemia. In an example the cancer is primary central nervous system lymphoma.

In an example, the nuclease treats the infection without causing reduction in efficacy of the therapy. In an embodiment, "without causing reduction in efficacy of the therapy" means the efficacy of the therapy compared to a reduction caused in patients by the administration of a broad-spectrum antibiotic (or an antibiotic disclosed herein) that kills a plurality of different species, wherein the plurality comprises the first species. In an embodiment, "without causing reduction in efficacy of the therapy" means the efficacy of the therapy is reduced by no more than 70, 80, 90 or 95% compared to administration of the therapy in the absence of treatment of the pathogenic bacterial infection (or compared to therapy as typically achieved in patients suffering from the disease or condition and receiving said therapy therefor).

This may be assessed, for example, by determining the duration of progression-free survival of the subject or treatment of the disease or condition, or overall survival of the subject; and/or by determining a reduction in one or more symptoms of the disease or condition.

In an example, the infection is treated completely or substantially completely. In another example, the infection is reduced (eg, by at least 80, 90 or 95% as determined by a marker of the infection or a symptom thereof). A marker may, for example, be CFUs of bacteria of the first species or strain per ml of a blood sample taken from the patient after the method has been carried out, eg, within 24 hours of that method being carried out, eg, from 1-12 hours or 1-24 hours after carrying out the method or from 1-12 hours or 1-24 hours after administering a RNA or DNA encoding the RNA to programme the nuclease in the subject. For example, the RNA is a guide RNA and the nuclease is Cas (eg, a Cas3 or a Cas9). The reduction may be compared to a sample taken from the subject immediately prior to the commencement of the method. Alternatively, the sample may be a stool, saliva or urine sample.

In an example, the invention increases overall survival rate in a human subject (compared to median overall survival rate in humans suffering from the same cancer and receiving the same cancer therapy treatment (eg, administration of the same immune checkpoint inhibitor, such as nivolumab, pembrolizumab or another antibody disclosed herein)). In an example any composition, or other product of the invention herein is provided for use in such method of treatment.

In an example, the method is practised on a population of human subjects and the median overall survival rate for the population is 120-250% (eg, 150-200%) of the median overall survival rate in humans suffering from the same cancer and receiving the same cancer therapy treatment (eg, administration of the same immune checkpoint inhibitor, such as nivolumab, pembrolizumab or another antibody disclosed herein). In an example any composition, or other product of the invention herein is provided for use in such method of treatment.

A "pathogenic bacterial infection" is a health-threatening infection of the subject, for example, a life-threatening infection. In an embodiment, a pathogenic bacterial infection is an infection requiring hospitalization or parenteral antimicrobials. The infection may be an acute bacterial infection, such as a systemic infection or a localised infection. Bacterial pathogens often cause infection in specific areas of the body. Others are generalists. A pathogenic bacterial infection is contrasted with an infection of commensal bacteria, such as commensal gut bacteria; in this case the bacteria do not cause an immediate health- or life-threatening situation.

The infection (or symptom thereof) can be any of the following:—

Bacterial vaginosis: this is caused by bacteria that change the vaginal microbiota caused by an overgrowth of bacteria that crowd out the Lactobacilli species that maintain healthy vaginal microbial populations.

Bacterial meningitis: this is a bacterial inflammation of the meninges, that is, the protective membranes covering the brain and spinal cord.

Bacterial pneumonia: this is a bacterial infection of the lungs.

Urinary tract infection: this is predominantly caused by bacteria. Symptoms include the strong and frequent sensation or urge to urinate, pain during urination, and urine that is cloudy. The main causal agent is *Escherichia coli*. Bacteria can ascend into the bladder or kidney and causing cystitis and nephritis.

Bacterial gastroenteritis: this is caused by enteric, pathogenic bacteria. These pathogenic species are usually distinct from the usually harmless bacteria of the normal gut flora. But a different strain of the same species may be pathogenic.

Bacterial skin infections: these include:

Impetigo, which is a highly contagious bacterial skin infection commonly seen in children. It is caused by *Staphylococcus aureus*, and *Streptococcus pyogenes*.

Erysipelas, which is an acute *streptococcus* bacterial infection of the deeper skin layers that spreads via with lymphatic system.

Cellulitis, which is a diffuse inflammation of connective tissue with severe inflammation of dermal and subcutaneous layers of the skin. Cellulitis can be caused by normal skin flora or by contagious contact, and usually occurs through open skin, cuts, blisters, cracks in the skin, insect bites, animal bites, burns, surgical wounds, intravenous drug injection, or sites of intravenous catheter insertion. In most cases it is the skin on the face or lower legs that is affected, though cellulitis can occur in other tissues.

In an example, the first bacteria are *Streptococcus* and the patient is suffering from chest infection, cellulitis or tonsillitis. In an example, the first bacteria are *Enterococcus* and the patient is suffering from bladder infection or septicaemia. In an example, the first bacteria are *Pseudomonas aeruginosa* and the patient is suffering from diarrhoea. In an example, the first bacteria are *E. coli* and the patient is suffering from diarrhoea.

2. The method of Clause 1, wherein the subject is a cancer patient and the therapy is a cancer therapy.

3. The method of Clause 2, wherein the therapy comprises administration of a haematopoietic stem cell transplant, chemotherapeutic agent, immune checkpoint inhibitor, immune checkpoint agonist or an immune cell (eg, T-cell and/or NK cell) enhancer; adoptive cell therapy (eg, CAR-T therapy); radiation or surgery.

In an example, the therapy is immunotherapy. Examples of suitable immunotherapy are administration of adoptive cell therapy (eg, CAR-T therapy), an immune checkpoint inhibitor, an immune checkpoint agonist or an immune cell (eg, T-cell and/or NK cell) enhancer. For example, administration of an anti-CTLA4, PD-1, PD-L1, PD-L2, LAG3, OX40, CD28, BTLA, CD137, CD27, HVEM, KIR, TIM-3, VISTA, ICOS, GITR, TIGIT or SIRPa antibody, such as administration of an antibody selected from ipilimumab (or YERVOY™), tremelimumab, nivolumab (or OPDIVO™) pembrolizumab (or KEYTRUDA™), pidilizumab, BMS-936559, durvalumab and atezolizumab, or a CAR-T therapy such as axicabtagene ciloleucel (Yescarta™) or tisagenlecleucel (Kymriah™).

In an example, the immune enhancer comprises an interleukin-2 (IL-2) or fragment or deletion mutant thereof.

In an example, the surgery comprises the removal of necrotic or cancerous tissue.

In an example, the chemotherapy comprises administration of a platinum-containing chemotherapy drug. In an example, the chemotherapy comprises administration of gefitinib.

In an example, the therapy comprises administering Cyclophosphamide, methotrexate and 5-fluorouracil (CMF); or doxorubicin and cyclophosphamide (AC); docetaxel, doxorubicin and cyclophosphamide (TAC); or doxorubicin, bleomycin, vinblastine and dacarbazine (ABVD); or mustine, vincristine, procarbazine and prednisolone (MOPP); cyclophosphamide, doxorubicin, vincristine and prednisolone (CHOP); bleomycin, etoposide and cisplatin (BEP); epirubicin, cisplatin and 5-fluorouracil (ECF); or epirubicin, cisplatin and capecitabine (ECX); methotrexate, vincristine, doxorubicin and cisplatin (MVAC); cyclophosphamide, doxorubicin and vincristine (CAV); or 5-fluorouracil, folinic acid and oxaliplatin (FOLFOX).

In an example, the cancer is breast cancer and the therapy comprises administering CMF or AC. In an example, the cancer is Hodgkin's lymphoma and the therapy comprises administering TAC, ABVD or MOPP. In an example, the cancer is Non-Hodgkin's lymphoma and the therapy comprises administering CHOP. In an example, the cancer is germ cell cancer and the therapy comprises administering BEP. In an example, the cancer is stomach cancer and the therapy comprises administering ECF or ECX. In an example, the cancer is bladder cancer and the therapy comprises administering MVAC. In an example, the cancer is lung cancer and the therapy comprises administering CAV. In an example, the cancer is colorectal cancer and the therapy comprises administering FOLFOX.

4. The method of Clause 3, wherein the therapy is an immune checkpoint inhibitor antibody.

Optionally the antibody is an anti-CTLA4, PD-1, PD-L1, PD-L2, LAG3, 0X40, CD28, BTLA, CD137, CD27, HVEM, KIR, TIM-3, VISTA, ICOS, GITR, TIGIT or SIRPa antibody. In an example, the antibody is an anti-PD-1 antibody. In an example, the antibody is an anti-PD-L1 antibody. In an example, the antibody is an anti-CTLA4 antibody.

5. The method of Clause 3, wherein the therapy is administration of an antibody selected from ipilimumab (or YERVOY™), tremelimumab, nivolumab (or OPDIVO™), pembrolizumab (or KEYTRUDA™), pidilizumab, BMS-936559, durvalumab and atezolizumab.

Optionally, the antibody (eg, anti-PD-L1 antibody) is administered with an anti-CTLA4 antibody (eg, ipilimumab or tremelimumab).

In an example, the an anti-PD-1 antibody herein is selected from nivolumab, pembrolizumab, pidillizumab, OPDIVO®, KEYTRUDA®, AMP-514, REGN2810, CT-011, BMS 936559, MPDL3280A and AMP-224.

In an example, the anti-CTLA4 antibody herein is selected from tremelimumab, YERVOY® and ipilimumab.

In an example the therapy is administration of an anti-KIR antibody, eg, lirilumab.

In an example, the checkpoint inhibitor is selected from an inhibitor of CTLA-4, PD-1, PD-L1, PD-L2, LAG-3, BTLA, B7H3, B7H4, TIM3, KIR, or A2aR. In certain aspects, the immune checkpoint inhibitor is a human programmed cell death 1 (PD-1) axis-binding antagonist. In some aspects, the PD-1 axis-binding antagonist is selected from the group consisting of a PD-1 binding antagonist, a PD-L1-binding antagonist and a PD-L2-binding antagonist. In certain aspects, the PD-1 axis-binding antagonist is a PD-1-binding antagonist. In some aspects, the PD-1-binding antagonist inhibits the binding of PD-1 to PD-L1 and/or PD-L2.

In some embodiments, the immune checkpoint inhibitor is a PD-L1 antagonist such as durvalumab, also known as MEDI4736, atezolizumab, also known as MPDL3280A, or avelumab, also known as MSB0010118C. In certain aspects, the immune checkpoint inhibitor is a PD-L2 antagonist such as rHIgM12B7. In some aspects, the immune checkpoint inhibitor is a LAG-3 antagonist such as IMP321 or BMS-986016. The immune checkpoint inhibitor may be an adenosine Ata receptor (A2aR) antagonist such as PBF-509.

In some embodiments, the antibody described herein (such as an anti-PD-1 antibody, an anti-PD-L1 antibody, or an anti-PD-L2 antibody) further comprises a human or murine constant region. In a still further aspect, the human constant region is selected from the group consisting of IgG1, IgG2, IgG2, IgG3, and IgG4. In a still further specific aspect, the human constant region is IgG1. In a still further aspect, the murine constant region is selected from the group consisting of IgG1, IgG2A, IgG2B, and IgG3. In a still further specific aspect, the antibody has reduced or minimal effector function. In a still further specific aspect, the minimal effector function results from production in prokaryotic, CHO, Cos or HEK cells. In a still further specific aspect the minimal effector function results from an "effector-less Fc mutation" or aglycosylation.

For example, the therapy comprises a haemopoietic stem cell transplant, eg, a bone marrow transplant (such as when the patient is a cancer patient, eg, a blood cancer or leukaemia patient).

For example, the therapy comprises a stem cell transplant, a skin graft, or an organ transplant, eg, a heart, liver, kidney or lung transplant.

6. The method of Clause 1 or 2, wherein the therapy is a tissue, organ or cell transplant.

7. The method of any preceding Clause, wherein the treatment of the bacterial infection is carried out simultaneously with the administration of the therapy to the subject.

8. The method of any one of Clauses 1 to 6, wherein the treatment of the bacterial infection is carried out immediately before administering the therapy to the subject.

In an example, the treatment of the bacterial infection is carried out no more than 7, 6, 5, 4, 3, 2, or 1 day, or 24, 12, 6, 5, 4, 3, 2, 1 or 0.5 hours before the therapy of the further disease or condition. In an example, the treatment of the bacterial infection is carried out no more than 7, 6, 5, 4, 3, 2, or 1 day, or 24, 12, 6, 5, 4, 3, 2, 1 or 0.5 hours after the therapy of the further disease or condition.

The treatment of the infection and the administration of the therapy may be carried out simultaneously or sequentially.

9. The method of any one of Clauses 1 to 6, wherein the treatment of the bacterial infection is carried out immediately after administering the therapy to the subject.

10. The method of any preceding Clause, wherein the method comprises administering to the subject a RNA (eg, a gRNA) or a nucleic acid that encodes an RNA for expression of the RNA in the subject, wherein the RNA complexes with the nuclease to program the nuclease to cut the target site in first bacteria comprised by the subject, thereby killing the first bacteria.

The RNA or nucleic acid is, for example, administered to the subject or patient orally, by IV injection, by subcutaneous injection or by inhalation.

11. The method of any preceding Clause, comprising administering a vector (eg, phage or plasmids) to the subject, wherein the vector encodes the programmable nuclease.

The nuclease is, for example, administered to the subject or patient orally, by IV injection, by subcutaneous injection or by inhalation.

12. The method of any one of Clauses 1 to 10, wherein the programmable nuclease is an endogenous nuclease (eg, Cas nuclease) of the first cells.

13. The method of any preceding Clause, wherein the efficacy of the therapy in the presence of the programmed nuclease is greater than the efficacy of the therapy in the presence of a broad-spectrum antibiotic.

In an example, the efficacy being greater is assessed by determining the duration of progression-free survival or treatment of the disease or condition; and/or by determining a reduction in one or more symptoms of the disease or condition. For example, this determination is compared to an analogous determination in a patient suffering from the disease or condition as well as the bacterial infection and being treated with the therapy and the antibiotic (rather than the nuclease killing of first bacteria as per the invention).

14. The method of any preceding Clause, wherein the efficacy of the therapy in the presence of the programmed nuclease is greater than the efficacy of the therapy in the presence of an antibiotic selected from methicillin, vancomycin, linezolid, daptomycin, quinupristin, dalfopristin; teicoplanin; cephalosporin; carbapenem; fluoroquinolone; aminoglycoside; colistin; erythromycin; clindamycin; beta-lactam; macrolide; amoxicillin; azithromycin; penicillin; ceftriaxone; azithromycin; ciprofloxacin; isoniazid (INH); rifampicin (RMP); amikacin; kanamycin; capreomycin; trimethoprim; itrofurantoin; cefalexin; amoxicillin; metronidazole (MTZ); cefixime; tetracycline; and meropenem.

15. The method of any preceding Clause, wherein the first bacteria is selected from (i) *Staphylococcus aureus* that is resistant to an antibiotic selected from methicillin, vancomycin, linezolid, daptomycin, quinupristin, dalfopristin and teicoplanin; (ii) *Pseudomonas aeuroginosa* that is resistant to an antibiotic selected from cephalosporins, carbapenems, fluoroquinolones, aminoglycosides and colistin; (iii) *Klebsiella* species that is resistant to carbapenem; (iv) *Streptococcus* species that is resistant to an antibiotic selected from erythromycin, clindamycin, beta-lactam, macrolide, amoxicillin, azithromycin and penicillin; (v) *Salmonella* species that is resistant to an antibiotic selected from ceftriaxone, azithromycin and ciprofloxacin; (vi) *Shigella* species that is resistant to ciprofloxacin or azithromycin; (vii) *Mycobacterium tuberculosis* that is resistant to an antibiotic selected from Resistance to isoniazid (INH), rifampicin (RMP), fluoroquinolone, amikacin, kanamycin, capreomycin and azithromycin; (viii) *Enterococcus* species that is resistant to vancomycin; (ix) Enterobacteriaceae species that is resistant to an antibiotic selected from cephalosporin and carbapenem; (x) *E. coli* that is resistant to an antibiotic selected from trimethoprim, itrofurantoin, cefalexin and amoxicillin; (xi) *Clostridium* species that is resistant to metronidazole (MTZ), fluoroquinolone or carbapenem; (xii) *Neisseria gonnorrhoea* that is resistant to an antibiotic selected from cefixime, ceftriaxone, azithromycin and tetracycline; (xiii) *Acinetobacter baumannii* that is resistant to an antibiotic selected from beta-lactam, meropenem and carbapenem; and (xiv) *Campylobacter* species that is resistant to ciprofloxacin or azithromycin.

16. The method of any preceding Clause, wherein the treatment of the infection treats or prevents a condition selected from vaginosis, meningitis, pneumonia, urinary tract infection, cystitis, nephritis, gastroenteritis, a skin infection, impetigo, erysipelas, dental infection and cellulitis.

17. The method of any preceding Clause, wherein the treatment of the infection treats or prevents septicaemia or sepsis in the subject.

In an example, the infection is a bloodstream infection.

18. The method of any preceding Clause, wherein the further disease or condition is a cancer; autoimmune disease or condition; viral infection or GI tract disease or condition. In an example, the cancer is metastatic. In an example, the cancer is melanoma. In an example, the cancer is a solid tumour with mismatch repair deficiency or microsatellite instability. In an example, the cancer is NSCLC. In an example, the cancer is HNSCC. In an example, the cancer is Hodgkin's lymphoma. In an example, the cancer is urothelial cancer. In an example, the cancer is lung cancer. In an example, the cancer is head and neck cancer. In an example, the cancer is head cancer. In an example, the cancer is neck cancer. In an example, the viral infection is a HIV, CMV or RSV infection.

19. The method of any preceding Clause, wherein the subject comprises bacteria (second bacteria) of one or more strains or species that are different to the first strain or species, wherein the genomes of the second bacteria do not comprise the target site, wherein the genomes of the second bacteria are not cut by the programmed nuclease in the subject, whereby second bacteria survive in the presence of the programmed nuclease in the patient; and wherein the therapy is efficacious in the presence of the second bacteria.

20. The method of Clause 19, wherein reduction in the second bacteria in patients (eg, in the gut microbiome) is associated with reduced efficacy of the therapy.

Optionally, the therapy is efficacious in the presence of the second bacteria in the gut of the subject.

Optionally, the first and/or second bacteria are present in the gut of the subject immediately prior to carrying out the method.

Optionally, the first and/or second bacteria are present in the blood of the subject immediately prior to carrying out the method.

Optionally, the first bacteria are present in the blood of the subject and the second bacteria are present in the gut of the subject immediately prior to carrying out the method.

Optionally, the first bacteria are present in the gut of the subject and the second bacteria are present in the blood of the subject immediately prior to carrying out the method.

Optionally, first bacteria in the blood of the subject is killed.

Optionally, the bacteria are gram positive bacteria. Optionally, the bacteria are gram negative bacteria.

Optionally, the first and second bacteria are capable of being killed by the same antibiotic. Optionally, the method does not comprise administering the antibiotic to the subject. In an example, the antibiotic is selected from methicillin, vancomycin, linezolid, daptomycin, quinupristin, dalfopristin; teicoplanin; cephalosporin; carbapenem; fluoroquinolone; aminoglycoside; colistin; erythromycin; clindamycin; beta-lactam; macrolide; amoxicillin; azithromycin; penicillin; ceftriaxone; azithromycin; ciprofloxacin; isoniazid (INH); rifampicin (RMP); amikacin; kanamycin; capreomycin; trimethoprim; itrofurantoin; cefalexin; amoxicillin; metronidazole (MTZ); cefixime; tetracycline; and meropenem. In an example, the antibiotic is selected from Aminoglycosides, Ampicillin, Amoxicillin, Amoxicillin or clavulanic acid, Carbapenems (e.g. imipenem), Piperacillin or tazobactam, Quinolones (e.g. ciprofloxacin), Tetracyclines, Chloramphenicol, Ticarcillin, Trimethoprim or sulfamethoxazole, penicillin, streptomycin, oxytetracycline and potentiated sulfonamides. In an example, the first bacteria are resistant to an antibiotic selected from Aminoglycosides, Ampicillin, Amoxicillin, Amoxicillin or clavulanic acid, Carbapenems (e.g. imipenem), Piperacillin or tazobactam, Quinolones (e.g. ciprofloxacin), Tetracyclines, Chloramphenicol, Ticarcillin, Trimethoprim or sulfamethoxazole, penicillin, streptomycin, oxytetracycline and potentiated sulfonamides. In an alternative, the antibiotic is selected from a beta-lactam, fluoroquinolone and macrolide.

Optionally, the first and second bacteria are bacteria of the same species, but are different strains of the species.

Optionally, the first and second bacteria are bacteria of the same genus, but are bacteria of different species of the genus.

Optionally, the first and second bacteria are bacteria of the same family, but are bacteria of different genera of the family.

Optionally, the first and second bacteria are gram positive bacteria.

Optionally, the first and second bacteria are gram-negative bacteria.

Optionally, the therapy is efficacious in the presence of the second bacteria.

Optionally, reduction in the second bacteria in patients is associated with reduced efficacy of the therapy. Optionally, reduction in the second bacteria in patients reduces efficacy of the therapy.

Optionally, the presence of the second bacteria in patients is associated with enhanced efficacy of the therapy. Optionally, the presence of the second bacteria in patients enhances efficacy of the therapy. For example, enhanced efficiency is efficiency compared to therapy in the absence or a reduced presence of the second bacteria, such as in the presence of an antibiotic that kills the second bacteria.

In an example, the therapy is efficacious in the presence of the second bacteria, wherein the disease or condition (or a symptom thereof) is reduced in the subject by at least 20, 30, 40, 50, 60, 70, 80, 90 or 95%. In an example, the therapy is efficacious in the presence of the second bacteria, wherein the progression of the disease or condition (or a symptom thereof) is reduced in the subject by at least 20, 30, 40, 50, 60, 70, 80, 90 or 95%. In an example, the therapy is efficacious in the presence of the second bacteria, wherein disease-free progression of the disease or condition (or a symptom thereof) is reduced in the subject by at least 20, 30, 40, 50, 60, 70, 80, 90 or 95%. In an example, the therapy is efficacious in the presence of the second bacteria, wherein the duration of the disease or condition (or a symptom thereof) is reduced in the subject by at least 20, 30, 40, 50, 60, 70, 80, 90 or 95%. In an example, the therapy is efficacious in the presence of the second bacteria, wherein the severity of the disease or condition (or a symptom thereof) is reduced in the subject by at least 20, 30, 40, 50, 60, 70, 80, 90 or 95%. In an example, the therapy is efficacious in the presence of the second bacteria, wherein the disease or condition (or a symptom thereof) is reduced for at least 1, 2, 3, 4, 5, 6, 7, 8, 9, 10, 11, 12, 13, 14, 21 or 28 days or for at least 1, 2, 3, 4 5, 6 or 12 months in the patient by at least 20, 30, 40, 50, 60, 70, 80, 90 or 95%. In an example, the therapy is efficacious in the presence of the second bacteria, wherein the disease or condition (or a symptom thereof) is treated for at least 1, 2, 3, 4, 5, 6, 7, 8, 9, 10, 11, 12, 13, 14, 21 or 28 days or for at least 1, 2, 3, 4 5, 6 or 12 months in the patient by at least 20, 30, 40, 50, 60, 70, 80, 90 or 95%. In an example, the therapy is efficacious in the presence of the second bacteria, wherein the disease or condition (or a symptom thereof) is undetectable for at least 1, 2, 3, 4, 5, 6, 7, 8, 9, 10, 11, 12, 13, 14, 21 or 28 days or for at least 1, 2, 3, 4 5, 6 or 12 months in the patient by at least 20, 30, 40, 50, 60, 70, 80, 90 or 95%.

21. The method of Clause 19 or 20, wherein the second bacteria are selected from the group consisting of *Akkermansia, Alistipes, Bacteroides, Barnesiella, Bifidobacterium, Clostridium, Collinsella, Enterococcus, Fusobacterium, Lactobacillus, Propionibacterium, Ruminococcus*, Segmented filamentous bacteria (SFB); *Veillonella, Prevotella, Escherichia* and *Streptococcus* bacteria.

In an example the second bacteria bacteria that produce short chain fatty acids (eg, butyrate-producing bacteria). In particular aspects, the species of bacteria produce butyrate. For example, the second bacteria are Clostridiales. The Clostridiales bacteria may be substantially or include bacteria in spore form. In particular aspects, the second bacteria are of the family Ruminococcaceae, Christensenellaceae, Clostridiaceae or Coriobacteriacease. In some embodiments, the Clostridiales (eg, *Clostridium*) bacteria comprise a first family and a second family. In some embodiments, the first family is selected from the group consisting of Ruminococcaceae, Christensenellaceae, Clostridiaceae and Coriobacteriacease, and the second family is not identical to the first family. In an example, the second bacteria are *Faecalibacterium prausnitzii, Ruminococcus albus, Ruminococcus bromii, Ruminococcus callidus, Ruminococcus flavefaciens, Ruminococcus champanellensis, Ruminococcus faecis, Ruminococcus gauvreauii, Ruminococcus gnavus, Ruminococcus hansenii, Ruminococcus hydrogenotrophicus, Ruminococcus lactaris, Ruminococcus luti, Ruminococcus obeum, Ruminococcus palustris, Ruminococcus pasteurii, Ruminococcus productus, Ruminococcus schinkii, Ruminococcus torques, Subdoligranulum variabile, Butyrivibrio fibrisolvens, Roseburia intestinalis, Anaerostipes caccae, Blautia obeum, Eubacterium nodatum* or *Eubacterium oxidoreducens*. In particular aspects, the second bacteria are *Faecalibacterium prausnitzii*. In an example the second bacteria are Firmicutes.

In certain embodiments, the first bacteria are Bacteroidia or Prevotellaceae, eg, Bacteroidetes or *Bacteroides*.

In an embodiment, the treatment results in or maintains a microbiome (eg, gut and/or blood microbiome) of the subject, which is beneficial for the immne checkpoint inhibitionor other therapy. In an example, the microbiome comprises a high relative abundance of one or more bacterial species from the phylum Firmicutes, class Clostridia, order Clostridiales, family Ruminococcaceae, genus *Ruminococcus*, genus *Hydrogenoanaerobacterium*, genus *Faecalibacterium*, phylum Actinobacteria, class Coriobacteriia, order Coriaobacteriales, family Coriobacteriaceae, domain Archaea, phylum Cyanobacteria, phylum Euryarchaeota or famly Christensenellaceae. Additionally or alternatively, the microbiome comprises a low relative abundance of bacteria from the genus *Dialister*, family Veillonellaceae, phylum Bacteroidetes, class Bacteroida, order Bacteroidales or family Prevotellaceae. Accordingly, a favorable microbial profile would have a higher relative abundance of one or more bacterial species from the phylum Firmicutes, class Clostridia, order Clostridiales, famiy Ruminococcaceae, genus *Ruminococcus*, genus *Hydrogenoanaerobacterium*, phylum Actinobacteria, class Coriobacteria, order Coriaobacteriales, family Coriobacteriaceae, domain Archaea, phylum Cyanobacteria, phylum Euryarchaeota or family Christensenellaceae, and/or has a decreased abundance of one or more bacterial species from genus *Dialister*, family Veillonellaceae, phylum Bacteroidetes, class Bacteroida, order Bacteroidales and/or family Prevotellaceae.

For example, the microbiome comprises a higher relative abundance of Firmicutes compared to Bacteroidetes, Bacteroida, Bacteroidales or Prevotellaceae. For example, the microbiome comprises a higher relative abundance of Firmicutes compared to Bacteroidetes, Bacteroida, Bacteroidales and Prevotellaceae.

Optionally, the second bacteria are selected from the group consisting of *Akkermansia muciniphila; Alistipes shahii; Bacteroides fragilis; Bacteroides uniformis; Barnesiella intestinihominis; Bacteroides dorei; Bifidobacterium adolescentis; Bifidobacterium breve; Bifidobacterium longum; Clostridium orbiscindens; Clostridium novyi; Clostridium perfringens; Collinsella aerofaciens; Enterococcus hirae; Fusobacterium nucleatum; Lactobacillus casei* Shirota; *L. casei* A047; *Lactobacillus rhamnosus; Propionibacterium granulosum; Ruminococcus gnavus*; Segmented filamentous bacteria (SFB); *Veillonella*; Lactobacilli; *Bacteroides*; Clostridia; *Prevotella; E. coli* Nissle; *Lactobacillus plantarum; Lactobacillus delbrueckii* (eg, subsp. *Bulgaricus*); *Lactobacillus paracasei; Lactobacillus acidophilus; Bifidobacterium infantis*; and *Streptococcus salivarius* (eg, subsp. *Thermophilus*). See "The microbiome in cancer immunotherapy: Diagnostic tools and therapeutic strategies"; Laurence Zitvogel et al; Science 23 Mar. 2018: Vol. 359, Issue 6382, pp. 1366-1370; DOI: 10.1126/science.aar6918.

In an example, the second bacteria are commensal bacteria in humans.

In an example, the first bacteria are comprised by gut microbiota, skin microbiota, oral cavity microbiota, throat microbiota, hair microbiota, armpit microbiota, vaginal microbiota, rectal microbiota, anal microbiota, ocular microbiota, nasal microbiota, tongue microbiota, lung microbiota, liver microbiota, kidney microbiota, genital microbiota, penile microbiota, scrotal microbiota, mammary gland microbiota, ear microbiota, urethra microbiota, labial microbiota, organ microbiota or dental microbiota.

In an example, the second bacteria are comprised by gut microbiota, skin microbiota, oral cavity microbiota, throat microbiota, hair microbiota, armpit microbiota, vaginal microbiota, rectal microbiota, anal microbiota, ocular microbiota, nasal microbiota, tongue microbiota, lung microbiota, liver microbiota, kidney microbiota, genital microbiota, penile microbiota, scrotal microbiota, mammary gland microbiota, ear microbiota, urethra microbiota, labial microbiota, organ microbiota or dental microbiota.

In an example, the first and/or second bacteria are blood-borne bacteria.

22. The method of any preceding Clause, wherein the first bacteria are selected from the group consisting *Staphylococcus, Streptococcus, Enterococcus, Helicobacter, Legionella, Heamophilus, Ghonnorhea, Acinetobacter, Escherichia, Klebsiella, Pseudomonas* or *Stenotrophomonas* bacteria.

*H. pylori* has been implicated in gastric cancer and gastric ulcers. Thus, in an example, the first bacteria are *H. pylori* and optionally the disease is a cancer, such as gastric cancer. In an embodiment, the therapy is chemotherapy or therapy with an immune checkpoint inhibitor (eg, an antibody). In an example, the first bacteria are *H. pylori* and the disease is gastric ulcer(s). In an embodiment, triple therapy for gastric ulcers is administered to the subject.

In an example, the first bacteria are Gram-negative bacteria and optionally the infection is a blood infection. In an example, the first bacteria are selected from *E. coli, P. aeruginosa* and *K. pneumoniae*, and optionally the infection is a blood infection.

23. The method of Clause 22, wherein the first bacteria are selected from the group consisting of *E. coli* (eg, EHEC *E. coli*), *C. dificile, V. cholera, Staphylococcus* (eg, *S. aureus* or MRSA), *Streptococcus pyogenes, Helicobacter pylori, Acinetobacter baumannii, Legionella, Pseudomonas aeruginosa* and *Klebsiella pneumoniae* bacteria.

In an example, the subject has been administered an immunosuppressant drug, or is on a course of an immunosuppressant drug, eg, a steroid, such as a corticosteroid.

24. A programmable nuclease for use in the method of any preceding Clause.
25. The method or nuclease of any preceding Clause, wherein the nuclease is a Cas nuclease (eg, a Cas 3 or 9), a meganuclease, a TALEN (Transcription activator-like effector nuclease) or zinc finger nuclease.
26. A CRISPR/Cas system comprising a nuclease according to Clause 24 or 25 for use in the method of any one of Clauses 1 to 23, wherein the nuclease is a Cas nuclease (eg, a Cas 3 or 9) and the system comprises one or more guide RNAs (gRNAs) or DNA encoding one or more guide RNAs, wherein each guide RNA is capable of programming the Cas nuclease to cut a target site comprised by the genomes of first bacteria.
27. A guide RNA or a DNA encoding a guide RNA for use in the system of Clause 26.
28. A guide RNA or a DNA encoding a guide RNA for use in the method of treating a pathogenic bacterial infection according to any one of Clauses 1 to 23, wherein the guide RNA is capable of programming the nuclease, wherein the nuclease is a Cas nuclease (eg, a Cas9, Cas3, Cas13, CasX, CasY or Cpf1 nuclease).
29. A nucleic acid vector comprising the guide RNA or DNA recited in any one of Clauses 26 to 28.
30. A nucleic acid vector encoding the nuclease of Clause 24 or 25 and optionally the guide RNA of Clause 29.
31. The vector of Clause 29 or 30 wherein the vector is a phage, phagemid plasmid (eg, conjugative plasmid) or transposon.

The phage are capable of infecting first bacteria and the phagemids are capable of producing such phage in the presence of a helper phage.

32. A pharmaceutical composition comprising a first nucleic acid vector (or a plurality thereof) encoding the nuclease of Clause 24 or 25 and a second nucleic acid vector (or a plurality thereof) encoding the guide RNA of Clause 29, the composition further comprising a pharmaceutically acceptable diluent, excipient or carrier.
33. A pharmaceutical composition comprising the CRISPR/Cas system of claim 26 and a pharmaceutically acceptable diluent, excipient or carrier.
34. A pharmaceutical composition comprising the vector of claim 31 and a pharmaceutically acceptable diluent, excipient or carrier.

Preventing a disease or condition herein may, for example, be reducing the risk of the disease or condition in the subject or patient.

In an alternative, instead of first bacteria, the infection is caused by first archaea and in this embodiment all of the features of the method and other configurations of the invention relating to killing first bacteria instead relate mutatis mutandis to killing first archaea.

In an embodiment, the method comprises carrying out the method of treating an acute microbial infection as described herein, and thus features of that method as described herein are combinable with the present method of treating a pathogenic bacterial infection (ie, where the pathogenic bacterial infection is the acute microbial infection in the first method). In an embodiment, the method comprises carrying out the method of durably treating a microbial infection as described herein, and thus features of that method as described herein are combinable with the present method of treating a pathogenic bacterial infection (ie, where the pathogenic bacterial infection is the microbial infection in the first method). Any of the optional features of the first method herein may apply mutatis mutandis to the present method of treating a pathogenic bacterial infection.

Aspects:—

Thus, the invention provides the following Aspects, which are optional features of Clauses above:—

1. The method of any one of Clauses 1-23, wherein the infection is reduced at least 100-fold by the first 30 minutes of carrying out step (b). Optionally, the infection is reduced at least 1000-fold by the first 30 minutes of carrying out step (b). Optionally, the reduction in infection persists for 30 minutes immediately after the first 30 minutes of carrying out step (b). For example, the reduction can be assessed by determining the difference in the number of bacteria of the first species or strain in (i) a sample taken from the subject (eg, a blood sample) immediately before commencement of the method and (ii) a sample (of the same type as the sample of (i), eg, a blood sample) taken from the subject at 30 minutes of the treatment. For example, the samples may be assessed for the difference in colony forming units (CFU)/ml sample, eg, when the samples have been plated on agar in respective petri dishes and incubated under identical conditions. Another example may use microscopic counting of bacteria in samples, or other routine methods know to the skilled addressee.
2. The method of any one of Clauses 1-23, wherein blood infection of the subject by the first bacteria is reduced at least 100- or 1000-fold by the first 30 minutes of carrying out step (b).
3. The method of Aspect 2, wherein the blood is infected with from $10^5$ to $10^{12}$ (eg, $10^7$ to $10^{12}$) CFU/ml of the first bacteria immediately before the treatment.
4. The method of any one of Clauses 1-23 or any preceding Aspect, wherein the method comprises administering to the subject a nucleic acid (eg, a RNA) and nuclease, wherein the nucleic acid complexes with the nuclease to program the nuclease to cut the target site in the first bacteria comprised by the subject.
5. The method of Aspect 4, wherein the nuclease is administered simultaneously or sequentially with the nucleic acid to the subject.
6. The method of Aspect 4, wherein the subject comprises the nuclease prior to administration of the nucleic acid to the subject.
7. The method of any one of Aspects 4 to 6, wherein a plurality phage are administered to the subject, wherein each phage comprises a copy of the nucleic acid, wherein the phage infect first bacteria comprised by the subject to deliver thereto the nucleic acid.
8. The method of Aspect 7, wherein the ratio of administered phage:first bacteria comprised by the subject is from 10 to 150. For example, the ratio is from 10 to 100, ie, a multiplicity of infection (MOI) of from 10 to 100.

The ratio can be determined, for example, using a sample (eg, a blood or gut sample) from a human or animal subject immediately before the treatment and determining the number of bacteria per ml of blood or gut sample. The amount of phage to be administered can then be worked out according to the determination using the sample.

9. The method of any one of Clauses 1-23 or any preceding Aspect, wherein the infection is an infection of the lungs, brain, skin, abdomen or urinary tract.
10. The method of any one of Clauses 1-23 or any preceding Aspect, wherein the subject has undergone surgery, is on an immunosuppressant medication, suffering from burns, suffering from diabetes, suffering from cancer or is suffering from a chronic disease.
11. The method of any one of Clauses 1-23 or any preceding Aspect, wherein the subject is a human over 65 years of age or is a paediatric patient.
12. The method of any one of Clauses 1-23 or any preceding Aspect, wherein the method treats or prevents sepsis in the subject.
13. The method of Clause 12, wherein at the start of the treatment, the subject (eg, a human) has a temperature of <36° C. or >38° C.; a heart rate of >90/min, a respiratory rate of >20 breaths/min or $PaCO_2$<4.3 kPa; and white blood cell count of <4000/mm$^3$ or >12,000/mm$^3$.
14. The method of Clause 12 or 13, wherein at the start of the treatment, the subject (eg, a human) has presence of two or more of the following: abnormal body temperature, abnormal heart rate, abnormal respiratory rate, abnormal blood gas and abnormal white blood cell count.

Immune Checkpoint Modulation

Immune checkpoints of the invention either turn up a signal (e.g., co-stimulatory molecules) or turn down a signal. Inhibitory immune checkpoint molecules that may be targeted by immune checkpoint modulation in the invention include adenosine A2A receptor (AZAR), B7-H3 (also known as CD276), B and T lymphocyte attenuator (BTLA), cytotoxic T-lymphocyte-associated protein 4 (CTLA-4, also known as CD 152), indoleamine 2,3-dioxygenase (IDO), killer-cell immunoglobulin (KIR), lymphocyte activation gene-3 (LAG3), programmed death 1 (PD-1), T-cell immunoglobulin domain and mucin domain 3 (TIM-3) and V-domain Ig suppressor of T cell activation (VISTA). In particular, the immune checkpoint inhibitors target the PD-1 axis and/or CTLA-4.

The immune checkpoint inhibitors may be drugs such as small molecules, recombinant forms of ligand or receptors, or, antibodies, such as human antibodies (e.g., WO2015016718; Pardoll, Nat Rev Cancer, 12(4): 252-64, 2012; both incorporated herein by reference). Known inhibitors of the immune checkpoint proteins or analogs thereof may be used, in particular chimerised, humanised or human forms of antibodies may be used. As the skilled person will know, alternative and/or equivalent names may be in use for certain antibodies mentioned in the present disclosure. Such alternative and/or equivalent names are interchangeable in the context of the present invention. For example it is known that lambrolizumab is also known under the alternative and equivalent names MK-3475 and pembrolizumab.

It is contemplated that any of the immune checkpoint inhibitors that are known in the art to stimulate immune responses may be used. This includes inhibitors that directly or indirectly stimulate or enhance antigen-specific T-lymphocytes. These immune checkpoint inhibitors include, without limitation, agents targeting immune checkpoint proteins and pathways involving PD-L2, LAG3, BTLA, B7H4 and TIM3. For example, LAG3 inhibitors known in the art include soluble LAG3 (IMP321, or LAG3-Ig disclosed in WO2009044273) as well as mouse or humanized antibodies blocking human LAG3 (e.g., IMP701 disclosed in WO2008132601), or fully human antibodies blocking human LAG3 (such as disclosed in EP 2320940). Another example is provided by the use of blocking agents towards BTLA, including without limitation antibodies blocking human BTLA interaction with its ligand (such as 4C7 disclosed in WO2011014438). Yet another example is provided by the use of agents neutralizing B7H4 including without limitation antibodies to human B7H4 (disclosed in WO 2013025779, and in WO2013067492) or soluble recombinant forms of B7H4 (such as disclosed in US20120177645). Yet another example is provided by agents neutralizing B7-H3, including without limitation antibodies neutralizing human B7-H3 (e.g. MGA271 disclosed as BRCA84D and derivatives in US 20120294796). Yet another example is provided by agents targeting TIM3, including without limitation antibodies targeting human TIM3 (e.g. as disclosed in WO 2013006490 A2 or the anti-human TIM3, blocking antibody F38-2E2 disclosed by Jones et ah, J Exp Med. 2008; 205(12):2763-79).

A. PD-1 Axis Antagonists

T cell dysfunction or anergy occurs concurrently with an induced and sustained expression of the inhibitory receptor, programmed death 1 polypeptide (PD-1). Thus, therapeutic targeting of PD-1 and other molecules which signal through interactions with PD-1, such as programmed death ligand 1 (PD-L1) and programmed death ligand 2 (PD-L2) is provided herein. PD-L1 is overexpressed in many cancers and is often associated with poor prognosis (Okazaki T et ah, Intern. Immun 2007 19(7):813). Thus, improved methods of treating cancer by inhibiting the PD-L1/PD-1 interaction in combination with modulating the microbiome is provided herein.

For example, PD-1 axis binding antagonists include a PD-1 binding antagonist, a PD-L1 binding antagonist and a PD-L2 binding antagonist. Alternative names for "PD-1" include CD279 and SLEB2. Alternative names for "PD-L1" include B7-H1, B7-4, CD274, and B7-H. Alternative names for "PD-L2" include B7-DC, Btdc, and CD273. In some embodiments, PD-1, PD-L1, and PD-L2 are human PD-1, PD-L1 and PD-L2.

In some embodiments, the PD-1 binding antagonist is a molecule that inhibits the binding of PD-1 to its ligand binding partners. In a specific aspect, the PD-1 ligand binding partners are PD-L1 and/or PD-L2. In another embodiment, a PD-L1 binding antagonist is a molecule that inhibits the binding of PD-L1 to its binding partners. In a specific aspect, PD-L1 binding partners are PD-1 and/or B7-1. In another embodiment, the PD-L2 binding antagonist is a molecule that inhibits the binding of PD-L2 to its binding partners. In a specific aspect, a PD-L2 binding partner is PD-1. The antagonist may be an antibody, an antigen binding fragment thereof, an immunoadhesin, a fusion protein, or oligopeptide. Exemplary antibodies are described in U.S. Pat. Nos. 8,735,553, 8,354,509, and 8,008, 449, all incorporated herein by reference. Other PD-1 axis antagonists for use in the methods provided herein are known in the art such as described in U.S. Patent Application No. US20140294898, US2014022021, and US20110008369, all incorporated herein by reference.

In some embodiments, the PD-1 binding antagonist is an anti-PD-1 antibody {e.g., a human antibody, a humanized antibody, or a chimeric antibody). In some embodiments, the anti-PD-1 antibody is selected from the group consisting of nivolumab, pembrolizumab, and CT-011. In some embodiments, the PD-1 binding antagonist is an immunoadhesin (e.g., an immunoadhesin comprising an extracellular or PD-1 binding portion of PDL1 or PD-L2 fused to a constant region (e.g., an Fc region of an immunoglobulin sequence). In some embodiments, the PD-1 binding antagonist is AMP-224. Nivolumab, also known as MDX-1106-04, MDX-1106, ONO-4538, BMS-936558, and OPDIVO®, is an anti-PD-1 antibody described in WO2006/121168. Pembrolizumab, also known as MK-3475, Merck 3475, lambrolizumab, KEYTRUDA®, and SCH-900475, is an anti-PD-1 antibody described in WO2009/114335. CT-011, also known as hBAT or hBAT-1, is an anti-PD-1 antibody described in WO2009/101611. AMP-224, also known as B7-DCIg, is a PD-L2-Fc fusion soluble receptor described in WO2010/027827 and WO2011/066342. Additional PD-1 binding antagonists include pidilizumab, also known as CT-011, MEDI0680, also known as AMP-514, and REGN2810.

In some embodiments, the immune checkpoint inhibitor is a PD-L1 antagonist such as durvalumab, also known as MEDI4736, atezolizumab, also known as MPDL3280A, or avelumab, also known as MSB00010118C. In certain aspects, the immune checkpoint inhibitor is a PD-L2 antagonist such as rHIgM12B7. In some aspects, the immune checkpoint inhibitor is a LAG-3 antagonist such as, but not limited to, IMP321, and BMS-986016. The immune checkpoint inhibitor may be an adenosine Ata receptor (A2aR) antagonist such as PBF-509.

In some embodiments, any antibody described herein (such as an anti-PD-1 antibody, an anti-PD-L1 antibody, or an anti-PD-L2 antibody) further comprises a human or murine constant region. In a still further aspect, the human constant region is selected from the group consisting of IgG1, IgG2, IgG2, IgG3, and IgG4. In a still further specific aspect, the human constant region is IgG1. In a still further aspect, the murine constant region is selected from the group consisting of IgG1, IgG2A, IgG2B, and IgG3. In a still further specific aspect, the antibody has reduced or minimal effector function. In a still further specific aspect, the minimal effector function results from production in prokaryotic cells. In a still further specific aspect the minimal effector function results from an "effector-less Fc mutation" or aglycosylation. Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxy amino acid, most commonly serine or threonine, although 5-hydroxyproline or 5-hydroxy lysine may also be used. Removal of glycosylation sites form an antibody is conveniently accomplished by altering the amino acid sequence such that one of the above-described tripeptide sequences (for N-linked glycosylation sites) is removed. The alteration may be made by substitution of an asparagine, serine or threonine residue within the glycosylation site another amino acid residue (e.g., glycine, alanine or a conservative substitution).

The antibody or antigen binding fragment thereof, may be made using methods known in the art, for example, by a process comprising culturing a host cell containing nucleic acid encoding any of the previously described anti-PD-L1, anti-PD-1, or anti-PD-L2 antibodies or antigen-binding fragment in a form suitable for expression, under conditions suitable to produce such antibody or fragment, and recovering the antibody or fragment.

B. CTLA-4

Another immune checkpoint that can be targeted in the methods provided herein is the cytotoxic T-lymphocyte-associated protein 4 (CTLA-4), also known as CD152. The complete cDNA sequence of human CTLA-4 has the Genbank accession number L15006. CTLA-4 is found on the surface of T cells and acts as an "off switch when bound to CD80 or CD86 on the surface of antigen-presenting cells. CTLA4 is a member of the immunoglobulin superfamily that is expressed on the surface of Helper T cells and transmits an inhibitory signal to T cells. CTLA4 is similar to the T-cell co-stimulatory protein, CD28, and both molecules bind to CD80 and CD86, also called B7-1 and B7-2 respectively, on antigen-presenting cells. CTLA4 transmits an inhibitory signal to T cells, whereas CD28 transmits a stimulatory signal. Intracellular CTLA4 is also found in regulatory T cells and may be important to their function. T cell activation through the T cell receptor and CD28 leads to increased expression of CTLA-4, an inhibitory receptor for B7 molecules.

In some embodiments, the immune checkpoint inhibitor is an anti-CTLA-4 antibody (e.g., a human antibody, a humanized antibody, or a chimeric antibody), an antigen binding fragment thereof, an immunoadhesin, a fusion protein, or oligopeptide.

Anti-human-CTLA-4 antibodies (or VH and/or VL domains derived therefrom) suitable for use in the present methods can be generated using methods well known in the art. Alternatively, art recognized anti-CTLA-4 antibodies can be used. For example, the anti-CTLA-4 antibodies disclosed in: U.S. Pat. No. 8,119,129, WO 01/14424, WO 98/42752; WO 00/37504 (CP675,206, also known as tremelimumab; formerly ticilimumab), U.S. Pat. No. 6,207,156; Hurwitz et al, 1998; can be used in the methods disclosed herein. The teachings of each of the aforementioned publications are hereby incorporated by reference. Antibodies that compete with any of these art-recognized antibodies for binding to CTLA-4 also can be used. For example, a humanized CTLA-4 antibody is described in International Patent Application No. WO2001014424, WO2000037504, and U.S. Pat. No. 8,017,114; all incorporated herein by reference.

An exemplary anti-CTLA-4 antibody is ipilimumab (also known as 10D1, MDX-010, MDX-101, and Yervoy®) or antigen binding fragments and variants thereof (see, e.g., WO01/14424). In other embodiments, the antibody comprises the heavy and light chain CDRs or VRs of ipilimumab. Accordingly, in one embodiment, the antibody comprises the CDR1, CDR2, and CDR3 domains of the VH region of ipilimumab, and the CDR1, CDR2 and CDR3 domains of the VL region of ipilimumab. In another embodiment, the antibody competes for binding with and/or binds to the same epitope on CTLA-4 as the above-mentioned antibodies. In another embodiment, the antibody has at least about 90% variable region amino acid sequence identity with the above-mentioned antibodies (e.g., at least about 90%, 95%, or 99% variable region identity with ipilimumab).

Other molecules for modulating CTLA-4 include soluble CTLA-4 ligands and receptors such as described in U.S. Pat. Nos. 5,844,905, 5,885,796 and International Patent Application Nos. WO1995001994 and WO1998042752; all incorporated herein by reference, and immunoadhesins such as described in U.S. Pat. No. 8,329,867, incorporated herein by reference.

C. Killer Immunoglobulin-Like Receptor (KIR)

Another immune checkpoint inhibitor for use in the present invention is an anti-KIR antibody. Anti-human-KIR antibodies (or VH/VL domains derived therefrom) suitable for use in the present methods can be generated using methods well known in the art.

Alternatively, art recognized anti-KIR antibodies can be used. The anti-KIR antibody can be cross-reactive with multiple inhibitory KIR receptors and potentiates the cytotoxicity of NK cells bearing one or more of these receptors. For example, the anti-KIR antibody may bind to each of KIR2D2DL1, KIR2DL2, and KIR2DL3, and potentiate NK cell activity by reducing, neutralizing and/or reversing inhibition of NK cell cytotoxicity mediated by any or all of these KIRs. In some aspects, the anti-KIR antibody does not bind KIR2DS4 and/or KIR2DS3. For example, monoclonal antibodies 1-7F9 (also known as IPH2101), 14F1, 1-6F1 and 1-6F5, described in WO 2006/003179, the teachings of which are hereby incorporated by reference, can be used. Antibodies that compete with any of these art-recognized antibodies for binding to KIR also can be used. Additional art-recognized anti-KIR antibodies which can be used include, for example, those disclosed in WO 2005/003168, WO 2005/009465, WO 2006/072625, WO 2006/072626, WO 2007/042573, WO 2008/084106, WO 2010/065939, WO 2012/071411 and WO 2012/160448.

An exemplary anti-KIR antibody is lirilumab (also referred to as BMS-986015 or IPH2102). In other embodiments, the anti-KIR antibody comprises the heavy and light chain complementarity determining regions (CDRs) or variable regions (VRs) of lirilumab. Accordingly, in one embodiment, the antibody comprises the CDR1, CDR2, and CDR3 domains of the heavy chain variable (VH) region of lirilumab, and the CDR1, CDR2 and CDR3 domains of the light chain variable (VL) region of lirilumab. In another embodiment, the antibody has at least about 90% variable region amino acid sequence identity with lirilumab.

Examples of cancers contemplated for treatment include lung cancer, head and neck cancer, breast cancer, pancreatic cancer, prostate cancer, renal cancer, bone cancer, testicular cancer, cervical cancer, gastrointestinal cancer, lymphomas, pre-neoplastic lesions in the lung, colon cancer, melanoma, metastatic melanoma, basal-cell skin cancer, squamous-cell skin cancer, dermatofibrosarcoma protuberans, Merkel cell carcinoma, Kaposi's sarcoma, keratoacanthoma, spindle cell tumours, sebaceous carcinomas, microcystic adnexal carcinoma, Paget's disease of the breast, atypical fibroxanthoma, leiomyosarcoma, and angiosarcoma, Lentigo Maligna, Lentigo Maligna Melanoma, Superficial Spreading Melanoma, Nodular Melanoma, Acral Lentiginous Melanoma, Desmoplastic Melanoma, and bladder cancer.

In some embodiments, the subject has cancer that is resistant (has been demonstrated to be resistant) to one or more anti-cancer therapies. In some embodiments, resistance to anti-cancer therapy includes recurrence of cancer or refractory cancer. Recurrence may refer to the reappearance of cancer, in the original site or a new site, after treatment. In some embodiments, resistance to anti-cancer therapy includes progression of the cancer during treatment with the anti-cancer therapy. In some embodiments, the cancer is at early stage or at late stage. The subject may have a cancer that expresses (has been shown to express e.g., in a diagnostic test) PD-L1 biomarker. In some embodiments, the patient's cancer expresses low PD-L1 biomarker. In some embodiments, the patient's cancer expresses high PD-L1 biomarker. The PD-L1 biomarker can be detected in the sample using a method selected from the group consisting of FACS, Western blot, ELISA, immunoprecipitation, immunohistochemistry, immunofluorescence, radioimmunoassay, dot blotting, immunodetection methods, HPLC, surface plasmon resonance, optical spectroscopy, mass spectrometery, HPLC, qPCR, RT-qPCR, multiplex qPCR or RT-qPCR, RNA-seq, microarray analysis, SAGE, MassARRAY technique, and FISH, and combinations thereof.

In some embodiments, the cancer has low levels of T cell infiltration. In some embodiments, the cancer has no detectable T cell infiltrate. In some embodiments, the cancer is a non-immunogenic cancer (e.g., non-immunogenic colorectal cancer and/or ovarian cancer).

For example, a therapeutically effective or sufficient amount of the immune checkpoint inhibitor, such as an antibody, is administered to a human will be in the range of about 0.01 to about 50 mg/kg of patient body weight whether by one or more administrations. In some embodiments, the antibody used is about 0.01 to about 45 mg/kg, about 0.01 to about 40 mg/kg, about 0.01 to about 35 mg/kg, about 0.01 to about 30 mg/kg, about 0.01 to about 25 mg/kg, about 0.01 to about 20 mg/kg, about 0.01 to about 15 mg/kg, about 0.01 to about 10 mg/kg, about 0.01 to about 5 mg/kg, or about 0.01 to about 1 mg/kg administered daily, for example. In some embodiments, the antibody is administered at 15 mg/kg. However, other dosage regimens may be useful. In one embodiment, an anti-PD-L1 antibody described herein is administered to a human at a dose of about 100 mg, about 200 mg, about 300 mg, about 400 mg, about 500 mg, about 600 mg, about 700 mg, about 800 mg, about 900 mg, about 1000 mg, about 1100 mg, about 1200 mg, about 1300 mg or about 1400 mg on day 1 of 21-day cycles. The dose may be administered as a single dose or as multiple doses (e.g., 2 or 3 doses), such as infusions. The progress of this therapy is easily monitored by conventional techniques.

Anti-Cancer and Other Therapies

In some embodiments, the immune checkpoint inhibitor may be administered in combination with at least one additional therapeutic. The additional therapy may be a cancer therapy such as radiation therapy, surgery, chemotherapy, gene therapy, DNA therapy, viral therapy, RNA therapy, immunotherapy, bone marrow transplantation, nanotherapy, monoclonal antibody therapy, or a combination of the foregoing. The additional therapy may be in the form of adjuvant or neoadjuvant therapy.

In an example, the therapy of the cancer (whether with or without administration of an immune checkpoint inhibitor) or any other disease (eg, viral infection or autoimmune disease) may radiation therapy, surgery, chemotherapy, gene therapy, DNA therapy, viral therapy, RNA therapy, immunotherapy, bone marrow transplantation, nanotherapy or monoclonal antibody therapy. The therapy may be a combination of the foregoing. An additional therapy may be administered In some embodiments, the therapy (or the additional cancer therapy) is the administration of a small molecule enzymatic inhibitor or anti-metastatic agent. In some embodiments, the additional therapy is the administration of side-effect limiting agents (e.g., agents intended to lessen the occurrence and/or severity of side effects of treatment, such as anti-nausea agents, etc.).

In some embodiments, the therapy (or the additional cancer therapy) is radiation therapy. In some embodiments, the therapy (or the additional cancer therapy) is surgery. In some embodiments, the therapy (or the additional cancer therapy) is a combination of radiation therapy and surgery. In some embodiments, the therapy (or the additional cancer therapy) is gamma irradiation. In some embodiments, the therapy (or the additional cancer therapy) is therapy targeting PBK/AKT/mTOR pathway, HSP90 inhibitor, tubulin inhibitor, apoptosis inhibitor, and/or chemopreventative agent. The therapy (or the additional cancer therapy) may be one or more of the chemotherapeutic agents known in the art.

Administration of any compound or therapy of the present embodiments to a patient will follow general protocols for the administration of such compounds, taking into account the toxicity, if any, of the agents. Therefore, in some embodiments there is a step of monitoring toxicity that is attributable to combination therapy.

The therapy can comprise or consist of administration to the subject of any of the following:—

1. Chemotherapy

A wide variety of chemotherapeutic agents may be used in accordance with the present embodiments. The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis.

Examples of chemotherapeutic agents include alkylating agents, such as thiotepa and cyclosphosphamide; alkyl sulfonates, such as busulfan, improsulfan, and piposulfan; aziridines, such as benzodopa, carboquone, meturedopa, and uredopa; ethylenimines and methylamelamines, including altretamine, triethylenemelamine, trietylenephosphoramide, triethiylenethiophosphoramide, and trimethylolomelamine; acetogenins (especially bullatacin and bullatacinone); a camptothecin (including the synthetic analogue topotecan); bryostatin; callystatin; CC-1065 (eg, its adozelesin, carzelesin and bizelesin synthetic analogues); cryptophycins (particularly cryptophycin 1 and cryptophycin 8); dolastatin; duocarmycin (eg, the synthetic analogues, KW-2189 and CB 1-TM1); eleutherobin; pancratistatin; a sarcodictyin; spongistatin; nitrogen mustards, such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, and uracil mustard; nitrosureas, such as carmustine, chlorozotocin, fotemustine, lomustine, nimustine, and ranimnustine; antibiotics, such as the enediyne antibiotics (e.g., calicheamicin, especially calicheamicin gammall and calicheamicin omegall); dynemicin, including dynemicin A; bisphosphonates, such as clodronate; an esperamicin; as well as neocarzinostatin chromophore and related chromoprotein enediyne antiobiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (eg, morpholino-doxorubicin, cyanomorpholino-doxorubicin, 2-pyrrolino-doxorubicin and deoxydoxorubicin), epirubicin, esorubicin, idarubicin, marcellomycin, mitomycins, such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, and zorubicin; anti-metabolites, such as methotrexate and 5-fluorouracil (5-FU); folic acid analogues, such as denopterin, pteropterin, and trimetrexate; purine analogs, such as fludarabine, 6-mercaptopurine, thiamiprine, and thioguanine; pyrimidine analogs, such as ancitabine, azacitidine, 6-azauridine, carmofur, cytarabine, dideoxyuridine, doxifluridine, enocitabine, and floxuridine; androgens, such as calusterone, dromostanolone propionate, epitiostanol, mepitiostane, and testolactone; anti-adrenals, such as mitotane and trilostane; folic acid replenisher, such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids, such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSKpolysaccharide complex; razoxane; rhizoxin; sizofiran; spirogermanium; tenuazonic acid; triaziquone; 2,2',2"-trichlorotriethylamine; trichothecenes (eg, T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; taxoids, e.g., paclitaxel and docetaxel gemcitabine; 6-thioguanine; mercaptopurine; platinum coordination complexes, such as cisplatin, oxaliplatin, and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DMFO); retinoids, such as retinoic acid; capecitabine; carboplatin, procarbazine, plicomycin, gemcitabien, navelbine, farnesyl-protein tansferase inhibitors, transplatinum, and pharmaceutically acceptable salts, acids, or derivatives of any of the above^

2. Radiotherapy

Other factors that cause DNA damage and have been used extensively include what are commonly known as γ-rays, X-rays, and/or the directed delivery of radioisotopes to tumour cells. Other forms of DNA damaging factors are also contemplated, such as microwaves, proton beam irradiation (U.S. Pat. Nos. 5,760,395 and 4,870,287), and UV-irradiation. It is most likely that all of these factors affect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 weeks), to single doses of 2000 to 6000 roentgens. Dosage ranges for radioisotopes vary widely, and depend on the half-life of the isotope, the strength and type of radiation emitted, and the uptake by the neoplastic cells.

3. Immunotherapy

The skilled artisan will understand that immunotherapies may be used in combination or in conjunction with the methods described herein. In the context of cancer treatment, immunotherapeutics generally rely on the use of immune effector cells and molecules to target and destroy cancer cells. Rituximab (RITUXAN®) is an example of an immunotherapy. The immune effector may be, for example, an antibody specific for a marker on the surface of a tumour cell. The antibody alone may serve as an effector of therapy or it may recruit other cells to actually effect cell killing. The antibody also may be conjugated to a drug or toxin (chemo therapeutic, radionuclide, ricin A chain, cholera toxin, pertussis toxin, etc.) and serve as a targeting agent. Alternatively, the effector may be a lymphocyte carrying a surface molecule that interacts, either directly or indirectly, with a tumour cell target. Various effector cells include cytotoxic T cells and NK cells.

In an example, the immunotherapy comprises adoptive cell therapy, such as CAR-T administration, eg, anti-CD19 or CD20 CAR-T administration.

In an example, the immunotherapy comprises or consists of administration of an IL-2 (eg, a truncated IL-2 or pegylated IL-2 or Fc-fused IL-2).

Antibody-drug conjugates have emerged as a breakthrough approach to the development of cancer therapeutics. Antibody-drug conjugates (ADCs) comprise monoclonal antibodies (MAbs) that are covalently linked to cell-killing drugs. This approach combines the high specificity of MAbs against their antigen targets with highly potent cytotoxic drugs, resulting in "armed" MAbs that deliver the payload (drug) to tumour cells with enriched levels of the antigen. Targeted delivery of the drug also minimizes its exposure in normal tissues, resulting in decreased toxicity and improved therapeutic index. The approval of two ADC drugs, ADCETRIS® (brentuximab vedotin) in 2011 and KADCYLA® (trastuzumab emtansine or T-DM1) in 2013 by FDA validated the approach. There are currently more than 30 ADC drug candidates in various stages of clinical trials for cancer treatment. As antibody engineering and linker-payload optimization are becoming more and more mature, the discovery and development of new ADCs are increasingly dependent on the identification and validation of new targets that are suitable to this approach and the generation of targeting MAbs. Two criteria for ADC targets are upregulated/high levels of expression in tumour cells and robust internalization.

In one aspect of immunotherapy, the tumour cell must bear some marker that is amenable to targeting, i.e., is not present on the majority of other cells. Many tumour markers exist and any of these may be suitable for targeting in the context of the present embodiments. Common tumour markers include CD20, carcinoembryonic antigen, tyrosinase (p97), gp68, TAG-72, HMFG, Sialyl Lewis Antigen, MucA, MucB, PLAP, laminin receptor, erb B, and pi 55. An alternative aspect of immunotherapy is to combine anticancer effects with immune stimulatory effects. Immune stimulating molecules also exist including: cytokines, such as IL-2, IL-4, IL-12, GM-CSF, gamma-IFN, chemokines, such as MIP-1, MCP-1, IL-8, and growth factors, such as FLT3 ligand.

4. Surgery

The cancer or other disease or condition may be treated by surgery in the invention.

Approximately 60% of persons with cancer will undergo surgery of some type, which includes preventative, diagnostic or staging, curative, and palliative surgery. Curative surgery includes resection in which all or part of cancerous tissue is physically removed, excised, and/or destroyed and may be used in conjunction with other therapies, such as the treatment of the present embodiments, chemotherapy, radiotherapy, hormonal therapy, gene therapy, immunotherapy, and/or alternative therapies. Tumour resection refers to physical removal of at least part of a tumour. In addition to tumour resection, treatment by surgery includes laser surgery, cryosurgery, electro surgery, and microscopically-controlled surgery (Mohs' surgery).

Upon excision of part or all of cancerous cells, tissue, or tumour, a cavity may be formed in the body. Treatment may be accomplished by perfusion, direct injection, or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

5. Bacterial Transplants

In an embodiment, the therapy comprises administering to the subject a bacterial transplant, eg, a faecal microbial transplant, comprising defined bacteria. For example, the transplant is any composition disclosed in WO2018064165, the disclosure of which (especially the compositions therein) are incorporated herein by reference in its entirety for possible application in the present invention. For example, the transplant is according to any of the following Paragraphs (tables nd sequence numbers referring to the tables and sequences in WO2018064165, which are explicitly incorporated herein for possible use in the Claims):—

1. A composition comprising at least one isolated or purified population of bacteria belonging to one or more of the families Ruminococcaceae, Clostridiaceae, Lachnospiraceae, Micrococcaceae, and/or Veilonellaceae.
2. A composition comprising at least two isolated or purified populations of bacteria belonging to one or more of the families Ruminococcaceae, Clostridiaceae, Lachnospiraceae, Micrococcaceae, and/or Veilonellaceae.
3. The composition of Paragraph 1 or Paragraph 2, wherein each of the populations of bacteria is present in the composition at a concentration of at least 10^3 CFU.
4. The composition of Paragraph 1 or Paragraph 2, wherein the composition is a live bacterial product or a live biotherapeutic product.
5. The composition of Paragraph 1 or Paragraph 2, wherein the at least one isolated or purified population bacteria or the at least two isolated or purified populations of bacteria are provided as bacterial spores.
6. The composition of Paragraph 1 or Paragraph 2, wherein the at least one population of bacteria or the at least two isolated or purified populations of bacteria belong to Clostridiales Family XII and/or Clostridiales Family XIII.
7. The composition of Paragraph 1 or Paragraph 2, wherein the at least one isolated or purified population bacteria or the at least two isolated or purified populations of bacteria belong to the family Ruminococcaceae and/or of the family Clostridiaceae.
8. The composition of Paragraph 1 or Paragraph 2, wherein the population of bacteria belonging to the family Ruminococcaceae is further defined as a population of bacteria belonging to the genus *Ruminococcus*.
9. The composition of Paragraph 8, wherein the population of bacteria belonging to the genus *Ruminococcus* is further defined as a population of bacteria belonging to the species *Ruminococcus bromii*.
10. The composition of Paragraph 1 or Paragraph 2, wherein the population of bacteria belonging to the family Ruminococcaceae is further defined as a population of bacteria belonging to the genus *Faecalibacterium*.
11. The composition of Paragraph 10, wherein the population of bacteria belonging to the genus *Faecalibacterium* is further defined as a population of bacteria belonging to the species *Faecalibacterium prausnitzii*.
12. The composition of Paragraph 1 or Paragraph 2, wherein the population of bacteria belonging to the family Micrococcaceae is further defined as a population of bacteria belonging to the genus *Rothia*.
13. The composition of Paragraph 1 or Paragraph 2, wherein the composition further comprises a population of bacteria belonging to the species *Porphyromonas pasteri*, the species *Clostridium hungatei*, the species *Phascolarctobacterium faecium*, the genus *Peptoniphilus*, and/or the class Mollicutes.
14. The composition of Paragraph 1 or Paragraph 2, wherein the composition is essentially free of populations of bacteria belonging to the order Bacteroidales.
15. The composition of Paragraph 1 or Paragraph 2, wherein the at least one isolated or purified population bacteria or the at least two isolated or purified populations of bacteria belongs to one or more of the species, subspecies or bacterial strains selected from the group consisting of the species in Table 1 with an enrichment index (ei) greater than 0.5.
16. The composition of Paragraph 1 or Paragraph 2, wherein the at least one isolated or purified population bacteria or the at least two isolated or purified populations of bacteria are selected from the group consisting of the species in Table 1 with an "ei" equal to 1.
17. The composition of Paragraph 1 or Paragraph 2, wherein the at least one isolated or purified population bacteria or the at least two isolated or purified populations of bacteria comprise a 16S ribosomal RNA (rRNA) nucleotide sequence that is at least 90% identical (eg, at least 91, 92, 93, 94, 95, 96, 97, 98 or 99% identical) to the 16S rRNA nucleotide sequence of bacteria identified by NCBI Taxonomy IDs selected from the group consisting of NCBI Taxonomy ID: 717959, 587, 758823, 649756, 44749, 671218, 1264, 1122135, 853, 484018, 46503, 54565, 290052, 216931, 575978, 433321, 1796646, 213810, 228924, 290054, 1509, 1462919, 29375, 337097, 1298596, 487174, 642492, 1735, 1297424, 742766, 46680, 132925, 411467, 1318465, 1852367, 1841857, 169679, 1175296, 259063, 172901, 39488, 57172, 28118, 166486, 28133, 1529, 694434, 1007096, 84030, 56774, 102148, 626947, 216933, 1348613, 1472417, 100176, 824, 1471761, 1297617, 288966, 1317125, 28197, 358743, 264639, 1265, 1335, 66219, 69473, 115117, 341220, 1732, 873513, 396504, 1796619, 45851, 2741, 105841, 86332, 1349822, 84037, 180311, 54291, 1217282, 762984, 1185412, 154046, 663278, 1543, 398512, 69825, 1841867, 1535, 1510, 84026, 1502, 1619234, 39497, 1544, 29343, 649762, 332095, 536633, 1033731, 574930, 742818, 177412, 1121308, 419208, 1673717, 55779, 28117, 626937, 180332, 1776382, 40519, 34062, 40518, 74426, 1216062, 293826, 850, 645466, 474960, 36835, 115544, 1515, 88431, 216932, 1417852, 39492, 1583, 420247, 118967, 169435, 37658, 138595, 31971, 100886, 1197717, 234908, 537007, 319644, 168384, 915173, 95159, 1816678, 626940, 501571, 1796620, 888727, 1147123, 376806, 1274356, 1267, 39495, 404403, 1348, 253314, 258515, 33033, 1118061, 357276, 214851, 320502, 217731, 246787, 29371, 649764, 901, 29374, 33043, 39778, 682400, 871665, 160404, 745368, 408, 1584, 333367, 47246, 1096246, 53342, 438033, 351091, 1796622, 1776384, 817, 48256, 720554, 500632, 36849, 301302, 879970, 655811, 264463, 1532, 285, 995, 242750, 29539, 1432052, 622312, 1796636, 1337051, 328814, 28446, 1492, 820, 39496, 52786, 1549, 1796618, 582, 46507, 109327, 1531, 1382, 33039, 311460, 230143, 216935, 539, 35519, 1681, 328813, 214853, 89014, 1121115, 1585974, 29466, 1363, 292800, 270498, 214856, 142877, 133926, 209880, 179628, 1121102, 105612, 1796615, 39777, 29353, 1579, 163665, 53443, 261299, 1302, 1150298, 938289, 358742, 471875, 938278, 1796613, 1118057, 1077144, 1737, 218205, 1121298, 684066, 433659, 52699, 204516, 706562, 253257, 328812, 1280, 147802, 58134, 1335613, 891, 585394, 1582, 235931, 308994, 1589, 1682, 1736, 28129, 178001, 551788, 2051, 856, 118562, 101070, 515619, 40215, 187979, 82979, 29363, 1776391, 1285191, 84112, 157688, 38304, 36850, 341694, 287, 75612, 818, 371674, 338188, 88164, 588581, 676965, 546271, 1236512, 178338, 862517, 157687, 158, 51048, 1583331, 529, 888745, 394340, 40545, 855, 553973, 938293, 93063, 708634, 179995, 1351, 476652, 1464038, 555088, 237576, 879566, 1852371, 742727, 1377, 35830, 997353, 218538, 83771, 1605, 28111, 131109, 46609, 690567, 46206, 155615, 51616, 40542, 203, 294, 1034346, 156456, 80866, 554406, 796942, 1002367, 29347, 796944, 61592, 487175, 1050201, 762948, 137732, 1211819, 1019, 272548, 1717, 384636, 216940, 2087, 45634, 466107, 1689, 47678, 575, 979627, 840, 1660, 1236517, 617123, 546, 28135, 82171, 483, 501496, 99656, 1379, 84032, 39483, 1107316, 584, 28124, 1033744, 657309, 536441, 76123, 1118060, 89152, 76122, 303, 1541, 507751, 515620, 38302, 53419, 726, 40324, 1796610, 988946, 1852370, 1017, 1168289, 76936, 94869, 1161098, 215580, 1125779, 327575, 549, 1450648 and 478.

18. The composition of Paragraph 1 or Paragraph 2, wherein the at least one isolated or purified population of bacteria or the at least two isolated or purified populations of bacteria are a species, subspecies or bacterial strains comprising a 16S rRNA gene sequence at least 80% identical (eg, at least 85, 90, 95 or 98% identical) to any one of the sequences of SEQ ID NOs: 1-876 in WO2018064165.

19. The composition of Paragraph 1 or Paragraph 2, wherein the at least one isolated or purified population bacteria or the at least two isolated or purified populations of bacteria belong to the species, subspecies or bacterial strains selected from the group consisting of *Bacteroides coagulans, Clostridium aldenense, Clostridium aldrichii, Clostridium alkalicellulosi, Clostridium amygdalinum, Clostridium asparagiforme, Clostridium cellulosi, Clostridium citroniae, Clostridium clariflavum* DSM 19732, *Clostridium clostridioforme, Clostridium colinum, Clostridium fimetarium, Clostridium hiranonis, Clostridium hungatei, Clostridium hylemonae* DSM 15053, *Clostridium indolis, Clostridium lactatifermentans, Clostridium leptum, Clostridium methylpentosum, Clostridium oroticum, Clostridium papyrosolvens* DSM 2782, *Clostridium populeti, Clostridium propionicum, Clostridium saccharolyticum, Clostridium scindens, Clostridium sporosphaeroides, Clostridium stercorarium, Clostridium straminisolvens, Clostridium sufflavum, Clostridium termitidis, Clostridium thermosuccino* genes, *Clostridium viride, Clostridium xylanolyticum, Desulfotomaculum guttoideum, Eubacterium rectale* ATCC 33656, *Eubacterium dolichum, Eubacterium eligens* ATCC 27750, *Eubacterium hallii, Eubacterium infirmum, Eubacterium siraeum, Eubacterium tenue, Ruminococcus torques, Acetanaerobacterium elongatum, Acetatifactor muris, Acetivibrio cellulolyticus, Acetivibrio ethanolgignens, Acholeplasma brassicae* 0502, *Acholeplasma parvum, Acholeplasma vituli, Acinetobacter junii, Actinobacillus porcinus, Actinomyces bowdenii, Actinomyces dentalis, Actinomyces odontolyticus, Acutalibacter muris, Aerococcus viridans, Aeromicrobium fastidiosum, Alistipes finegoldii, Alistipes obesi, Alistipes onderdonkii, Alistipes putredinis, Alistipes shahii, Alistipes shahii* WAL 8301, *Alistipes timonensis* JC136, *Alkalibacter saccharofermentans, Alkaliphilus metalliredigens* QYMF, *Allisonella histaminiformans, Allobaculum stercoricanis* DSM 13633, *Alloprevotella rava, Alloprevotella tannerae, Anaerobacterium chartisolvens, Anaerobiospirillum thomasii, Anaerobium acetethylicum, Anaerococcus octavius* NCTC 9810, *Anaerococcus provenciensis, Anaerococcus vaginalis* ATCC 51170, *Anaerocolumna jejuensis, Anaerofilum agile, Anaerofustis stercorihominis, Anaeroglobus geminatus, Anaeromassilibacillus senegalensis, Anaeroplasma abactoclasticum, Anaerorhabdus furcosa, Anaerosporobacter mobilis, Anaerostipes butyraticus, Anaerostipes caccae, Anaerostipes hadrus, Anaerotruncus colihominis, Anaerovorax odorimutans, Anoxybacillus rupiensis, Aquabacterium limnoticum, Arcobacter butzleri, Arthrospira platensis, Asaccharobacter celatus, Atopobium parvulum, Bacteroides caccae, Bacteroides caecimuris, Bacteroides cellulosilyticus, Bacteroides clarus* YIT 12056, *Bacteroides dorei, Bacteroides eggerthii, Bacteroides finegoldii, Bacteroides fragilis, Bacteroides gallinarum, Bacteroides massiliensis, Bacteroides oleiciplenus* YIT 12058, *Bacteroides plebeius* DSM 17135, *Bacteroides rodentium* JCM 16496, *Bacteroides thetaiotaomicron, Bacteroides uniformis, Bacteroides xylanisolvens* XB1A, *Bacteroides xylanolyticus, Barnesiella intestinihominis, Beduini massiliensis, Bifidobacterium bifidum, Bifidobacterium dentium, Bifidobacterium longum* subsp. *infantis, Blautia caecimuris, Blautia coccoides, Blautia faecis, Blautia glucerasea, Blautia hansenii* DSM 20583, *Blautia hydrogenotrophica, Blautia luti, Blautia luti* DSM 14534, *Blautia wexlerae* DSM 19850, *Budvicia aquatica, Butyricicoccus pullicaecorum, Butyricimonas paravirosa, Butyrivibrio crossotus, Caldicoprobacter oshimai, Caloramator coolhaasii, Caloramator proteoclasticus, Caloramator quimbayensis, Campylobacter gracilis, Campylobacter rectus, Campylobacter ureolyticus* DSM 20703, *Capnocytophaga gingivalis, Capnocytophaga leadbetteri, Capnocytophaga sputigena, Casaltella massiliensis, Catabacter hongkongensis, Catenibacterium mitsuokai, Christensenella minuta, Christensenella timonensis, Chryseobacterium taklimakanense, Citrobacter freundii, Cloacibacillus porcorum, Clostridioides difficile* ATCC 9689=DSM 1296, *Clostridium amylolyticum, Clostridium bowmanii, Clostridium butyricum, Clostridium cadaveris, Clostridium colicanis, Clostridium gasigenes, Clostridium lentocellum* DSM 5427, *Clostridium oceanicum, Clostridium oryzae, Clostridium paraputrificum, Clostridium pascui, Clostridium perfringens, Clostridium quinii, Clostridium saccharobutylicum, Clostridium sporogenes, Clostridium ventriculi, Collinsella aerofaciens, Comamonas testosteroni, Coprobacter fastidiosus* NSB1, *Coprococcus eutactus, Corynebacterium diphtheriae, Corynebacterium durum, Corynebacterium mycetoides, Corynebacterium pyruviciproducens* ATCC BAA-1742, *Corynebacterium tuberculostearicum, Culturomica massiliensis, Cuneatibacter caecimuris, Defluviitalea saccharophila, Delftia acidovorans, Desulfitobacterium chlororespirans, Desulfitobacterium metallire-* ducens, Desulfosporosinus acididurans, Desulfotomaculum halophilum, Desulfotomaculum intricatum, Desulfotomaculum tongense, Desulfovibrio desulfuricans subsp. desulfuricans, Desulfovibrio idahonensis, Desulfovibrio litoralis, Desulfovibrio piger, Desulfovibrio simplex, Desulfovibrio zosterae, Desulfuromonas acetoxidans, Dethiobacter alkaliphilus AHT 1, Dethiosulfatibacter aminovorans, Dialister invisus, Dialister propionicifaciens, Dielma fastidiosa, Dietzia alimentaria 72, Dorea longicatena, Dysgonomonas gadei ATCC BAA-286, Dysgonomonas mossii, Eggerthella lenta, Eikenella corrodens, Eisenbergiella tayi, Emergencia timonensis, Enorma massiliensis phi, Enterococcus faecalis, Enterorhabdus muris, Ethanoligenens harbinense YUAN-3, Eubacterium coprostanoligenes, Eubacterium limosum, Eubacterium oxidoreducens, Eubacterium sulci ATCC 35585, Eubacterium uniforme, Eubacterium ventriosum, Eubacterium xylanophilum, Extibacter muris, Ezakiella peruensis, Faecalibacterium prausnitzii, Faecalicoccus acidiformans, Faecalitalea cylindroides, Filifactor villosus, Flavonifractor plautii, Flintibacter butyricus, Frisingicoccus caecimuris, Fucophilus fucoidanolyticus, Fusicatenibacter saccharivorans, Fusobacterium mortiferum, Fusobacterium nucleatum subsp. vincentii, Fusobacterium simiae, Fusobacterium varium, Garciella nitratireducens, Gemella haemolysans, Gemmiger Gordonibacter urolithinfaciens, Gracilibacter thermotolerans JW/YJL-S1, Granulicatella elegans, Guggenheimella bovis, Haemophilus haemolyticus, Helicobacter typhlonius, Hespellia stercorisuis, Holdemanella biformis, Holdemania massiliensis AP2, Howardella ureilytica, Hungatella effluvii, Hungatella hathewayi, Hydrogenoanaerobacterium saccharovorans, Ihubacter massiliensis, Intestinibacter bartlettii, Intestinimonas butyriciproducens, Irregularibacter muris, Kiloniella laminariae DSM 19542, Kroppenstedtia guangzhouensis, Lachnoanaerobaculum orale, Lachnoanaerobaculum umeaense, Lachnoclostridium phytofermentans, Lactobacillus acidophilus, Lactobacillus algidus, Lactobacillus animalis, Lactobacillus casei, Lactobacillus delbrueckii, Lactobacillus formicalis, Lactobacillus iners, Lactobacillus pentosus, Lactobacillus rogosae, Lactococcus garvieae, Lactonifactor longoviformis, Leptotrichia buccalis, Leptotrichia hofstadii, Leptotrichia hongkongensis, Leptotrichia wadei, Leuconostoc inhae, Levyella massiliensis, Loriellopsis cavernicola, Lutispora thermophila, Marinilabilia salmonicolor JCM 21150, Marvinbryantia formatexigens, Mesoplasma photuris, Methanobrevibacter smithii ATCC 35061, Methanomassiliicoccus luminyensis BIO, Methylobacterium extorquens, Mitsuokella jalaludinii, Mobilitalea sibirica, Mobiluncus curtisii, Mogibacterium pumilum, Mogibacterium timidum, Moorella glycerini, Moorella humiferrea, Moraxella nonliquefaciens, Moraxella osloensis, Morganella morganii, Moryella indoligenes, Muribaculum intestinale, Murimonas intestini, Natranaerovirga pectinivora, Neglecta timonensis, Neisseria cinerea, Neisseria oralis, Nocardioides mesophilus, Novibacillus thermophilus, Ochrobactrum anthropi, Odoribacter splanchnicus, Olsenella profusa, Olsenella uli, Oribacterium asaccharolyticum ACB7, Oribacterium sinus, Oscillibacter ruminantium GHJ, Oscillibacter valericigenes, Oxobacter pfennigii, Pantoea agglomerans, Papillibacter cinnamivorans, Parabacteroides faecis, Parabacteroides goldsteinii, Parabacteroides gordonii, Parabacteroides merdae, Parasporobacterium paucivorans, Parasutterella excrementihominis, Parasutterella secunda, Parvimonas micra, Peptococcus niger, Peptoniphilus duerdenii ATCC BAA-1640, Peptoniphilus grossensis ph5, Peptoniphilus koenoeneniae, Peptoniphilus senegalensis JC140, Peptostreptococcus stomatis, Phascolarctobacterium succinatutens, Phocea massiliensis, Pontibacter indicus, Porphyromonas bennonis, Porphyromonas endodontalis, Porphyromonas pasteri, Prevotella bergensis, Prevotella buccae ATCC 33574, Prevotella denticola, Prevotella enoeca, Prevotella fusca JCM 17724, Prevotella loescheii, Prevotella nigrescens, Prevotella oris, Prevotella pollens ATCC 700821, Prevotella stercorea DSM 18206, Prev ote llamas silia timonensis, Propionispira arcuata, Proteus mirabilis, Providencia rettgeri, Pseudobacteroides cellulosolvens ATCC 35603=DSM 2933, Pseudobutyrivibrio ruminis, Pseudoflavonifr actor capillosus ATCC 29799, Pseudomonas aeruginosa, Pseudomonas fluorescens, Pseudomonas mandelii, Pseudomonas nitroreducens, Pseudomonas putida, Raoultella ornithinolytica, Raoultella planticola, Raoultibacter massiliensis, Robinsoniella peoriensis, Romboutsia timonensis, Roseburia faecis, Roseburia hominis A2-183, Roseburia intestinalis, Roseburia inulinivorans DSM 16841, Rothia dentocariosa ATCC 17931, Ruminiclostridium thermocellum, Ruminococcus albus, Ruminococcus bromii, Ruminococcus callidus, Ruminococcus champanellensis 18P13=JCM 17042, Ruminococcus faecis JCM 15917, Ruminococcus flavefaciens, Ruminococcus gauvreauii, Ruminococcus lactaris ATCC 29176, Rummeliibacillus pycnus, Saccharofermentans acetigenes, Scardovia wiggsiae, Schlegelella thermodepolymerans, Sedimentibacter hongkongensis, Selenomonas sputigena ATCC 35185, Slackia exigua ATCC 700122, Slackia piriformis YIT 12062, Solitalea canadensis, Solobacterium moorei, Sphingomonas aquatilis, Spiroplasma alleghenense, Spiroplasma chinense, Spiroplasma chrysopicola, Spiroplasma culicicola, Spiroplasma lampyridicola, Sporobacter termitidis, Staphylococcus aureus, Stenotrophomonas maltophilia, Stomatobaculum longum, Streptococcus agalactiae ATCC 13813, Streptococcus cristatus, Streptococcus equinus, Streptococcus gordonii, Streptococcus lactarius, Streptococcus parauberis, Subdoligranulum variabile, Succinivibrio dextrinosolvens, Sutterella stercoricanis, Sutterella wadsworthensis, Syntrophococcus sucromutans, Syntrophomonas zehnderi OL-4, Terrisporobacter mayombei, Thermoleophilum album, Treponema denticola, Treponema socranskii, Tyzzerella nexilis DSM 1787, Vallitalea guaymasensis, Vallitalea pronyensis, Vampirovibrio chlorellavorus, Veillonella atypica, Veillonella denticariosi, Veillonella dispar, Veillonella parvula, Victivallis vadensis, Vulcanibacillus modesticaldus and Weissella confusa.

In an example, the transplant comprises or consists of SER-109 or SER-262 (and optionally the condition is a C. dificile infection); VE202 or SER-287 (and optionally the disease is ulcerative colitis); SER-301 (and optionally the disease is IBD); SER-401 (and optionally the condition is a cancer; eg, wherein the therapy further comprises administration of an anti-PD-1 axis antibody, eg, an anti-PD-1 antibody); VE800 or SER-155 (and optionally the therapy further comprises the administration of a transplant, eg, a haematopoietic stem cell or solid organ transplant); EDP1066 or EDP1815 (and optionally the disease is an inflammatory condition, eg, colitis, Crohn's disease, asthma, rheumatoid arthritis (RA), psoriasis, dermatitis (eg, atopic dermatitis) or IBD); or EDP1503 (and the disease is a cancer, eg, colorectal cancer, renal cell carcinoma, melanoma or a PD-1 relapsed cancer). In an example, the therapy comprises the administration of SGM-1019, SG-2-0776 or EB8018 (and optionally the disease or condition is NASH or IBD or an inflammatory condition, eg, colitis, Crohn's disease, asthma, rheumatoid arthritis (RA), psoriasis and dermatitis (eg, atopic dermatitis). Those starting "VE" are developed by Vadanta Biosciences, SER are developed by Seres Therapeutics, EDP are developed by Evelo Biosciences, SG are developed by Second Genome and EB are developed by Enterome.

In an example, the disease or condition herein is an inflammatory condition, eg, colitis, Crohn's disease, asthma, rheumatoid arthritis (RA), psoriasis, dermatitis (eg, atopic dermatitis) or IBD.

6. Other Agents

It is contemplated that other agents may be used in combination with certain aspects of the present embodiments to improve the therapeutic efficacy of treatment. These additional agents include agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Increases in intercellular signalling by elevating the number of GAP junctions would increase the anti-hyperproliferative effects on the neighbouring hyperproliferative cell population. In other embodiments, cytostatic or differentiation agents can be used in combination with certain aspects of the present embodiments to improve the anti-hyperproliferative efficacy of the treatments. Inhibitors of cell adhesion are contemplated to improve the efficacy of the present embodiments. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with certain aspects of the present embodiments to improve the treatment efficacy.

Diseases and Conditions

Optionally, the disease or condition is selected from
(a) A neurodegenerative disease or condition;
(b) A brain disease or condition;
(c) A CNS disease or condition;
(d) Memory loss or impairment;
(e) A heart or cardiovascular disease or condition, eg, heart attack, stroke or atrial fibrillation;
(f) A liver disease or condition;
(g) A kidney disease or condition, eg, chronic kidney disease (CKD);
(h) A pancreas disease or condition;
(i) A lung disease or condition, eg, cystic fibrosis or COPD;
(j) A gastrointestinal disease or condition;
(k) A throat or oral cavity disease or condition;
(l) An ocular disease or condition;
(m) A genital disease or condition, eg, a vaginal, labial, penile or scrotal disease or condition;
(n) A sexually-transmissible disease or condition, eg, gonorrhea, HIV infection, syphilis or *Chlamydia* infection;
(o) An ear disease or condition;
(p) A skin disease or condition;
(q) A heart disease or condition;
(r) A nasal disease or condition
(s) A haematological disease or condition, eg, anaemia, eg, anaemia of chronic disease or cancer;
(t) A viral infection;
(u) A pathogenic bacterial infection;
(v) A cancer;
(w) An autoimmune disease or condition, eg, SLE;
(x) An inflammatory disease or condition, eg, rheumatoid arthritis, psoriasis, eczema, asthma, ulcerative colitis, colitis, Crohn's disease or IBD;
(y) Autism;
(z) ADHD;
(aa) Bipolar disorder;
(bb) ALS [Amyotrophic Lateral Sclerosis];
(cc) Osteoarthritis;
(dd) A congenital or development defect or condition;
(ee) Miscarriage;
(ff) A blood clotting condition;
(gg) Bronchitis;
(hh) Dry or wet AMD;
(ii) Neovascularisation (eg, of a tumour or in the eye);
(jj) Common cold;
(kk) Epilepsy;
(ll) Fibrosis, eg, liver or lung fibrosis;
(mm) A fungal disease or condition, eg, thrush;
(nn) A metabolic disease or condition, eg, obesity, anorexia, diabetes, Type I or Type II diabetes.
(oo) Ulcer(s), eg, gastric ulceration or skin ulceration;
(pp) Dry skin;
(qq) Sjogren's syndrome;
(rr) Cytokine storm;
(ss) Deafness, hearing loss or impairment;
(tt) Slow or fast metabolism (ie, slower or faster than average for the weight, sex and age of the subject);
(uu) Conception disorder, eg, infertility or low fertility;
(vv) Jaundice;
(ww) Skin rash;
(xx) Kawasaki Disease;
(yy) Lyme Disease;
(zz) An allergy, eg, a nut, grass, pollen, dust mite, cat or dog fur or dander allergy;
(aaa) Malaria, typhoid fever, tuberculosis or cholera;
(bbb) Depression;
(ccc) Mental retardation;
(ddd) Microcephaly;
(eee) Malnutrition;
(fff) Conjunctivitis;
(ggg) Pneumonia;
(hhh) Pulmonary embolism;
(iii) Pulmonary hypertension;
(jjj) A bone disorder;
(kkk) Sepsis or septic shock;
(lll) Sinusitus;
(mmm) Stress (eg, occupational stress);
(nnn) Thalassaemia, anaemia, von Willebrand Disease, or haemophilia;
(ooo) Shingles or cold sore;
(ppp) Menstruation;
(qqq) Low sperm count.

Neurodegenerative or CNS Diseases or Conditions for Treatment or Prevention by the Method In an example, the neurodegenerative or CNS disease or condition is selected from the group consisting of Alzheimer disease, geriopsychosis, Down syndrome, Parkinson's disease, Creutzfeldt-jakob disease, diabetic neuropathy, Parkinson syndrome, Huntington's disease, Machado-Joseph disease, amyotrophic lateral sclerosis, diabetic neuropathy, and Creutzfeldt Creutzfeldt-Jakob disease. For example, the disease is Alzheimer disease. For example, the disease is Parkinson syndrome.

In an example, wherein the method of the invention is practised on a human or animal subject for treating a CNS or neurodegenerative disease or condition, the method causes downregulation of Treg cells in the subject, thereby promoting entry of systemic monocyte-derived macrophages and/or Treg cells across the choroid plexus into the brain of the subject, whereby the disease or condition (eg, Alzheimer's disease) is treated, prevented or progression thereof is reduced. In an embodiment the method causes an increase of IFN-gamma in the CNS system (eg, in the brain and/or CSF) of the subject. In an example, the method restores nerve fibre and/or reduces the progression of nerve fibre damage. In an example, the method restores nerve myelin and/or reduces the progression of nerve myelin damage. In an example, the method of the invention treats or prevents a disease or condition disclosed in WO2015136541 and/or the method can be used with any method disclosed in WO2015136541 (the disclosure of this document is incorporated by reference herein in its entirety, eg, for providing disclosure of such methods, diseases, conditions and potential therapeutic agents that can be administered to the subject for effecting treatment and/or prevention of CNS and neurodegenerative diseases and conditions, eg, agents such as immune checkpoint inhibitors, eg, anti-PD-1, anti-PD-L1, anti-TIM3 or other antibodies disclosed therein).

Cancers for Treatment or Prevention by the Method

Cancers that may be treated include tumours that are not vascularized, or not substantially vascularized, as well as vascularized tumours. The cancers may comprise non-solid tumours (such as haematological tumours, for example, leukaemias and lymphomas) or may comprise solid tumours. Types of cancers to be treated with the invention include, but are not limited to, carcinoma, blastoma, and sarcoma, and certain leukaemia or lymphoid malignancies, benign and malignant tumours, and malignancies e.g., sarcomas, carcinomas, and melanomas. Adult tumours/cancers and paediatric tumours/cancers are also included.

Haematologic cancers are cancers of the blood or bone marrow. Examples of haematological (or haematogenous) cancers include leukaemias, including acute leukaemias (such as acute lymphocytic leukaemia, acute myelocytic leukaemia, acute myelogenous leukaemia and myeloblasts, promyelocytic, myelomonocytic, monocytic and erythroleukaemia), chronic leukaemias (such as chronic myelocytic (granulocytic) leukaemia, chronic myelogenous leukaemia, and chronic lymphocytic leukaemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukaemia and myelodysplasia.

Solid tumours are abnormal masses of tissue that usually do not contain cysts or liquid areas. Solid tumours can be benign or malignant. Different types of solid tumours are named for the type of cells that form them (such as sarcomas, carcinomas, and lymphomas). Examples of solid tumours, such as sarcomas and carcinomas, include fibrosarcoma, myxosarcoma, liposarcoma, chondrosarcoma, osteosarcoma, and other sarcomas, synovioma, mesothelioma, Ewing's tumour, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumour, cervical cancer, testicular tumour, seminoma, bladder carcinoma, melanoma, and CNS tumours (such as a glioma (such as brainstem glioma and mixed gliomas), glioblastoma (also known as glioblastoma multiforme) astrocytoma, CNS lymphoma, germinoma, medulloblastoma, Schwannoma craniopharyogioma, ependymoma, pineaioma, hemangioblastoma, acoustic neuroma, oligodendroglioma, menangioma, neuroblastoma, retinoblastoma and brain metastases).

In an example, the cancer is a haematological cancer. In an example, the cancer is NSCLC. In an example, the cancer is renal cell carcinoma. In an example, the cancer is urothelial carcinoma. In an example, the cancer is melanoma.

Autoimmune Diseases for Treatment or Prevention by the Method

Acute Disseminated Encephalomyelitis (ADEM)
Acute necrotizing hemorrhagic leukoencephalitis
Addison's disease
Agammaglobulinemia
Alopecia areata
Amyloidosis
Ankylosing spondylitis
Anti-GBM/Anti-TBM nephritis
Antiphospholipid syndrome (APS)
Autoimmune angioedema
Autoimmune aplastic anemia
Autoimmune dysautonomia
Autoimmune hepatitis
Autoimmune hyperlipidemia
Autoimmune immunodeficiency
Autoimmune inner ear disease (AIED)
Autoimmune myocarditis
Autoimmune oophoritis
Autoimmune pancreatitis
Autoimmune retinopathy
Autoimmune thrombocytopenic purpura (ATP)
Autoimmune thyroid disease
Autoimmune urticaria
Axonal & neuronal neuropathies
Balo disease
Behcet's disease
Bullous pemphigoid
Cardiomyopathy
Castleman disease
Celiac disease
Chagas disease
Chronic fatigue syndrome
Chronic inflammatory demyelinating polyneuropathy (CIDP)
Chronic recurrent multifocal ostomyelitis (CRMO)
Churg-Strauss syndrome
Cicatricial pemphigoid/benign mucosal pemphigoid
Crohn's disease
Cogans syndrome
Cold agglutinin disease
Congenital heart block
Coxsackie myocarditis
CREST disease
Essential mixed cryoglobulinemia
Demyelinating neuropathies
Dermatitis herpetiformis
Dermatomyositis Devic's disease (neuromyelitis optica)
Discoid lupus
Dressler's syndrome
Endometriosis
Eosinophilic esophagitis
Eosinophilic fasciitis
Erythema nodosum
Experimental allergic encephalomyelitis
Evans syndrome
Fibromyalgia
Fibrosing alveolitis
Giant cell arteritis (temporal arteritis)
Giant cell myocarditis
Glomerulonephritis
Goodpasture's syndrome
Granulomatosis with Polyangiitis (GPA) (formerly called Wegener's Granulomatosis)
Graves' disease
Guillain-Barre syndrome
Hashimoto's encephalitis
Hashimoto's thyroiditis
Hemolytic anemia
Henoch-Schonlein purpura
Herpes gestationis
Hypogammaglobulinemia
Idiopathic thrombocytopenic purpura (ITP)
IgA nephropathy
IgG4-related sclerosing disease
Immunoregulatory lipoproteins
Inclusion body myositis
Interstitial cystitis
Juvenile arthritis
Juvenile diabetes (Type 1 diabetes)
Juvenile myositis
Kawasaki syndrome
Lambert-Eaton syndrome
Leukocytoclastic vasculitis
Lichen planus
Lichen sclerosus
Ligneous conjunctivitis
Linear IgA disease (LAD)
Lupus (SLE)
Lyme disease, chronic
Meniere's disease
Microscopic polyangiitis
Mixed connective tissue disease (MCTD)
Mooren's ulcer
Mucha-Habermann disease
Multiple sclerosis
Myasthenia gravis
Myositis
Narcolepsy
Neuromyelitis optica (Devic's)
Neutropenia
Ocular cicatricial pemphigoid
Optic neuritis
Palindromic rheumatism
PANDAS (Pediatric Autoimmune Neuropsychiatric Disorders Associated with *Streptococcus*)
Paraneoplastic cerebellar degeneration
Paroxysmal nocturnal hemoglobinuria (PNH)
Parry Romberg syndrome
Parsonnage-Turner syndrome
Pars planitis (peripheral uveitis)
Pemphigus
Peripheral neuropathy
Perivenous encephalomyelitis
Pernicious anemia
POEMS syndrome
Polyarteritis nodosa
Type I, II, & III autoimmune polyglandular syndromes
Polymyalgia rheumatica
Polymyositis
Postmyocardial infarction syndrome
Postpericardiotomy syndrome
Progesterone dermatitis
Primary biliary cirrhosis
Primary sclerosing cholangitis
Psoriasis
Psoriatic arthritis
Idiopathic pulmonary fibrosis
Pyoderma gangrenosum
Pure red cell aplasia
Raynauds phenomenon
Reactive Arthritis
Reflex sympathetic dystrophy
Reiter's syndrome
Relapsing polychondritis
Restless legs syndrome
Retroperitoneal fibrosis
Rheumatic fever
Rheumatoid arthritis
Sarcoidosis
Schmidt syndrome
Scleritis
Scleroderma
Sjogren's syndrome
Sperm & testicular autoimmunity
Stiff person syndrome
Subacute bacterial endocarditis (SBE)
Susac's syndrome
Sympathetic ophthalmia
Takayasu's arteritis
Temporal arteritis/Giant cell arteritis
Thrombocytopenic purpura (TTP)
Tolosa-Hunt syndrome
Transverse myelitis
Type 1 diabetes
Ulcerative colitis
Undifferentiated connective tissue disease (UCTD)
Uveitis
Vasculitis
Vesiculobullous dermatosis
Vitiligo
Wegener's granulomatosis (now termed Granulomatosis with Polyangiitis (GPA).

Inflammatory Diseases for Treatment or Prevention by the Method
    Alzheimer's
    ankylosing spondylitis
    arthritis (osteoarthritis, rheumatoid arthritis (RA), psoriatic arthritis)
    asthma
    atherosclerosis
    Crohn's disease
    colitis
    dermatitis
    diverticulitis
    fibromyalgia
    hepatitis
    irritable bowel syndrome (IBS)

systemic lupus erythematous (SLE)
nephritis
Parkinson's disease
ulcerative colitis.

Concepts:—

The invention provides the following Concepts.

1. A programmable nuclease for use in a method of treating an acute microbial infection of a subject, wherein the microbial infection is caused by microbes of a first species or strain and the nuclease is programmable to cut a target site comprised by the genomes of microbes that have infected the subject, whereby microbes of the first species or strain are killed, or growth or proliferation of the microbes is reduced, the treatment method comprising exposing the subject to the nuclease wherein the nuclease is programmed to cut the target site, whereby genomes of the microbes comprised by the subject are cut and acute microbial infection of the subject is treated.
2. A programmable nuclease for use in a method of durably treating a microbial (eg, bacterial) infection of a subject, wherein the microbial infection is caused by microbes of a first species or strain and the nuclease is programmable to cut a target site comprised by the genomes of microbes that have infected the subject, whereby microbes of the first species or strain are durably killed, or growth or proliferation of the microbes is reduced, the treatment method comprising exposing the subject to the nuclease wherein the nuclease is programmed to cut the target site, whereby genomes of the microbes comprised by the subject are cut and microbial infection of the subject is durably treated.
3. The nuclease of Concept 2, wherein the nuclease (eg, programmed nuclease) and/or a nucleic acid that programs the nuclease to recognise and cut the target site is administered to the subject at a first time (T1) and at a second time (T2) wherein T2 is at least 1 hour after T1.
4. The nuclease of any preceding Concept, wherein the method comprises reducing the infection at least 100-fold by the first 30 minutes (eg, by the first 15 minutes) of the treatment.
5. The nuclease of any preceding Concept, wherein the method comprises maintaining reduction of the infection by at least 100-fold for at least 60 minutes (eg, at least 120 minutes) after exposing the subject to the programmed nuclease.
6. The nuclease of any preceding Concept, wherein the method comprises reducing the infection such that the reduction in infection persists for 30 minutes immediately after the first 30 minutes of the treatment.
7. The nuclease of any preceding Concept, wherein the method comprises administering to the subject a RNA or a nucleic acid that encodes an RNA for expression of the RNA in the subject, wherein the RNA complexes with the nuclease to program the nuclease to cut the target site in microbes comprised by the subject.
8. The nuclease of Concept 7, wherein the nuclease is administered simultaneously or sequentially with the RNA or nucleic acid to the subject.
9. The nuclease of Concept 7, wherein the subject comprises the nuclease prior to administration of the RNA or nucleic acid to the subject.
10. The nuclease of any one of Concepts 7 to 9, wherein a plurality of viruses (eg, phage) are administered to the subject, wherein each virus comprises a copy of the nucleic acid, wherein the viruses infect the microbes comprised by the subject to deliver thereto the nucleic acid.
11. The nuclease of Concept 10, wherein the ratio of administered viruses:microbes comprised by the subject is from 10 to 150.
12. The nuclease according to any preceding Concept, wherein the subject is a human or animal, optionally wherein the subject is a human over 65 years of age or is a paediatric patient.
13. The nuclease according to Concept 12, wherein the infection is an infection of the lungs, abdomen or urinary tract; or wherein the subject has undergone surgery, is on an immunosuppressant medication and/or is suffering from a chronic disease.
14. The nuclease according to any preceding Concept, wherein the infection is reduced by at least 90% for 1 hour or more, optionally by the first 30 minutes (eg, by the first 15 minutes) of the treatment.
15. The nuclease according to any preceding Concept, wherein the method comprises reducing the infection at least 100-fold by the first 30 minutes (eg, by the first 15 minutes) of the treatment; and wherein reduction of the infection by at least 100-fold is maintained for at least 60 minutes (eg, at least 120, 145 or 180 minutes) after exposing the subject to the programmed nuclease.
16. The nuclease according to any one of Concepts 12 to 15, wherein the method treats or prevents septicaemia and/or sepsis (eg, septic shock) in the subject.
17. The nuclease of Concept 16, wherein at the start of the treatment, the subject (eg, a human) has a temperature of <36° C. or >38° C.; a heart rate of >90/min, a respiratory rate of breaths/min or $PaCO_2$<43 kPa; and white blood cell count of <4000/mm$^3$ or >12,000/mm$^3$.
18. The nuclease of Concept 16 or 17, wherein at the start of the treatment, the subject (eg, a human) has presence of two or more of the following: abnormal body temperature, abnormal heart rate, abnormal respiratory rate, abnormal blood gas and abnormal white blood cell count.
19. The nuclease of any preceding Concept, wherein the subject is a human or animal and the microbes are bacteria (eg, *E. coli* or *C. dificile*), wherein blood infection of the subject by the bacteria is reduced at least 100- or 1000-fold by the first 30 minutes (eg, by the first 15 minutes) of the treatment.
20. The nuclease of any one of Concepts 12 to 19, wherein the blood of the subject is infected with from 10$^7$ to 10$^{12}$ CFU/ml of the bacteria immediately before the treatment.
21. The nuclease according to any one of Concepts 1 to 11, wherein the subject is a plant.
22. The nuclease according to any preceding Concept, wherein the microbes are bacteria.
23. The nuclease according to Concept 22, wherein the bacteria are gram positive bacteria.
24. The nuclease according to Concept 22 or 23, wherein the bacteria are *Staphylococcus, Streptococcus, Enterococcus, Legionella, Heamophilus, Ghonnorhea, Acinetobacter, Escherichia, Klebsiella, Pseudomonas* or *Stenotrophomonas* bacteria (eg, *E. coli* (eg, EHEC *E. coli*), *C. dificile, V. cholera, Staphylococcus* (eg, *S. aureus* or MRSA), *Streptococcus pyogenes, Acinetobacter baumannii, Legionella, Pseudomonas aeruginosa, Klebsiella pneumoniae* bacteria).
25. The nuclease according to any preceding Concept, wherein the nuclease is a Cas nuclease (eg, a Cas 3 or 9), a meganuclease, a TALEN (Transcription activator-like effector nuclease) or zinc finger nuclease.
26. A plurality of viruses (eg, phage or phagemids for producing phage) for use with the nuclease of any preceding Concept in the method of treatment, wherein each virus comprises a copy of a nucleic acid as defined in any one of Concepts 7 to 9, wherein the viruses are capable of infecting microbes comprised by the subject to deliver thereto the nucleic acid.
27. A composition comprising a plurality of nucleic acids for programming the nuclease of any one of Concepts 1 to 25 in the method of treatment, wherein each nucleic acid is a nucleic acid as defined in any one of Concepts 7 to 9.
28. A CRISPR/Cas system comprising a nuclease according to any preceding Concept for use in the method of treatment, wherein the nuclease is a Cas nuclease (eg, a Cas 3 or 9) and the system comprises one or more guide RNAs or DNA encoding one or more guide RNAs, wherein each guide RNA is capable of programming the Cas nuclease to cut a target site comprised by the genomes of the microbes.
29. A guide RNA or a DNA encoding a guide RNA for use in the system of Concept 28 for use in the method of treating an acute microbial infection in the subject, eg, septicaemia or sepsis.
30. A nucleic acid vector comprising the guide RNA or DNA recited in Concept 27 or 29.
31. The vector of Concept 30 wherein the vector is a phage, phagemid, viriophage, virus, plasmid (eg, conjugative plasmid) or transposon.
32. An anti-sepsis or anti-septicaemia composition for administration to a human or animal for treating sepsis or septicaemia, the composition comprising a plurality of vectors, wherein each vector is according to Concept 30 or 31.
33. A method of treating an acute microbial infection of a subject, wherein the method is as defined by any preceding Concept.
34. Use of a nuclease, plurality of viruses, system, guide RNA, DNA or vector of any one of Concepts 1 to 26 and 28 to 30, in the manufacture of a composition for carrying out a method of treatment as defined by any preceding Concept, wherein the subject is an organism other than a human or animal.
35. Use of a nuclease, plurality of viruses, system, guide RNA, DNA or vector of any one of Concepts 1 to 26 and 28 to 30, in the manufacture of a composition for carrying out an ex vivo method of treatment of a microbial infection of a substrate, wherein the microbial infection is caused by microbes of a first species or strain and the nuclease is programmable to cut a target site comprised by the genomes of microbes that have infected the substrate, whereby microbes of the first species or strain are killed, or growth or proliferation of the microbes is reduced, the treatment method comprising exposing the subject to the nuclease wherein the nuclease is programmed to cut the target site, whereby genomes of the microbes comprised by the subject are cut and acute microbial infection of the substrate is treated.
36. Use of a programmable nuclease in the manufacture of a composition for carrying out an ex vivo method of treatment of a microbial infection of a substrate, wherein the microbial infection is caused by microbes of a first species or strain and the nuclease is programmable to cut a target site comprised by the genomes of microbes that have infected the substrate, whereby microbes of the first species or strain are killed, or growth or proliferation of the microbes is reduced, the treatment method comprising exposing the subject to the nuclease wherein the nuclease is programmed to cut the target site, whereby genomes of the microbes comprised by the subject are cut and acute microbial infection of the substrate is treated.
37. The use of Concept 34, 35 or 36, wherein the nuclease (eg, programmed nuclease) and/or a nucleic acid that programs the nuclease to recognise and cut the target site is administered to the subject or substrate at a first time (T1) and at a second time (T2) wherein T2 is at least 1 hour after T1.
38. The use of any one of Concepts 34 to 37, wherein the infection is reduced at least 100-fold by the first 30 minutes (eg, by the first 15 minutes) of the treatment.
39. The use of any one of Concepts 34 to 38, wherein the reduction of the infection is maintained by at least 100-fold for at least 60 minutes (eg, at least 120 minutes) after exposing the subject to the programmed nuclease.
40. The use of any one of Concepts 34 to 39, wherein the reduction in infection persists for 30 minutes immediately after the first 30 minutes of the treatment.
41. The use of any one of Concepts 34 to 40, wherein the method comprises administering to the subject or substrate a RNA or a nucleic acid that encodes an RNA for expression of the RNA in or on the subject or substrate, wherein the RNA complexes with the nuclease to program the nuclease to cut the target site in microbes comprised by the subject or substrate.
42. The use of Concept 41, wherein the nuclease is administered simultaneously or sequentially with the RNA or nucleic acid to the subject or substrate.
43. The use of Concept 41, wherein the subject or substrate comprises the nuclease prior to administration of the RNA or nucleic acid.
44. The use of any one of Concepts 41 to 43, wherein a plurality of viruses (eg, phage) are administered to the subject or substrate, wherein each virus comprises a copy of the nucleic acid, wherein the viruses infect the microbes comprised by the subject or substrate to deliver thereto the nucleic acid.
45. The use of Concept 44, wherein the ratio of administered viruses:microbes is from 10 to 150.
46. The use of any one of Concepts 34 to 45, wherein the infection is reduced by at least 90% for 1 hour or more, optionally by the first 30 minutes (eg, by the first 15 minutes) of the treatment.
47. The use of any one of Concepts 34 to 46, wherein the infection is reduced at least 100-fold by the first 30 minutes (eg, by the first 15 minutes) of the treatment; and wherein reduction of the infection by at least 100-fold is maintained for at least 60 minutes (eg, at least 120, 145 or 180 minutes) after exposing the subject or substrate to the programmed nuclease.
48. The use of any one of Concepts 34 to 47, wherein the subject is a plant; or wherein the substrate is a metallic, plastic, concrete, stone, wood, glass or ceramic substrate.
49. The use of any one of Concepts 34 to 48, wherein the microbes are bacteria.
50. The use according to Concept 49, wherein the bacteria are gram positive bacteria.
51. The use according to Concept 49 or 50, wherein the bacteria are *Staphylococcus, Streptococcus, Enterococ-* cus, Legionella, Heamophilus, Ghonnorhea, Acinetobacter, Escherichia, Klebsiella, Pseudomonas or Stenotrophomonas bacteria (eg, E. coli (eg, EHEC E. coli), C. dificile, V. cholera, Staphylococcus (eg, S. aureus or MRSA), Streptococcus pyogenes, Acinetobacter baumannii, Legionella, Pseudomonas aeruginosa, Klebsiella pneumoniae bacteria).

52. The use of any one of Concepts 34 to 51, wherein the nuclease is a Cas nuclease (eg, a Cas 3 or 9), a meganuclease, a TALEN (Transcription activator-like effector nuclease) or zinc finger nuclease.

EMBODIMENTS

1. A method for treating a pathogenic bacterial infection in a human or animal subject caused by bacteria (first bacteria) of a first species or strain, the method comprising selectively killing first bacteria comprised by the subject by cutting a target site comprised by the genomes of the first bacteria, wherein the cutting is carried out using a programmable nuclease that is programmed to cut the target site, wherein the subject is suffering from a further disease or condition other than the pathogenic bacterial infection and the method comprises administering a therapy to the subject for treating or preventing the further disease or condition, wherein the nuclease treats the infection and the therapy is efficacious in the presence of the programmed nuclease to treat or prevent the disease or condition.
2. The method of Embodiment 1, wherein the subject is a cancer patient and the therapy comprises administration of a haematopoietic stem cell transplant, chemotherapeutic agent, immune checkpoint inhibitor, immune checkpoint agonist or an immune cell enhancer; adoptive cell therapy; radiation or surgery.
3. The method of Embodiment 2, wherein the therapy is an immune checkpoint inhibitor antibody, or an antibody selected from ipilimumab (or YERVOY®), tremelimumab, nivolumab (or OPDIVO®), pembrolizumab (or KEYTRUDA®), pidilizumab, BMS-936559, durvalumab (or IMFINZI®) and atezolizumab (or TECENTRIQ®).
4. The method of Embodiment 1, wherein the therapy is a tissue, organ or cell transplant.
5. The method of Embodiment 1, wherein the treatment of the bacterial infection is carried out simultaneously with the administration of the therapy to the subject.
6. The method of Embodiment 1, wherein the treatment of the bacterial infection is carried out immediately before or after administering the therapy to the subject.
7. The method of Embodiment 1, wherein the method comprises administering to the subject a or a nucleic acid that encodes an RNA for expression of the RNA in the subject, wherein the RNA complexes with the nuclease to program the nuclease to cut the target site in first bacteria comprised by the subject, thereby killing the first bacteria.
8. The method of Embodiment 1, comprising administering a nucleic acid vector to the subject, wherein the vector encodes the programmable nuclease.
9. The method of Embodiment 1, wherein the programmable nuclease is an endogenous nuclease of the first cells.
10. The method of Embodiment 1, wherein the efficacy of the therapy in the presence of the programmed nuclease is greater than the efficacy of the therapy in the presence of a broad-spectrum antibiotic.
11. The method of Embodiment 1, wherein the efficacy of the therapy in the presence of the programmed nuclease is greater than the efficacy of the therapy in the presence of an antibiotic selected from methicillin, vancomycin, linezolid, daptomycin, quinupristin, dalfopristin; teicoplanin; cephalosporin; carbapenem; fluoroquinolone; aminoglycoside; colistin; erythromycin; clindamycin; beta-lactam; macrolide; amoxicillin; azithromycin; penicillin; ceftriaxone; azithromycin; ciprofloxacin; isoniazid (INH); rifampicin (RMP); amikacin; kanamycin; capreomycin; trimethoprim; itrofurantoin; cefalexin; amoxicillin; metronidazole (MTZ); cefixime; tetracycline; and meropenem.
12. The method of Embodiment 1, wherein the first bacteria is selected from (i) Staphylococcus aureus that is resistant to an antibiotic selected from methicillin, vancomycin, linezolid, daptomycin, quinupristin, dalfopristin and teicoplanin; (ii) Pseudomonas aeuroginosa that is resistant to an antibiotic selected from cephalosporins, carbapenems, fluoroquinolones, aminoglycosides and colistin; (iii) Klebsiella species that is resistant to carbapenem; (iv) Streptoccocus species that is resistant to an antibiotic selected from erythromycin, clindamycin, beta-lactam, macrolide, amoxicillin, azithromycin and penicillin; (v) Salmonella species that is resistant to an antibiotic selected from ceftriaxone, azithromycin and ciprofloxacin; (vi) Shigella species that is resistant to ciprofloxacin or azithromycin; (vii) Mycobacterium tuberculosis that is resistant to an antibiotic selected from Resistance to isoniazid (INH), rifampicin (RMP), fluoroquinolone, amikacin, kanamycin, capreomycin and azithromycin; (viii) Enterococcus species that is resistant to vancomycin; (ix) Enterobacteriaceae species that is resistant to an antibiotic selected from cephalosporin and carbapenem; (x) E. coli that is resistant to an antibiotic selected from trimethoprim, itrofurantoin, cefalexin and amoxicillin; (xi) Clostridium species that is resistant to metronidazole (MTZ), fluoroquinolone or carbapenem; (xii) Neisseria gonnorrhoea that is resistant to an antibiotic selected from cefixime, ceftriaxone, azithromycin and tetracycline; (xiii) Acinetoebacter baumannii that is resistant to an antibiotic selected from beta-lactam, meropenem and carbapenem; and (xiv) Campylobacter species that is resistant to ciprofloxacin or azithromycin.
13. The method of Embodiment 1, wherein the treatment of the infection treats or prevents in the subject a condition selected from vaginosis, meningitis, pneumonia, urinary tract infection, cystitis, nephritis, gastroenteritis, a skin infection, impetigo, erysipelas, cellulitis, septicaemia or sepsis in the subject.
14. The method of Embodiment 1, wherein the further disease or condition is a cancer; autoimmune disease or condition; or GI tract disease or condition.
15. The method of Embodiment 1, wherein the subject comprises bacteria (second bacteria) of one or more strains or species that are different to the first strain or species, wherein the genomes of the second bacteria do not comprise the target site, wherein the genomes of the second bacteria are not cut by the programmed nuclease in the subject, whereby second bacteria survive in the presence of the programmed nuclease in the patient; and wherein the therapy is efficacious in the presence of the second bacteria.

16. The method of Embodiment 15, wherein reduction in the second bacteria in patients is associated with reduced efficacy of the therapy.
17. The method of Embodiment 15, wherein the second bacteria are selected from the group consisting of *Akkermansia, Alistipes, Bacteroides, Barnesiella, Bifidobacterium, Clostridium, Collinsella, Enterococcus, Fusobacterium, Lactobacillus, Propionibacterium, Ruminococcus*, Segmented filamentous bacteria (SFB); *Veillonella, Prevotella, Escherichia* and *Streptococcus* bacteria.
18. The method of Embodiment 1, wherein the first bacteria are selected from the group consisting of *E. coli, C. dificile, V. cholera, Staphylococcus, Streptococcus pyogenes, Acinetobacter baumannii, Legionella, Pseudomonas aeruginosa* and *Klebsiella pneumoniae* bacteria.
19. The method of Embodiment 1, wherein the nuclease is a Cas nuclease, a meganuclease, a Transcription activator-like effector nuclease (TALEN) or zinc finger nuclease.
20. A method for treating a pathogenic bacterial infection in a cancer patient caused by bacteria (first bacteria) of a first species or strain, the method comprising selectively killing first bacteria comprised by the subject by cutting a target site comprised by the genomes of the first bacteria, wherein the cutting is carried out using a Cas nuclease that is programmed by guide RNA to cut the target site, wherein the method comprises administering an immunotherapy to the subject for treating cancer in the patient, wherein the nuclease treats the infection and the immunotherapy is efficacious in the presence of the programmed nuclease to treat the cancer.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine study, numerous equivalents to the specific procedures described herein. Such equivalents are considered to be within the scope of this invention and are covered by the claims. All publications and patent applications mentioned in the specification are indicative of the level of skill of those skilled in the art to which this invention pertains. All publications and patent applications and all US equivalent patent applications and patents are herein incorporated by reference to the same extent as if each individual publication or patent application was specifically and individually indicated to be incorporated by reference. The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps The term "or combinations thereof" or similar as used herein refers to all permutations and combinations of the listed items preceding the term. For example, "A, B, C, or combinations thereof is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

Any part of this disclosure may be read in combination with any other part of the disclosure, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

The present invention is described in more detail in the following non limiting Examples.

EXAMPLES

Precision Fast Bacteria Killing with Programmable Nucleases

The examples provide a method for fast and precision killing of *Escherichia coli* and *Clostridium dificile* strains. As a model programmable nuclease system, we used a CRISPR guided vector (CGV™) system to specifically target enterohemorrhagic *E. coli* (EHEC) and probiotic *coli* Nissle.

Example 1. Precision Killing of Target Strain Enterohemorrhagic *E. coli* (EHEC)

1.1. Design, Construction and Delivery of CRISPR Guided Vector (CGV) System Targeting *E. coli* (EHEC) ATCC43888.

The invention provides a CGV system to specifically target enterohemorrhagic *E. coli* (EHEC) ATCC43888 (a human fecal isolate obtained from the American Type Culture Collection). The CGV system comprises two vectors: (a) a vector containing a tracrRNA and the Cas9 protein from *Streptococcus pyogenes* (SpCas); (b) a vector containing a guide RNA (gRNA) that comprises a nucleotide sequence capable of hybridizing to a target sequence in the host cells to guide SpCas9 to the target sequence. To enable specific killing of *E. coli* (EHEC) ATCC43888, a particular sequence from the genome of this strain was chosen to target. Specifically, the sequence contains 20 nucleotides from the 23S ribosomal RNA gene from *E. coli* (EHEC)

ATCC43888. Additionally, the 5'-NGG protospacer adjacent motif (PAM) was located adjacent to the selected target sequence. The selected target sequence in the 23S rRNA gene can be found in Table 3.

1.2 Characterization of the CGV System Targeting *E. coli* (EHEC) ATCC43888.

Figure 1B:
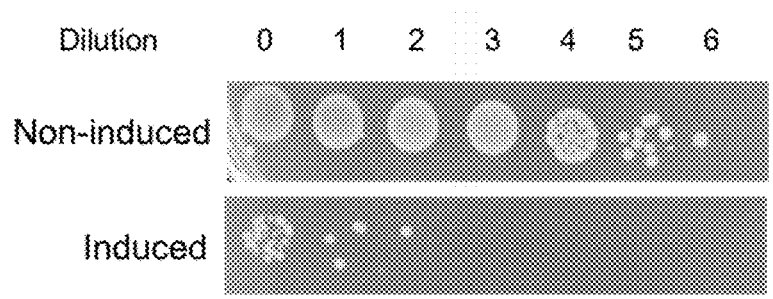

To establish the CGV system functionality in mediating sequence-specific killing in *E. coli* (EHEC) ATCC43888, the system was transformed into *E. coli* (EHEC) ATCC43888 cells. Overnight cultures were diluted 1:100 in fresh lysogeny broth (LB) and grown to mid-exponential phase OD600 ~0.6. The CRISPR system was induced by adding theophylline and arabinose (2 mM theophylline and 1% arabinose), and survival of the strain was followed over time by plating the cultures in serial dilutions every 15 minutes, for 1 h (FIG. 1B). CRISPR induction in *E. coli* (EHEC) surprisingly triggered a rapid killing of the cells, achieving 99.98% killing within 30 minutes of induction (FIG. 1A).

Example 2. In Vivo CRISPR Killing of Target Strain Enterohemorrhagic *E. coli* (EHEC) in *Galleria mellonella* Larvae In Vivo Infection Model 2.1. CRISPR Efficacy Against *E. coli* (EHEC) ATCC43888 Infections in *Galleria mellonella*

Figure 2:
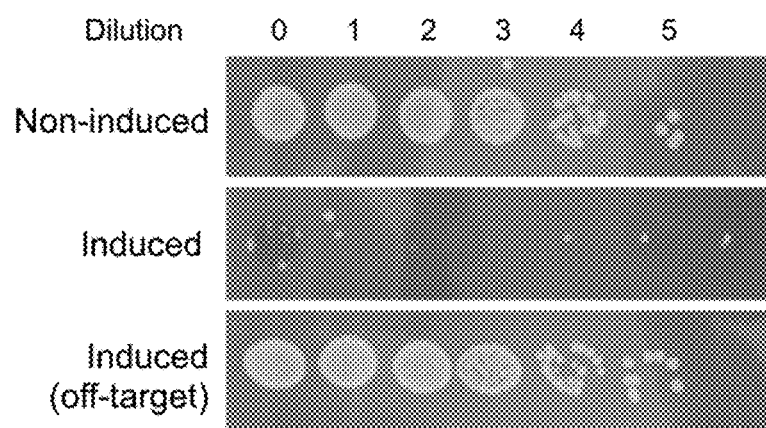
FIG. 2 shows CRISPR killing of target strain *Escherichia coli* (EHEC) ATCC43888 in *Galleria mellonella* larvae. *G. mellonella* larvae were delivered injections of bacteria behind the final left proleg. Approximately 1 h after the injection, CRISPR inducers were administered behind the final right proleg. Larvae were incubated at 37° C. for 2 h and sacrificed. Control bacteria carrying an off-target single guide RNA plasmid were also injected in the control group.
Figure 3:
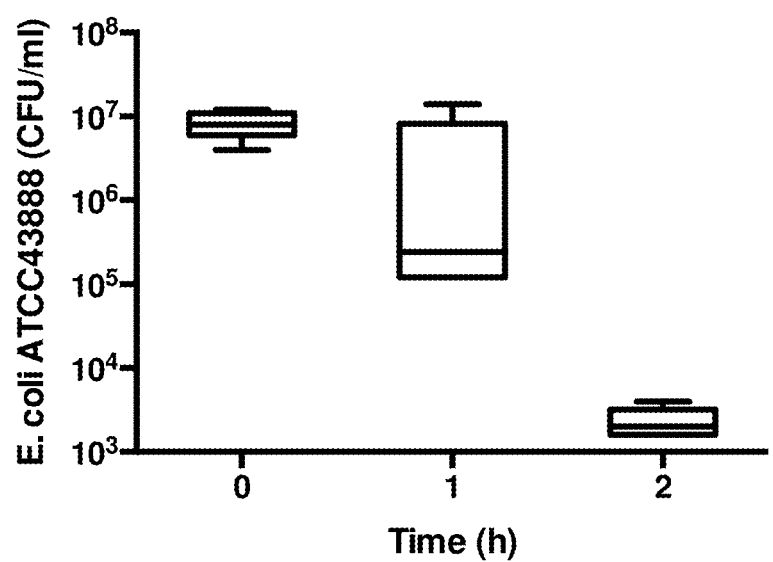
FIG. 3 shows *E. coli* ATCC43888 count over time.

CRISPR killing of target strain *E. coli* (EHEC) ATCC43888 was tested in *G. mellonella* in vivo infection model. To this aim, *G. mellonella* larvae were delivered injections of bacteria $10^8$ CFU *E. coli* (EHEC) ATCC43888 behind the final left proleg. Approximately 1 h after the injection, CRISPR inducers (2 mM theophylline and 1% arabinose) were administered behind the final right proleg. Larvae were incubated at 37° C. and they were sacrificed after 1 and 2 h after induction. As shown in FIGS. 2 and 3, CRISPR induction killed 99% of the population after 2 h, as compared to the off-target control.

2.2. Survival Curves of *G. mellonella* Larvae Infected with Enterohemorrhagic *E. coli* (EHEC).

Figure 4:
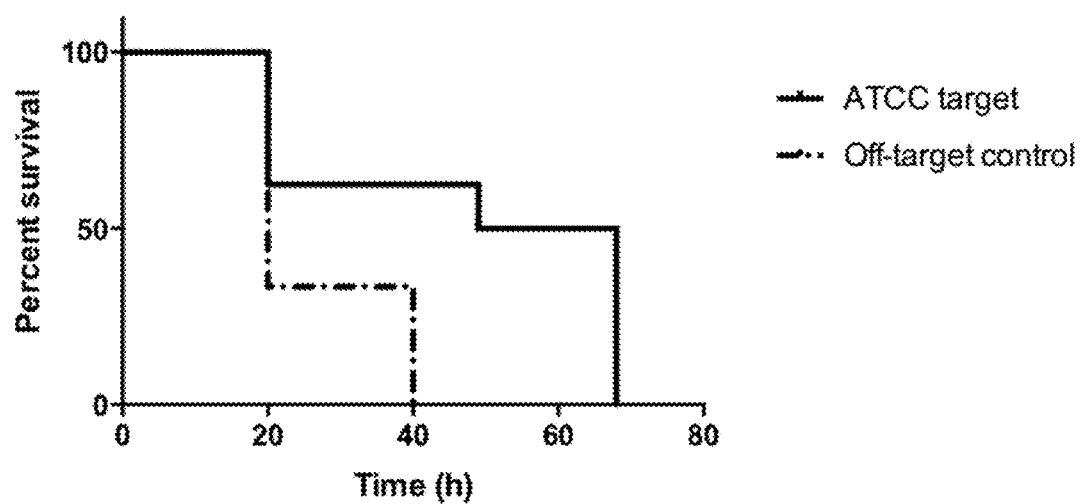
FIG. 4 shows Kaplan-Meier survival curves of *Galleria mellonella* larvae infected with *Escherichia coli* (EHEC) ATCC43888. CRISPR induction significantly improves survival of the larvae (black line) compared to the off-target control carrying an off-target single guide RNA plasmid (dashed line).

*G. mellonella* larvae were delivered injections of bacteria ($8\times10^4$ CFU *E. coli* ATCC43888) behind the final left proleg. Approximately 1 h after the injection, CRISPR inducers (2 mM theophylline and 1% arabinose) were administered behind the final right proleg. Larvae were incubated at 37° C. and survival was monitored for 115 h, with death indicated by lack of movement and unresponsiveness to touch. CRISPR killing of target strain *E. coli* (EHEC) ATCC43888 in *G. mellonella* larvae significantly improved survival of the larvae compared to the off-target control (FIG. 4) (log-rank test, P<0.03).

Example 3. Precision Killing of Target Strain Probiotic *E. coli* Nissle 1917

3.1. Design, Construction and Delivery of CRISPR Guided Vector (CGV) System Targeting *E. coli* Nissle 1917.

The invention provides a CGV system to specifically target *E. coli* Nissle 1917. The CGV system comprises two vectors: (a) a vector containing a tracrRNA and the Cas9 from *Streptococcus pyogenes* (SpCas); (b) a vector containing a guide RNA (gRNA) that comprises a nucleotide sequence capable of hybridizing to a target sequence in the host cells to guide SpCas9 to the target sequence. To enable specific killing of *E. coli* Nissle 1917, a specific sequence from the genome of this strain was chosen to target. Specifically, the sequence contains 20 nucleotides from the pks gene from *E. coli* Nissle 1917. Additionally, the 5'-NGG protospacer adjacent motif (PAM) was located adjacent to the selected target sequence. The selected target sequence in the pks gene can be found in Table 3.

Furthermore, a different genome target was selected to specifically kill *E. coli* Nissle 1917. The sequence contains 20 nucleotides from the yapH gene. Additionally, the 5'-NGG protospacer adjacent motif (PAM) was located adjacent to the selected target sequence. The selected target sequence in yapH gene can be found in Table 3.

3.2. Construction and Delivery of CRISPR Guided Vectors (CGV) Targeting *E. coli* Nissle 1917

Figure 5B:
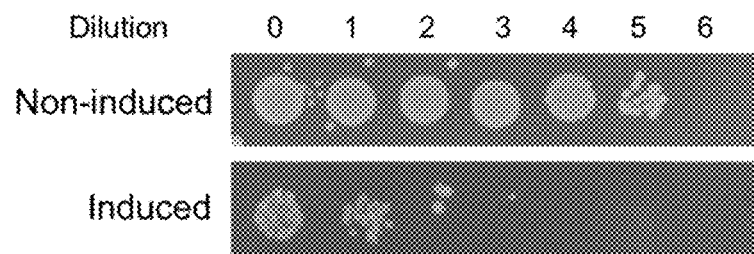
Figure 6B:
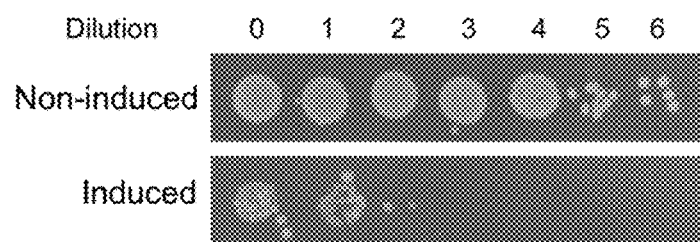

To establish CGVs functionality in mediating sequence-specific killing in *E. coli* Nissle 1917, the CGV system was transformed into *E. coli* Nissle 1917 cells. Overnight cultures were diluted 1:100 in fresh lysogeny broth (LB) and grown to mid-exponential phase OD600 ~0.6. The CRISPR system was induced by adding theophylline and arabinose (2 mM theophylline and 1% arabinose), and survival of the strain was followed over time by plating the cultures in serial dilutions every 15 minutes, for 3 h (FIGS. 5B and 6B). FIGS. 5B and 6A show CRISPR killing assay in *E. coli* Nissle 1917, targeting pks gene and yapH gene, respectively. In both cases, CRISPR induction triggers a rapid killing of *E. coli* Nissle 1917 cells, achieving 99.98% killing within only 15 minutes of induction.

Example 4. In Vitro CRISPR Killing of *Clostridium difficile* by Conjugative Plasmid Vectors and Cas3

This experiment involves the precision killing of *Clostridium difficile* using a gRNA-encoding CRISPR array that is delivered from a probiotic carrier bacterial species by conjugative plasmids as vectors (which we call CRISPR guided vectors (CGV™)). A carrier bacterium (*E. coli* donor strain containing the CRISPR guided vector (CGV™)) was mated with *Clostridium difficile* which was killed upon delivery of the CGV™ containing the designed array. This CGV™ harnessed the endogenous Cas3 machinery of *Clostridium difficile* 630Δerm. A 100% killing of *Clostridium difficile* cells was achieved.

Introduction

*Clostridium difficile* (*C. difficile*) is a spore-forming human opportunistic pathogen that can asymptomatically colonize the intestine of healthy individuals. The two main risk factors for contracting *C. difficile*-associated diseases, such as nosocomial diarrhea, are age and antibiotic treatment and can have fatal consequences. *C. difficile* 630Δerm, the subject of our study, is a well-characterized strain and it is widely used for the generation of mutant specimens.

Study Objectives

Objective 1: Delivery of CGVs by Conjugation.

A CRISPR guided vector (CGV) containing an array to specifically target and kill *C. difficile* was designed and assembled. The same CGV lacking the array was assembled to use as a control for conjugation efficiency. Both CGVs were transformed into the carrier strain *Escherichia coli* CA434, which was used as a donor strain to conjugate the plasmid into our strain of interest *C. difficile* 630Δerm.

Objective 2: Harnessing *Clostridium difficile* Endogenous Cas3 Machinery.

Upon transcription of the delivered CRISPR array in the recipient target strain *C. difficile*, the endogenous Cas3 was guided to cut its own DNA; leading to bacterial death.

Objective 3: Eradication of *Clostridium difficile* 630Δerm.

Achievement of efficient killing of transconjugant *C. difficile* cells using designed CGVs.

Materials and Methods
Bacterial Strains and Growth Conditions

*E. coli* strain CA434 was acquired from Chain Biotech. It was cultured on nutrient-rich media (2×YT) and grown overnight at 37° C. and 250 rpm. Medium was supplemented with 12.5 μg/mL of thiamphenicol when required to maintain the CGVs.

*Clostridium difficile* 630Δerm was grown on BHI agar supplemented with 5 g/L of yeast extract, 0.03% L-cystein, 250 ug/ml D-cycloserine and 8 ug/ml of cefoxitin (BHIS+CC). *C. difficile* was grown overnight in a Coy vinyl anaerobic cabinet in an atmosphere of 92% $N_2$, 6% $CO_2$ and 2% H2 at 37° C. The mating of the donor CA434 and *C. difficile* was grown on plain BHI agar to allow for growth of the donor strain. Thiamphenicol was added to BHIS+CC plates to a final concentration of 12.5 μg/mL for selection of transconjugants after mating. All plates were dried for 1.5 hours and transferred, along with the broth version of this medium, to the anaerobic chamber at least 3 hours before use.

CGV Transfer Procedures

Carrier cells of *E. coli* CA434 were obtained by electroporation of either of our CGVs (control vector pMTL84151-FJ797649 and CRISPR vector pMTL84151-cdCRISPR1). In order to do that, overnight cultures of *E. coli* CA434 were diluted 1:100 in fresh 2×YT medium without selection and grown to OD600 ~0.5. Then, they were made electrocompetent by standard procedures (Sharan et al., 2009). Electrocompetent cells were transformed with either plasmid pMTL84151-FJ797649 or pMTL84151-cdCRISPR1 and recovered in 2×YT for 1 h at 37° C. with shaking (250 rpm). Finally, they were plated on LB agar supplemented with 12.5 μg/mL thiamphenicol for selection of transformants. Transformants were grown in liquid 2×YT supplemented with 12.5 μg/mL thiamphenicol at 37° C. and 250 rpm for mating with *C. difficile*. 1 ml of donor cells was centrifuged at 4000×g for 2 minutes, supernatant removed and carefully washed with 400 μl of PBS. After a second centrifugation cycle the pellet was transferred to the anaerobic chamber for mating with *C. difficile* in BHI non-selective plates. *C. difficile* was prepared for mating following a modified protocol (Des Purdy et al., 2002). *C. difficile* 630Δerm was incubated overnight in selective BHIS+CC plates, from which, a scrape was inoculated overnight in 1 ml of non-selective BHI and incubated overnight for mating. 200 μl of that culture was used to resuspend the pelleted donor cells and mixed culture was plated in 20 μl spots on top of non-selective BHI plates. The mating was incubated 24h to allow for conjugation. After incubation, the whole plate was thoroughly scraped with a sterile inoculation loop, resuspended in BHI and serial dilutions were plated on BHI+CC plates to prevent growth of donor *E. coli* and on BHI+CC supplemented with thiamphenicol for additional selection of transconjugants. Single colonies were counted after 48 hours.

Results

Figure 7:
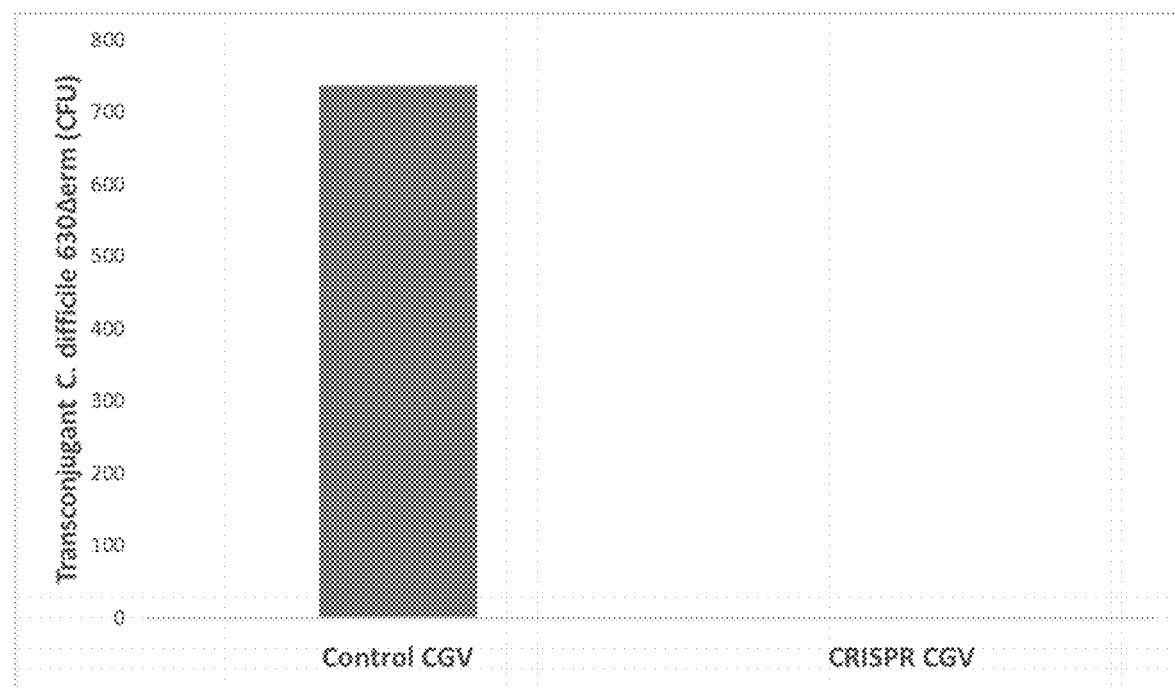
FIG. 7 shows complete killing of transconjugant *C. difficile*. The complete precision killing of *Clostridium difficile* using a gRNA-encoding CRISPR array that was delivered from a probiotic carrier bacterial species by conjugative plasmids as vectors is shown. A carrier bacterium (*E. coli* donor strain containing the vectors was mated with *Clostridium difficile* which was killed upon delivery of the designed array. This harnessed the endogenous Cas3 machinery of *Clostridium difficile*. A 100% killing of *Clostridium difficile* cells was achieved and is shown in this figure.

Replicates of BHI+CC+Thiamphenicol plates, selecting for *C. difficile* transconjugants carrying the control CGV, showed a consistent number of colonies resulting in about ~600-750 CFUs per mating experiment. For the mating of *C. difficile* with *E. coli* CA434 carrying the CGV with the CRISPR array the plates were empty, no colonies were observed. This translates into 100% killing of transconjugant *C. difficile* 630Δerm cells receiving the CRISPR array (see FIG. 7: Killing of transconjugant *C. difficile* 630Δerm).

DISCUSSION AND CONCLUSIONS

The results of this experiment show that we could successfully conjugate CGVs containing the desired CRISPR arrays into *C. difficile* 630Δerm from an *E. coli* carrier bacterium. We could also successfully harness *C. difficile* endogenous Cas3 machinery for very efficient CRISPR killing.

REFERENCES

Purdy D, O'Keeffe T A, Elmore M, Herbert M, McLeod A, Bokori-Brown M, Ostrowski A, Minton N P. (2002) Conjugative transfer of clostridial shuttle vectors from *Escherichia coli* to *Clostridium difficile* through circumvention of the restriction barrier. Molec. Microbiology 46(2), 439-452

Sharan, S. K., Thomason, L. C., Kuznetsov, S. G., and Court, D. L. (2009) Recombineering: a homologous recombination-based method of genetic engineering. Nat. Protoc. 4, 206-223

TABLE 1

Example Bacteria
Optionally, the bacteria are selected from this Table.

| | | | | |
|---|---|---|---|---|
| Abiotrophia | Acidocella | Actinomyces | Alkalilimnicola | Aquaspirillum |
| Abiotrophia defectiva | Acidocella aminolytica | Actinomyces bovis Actinomyces | Alkalilimnicola ehrlichii | Aquaspirillum polymorphum |
| Acaricomes | Acidocella facilis | denticolens | Alkaliphilus | Aquaspirillum |
| Acaricomes phytoseiuli | Acidomonas Acidomonas | Actinomyces europaeus | Alkaliphilus oremlandii | putridiconchylium Aquaspirillum |
| Acetitomaculum | methanolica | Actinomyces | Alkaliphilus | serpens |
| Acetitomaculum ruminis | Acidothermus Acidothermus | georgiae Actinomyces | transvaalensis Allochromatium | Aquimarina Aquimarina |
| Acetivibrio | cellulolyticus | gerencseriae | Allochromatium | latercula |
| Acetivibrio cellulolyticus | Acidovorax Acidovorax | Actinomyces hordeovulneris | vinosum Alloiococcus | Arcanobacterium Arcanobacterium |
| Acetivibrio | anthurii | Actinomyces | Alloiococcus otitis | haemolyticum |
| ethanolgignens | Acidovorax caeni | howellii | Allokutzneria | Arcanobacterium |
| Acetivibrio multivorans | Acidovorax cattleyae | Actinomyces hyovaginalis | Allokutzneria albata Altererythrobacter | pyogenes Archangium |
| Acetoanaerobium | Acidovorax citrulli | Actinomyces | Altererythrobacter | Archangium |
| Acetoanaerobium noterae | Acidovorax defluvii | israelii Actinomyces | ishigakiensis Altermonas | gephyra Arcobacter |
| Acetobacter | Acidovorax | johnsonii | Altermonas | Arcobacter butzleri |
| Acetobacter aceti | delafieldii | Actinomyces | haloplanktis | Arcobacter |
| Acetobacter cerevisiae | Acidovorax facilis Acidovorax | meyeri Actinomyces | Altermonas macleodii | cryaerophilus Arcobacter |
| Acetobacter | konjaci | naeslundii | Alysiella | halophilus |

TABLE 1-continued

Example Bacteria
Optionally, the bacteria are selected from this Table.

| | | | | |
|---|---|---|---|---|
| cibinongensis | Acidovorax | Actinomyces neuii | Alysiella crassa | Arcobacter |
| Acetobacter | temperans | Actinomyces | Alysiella filiformis | nitrofigilis |
| estunensis | Acidovorax | odontolyticus | Aminobacter | Arcobacter |
| Acetobacter | valerianellae | Actinomyces oris | Aminobacter | skirrowii |
| fabarum | Acinetobacter | Actinomyces | aganoensis | Arhodomonas |
| Acetobacter | Acinetobacter | radingae | Aminobacter | Arhodomonas |
| ghanensis | baumannii | Actinomyces | aminovorans | aquaeolei |
| Acetobacter | Acinetobacter | slackii | Aminobacter | Arsenophonus |
| indonesiensis | baylyi | Actinomyces | niigataensis | Arsenophonus |
| Acetobacter | Acinetobacter | turicensis | Aminobacterium | nasoniae |
| lovaniensis | bouvetii | Actinomyces | Aminobacterium | Arthrobacter |
| Acetobacter | Acinetobacter | viscosus | mobile | Arthrobacter agilis |
| malorum | calcoaceticus | Actinoplanes | Aminomonas | Arthrobacter albus |
| Acetobacter | Acinetobacter | Actinoplanes | Aminomonas | Arthrobacter |
| nitrogenifigens | gerneri | auranticolor | paucivorans | aurescens |
| Acetobacter oeni | Acinetobacter | Actinoplanes | Ammoniphilus | Arthrobacter |
| Acetobacter | haemolyticus | brasiliensis | Ammoniphilus | chlorophenolicus |
| orientalis | Acinetobacter | Actinoplanes | oxalaticus | Arthrobacter |
| Acetobacter | johnsonii | consettensis | Ammoniphilus | citreus |
| orleanensis | Acinetobacter junii | Actinoplanes | oxalivorans | Arthrobacter |
| Acetobacter | Acinetobacter | deccanensis | Amphibacillus | crystallopoietes |
| pasteurianus | lwoffi | Actinoplanes | Amphibacillus | Arthrobacter |
| Acetobacter | Acinetobacter | derwentensis | xylanus | cumminsii |
| pornorurn | parvus | Actinoplanes | Amphritea | Arthrobacter |
| Acetobacter | Acinetobacter | digitatis | Amphritea balenae | globiformis |
| senegalensis | radioresistens | Actinoplanes | Amphritea japonica | Arthrobacter |
| Acetobacter | Acinetobacter | durhamensis | Amycolatopsis | histidinolovorans |
| xylinus | schindleri | Actinoplanes | Amycolatopsis alba | Arthrobacter ilicis |
| Acetobacterium | Acinetobacter soli | ferrugineus | Amycolatopsis | Arthrobacter luteus |
| Acetobacterium | Acinetobacter | Actinoplanes | albidoflavus | Arthrobacter |
| bakii | tandoii | globisporus | Amycolatopsis | methylotrophus |
| Acetobacterium | Acinetobacter | Actinoplanes | azurea | Arthrobacter |
| carbinolicum | tjernbergiae | humidus | Amycolatopsis | mysorens |
| Acetobacterium | Acinetobacter | Actinoplanes | coloradensis | Arthrobacter |
| dehalogenans | towneri | italicus | Amycolatopsis | nicotianae |
| Acetobacterium | Acinetobacter | Actinoplanes | lurida | Arthrobacter |
| fimetarium | ursingii | liguriensis | Amycolatopsis | nicotinovorans |
| Acetobacterium | Acinetobacter | Actinoplanes | mediterranei | Arthrobacter |
| malicum | venetianus | lobatus | Amycolatopsis | oxydans |
| Acetobacterium | Acrocarpospora | Actinoplanes | rifamycinica | Arthrobacter |
| paludosum | Acrocarpospora | missouriensis | Amycolatopsis | pascens |
| Acetobacterium | corrugata | Actinoplanes | rubida | Arthrobacter |
| tundrae | Acrocarpospora | palleronii | Amycolatopsis | phenanthrenivorans |
| Acetobacterium | macrocephala | Actinoplanes | sulphurea | Arthrobacter |
| wieringae | Acrocarpospora | philippinensis | Amycolatopsis | polychromogenes |
| Acetobacterium | pleiomorpha | Actinoplanes | tolypomycina | Atrhrobacter |
| woodii | Actibacter | rectilineatus | Anabaena | protophormiae |
| Acetofilamentum | Actibacter | Actinoplanes | Anabaena cylindrica | Arthrobacter |
| Acetofilamentum | sediminis | regularis | Anabaena flosaquae | psychrolactophilus |
| rigidum | Actinoalloteichus | Actinoplanes | Anabaena variabilis | Arthrobacter |
| Acetohalobium | Actinoalloteichus | teichomyceticus | Anaeroarcus | ramosus |
| Acetohalobium | cyanogriseus | Actinoplanes | Anaeroarcus | Arthrobacter |
| arabaticum | Actinoalloteichus | utahensis | burkinensis | sulfonivorans |
| Acetomicrobium | hymeniacidonis | Actinopolyspora | Anaerobaculum | Arthrobacter |
| Acetomicrobium | Actinoalloteichus | Actinopolyspora | Anaerobaculum | sulfureus |
| faecale | spitiensis | halophila | mobile | Arthrobacter |
| Acetomicrobium | Actinobaccillus | Actinopolyspora | Anaerobiospirillum | uratoxydans |
| flavidum | Actinobacillus | mortivallis | Anaerobiospirillum | Arthrobacter |
| Acetonema | capsulatus | Actinosynnema | succiniciproducens | ureafaciens |
| Acetonema longum | Actinobacillus | Actinosynnema | Anaerobiospirillum | Arthrobacter |
| Acetothermus | delphinicola | mirum | thomasii | viscosus |
| Acetothermus | Actinobacillus | Actinotalea | Anaerococcus | Arthrobacter |
| paucivorans | hominis | Actinotalea | Anaerococcus | woluwensis |
| Acholeplasma | Actinobacillus | fermentans | hydrogenalis | Asaia |
| Acholeplasma | indolicus | Aerococcus | Anaerococcus | Asaia bogorensis |
| axanthum | Actinobacillus | Aerococcus | lactolyticus | Asanoa |
| Acholeplasma | lignieresii | sanguinicola | Anaerococcus | Asanoa ferruginea |
| brassicae | Actinobacillus | Aerococcus urinae | prevotii | Asticcacaulis |
| Acholeplasma | minor | Aerococcus | Anaerococcus | Asticcacaulis |
| cavigenitalium | Actinobacillus | urinaeequi | tetradius | biprosthecium |
| Acholeplasma | muris | Aerococcus | Anaerococcus | Asticcacaulis |
| equifetale | Actinobacillus | urinaehominis | vaginalis | excentricus |
| Acholeplasma | pleuropneumoniae | Aerococcus | Anaerofustis | Atopobacter |
| granularum | Actinobacillus | viridans | Anaerofustis | Atopobacter |
| Acholeplasma | porcinus | Aeromicrobium | stercorihominis | phocae |
| hippikon | Actinobacillus | Aeromicrobium | Anaeromusa | Atopobium |
| Acholeplasma | rossii | erythreum | Anaeromusa | Atopobium fossor |

TABLE 1-continued

Example Bacteria
Optionally, the bacteria are selected from this Table.

| | | | | |
|---|---|---|---|---|
| laidlawii | Actinobacillus | Aeromonas | acidaminophila | Atopobium |
| Acholeplasma | scotiae | Aeromonas | Anaeromyxobacter | minutum |
| modicum | Actinobacillus | allosaccharophila | Anaeromyxobacter | Atopobium |
| Acholeplasma | seminis | Aeromonas | dehalogenans | parvulum |
| morum | Actinobacillus | bestiarum | Anaerorhabdus | Atopobium rimae |
| Acholeplasma | succinogenes | Aeromonas caviae | Anaerorhabdus | Atopobium vaginae |
| multilocale | Actinobaccillus | Aeromonas | furcosa | Aureobacterium |
| Acholeplasma | suis | encheleia | Anaerosinus | Aureobacterium |
| oculi | Actinobacillus | Aeromonas | Anaerosinus | barkeri |
| Acholeplasma | ureae | enteropelogenes | glycerini | Aurobacterium |
| palmae | Actinobaculum | Aeromonas | Anaerovirgula | Aurobacterium |
| Acholeplasma | Actinobaculum | eucrenophila | Anaerovirgula | liquefaciens |
| parvum | massiliense | Aeromonas | multivorans | Avibacterium |
| Acholeplasma | Actinobaculum | ichthiosmia | Ancalomicrobium | Avibacterium avium |
| pleciae | schaalii | Aeromonas | Ancalomicrobium | Avibacterium |
| Acholeplasma | Actinobaculum | jandaei | adetum | gallinarum |
| vituli | suis | Aeromonas media | Ancylobacter | Avibacterium |
| Achromobacter | Actinomyces | Aeromonas | Ancylobacter | paragallinarum |
| Achromobacter | urinale | popoffii | aquaticus | Avibacterium |
| denitrificans | Actinocatenispora | Aeromonas sobria | Aneurinibacillus | volantium |
| Achromobacter | Actinocatenispora | Aeromonas veronii | Aneurinibacillus | Azoarcus |
| insolitus | rupis | Agrobacterium | aneurinilyticus | Azoarcus indigens |
| Achromobacter | Actinocatenispora | Agrobacterium | Aneurinibacillus | Azoarcus |
| piechaudii | thailandica | gelatinovorum | migulanus | tolulyticus |
| Achromobacter | Actinocatenispora | Agrococcus | Aneurinibacillus | Azoarcus |
| ruhlandii | sera | Agrococcus | thermoaerophilus | toluvorans |
| Achromobacter | Actinocorallia | citreus | Angiococcus | Azohydromonas |
| spanius | Actinocorallia | Agrococcus | Angiococcus | Azohydromonas |
| Acidaminobacter | aurantiaca | jenensis | disciformis | australica |
| Acidaminobacter | Actinocorallia | Agromonas | Angulomicrobium | Azohydromonas |
| hydrogenoformans | aurea | Agromonas | Angulomicrobium | lata |
| Acidaminococcus | Actinocorallia | oligotrophica | tetraedrale | Azomonas |
| Acidaminococcus | cavernae | Agromyces | Anoxybacillus | Azomonas agilis |
| fermentans | Actinocorallia | Agromyces | Anoxybacillus | Azomonas insignis |
| Acidaminococcus | glomerata | fucosus | pushchinoensis | Azomonas |
| intestini | Actinocorallia | Agromyces | Aquabacterium | macrocytogenes |
| Acidicaldus | herbida | hippuratus | Aquabacterium | Azorhizobium |
| Acidicaldus | Actinocorallia | Agromyces | commune | Azorhizobium |
| organivorans | libanotica | luteolus | Aquabacterium | caulinodans |
| Acidimicrobium | Actinocorallia | Agromyces | parvum | Azorhizophilus |
| Acidimicrobium | longicatena | mediolanus | | Azorhizophilus |
| ferrooxidans | Actinomadura | Agromyces | | paspali |
| Acidiphilium | Actinomadura alba | ramosus | | Azospirillum |
| Acidiphilium | Actinomadura | Agromyces | | Azospirillum |
| acidophilum | atramentaria | rhizospherae | | brasilense |
| Acidiphilium | Actinomadura | Akkermansia | | Azospirillum |
| angustum | bangladeshensis | Akkermansia | | halopraeferens |
| Acidiphilium | Actinomadura | muciniphila | | Azospirillum |
| cryptum | catellatispora | Albidiferax | | irakense |
| Acidiphilium | Actinomadura | Albidiferax | | Azotobacter |
| multivorum | chibensis | ferrireducens | | Azotobacter |
| Acidiphilium | Actinomadura | Albidovulum | | beijerinckii |
| organovorum | chokoriensis | Albidovulum | | Azotobacter |
| Acidiphilium | Actinomadura | inexpectatum | | chroococcum |
| rubrum | citrea | Alcaligenes | | Azotobacter |
| Acidisoma | Actinomadura | Alcaligenes | | nigricans |
| Acidisoma | coerulea | denitrificans | | Azotobacter |
| sibiricum | Actinomadura | Alcaligenes | | salinestris |
| Acidisoma tundrae | echinospora | faecalis | | Azotobacter |
| Acidisphaera | Actinomadura | Alcanivorax | | vinelandii |
| Acidisphaera | fibrosa | Alcanivorax | | |
| rubrifaciens | Actinomadura | borkumensis | | |
| Acidithiobacillus | formosensis | Alcanivorax | | |
| Acidithiobacillus | Actinomadura | jadensis | | |
| albertensis | hibisca | Algicola | | |
| Acidithiobacillus | Actinomadura | Algicola | | |
| caldus | kijaniata | bacteriolytica | | |
| Acidithiobacillus | Actinomadura | Alicyclobacillus | | |
| ferrooxidans | latina | Alicyclobacillus | | |
| Acidithiobacillus | Actinomadura | disulfidooxidans | | |
| thiooxidans | livida | Alicyclobacillus | | |
| Acidobacterium | Actinomadura | sendaiensis | | |
| Acidobacterium | luteofluorescens | Alicyclobacillus | | |
| capsulatum | Actinomadura | vulcanalis | | |
| | macra | Alishewanella | | |
| | Actinomadura | Alishewanella | | |
| | madurae | fetalis | | |

TABLE 1-continued

Example Bacteria
Optionally, the bacteria are selected from this Table.

|  |  |  |  |  |
|---|---|---|---|---|
|  | *Actinomadura oligospora* | *Alkalibacillus* |  |  |
|  | *Actinomadura pelletieri* | *Alkalibacillus haloalkaliphilus* |  |  |
|  | *Actinomadura rubrobrunea* |  |  |  |
|  | *Actinomadura rugatobispora* |  |  |  |
|  | *Actinomadura umbrina* |  |  |  |
|  | *Actinomadura verrucosospora* |  |  |  |
|  | *Actinomadura vinacea* |  |  |  |
|  | *Actinomadura viridilutea* |  |  |  |
|  | *Actinomadura viridis* |  |  |  |
|  | *Actinomadura yumaensis* |  |  |  |
| *Bacillus* [see below] | *Bacteroides* | *Bibersteinia* | *Borrelia* | *Brevinema* |
| *Bacteriovorax* | *Bacteroides* | *Bibersteinia trehalosi* | *Borrelia afzelii* | *Brevinema andersonii* |
| *Bacteriovorax stolpii* | *Bacteroides caccae* | *Bifidobacterium* | *Borrelia americana* | *Brevundimonas* |
|  | *Bacteroides coagulans* | *Bifidobacterium adolescentis* | *Borrelia burgdorferi* | *Brevundimonas alba* |
|  | *Bacteroides eggerthii* | *Bifidobacterium angulatum* | *Borrelia carolinensis* | *Brevundimonas aurantiaca* |
|  | *Bacteroides fragilis* | *Bifidobacterium animalis* | *Borrelia coriaceae* | *Brevundimonas diminuta* |
|  | *Bacteroides galacturonicus* | *Bifidobacterium asteroides* | *Borrelia garinii* | *Brevundimonas intermedia* |
|  | *Bacteroides helcogenes* | *Bifidobacterium bifidum* | *Borrelia japonica* | *Brevundimonas subvibrioides* |
|  | *Bacteroides ovatus* | *Bifidobacterium boum* | *Bosea* | *Brevundimonas vancanneytii* |
|  | *Bacteroides pectinophilus* | *Bifidobacterium breve* | *Bosea minatitlanensis* | *Brevundimonas variabilis* |
|  | *Bacteroides pyogenes* | *Bifidobacterium catenulatum* | *Bosea thiooxidans* | *Brevundimonas vesicularis* |
|  | *Bacteroides salyersiae* | *Bifidobacterium choerinum* | *Brachybacterium* | *Brochothrix* |
|  | *Bacteroides stercoris* | *Bifidobacterium coryneforme* | *Brachybacterium alimentarium* | *Brochothrix campestris* |
|  | *Bacteroides suis* | *Bifidobacterium cuniculi* | *Brachybacterium faecium* | *Brochothrix thermosphacta* |
|  | *Bacteroides tectus* | *Bifidobacterium dentium* | *Brachybacterium paraconglomeratum* | *Brucella* |
|  | *Bacteroides thetaiotaomicron* | *Bifidobacterium gallicum* | *Brachybacterium rhamnosum* | *Brucella canis* |
|  | *Bacteroides uniformis* | *Bifidobacterium gallinarum* | *Brachybacterium tyrofermentans* | *Brucella neotomae* |
|  | *Bacteroides ureolyticus* | *Bifidobacterium indicum* | *Brachyspira* | *Bryobacter* |
|  | *Bacteroides vulgatus* | *Bifidobacterium longum* | *Brachyspira alvinipulli* | *Bryobacter aggregatus* |
|  | *Balnearium* | *Bifidobacterium magnum* *Bifidobacterium* | *Brachyspira hyodysenteriae* | *Burkholderia* |
|  | *Balnearium lithotrophicum* | *merycicum* | *Brachyspira innocens* | *Burkholderia ambifaria* |
|  | *Balneatrix* | *Bifidobacterium minimum* | *Brachyspira murdochii* | *Burkholderia andropogonis* |
|  | *Balneatrix alpica* | *Bifidobacterium pseudocatenulatum* | *Brachyspira pilosicoli* | *Burkholderia anthina* |
|  | *Balneola* | *Bifidobacterium pseudolongum* | *Bradyrhizobium* | *Burkholderia caledonica* |
|  | *Balneola vulgaris* | *Bifidobacterium pullorum* | *Bradyrhizobium canariense* | *Burkholderia caryophylli* |
|  | *Barnesiella* | *Bifidobacterium ruminantium* | *Bradyrhizobium elkanii* | *Burkholderia cenocepacia* |
|  | *Barnesiella viscericola* | *Bifidobacterium saeculare* | *Bradyrhizobium japonicum* | *Burkholderia cepacia* |
|  | *Bartonella* | *Bifidobacterium subtile* | *Bradyrhizobium liaoningense* | *Burkholderia cocovenenans* |
|  | *Bartonella alsatica* | *Bifidobacterium thermophilum* | *Brenneria* | *Burkholderia dolosa* |
|  | *Bartonella bacilliformis* | *Bilophila* | *Brenneria alni* | *Burkholderia fungorum* |
|  | *Bartonella clarridgeiae* | *Bilophila wadsworthia* | *Brenneria nigrifluens* | *Burkholderia glathei* |
|  | *Bartonella doshiae* | *Biostraticola* | *Brenneria quercina* | *Burkholderia* |
|  | *Bartonella elizabethae* | *Biostraticola tofi* | *Brenneria quercina* |  |
|  | *Bartonella* | *Bizionia* | *Brenneria salicis* |  |
|  |  | *Bizionia argentinensis* | *Brevibacillus* |  |
|  |  |  | *Brevibacillus agri* |  |
|  |  |  | *Brevibacillus borstelensis* |  |

TABLE 1-continued

Example Bacteria
Optionally, the bacteria are selected from this Table.

| | | | |
|---|---|---|---|
| grahamii | Blastobacter | Brevibacillus brevis | glumae |
| Bartonella | Blastobacter capsulatus | Brevibacillus | Burkholderia |
| henselae | Blastobacter | centrosporus | graminis |
| Bartonella | denitrificans | Brevibacillus | Burkholderia |
| rochalimae | Blastococcus | choshinensis | kururiensis |
| Bartonella | Blastococcus | Brevibacillus | Burkholderia |
| vinsonii | aggregatus | invocatus | multivorans |
| Bavariicoccus | Blastococcus | Brevibacillus | Burkholderia |
| Bavariicoccus | saxobsidens | laterosporus | phenazinium |
| seileri | Blastochloris | Brevibacillus | Burkholderia |
| Bdellovibrio | Blastochloris | parabrevis | plantarii |
| Bdellovibrio | viridis | Brevibacillus | Burkholderia |
| bacteriovorus | Blastomonas | reuszeri | pyrrocinia |
| Bdellovibrio | Blastomonas | Brevibacterium | Burkholderia |
| exovorus | natatoria | Brevibacterium | silvatlantica |
| Beggiatoa | Blastopirellula | abidum | Burkholderia |
| Beggiatoa alba | Blastopirellula | Brevibacterium | stabilis |
| Beijerinckia | marina | album | Burkholderia |
| Beijerinckia | Blautia | Brevibacterium | thailandensis |
| derxii | Blautia coccoides | aurantiacum | Burkholderia |
| Beijerinckia | Blautia hansenii | Brevibacterium | tropica |
| fluminensis | Blautia producta | celere | Burkholderia |
| Beijerinckia | Blautia wexlerae | Brevibacterium | unamae |
| indica | Bogoriella | epidermidis | Burkholderia |
| Beijerinckia | Bogoriella | Brevibacterium | vietnamiensis |
| mobilis | caseilytica | frigoritolerans | Buttiauxella |
| Belliella | Bordetella | Brevibacterium | Buttiauxella |
| Belliella baltica | Bordetella avium | halotolerans | agrestis |
| Bellilinea | Bordetella | Brevibacterium | Buttiauxella |
| Bellilinea | bronchiseptica | iodinum | brennerae |
| caldifistulae | Bordetella hinzii | Brevibacterium | Buttiauxella |
| Belnapia | Bordetella holmesii | linens | ferragutiae |
| Belnapia | Bordetella parapertussis | Brevibacterium | Buttiauxella |
| moabensis | Bordetella pertussis | lyticum | gaviniae |
| Bergeriella | Bordetella petrii | Brevibacterium | Buttiauxella |
| Bergeriella | Bordetella trematum | mcbrellneri | izardii |
| denitrificans | | Brevibacterium | Buttiauxella |
| Beutenbergia | | otitidis | noackiae |
| Beutenbergia | | Brevibacterium | Buttiauxella |
| cavernae | | oxydans | warmboldiae |
| | | Brevibacterium | Butyrivibrio |
| | | paucivorans | Butyrivibrio |
| | | Brevibacterium | fibrisolvens |
| | | stationis | Butyrivibrio |
| | | | hungatei |
| | | | Butyrivibrio |
| | | | proteoclasticus |

Bacillus
| | | | | |
|---|---|---|---|---|
| B. acidiceler | B. aminovorans | B. glucanolyticus | B. taeanensis | B. lautus |
| B. acidicola | B. amylolyticus | B. gordonae | B. tequilensis | B. lehensis |
| B. acidiproducens | B. andreesenii | B. gottheilii | B. thermantarcticus | B. lentimorbus |
| B. acidocaldarius | B. aneurinilyticus | B. graminis | B. thermoaerophilus | B. lentus |
| B. acidoterrestris | B. anthracis | B. halmapalus | B. thermoamylovorans | B. licheniformis |
| B. aeolius | B. aquimaris | B. haloalkaliphilus | B. thermocatenulatus | B. ligniniphilus |
| B. aerius | B. arenosi | B. halochares | B. thermocloacae | B. litoralis |
| B. aerophilus | B. arseniciselenatis | B. halodenitrificans | B. thermocopriae | B. locisalis |
| B. agaradhaerens | B. arsenicus | B. halodurans | B. thermodenitrificans | B. luciferensis |
| B. agri | B. aurantiacus | B. halophilus | B. thermoglucosidasius | B. luteolus |
| B. aidingensis | B. arvi | B. halosaccharovorans | B. thermolactis | B. luteus |
| B. akibai | B. aryabhattai | B. hemicellulosilyticus | B. thermoleovorans | B. macauensis |
| B. alcalophilus | B. asahii | B. hemicentroti | B. thermophilus | B. macerans |
| B. algicola | B. atrophaeus | B. herbersteinensis | B. thermoruber | B. macquariensis |
| B. alginolyticus | B. axarquiensis | B. horikoshii | B. thermosphaericus | B. macyae |
| B. alkalidiazotrophicus | B. azotofixans | B. horneckiae | B. thiaminolyticus | B. malacitensis |
| B. alkalinitrilicus | B. azotoformans | B. horti | B. thioparans | B. mannanilyticus |
| B. alkalisediminis | B. badius | B. huizhouensis | B. thuringiensis | B. marisflavi |
| B. alkalitelluris | B. barbaricus | B. humi | B. tianshenii | B. marismortui |
| B. altitudinis | B. bataviensis | B. hwajinpoensis | B. trypoxylicola | B. marmarensis |
| B. alveayuensis | B. beijingensis | B. idriensis | B. tusciae | B. massiliensis |
| B. alvei | B. benzoevorans | B. indicus | B. validus | B. megaterium |
| B. amyloliquefaciens | B. beringensis | B. infantis | B. vallismortis | B. mesonae |
| B. a. subsp. amyloliquefaciens | B. berkeleyi | B. infernus | B. vedderi | B. methanolicus |
| B. a. subsp. plantarum | B. beveridgei | B. insolitus | B. velezensis | B. methylotrophicus |
| B. dipsosauri | B. bogoriensis | B. invictae | B. vietnamensis | B. migulanus |
| B. drentensis | B. boroniphilus | B. iranensis | B. vireti | B. mojavensis |
| B. edaphicus | B. borstelensis | B. isabeliae | B. vulcani | B. mucilaginosus |

TABLE 1-continued

Example Bacteria
Optionally, the bacteria are selected from this Table.

| | | | | |
|---|---|---|---|---|
| B. ehimensis | B. brevis Migula | B. isronensis | B. wakoensis | B. muralis |
| B. eiseniae | B. butanolivorans | B. jeotgali | B. weihenstephanensis | B. murimartini |
| B. enclensis | B. canaveralius | B. kaustophilus | B. xiamenensis | B. mycoides |
| B. endophyticus | B. carboniphilus | B. kobensis | B. xiaoxiensis | B. naganoensis |
| B. endoradicis | B. cecembensis | B. kochii | B. zhanjiangensis | B. nanhaiensis |
| B. farraginis | B. cellulosilyticus | B. kokeshiiformis | B. peoriae | B. nanhaiisediminis |
| B. fastidiosus | B. centrosporus | B. koreensis | B. persepolensis | B. nealsonii |
| B. fengqiuensis | B. cereus | B. korlensis | B. persicus | B. neidei |
| B. firmus | B. chagannorensis | B. kribbensis | B. pervagus | B. neizhouensis |
| B. flexus | B. chitinolyticus | B. krulwichiae | B. plakortidis | B. niabensis |
| B. foraminis | B. chondroitinus | B. laevolacticus | B. pocheonensis | B. niacini |
| B. fordii | B. choshinensis | B. larvae | B. polygoni | B. novalis |
| B. formosus | B. chungangensis | B. laterosporus | B. polymyxa | B. oceanisediminis |
| B. fortis | B. cibi | B. salexigens | B. popilliae | B. odysseyi |
| B. fumarioli | B. circulans | B. saliphilus | B. pseudalcalophilus | B. okhensis |
| B. funiculus | B. clarkii | B. schlegelii | B. pseudofirmus | B. okuhidensis |
| B. fusiformis | B. clausii | B. sediminis | B. pseudomycoides | B. oleronius |
| B. galactophilus | B. coagulans | B. selenatarsenatis | B. psychrodurans | B. oryzaecorticis |
| B. galactosidilyticus | B. coahuilensis | B. selenitireducens | B. psychrophilus | B. oshimensis |
| B. galliciensis | B. cohnii | B. seohaeanensis | B. psychrosaccharolyticus | B. pabuli |
| B. gelatini | B. composti | B. shacheensis | B. psychrotolerans | B. pakistanensis |
| B. gibsonii | B. curdlanolyticus | B. shackletonii | B. pulvifaciens | B. pallidus |
| B. ginsengi | B. cycloheptanicus | B. siamensis | B. pumilus | B. pallidus |
| B. ginsengihumi | B. cytotoxicus | B. silvestris | B. purgationiresistens | B. panacisoli |
| B. ginsengisoli | B. daliensis | B. simplex | B. pycnus | B. panaciterrae |
| B. globisporus | B. decisifrondis | B. siralis | B. qingdaonensis | B. pantothenticus |
| (eg, B. g. subsp. | B. decolorationis | B. smithii | B. qingshengii | B. parabrevis |
| Globisporus; | B. deserti | B. soli | B. reuszeri | B. paraflexus |
| or B. g. subsp. | | B. solimangrovi | B. rhizosphaerae | B. pasteurii |
| Marinus) | | B. solisalsi | B. rigui | B. patagoniensis |
| | | B. songklensis | B. ruris | |
| | | B. sonorensis | B. safensis | |
| | | B. sphaericus | B. salarius | |
| | | B. sporothermodurans | | |
| | | B. stearothermophilus | | |
| | | B. stratosphericus | | |
| | | B. subterraneus | | |
| | | B. subtilis | | |
| | | (eg, B. s. subsp. | | |
| | | Inaquosorum; | | |
| | | or B. s. subsp. | | |
| | | Spizizeni; | | |
| | | or B. s. subsp. | | |
| | | Subtilis) | | |

| | | | | |
|---|---|---|---|---|
| Caenimonas | Campylobacter | Cardiobacterium | Catenuloplanes | Curtobacterium |
| Caenimonas koreensis | Campylobacter coli | Cardiobacterium hominis | Catenuloplanes atrovinosus | Curtobacterium albidum |
| Caldalkalibacillus | Campylobacter concisus | Carnimonas | Catenuloplanes castaneus | Curtobacterium citreus |
| Caldalkalibacillus uzonensis | Campylobacter curvus | Carnimonas nigrificans | Catenuloplanes crispus | |
| Caldanaerobacter | Campylobacter fetus | Carnobacterium alterfunditum | Catenuloplanes indicus | |
| Caldanaerobacter subterraneus | Campylobacter gracilis | Carnobacterium divergens | Catenuloplanes japonicus | |
| Caldanaerobius | Campylobacter helveticus | Carnobacterium funditum | Catenuloplanes nepalensis | |
| Caldanaerobius fijiensis | Campylobacter hominis | Carnobacterium gallinarum | Catenuloplanes niger | |
| Caldanaerobius polysaccharolyticus | Campylobacter hyointestinalis | Carnobacterium maltaromaticum | Chryseobacterium | |
| Caldanaerobius zeae | Campylobacter jejuni | Carnobacterium mobile | Chryseobacterium balustinum | |
| Caldanaerovirga | Campylobacter lari | Carnobacterium viridans | Citrobacter | |
| Caldanaerovirga acetigignens | Campylobacter mucosalis | Caryophanon | C. amalonaticus | |
| Caldicellulosiruptor | Campylobacter rectus | Caryophanon latum | C. braakii | |
| Caldicellulosiruptor bescii | Campylobacter showae | Caryophanon tenue | C. diversus | |
| Caldicellulosiruptor kristjanssonii | Campylobacter sputorum | Catellatospora | C. farmeri | |
| Caldicellulosiruptor owensensis | Campylobacter upsaliensis | Catellatospora citrea | C. freundii | |
| | Capnocytophaga | Catellatospora methionotrophica | C. gillenii | |
| | Capnocytophaga canimorsus | Catenococcus | C. koseri | |
| | Capnocytophaga | | C. murliniae | |
| | | | C. pasteurii[1] | |
| | | | C. rodentium | |
| | | | C. sedlakii | |
| | | | C. werkmanii | |
| | | | C. youngae | |

TABLE 1-continued

Example Bacteria
Optionally, the bacteria are selected from this Table.

| | | | |
|---|---|---|---|
| | cynodegmi | Catenococcus | Clostridium |
| | Capnocytophaga | thiocycli | (see below) |
| | gingivalis | | Coccochloris |
| | Capnocytophaga | | Coccochloris |
| | granulosa | | elabens |
| | Capnocytophaga | | Corynebacterium |
| | haemolytica | | Corynebacterium |
| | Capnocytophaga | | flavescens |
| | ochracea | | Corynebacterium |
| | Capnocytophaga | | variabile |
| | sputigena | | |

Clostridium
Clostridium absonum, Clostridium aceticum, Clostridium acetireducens, Clostridium acetobutylicum, Clostridium acidisoli, Clostridium aciditolerans, Clostridium acidurici, Clostridium aerotolerans, Clostridium aestuarii, Clostridium akagii, Clostridium aldenense, Clostridium aldrichii, Clostridium algidicarni, Clostridium algidixylanolyticum, Clostridium algifaecis, Clostridium algoriphilum, Clostridium alkalicellulosi, Clostridium aminophilum, Clostridium aminovalericum, Clostridium amygdalinum, Clostridium amylolyticum, Clostridium arbusti, Clostridium arcticum, Clostridium argentinense, Clostridium asparagiforme, Clostridium aurantibutyricum, Clostridium autoethanogenum, Clostridium baratii, Clostridium barkeri, Clostridium bartlettii, Clostridium beijerinckii, Clostridium bifermentans, Clostridium bolteae, Clostridium bornimense, Clostridium botulinum, Clostridium bowmanii, Clostridium bryantii, Clostridium butyricum, Clostridium cadaveris, Clostridium caenicola, Clostridium caminithermale, Clostridium carboxidivorans, Clostridium carnis, Clostridium cavendishii, Clostridium celatum, Clostridium celerecrescens, Clostridium cellobioparum, Clostridium cellulofermentans, Clostridium cellulolyticum, Clostridium cellulosi, Clostridium cellulovorans, Clostridium chartatabidum, Clostridium chauvoei, Clostridium chromiireducens, Clostridium citroniae, Clostridium clariflavum, Clostridium clostridioforme, Clostridium coccoides, Clostridium cochlearium, Clostridium colletant, Clostridium colicanis, Clostridium colinum, Clostridium collagenovorans, Clostridium cylindrosporum, Clostridium difficile, Clostridium diolis, Clostridium disporicum, Clostridium drakei, Clostridium durum, Clostridium estertheticum, Clostridium estertheticum estertheticum, Clostridium estertheticum laramiense, Clostridium fallax, Clostridium felsineum, Clostridium fervidum, Clostridium fimetarium, Clostridium formicaceticum, Clostridium frigidicarnis, Clostridium frigoris, Clostridium ganghwense, Clostridium gasigenes, Clostridium ghonii, Clostridium glycolicum, Clostridium glycyrrhizinilyticum, Clostridium grantii, Clostridium haemolyticum, Clostridium halophilum, Clostridium hastiforme, Clostridium hathewayi, Clostridium herbivorans, Clostridium hiranonis, Clostridium histolyticum, Clostridium homopropionicum, Clostridium huakuii, Clostridium hungatei, Clostridium hydrogeniformans, Clostridium hydroxybenzoicum, Clostridium hylemonae, Clostridium jejuense, Clostridium indolis, Clostridium innocuum, Clostridium intestinale, Clostridium irregulare, Clostridium isatidis, Clostridium josui, Clostridium kluyveri, Clostridium lactatifermentans, Clostridium lacusfryxellense, Clostridium laramiense, Clostridium lavalense, Clostridium lentocellum, Clostridium lentoputrescens, Clostridium leptum, Clostridium limosum, Clostridium litorale, Clostridium lituseburense, Clostridium ljungdahlii, Clostridium lortetii, Clostridium lundense, Clostridium magnum, Clostridium malenominatum, Clostridium mangenotii, Clostridium mayombei, Clostridium methoxybenzovorans, Clostridium methylpentosum, Clostridium neopropionicum, Clostridium nexile, Clostridium nitrophenolicum, Clostridium novyi, Clostridium oceanicum, Clostridium orbiscindens, Clostridium oroticum, Clostridium oxalicum, Clostridium papyrosolvens, Clostridium paradoxum, Clostridium paraperfringens (Alias: C. welchii), Clostridium paraputrificum, Clostridium pascui, Clostridium pasteurianum, Clostridium peptidivorans, Clostridium perenne, Clostridium perfringens, Clostridium pfennigii, Clostridium phytofermentans, Clostridium piliforme, Clostridium polysaccharolyticum, Clostridium populeti, Clostridium propionicum, Clostridium proteoclasticum, Clostridium proteolyticum, Clostridium psychrophilum, Clostridium puniceum, Clostridium purinilyticum, Clostridium putrefaciens, Clostridium putrificum, Clostridium quercicolum, Clostridium quinii, Clostridium ramosum, Clostridium rectum, Clostridium roseum, Clostridium saccharobutylicum, Clostridium saccharogumia, Clostridium saccharolyticum, Clostridium saccharoperbutylacetonicum, Clostridium sardiniense, Clostridium sartagoforme, Clostridium scatologenes, Clostridium schirmacherense, Clostridium scindens, Clostridium septicum, Clostridium sordellii, Clostridium sphenoides, Clostridium spiroforme, Clostridium sporogenes, Clostridium sporosphaeroides, Clostridium stercorarium, Clostridium stercorarium leptospartum, Clostridium stercorarium stercorarium, Clostridium stercorarium thermolacticum, Clostridium sticklandii, Clostridium straminisolvens, Clostridium subterminale, Clostridium sufflavum, Clostridium sulfidigenes, Clostridium symbiosum, Clostridium tagluense, Clostridium tepidiprofundi, Clostridium termitidis, Clostridium tertium, Clostridium tetani, Clostridium tetanomorphum, Clostridium thermaceticum, Clostridium thermautotrophicum, Clostridium thermoalcaliphilum, Clostridium thermobutyricum, Clostridium thermocellum, Clostridium thermocopriae, Clostridium thermohydrosulfuricum, Clostridium thermolacticum, Clostridium thermopalmarium, Clostridium thermopapyrolyticum, Clostridium thermosaccharolyticum, Clostridium thermosuccinogenes, Clostridium thermosulfurigenes, Clostridium thiosulfatireducens, Clostridium tyrobutyricum, Clostridium uliginosum, Clostridium ultunense, Clostridium villosum, Clostridium vincentii, Clostridium viride, Clostridium xylanolyticum, Clostridium xylanovorans

| | | | |
|---|---|---|---|
| Dactylosporangium | Deinococcus | Delftia | Echinicola |
| Dactylosporangium aurantiacum | Deinococcus aerius | Delftia acidovorans | Echinicola pacifica |
| Dactylosporangium fulvum | Deinococcus apachensis | Desulfovibrio | Echinicola vietnamensis |
| Dactylosporangium matsuzakiense | Deinococcus aquaticus | Desulfovibrio desulfuricans | |
| Dactylosporangium | Deinococcus | Diplococcus | |
| | | Diplococcus | |

TABLE 1-continued

Example Bacteria
Optionally, the bacteria are selected from this Table.

| | | | |
|---|---|---|---|
| *roseum* | *aquatilis* | *pneumoniae* | |
| *Dactylosporangium thailandense* | *Deinococcus caeni* | | |
| *Dactylosporangium vinaceum* | *Deinococcus radiodurans* | | |
| | *Deinococcus radiophilus* | | |

| | | | |
|---|---|---|---|
| *Enterobacter* | *Enterobacter kobei* | *Faecalibacterium* | *Flavobacterium* |
| *E. aerogenes* | *E. ludwigii* | *Faecalibacterium prausnitzii* | *Flavobacterium antarcticum* |
| *E. amnigenus* | *E. mori* | *Fangia* | *Flavobacterium aquatile* |
| *E. agglomerans* | *E. nimipressuralis* | *Fangia hongkongensis* | *Flavobacterium aquidurense* |
| *E. arachidis* | *E. oryzae* | *Fastidiosipila* | *Flavobacterium balustinum* |
| *E. asburiae* | *E. pulveris* | *Fastidiosipila sanguinis* | *Flavobacterium croceum* |
| *E. cancerogenous* | *E. pyrinus* | *Fusobacterium* | *Flavobacterium cucumis* |
| *E. cloacae* | *E. radicincitans* | *Fusobacterium nucleatum* | *Flavobacterium daejeonense* |
| *E. cowanii* | *E. taylorae* | | *Flavobacterium defluvii* |
| *E. dissolvens* | *E. turicensis* | | *Flavobacterium degerlachei* |
| *E. gergoviae* | *E. sakazakii* | | *Flavobacterium denitrificans* |
| *E. helveticus* | *Enterobacter soli* | | *Flavobacterium filum* |
| *E. hormaechei* | *Enterococcus* | | *Flavobacterium flevense* |
| *E. intermedius* | *Enterococcus durans* | | *Flavobacterium frigidarium* |
| | *Enterococcus faecalis* | | *Flavobacterium mizutaii* |
| | *Enterococcus faecium* | | *Flavobacterium okeanokoites* |
| | *Erwinia* | | |
| | *Erwinia hapontici* | | |
| | *Escherichia* | | |
| | *Escherichia coli* | | |

| | | | |
|---|---|---|---|
| *Gaetbulibacter* | *Haemophilus* | *Ideonella* | *Janibacter* |
| *Gaetbulibacter saemankumensis* | *Haemophilus aegyptius* | *Ideonella azotifigens* | *Janibacter anophelis* |
| *Gallibacterium* | *Haemophilus aphrophilus* | *Idiomarina* | *Janibacter corallicola* |
| *Gallibacterium anatis* | *Haemophilus felis* | *Idiomarina abyssalis* | *Janibacter limosus* |
| *Gallicola* | *Haemophilus gallinariim* | *Idiomarina baltica* | *Janibacter melonis* |
| *Gallicola barnesae* | *Haemophilus haemolyticus* | *Idiomarina fontislapidosi* | *Janibacter terrae* |
| *Garciella* | *Haemophilus influenzae* | *Idiomarina loihiensis* | *Jannaschia* |
| *Garciella nitratireducens* | *Haemophilus paracuniculus* | *Idiomarina ramblicola* | *Jannaschia cystaugens* |
| *Geobacillus* | *Haemophilus parahaemolyticus* | *Idiomarina seosinensis* | *Jannaschia helgolandensis* |
| *Geobacillus thermoglucosidasius* | *Haemophilus parainfluenzae* | *Idiomarina zobellii* | *Jannaschia pohangensis* |
| *Geobacillus stearothermophilus* | *Haemophilus paraphrohaemolyticus* | *Ignatzschineria* | *Jannaschia rubra* |
| *Geobacter* | *Haemophilus parasuis* | *Ignatzschineria larvae* | *Janthinobacterium* |
| *Geobacter bemidjiensis* | *Haemophilus pittmaniae* | *Ignavigranum* | *Janthinobacterium agaricidamnosum* |
| *Geobacter bremensis* | *Hafnia* | *Ignavigranum ruoffiae* | *Janthinobacterium lividum* |
| *Geobacter chapellei* | *Hafnia alvei* | *Ilumatobacter* | *Jejuia* |
| *Geobacter grbiciae* | *Hahella* | *Ilumatobacter fluminis* | *Jejuia pallidilutea* |
| *Geobacter hydrogenophilus* | *Hahella ganghwensis* | *Ilyobacter* | *Jeotgalibacillus* |
| *Geobacter lovleyi* | *Halalkalibacillus* | *Ilyobacter delafieldii* | *Jeotgalibacillus alimentarius* |
| *Geobacter metallireducens* | *Halalkalibacillus halophilus* | *Ilyobacter insuetus* | *Jeotgalicoccus* |
| *Geobacter pelophilus* | *Helicobacter* | *Ilyobacter polytropus* | *Jeotgalicoccus halotolerans* |
| *Geobacter pickeringii* | *Helicobacter pylori* | *Ilyobacter tartaricus* | |
| *Geobacter sulfurreducens* | | | |
| *Geodermatophilus* | | | |
| *Geodermatophilus obscurus* | | | |
| *Gluconacetobacter* | | | |
| *Gluconacetobacter xylinus* | | | |
| *Gordonia* | | | |
| *Gordonia* | | | |

TABLE 1-continued

Example Bacteria
Optionally, the bacteria are selected from this Table.

| | | | | |
|---|---|---|---|---|
| *rubripertincta* | | | | |
| *Kaistia* | *Labedella* | *Listeria ivanovii* | *Micrococcus* | *Nesterenkonia* |
| *Kaistia adipata* | *Labedella gwakjiensis* | *L. marthii* | *Micrococcus luteus* | *Nesterenkonia holobia* |
| *Kaistia soli* | *Labrenzia* | *L. monocytogenes* | *Micrococcus lylae* | *Nocardia* |
| *Kangiella* | *Labrenzia aggregata* | *L. newyorkensis* | *Moraxella* | *Nocardia argentinensis* |
| *Kangiella aquimarina* | *Labrenzia alba* | *L. riparia* | *Moraxella bovis* | *Nocardia corallina* |
| *Kangiella koreensis* | *Labrenzia alexandrii* | *L. rocourtiae* | *Moraxella* | *Nocardia nonliquefaciens* |
| *Kerstersia* | *Labrenzia marina* | *L. seeligeri* | *Moraxella osloensis* | *Nocardia otitidiscaviarum* |
| *Kerstersia gyiorum* | *Labrys* | *L. weihenstephanensis* | *Nakamurella* | |
| *Kiloniella* | *Labrys methylaminiphilus* | *L. welshimeri* | *Nakamurella multipartita* | |
| *Kiloniella laminariae* | *Labrys miyagiensis* | *Listonella* | *Nannocystis* | |
| *Klebsiella* | *Labrys monachus* | *Listonella anguillarum* | *Nannocystis pusilla* | |
| *K. granulomatis* | *Labrys okinawensis* | *Macrococcus* | *Natranaerobius* | |
| *K. oxytoca* | *Labrys portucalensis* | *Macrococcus bovicus* | *Natranaerobius thermophilus* | |
| *K. pneumoniae* | *Lactobacillus* [see below] | *Marinobacter* | *Natranaerobius trueperi* | |
| *K. terrigena* | *Laceyella* | *Marinobacter algicola* | *Naxibacter* | |
| *K. variicola* | *Laceyella putida* | *Marinobacter bryozoorum* | *Naxibacter alkalitolerans* | |
| *Kluyvera* | *Lechevalieria* | *Marinobacter flavimaris* | *Neisseria* | |
| *Kluyvera ascorbata* | *Lechevalieria aerocolonigenes* | *Meiothermus* | *Neisseria cinerea* | |
| *Kocuria* | *Legionella* [see below] | *Meiothermus ruber* | *Neisseria denitrificans* | |
| *Kocuria roasea* | *Listeria* | *Methylophilus* | *Neisseria gonorrhoeae* | |
| *Kocuria varians* | *L. aquatica* | *Methylophilus methylotrophus* | *Neisseria lactamica* | |
| *Kurthia* | *L. booriae* | *Microbacterium* | *Neisseria mucosa* | |
| *Kurthia zopfii* | *L. cornellensis* | *Microbacterium ammoniaphilum* | *Neisseria sicca* | |
| | *L. fleischmannii* | *Microbacterium arborescens* | *Neisseria subflava* | |
| | *L. floridensis* | *Microbacterium liquefaciens* | *Neptunomonas* | |
| | *L. grandensis* | *Microbacterium oxydans* | *Neptunomonas japonica* | |
| | *L. grayi* | | | |
| | *L. innocua* | | | |

| | | | | |
|---|---|---|---|---|
| *Lactobacillus* | | | | |
| *L. acetotolerans* | *L. catenaformis* | *L. mali* | *L. parakefiri* | *L. sakei* |
| *L. acidifarinae* | *L. ceti* | *L. manihotivorans* | *L. paralimentarius* | *L. salivarius* |
| *L. acidipiscis* | *L. coleohominis* | *L. mindensis* | *L. paraplantarum* | *L. sanfranciscensis* |
| *L. acidophilus* | *L. collinoides* | *L. mucosae* | *L. pentosus* | *L. satsumensis* |
| *Lactobacillus agilis* | *L. composti* | *L. murinus* | *L. perolens* | *L. secaliphilus* |
| *L. algidus* | *L. concavus* | *L. nagelii* | *L. plantarum* | *L. sharpeae* |
| *L. alimentarius* | *L. coryniformis* | *L. namurensis* | *L. pontis* | *L. siliginis* |
| *L. amylolyticus* | *L. crispatus* | *L. nantensis* | *L. protectus* | *L. spicheri* |
| *L. amylophilus* | *L. crustorum* | *L. oligofermentans* | *L. psittaci* | *L. suebicus* |
| *L. amylotrophicus* | *L. curvatus* | *L. oris* | *L. rennini* | *L. thailandensis* |
| *L. amylovorus* | *L. delbrueckii* subsp. *bulgaricus* | *L. panis* | *L. reuteri* | *L. ultunensis* |
| *L. animalis* | *L. delbrueckii* subsp. *delbrueckii* | *L. pantheris* | *L. rhamnosus* | *L. vaccinostercus* |
| *L. antri* | *L. delbrueckii* subsp. *lactis* | *L. parabrevis* | *L. rimae* | *L. vaginalis* |
| *L. apodemi* | *L. dextrinicus* | *L. parabuchneri* | *L. rogosae* | *L. versmoldensis* |
| *L. aviarius* | *L. diolivorans* | *L. paracasei* | *L. rossiae* | *L. vini* |
| *L. bifermentans* | *L. equi* | *L. paracollinoides* | *L. ruminis* | *L. vitulinus* |
| *L. brevis* | *L. equigenerosi* | *L. parafarraginis* | *L. saerimneri* | *L. zeae* |
| *L. buchneri* | *L. farraginis* | *L. homohiochii* | *L. jensenii* | *L. zymae* |
| *L. camelliae* | *L. farciminis* | *L. iners* | *L. johnsonii* | *L. gastricus* |
| *L. casei* | *L. fermentum* | *L. ingluviei* | *L. kalixensis* | *L. ghanensis* |
| *L. kitasatonis* | *L. fornicalis* | *L. intestinalis* | *L. kefiranofaciens* | *L. graminis* |
| *L. kunkeei* | *L. fructivorans* | *L. fuchuensis* | *L. kefiri* | *L. hammesii* |
| *L. leichmannii* | *L. frumenti* | *L. gallinarum* | *L. kimchii* | *L. hamsteri* |
| *L. lindneri* | | *L. gasseri* | *L. helveticus* | *L. harbinensis* |
| *L. malefermentans* | | | *L. hilgardii* | *L. hayakitensis* |

| | | | | |
|---|---|---|---|---|
| *Legionella* | | | | |
| *Legionella adelaidensis* | *Legionella drancourtii* | *Candidatus Legionella jeonii* | *Legionella quinlivanii* | |
| *Legionella anisa* | *Legionella dresdenensis* | *Legionella jordanis* | *Legionella rowbothamii* | |
| *Legionella beliardensis* | *Legionella drozanskii* | *Legionella lansingensis* | *Legionella rubrilucens* | |
| *Legionella* | | | | |

TABLE 1-continued

Example Bacteria
Optionally, the bacteria are selected from this Table.

| | | | |
|---|---|---|---|
| birminghamensis | Legionella dumoffii | Legionella londiniensis | Legionella sainthelensi |
| Legionella bozemanae | Legionella erythra | Legionella longbeachae | Legionella santicrucis |
| Legionella brunensis | Legionella fairfieldensis | Legionella lytica | Legionella shakespearei |
| Legionella busanensis | Legionella fallonii | Legionella maceachernii | Legionella spiritensis |
| Legionella cardiaca | Legionella feeleii | Legionella massiliensis | Legionella steelei |
| Legionella cherrii | Legionella geestiana | Legionella micdadei | Legionella steigerwaltii |
| Legionella cincinnatiensis | Legionella genomospecies | Legionella monrovica | Legionella taurinensis |
| Legionella clemsonensis | Legionella gormanii | Legionella moravica | Legionella tucsonensis |
| Legionella donaldsonii | Legionella gratiana | Legionella nagasakiensis | Legionella tunisiensis |
| | Legionella gresilensis | Legionella nautarum | Legionella wadsworthii |
| | Legionella hackeliae | Legionella norrlandica | Legionella waltersii |
| | Legionella impletisoli | Legionella oakridgensis | Legionella worsleiensis |
| | Legionella israelensis | Legionella parisiensis | Legionella yabuuchiae |
| | Legionella jamestowniensis | Legionella pittsburghensis | |
| | | Legionella pneumophila | |
| | | Legionella quateirensis | |
| Oceanibulbus | Paenibacillus | Prevotella | Quadrisphaera |
| Oceanibulbus indolifex | Paenibacillus thiaminolyticus | Prevotella albensis | Quadrisphaera granulorum |
| Oceanicaulis | Pantoea | Prevotella amnii | Quatrionicoccus |
| Oceanicaulis alexandrii | Pantoea agglomerans | Prevotella bergensis | Quatrionicoccus australiensis |
| Oceanicola | Paracoccus | Prevotella bivia | Quinella |
| Oceanicola batsensis | Paracoccus alcaliphilus | Prevotella brevis | Quinella ovalis |
| Oceanicola granulosus | Paucimonas | Prevotella bryantii | Ralstonia |
| Oceanicola nanhaiensis | Paucimonas lemoignei | Prevotella buccae | Ralstonia eutropha |
| Oceanimonas | Pectobacterium | Prevotella buccalis | Ralstonia insidiosa |
| Oceanimonas baumannii | Pectobacterium aroidearum | Prevotella copri | Ralstonia mannitolilytica |
| Oceaniserpentilla | Pectobacterium atrosepticum | Prevotella dentalis | Ralstonia pickettii |
| Oceaniserpentilla haliotis | Pectobacterium betavasculorum | Prevotella denticola | Ralstonia pseudosolanacearum |
| Oceanisphaera | Pectobacterium cacticida | Prevotella disiens | Ralstonia syzygii |
| Oceanisphaera donghaensis | Pectobacterium carnegieana | Prevotella histicola | Ralstonia solanacearum |
| Oceanisphaera litoralis | Pectobacterium carotovorum | Prevotella intermedia | Ramlibacter |
| Oceanithermus | Pectobacterium chrysanthemi | Prevotella maculosa | Ramlibacter henchirensis |
| Oceanithermus desulfurans | Pectobacterium cypripedii | Prevotella marshii | Ramlibacter tataouinensis |
| Oceanithermus profundus | Pectobacterium rhapontici | Prevotella melaninogenica | Raoultella |
| Oceanobacillus | Pectobacterium wasabiae | Prevotella micans | Raoultella ornithinolytica |
| Oceanobacillus caeni | Planococcus | Prevotella multiformis | Raoultella planticola |
| Oceanospirillum | Planococcus citreus | Prevotella nigrescens | Raoultella terrigena |
| Oceanospirillum linum | Planomicrobium | Prevotella oralis | Rathayibacter |
| | Planomicrobium okeanokoites | Prevotella oris | Rathayibacter caricis |
| | Plesiomonas | Prevotella oulorum | Rathayibacter festucae |
| | Plesiomonas shigelloides | Prevotella pallens | Rathayibacter iranicus |
| | Proteus | Prevotella salivae | Rathayibacter rathayi |
| | Proteus vulgaris | Prevotella stercorea | Rathayibacter toxicus |
| | | Prevotella tannerae | |
| | | Prevotella | |

TABLE 1-continued

Example Bacteria
Optionally, the bacteria are selected from this Table.

| | | | timonensis | Rathayibacter |
| | | | Prevotella | tritici |
| | | | veroralis | Rhodobacter |
| | | | Providencia | Rhodobacter |
| | | | Providencia | sphaeroides |
| | | | stuartii | Ruegeria |
| | | | Pseudomonas | Ruegeria |
| | | | Pseudomonas | gelatinovorans |
| | | | aeruginosa | |
| | | | Pseudomonas | |
| | | | alcaligenes | |
| | | | Pseudomonas | |
| | | | anguillispetica | |
| | | | Pseudomonas | |
| | | | fluorescens | |
| | | | Pseudoalteromonas | |
| | | | haloplanktis | |
| | | | Pseudomonas | |
| | | | mendocina | |
| | | | Pseudomonas | |
| | | | pseudoalcaligenes | |
| | | | Pseudomonas | |
| | | | putida | |
| | | | Pseudomonas | |
| | | | tutzeri | |
| | | | Pseudomonas | |
| | | | syringae | |
| | | | Psychrobacter | |
| | | | Psychrobacter | |
| | | | faecalis | |
| | | | Psychrobacter | |
| | | | phenylpyruvicus | |
| Saccharococcus | Sagittula | Sanguibacter | Stenotrophomonas | Tatlockia |
| Saccharococcus thermophilus | Sagittula stellata | Sanguibacter keddieii | Stenotrophomonas maltophilia | Tatlockia maceachernii |
| Saccharomonospora | Salegentibacter | Sanguibacter | Streptococcus | Tatlockia |
| Saccharomonospora azurea | Salegentibacter salegens | suarezii | [also see below] | micdadei |
| Saccharomonospora cyanea | Salimicrobium | Saprospira | Streptomyces | Tenacibaculum |
| Saccharomonospora viridis | Salimicrobium album | Saprospira grandis | Streptomyces achromogenes | Tenacibaculum amylolyticum |
| Saccharophagus | Salinibacter | Sarcina | Streptomyces cesalbus | Tenacibaculum discolor |
| Saccharophagus degradans | Salinibacter ruber | Sarcina maxima | Streptomyces | Tenacibaculum |
| Saccharopolyspora | Salinicoccus | Sarcina ventriculi | cescaepitosus | gallaicum |
| Saccharopolyspora erythraea | Salinicoccus alkaliphilus | Sebaldella | Streptomyces cesdiastaticus | Tenacibaculum lutimaris |
| Saccharopolyspora gregorii | Salinicoccus | Sebaldella termitidis | Streptomyces | Tenacibaculum |
| Saccharopolyspora hirsuta | Salinicoccus hispanicus | Serratia | cesexfoliatus | mesophilum |
| Saccharopolyspora hordei | Salinicoccus roseus | Serratia fonticola | Streptomyces | Tenacibaculum |
| Saccharopolyspora rectivirgula | Salinispora | Serratia marcescens | fimbriatus | skagerrakense |
| Saccharopolyspora spinosa | Salinispora arenicola | Sphaerotilus | Streptomyces fradiae | Tepidanaerobacter |
| Saccharopolyspora taberi | Salinispora tropica | Sphaerotilus natans | Streptomyces fulvissimus | Tepidanaerobacter syntrophicus |
| Saccharothrix | Salinivibrio | Sphingobacterium | Streptomyces griseoruber | Tepidibacter |
| Saccharothrix australiensis | Salinivibrio costicola | Sphingobacterium multivorum | Streptomyces griseus | Tepidibacter formicigenes |
| Saccharothrix coeruleofusca | Salmonella | Staphylococcus [see below] | Streptomyces lavendulae | Tepidibacter thalassicus |
| Saccharothrix espanaensis | Salmonella bongori | | Streptomyces phaeochromogenes | Thermus |
| Saccharothrix longispora | Salmonella enterica | | Streptomyces thermodiastaticus | Thermus aquaticus |
| Saccharothrix mutabilis | Salmonella subterranea | | Streptomyces tubercidicus | Thermus filiformis |
| Saccharothrix syringae | Salmonella typhi | | | Thermus thermophilus |

TABLE 1-continued

Example Bacteria
Optionally, the bacteria are selected from this Table.

*Saccharothrix tangerinus*
*Saccharothrix texasensis*

| *Staphylococcus* | | | |
|---|---|---|---|
| *S. arlettae* | *S. equorum* | *S. microti* | *S. schleiferi* |
| *S. agnetis* | *S. felis* | *S. muscae* | *S. sciuri* |
| *S. aureus* | *S. fleurettii* | *S. nepalensis* | *S. simiae* |
| *S. auricularis* | *S. gallinarum* | *S. pasteuri* | *S. simulans* |
| *S. capitis* | *S. haemolyticus* | *S. petrasii* | *S. stepanovicii* |
| *S. caprae* | *S. hominis* | *S. pettenkoferi* | *S. succinus* |
| *S. carnosus* | *S. hyicus* | *S. piscifermentans* | *S. vitulinus* |
| *S. caseolyticus* | *S. intermedius* | *S. pseudintermedius* | *S. warneri* |
| *S. chromogenes* | *S. kloosii* | *S. pseudolugdunensis* | *S. xylosus* |
| *S. cohnii* | *S. leei* | *S. pulvereri* | |
| *S. condimenti* | *S. lentus* | *S. rostri* | |
| *S. delphini* | *S. lugdunensis* | *S. saccharolyticus* | |
| *S. devriesei* | *S. lutrae* | *S. saprophyticus* | |
| *S. epidermidis* | *S. lyticans* | | |
| | *S. massiliensis* | | |

| *Streptococcus* | | | |
|---|---|---|---|
| *Streptococcus agalactiae* | *Streptococcus infantarius* | *Streptococcus orisratti* | *Streptococcus thermophilus* |
| *Streptococcus anginosus* | *Streptococcus iniae* | *Streptococcus parasanguinis* | *Streptococcus sanguinis* |
| *Streptococcus bovis* | *Streptococcus intermedius* | *Streptococcus peroris* | *Streptococcus sobrinus* |
| *Streptococcus canis* | *Streptococcus lactarius* | *Streptococcus pneumoniae* | *Streptococcus suis* |
| *Streptococcus constellatus* | *Streptococcus milleri* | *Streptococcus pseudopneumoniae* | *Streptococcus uberis* |
| *Streptococcus downei* | *Streptococcus mitis* | *Streptococcus pyogenes* | *Streptococcus vestibularis* |
| *Streptococcus dysgalactiae* | *Streptococcus mutans* | *Streptococcus ratti* | *Streptococcus viridans* |
| *Streptococcus equines* | *Streptococcus oralis* | *Streptococcus salivariu* | *Streptococcus zooepidemicus* |
| *Streptococcus faecalis* | *Streptococcus tigurinus* | | |
| *Streptococcus ferus* | | | |

| | | | | |
|---|---|---|---|---|
| *Uliginosibacterium* | *Vagococcus* | *Vibrio* | *Virgibacillus* | *Xanthobacter* |
| *Uliginosibacterium gangwonense* | *Vagococcus carniphilus* | *Vibrio aerogenes* | *Virgibacillus halodenitrificans* | *Xanthobacter agilis* |
| *Ulvibacter* | *Vagococcus elongatus* | *Vibrio aestuarianus* | *Virgibacillus pantothenticus* | *Xanthobacter aminoxidans* |
| *Ulvibacter litoralis* | *Vagococcus fessus* | *Vibrio albensis* | *Weissella* | *Xanthobacter autotrophicus* |
| *Umezawaea* | *Vagococcus fluvialis* | *Vibrio alginolyticus* | *Weissella cibaria* | *Xanthobacter flavus* |
| *Umezawaea tangerina* | *Vagococcus lutrae* | *Vibrio campbellii* | *Weissella confusa* | *Xanthobacter tagetidis* |
| *Undibacterium* | *Vagococcus salmoninarum* | *Vibrio cholerae* | *Weissella halotolerans* | *Xanthobacter viscosus* |
| *Undibacterium pigrum* | *Variovorax* | *Vibrio cincinnatiensis* | *Weissella hellenica* | *Xanthomonas* |
| *Ureaplasma* | *Variovorax boronicumulans* | *Vibrio coralliilyticus* | *Weissella kandleri* | *Xanthomonas albilineans* |
| *Ureaplasma urealyticum* | *Variovorax dokdonensis* | *Vibrio cyclitrophicus* | *Weissella koreensis* | *Xanthomonas alfalfae* |
| *Ureibacillus* | *Variovorax paradoxus* | *Vibrio diazotrophicus* | *Weissella minor* | *Xanthomonas arboricola* |
| *Ureibacillus composti* | *Variovorax soli* | *Vibrio fluvialis* | *Weissella paramesenteroides* | *Xanthomonas axonopodis* |
| *Ureibacillus suwonensis* | *Veillonella* | *Vibrio furnissii* | *Weissella soli* | *Xanthomonas campestris* |
| *Ureibacillus terrenus* | *Veillonella atypica* | *Vibrio gazogenes* | *Weissella thailandensis* | *Xanthomonas citri* |
| *Ureibacillus thermophilus* | *Veillonella caviae* | *Vibrio halioticoli* | *Weissella viridescens* | *Xanthomonas codiaei* |
| *Ureibacillus thermosphaericus* | *Veillonella criceti* | *Vibrio harveyi* | *Williamsia* | *Xanthomonas cucurbitae* |
| | *Veillonella dispar* | *Vibrio ichthyoenteri* | *Williamsia marianensis* | *Xanthomonas euvesicatoria* |
| | *Veillonella montpellierensis* | *Vibrio mediterranei* | *Williamsia maris* | *Xanthomonas fragariae* |
| | *Veillonella parvula* | *Vibrio metschnikovii* | *Williamsia serinedens* | *Xanthomonas fuscans* |
| | *Veillonella ratti* | *Vibrio mytili* | *Winogradskyella* | *Xanthomonas gardneri* |
| | *Veillonella rodentium* | *Vibrio natriegens* | *Winogradskyella thalassocola* | *Xanthomonas* |
| | *Venenivibrio* | *Vibrio navarrensis* | *Wolbachia* | |
| | *Venenivibrio stagnispumantis* | *Vibrio nereis* | *Wolbachia persica* | |
| | *Verminephrobacter* | *Vibrio nigripulchritudo* | *Wolinella* | |
| | *Verminephrobacter eiseniae* | *Vibrio ordalii* | *Wolinella succinogenes* | |
| | *Verrucomicrobium* | *Vibrio orientalis* | | |
| | *Verrucomicrobium spinosum* | *Vibrio parahaemolyticus* | | |

TABLE 1-continued

Example Bacteria
Optionally, the bacteria are selected from this Table.

| | | | | |
|---|---|---|---|---|
| | | Vibrio pectenicida | Zobellia | hortorum |
| | | Vibrio penaeicida | Zobellia | Xanthomonas |
| | | Vibrio | galactanivorans | hyacinthi |
| | | proteolyticus | Zobellia uliginosa | Xanthomonas |
| | | Vibrio shilonii | Zoogloea | perforans |
| | | Vibrio splendidus | Zoogloea | Xanthomonas |
| | | Vibrio tubiashii | ramigera | phaseoli |
| | | Vibrio vulnificus | Zoogloea | Xanthomonas |
| | | | resiniphila | pisi |
| | | | | Xanthomonas |
| | | | | populi |
| | | | | Xanthomonas |
| | | | | theicola |
| | | | | Xanthomonas |
| | | | | translucens |
| | | | | Xanthomonas |
| | | | | vesicatoria |
| | | | | Xylella |
| | | | | Xylella |
| | | | | fastidiosa |
| | | | | Xylophilus |
| | | | | Xylophilus |
| | | | | ampelinus |
| Xenophilus | Yangia | Yersinia | Zooshikella | Zobellella |
| Xenophilus azovorans | Yangia pacifica | mollaretii | Zooshikella | Zobellella |
| Xenorhabdus | Yaniella | Yersinia | ganghwensis | denitrificans |
| Xenorhabdus beddingii | Yaniella flava | philomiragia | Zunongwangia | Zobellella |
| Xenorhabdus bovienii | Yaniella | Yersinia pestis | Zunongwangia | taiwanensis |
| Xenorhabdus | halotolerans | Yersinia | profunda | Zeaxanthinibacter |
| cabanillasii | Yeosuana | pseudotuberculosis | Zymobacter | Zeaxanthinibacter |
| Xenorhabdus doucetiae | Yeosuana | Yersinia rohdei | Zymobacter | enoshimensis |
| Xenorhabdus griffiniae | aromativorans | Yersinia ruckeri | palmae | Zhihengliuella |
| Xenorhabdus hominickii | Yersinia | Yokenella | Zymomonas | Zhihengliuella |
| Xenorhabdus | Yersinia aldovae | Yokenella | Zymomonas | halotolerans |
| koppenhoeferi | Yersinia bercovieri | regensburgei | mobilis | Xylanibacterium |
| Xenorhabdus | Yersinia | Yonghaparkia | Zymophilus | Xylanibacterium |
| nematophila | enterocolitica | Yonghaparkia | Zymophilus | ulmi |
| Xenorhabdus poinarii | Yersinia | alkaliphila | paucivorans | |
| Xylanibacter | entomophaga | Zavarzinia | Zymophilus | |
| Xylanibacter oryzae | Yersinia | Zavarzinia | raffinosivorans | |
| | frederiksenii | compransoris | | |
| | Yersinia intermedia | | | |
| | Yersinia kristensenii | | | |

TABLE 2

Systemic inflammatory response syndrome

| Finding | Value |
|---|---|
| Temperature | <36° C. (96.8° F.) or >38° C. (100.4° F.) |
| Heart rate | >90/min |
| Respiratory rate | >20/min or PaCO2 < 32 mmHg (4.3 kPa) |
| WBC | <4 × 10$^9$/L (<4000/mm$^3$), >12 × 10$^9$/L (>12,000/mm$^3$), or 10% bands |

TABLE 3

Sequences of genomic targets to selectively CRISPR-kill E. coli strains. The 3-bp PAM are shown in bold type (ie, tgg, agg and cgg). Expected SpCas9-gRNA cleavage sites are indicated by vertical arrows (3 bp upstream of the PAM).

| Target strain | Target gene | Genomic target sequence |
|---|---|---|
| E. coli (EHEC) ATCC43888 | 23S ribosomal RNA | taggtgaagtccctcgcggatgg (SEQ ID NO: 1) |
| E. coli Nissle 1917 | yapH | cacccgcattacctttatgcagg (SEQ ID NO: 2) |
| E. coli Nisslte 1917 | pks | gcgcgggtgtggttgtgcttcgg (SEQ ID NO: 3) |

TABLE 4

Sequences of aenomic targets & Cas to selectively CRISPR-kill C dificile (a) Overview of design spacers in pMTL84151 - cdCRISPR1 targeting C. difficile

| Gene | Name | PAM | target |
|------|------|-----|--------|
| tcdA | TA2 | CCA | ACACCTTAACCCAGCCATAGAGTCTGATAATAACTTC (SEQ ID NO: 4) |
| tcdB | TB2 | CCA | GACTTATTTGAGTCTATAGAGAAACCTAGTTCAGTAA (SEQ ID NO: 5) |
| rRNA-1 | TRR1 | CCT | TCGACGACTTCTTCCAAAAGGTTAGATAATCGGCTTC (SEQ ID NO: 6) |
| rRNA-2 | TRR2 | CCA | GTACAGGATGGACCCGCGTCTGATTAGCTAGTTGGTA (SEQ ID NO: 7) |
| gyrA | TAR1 | CCA | TCCTCATGGAGATACTGCTGTTTATTATGCTATGGTA (SEQ ID NO: 8) |

(b) Cas3 sequence (SEQ ID NO: 9)
Sequence

TCAAATAAATTGGTCTATTTCATTACTTATAAGCACACCTTTACCAAATA
TCTGTTTTGTATGCTTATTTTCGTATATATCATATTTATATAAAAGTATT
TTTAAATCTTCAAGACCTTTCACCTGTATGTCAATTACATTTTGTTTAGC
TTTATATATTGGTAAATTTACAGTTTTTTTAATTATCTCTCTTCTTGCTT
TTTTTCTCTTAGACTTTATTTTATTTATCAATTGTCTATCATCATTACTA
TATGCATTTATAAGCTCTTGTCCCAACTCTTCATAATCTTTGATTAAAGT
TTCTTCAATTTTATTATATATATCCTCTGGAATTACTGTATATCCTTCAA
TATTTCTAAGTATATTTTGTGCATCTTTAGAACCTAAACTATATGGCGTT
ATAGTATCTAAAATATTTAAAGCACTGGTAAATCTCTTTTCAAAAGCTGT
ACCTTCTAGACTTTCTTTAGAGTATAGTATCTTAACCATTTCTACCTTAT
ATTTTTCTTTCATCTTCACACATTCTTTTCCATTTATAAAGTTTTCAGT
AGCTCAAGTCCTTTTTCTACAATATCCTTATCATAAATACTACCTATTCC
TGTAGCTTTTTCTGTATATATAAATATATTTGGGCTATTTTCTTCATACT
CACGACTTCTATAACATCTACCAAATCGTTGAAATAGACTGTCAAGTGTT
GAATTTTCTGTATGAAGCTCATCAAAATCAATATCAAGGGATGCTTCCAC
TAATTGTGTAGTAATCCAAATACCATTACTATCACTATCTGCAAATTCTT
TTATATATTTTTCTAATTTTGCTCTATCTTCTTGTATATACATAGAATGT
AAAAGATTTAAGTTGACATCTATTCCTTTTGGCTTAACTATTTCTTCTAT
TAACTCATATTTTTCTACAGCACTTTTAACTGTATTTACTATTACAAGAA
CTTTTTTATTCATTCCACTTTGTATTATTTTACCTAAGTTTTCATCTATT
GAATTTTCTACAATAGACACACAATGTCTTATTTTTTCTGTATTACATGT
CAATTCAGCTAAGTTACTATTCATTACACCTCTTTTTTTTAATTCATCTA
TATATATGGTTGGCATAGTAGCTGTCATTATCATAAATCTGCCACCTATC
TTATGTATCATTTCTATACCTTTTACCAATACAGCTGCTATTTCTGGTGA
ATATGCTTGTATCTCATCTATTACTACTTTTGAATATGCTAATGTTGAGT
ACACTTTTTCATACCCTCTATACAAAAAAGGAAATTTAAATATTTGGTCT
ATTGTAGAAAATGTCAGTTTGCAAGATAATAACTTTGCTAAATCTACAAT
CTCACTTGAATTTTCTTGATTACTTTCTTCTAGATAATCTATTGCTGTTG
AATGTAACAAACCTAAGAATGTATCATTTGATTCTCCAACTCCAACTATA
TTTTTTGCTCTATCAAATAATGCATTTATACTTACTCTTAATGGAAGTGT
AAAAAATGCCTTGTCTTTATCTATCCAAATTAAGGCAGTTTCTGTTTTTC
CCATTCCTGTAGGTGCAATCAGTATTATATTCTTATTTCTATTAGATTTA
GCAAATGATTGAGCCTCTCTCAAACTACCAAACTCTTTCATTAAATAATT
TTCTGTCTGTTCTCCTATATTTATAACATTATTGCATTCCACAACTTCAT
GAGCAGAAGCACTGTGGTCTAATCTATGTAGTATTCCTTTTAACATAATA
TATAAATTATAGTACTTGTGATTTTTATCTATTCTTTTTTCTACACTTTG
TAGATATACTTTACTCAATTTTTCTGTTTTTATTGGATATCTAACTTTAA
ATTCATGCTGTAGTTCATAAACTTTATTTATTAAATCTTCATCTAATATT
TTTTGTATTAAATTTTTAAAATCTTTATCTATAAAGATATCTCTTTCATG
ATGATATACAATAACTTGATTTAATACTGCTCTAAGTTCTTTATTTTTTT
TCCTGTCTATATAACTATAATCAATAAATGCAGGAGAAAGATAATTATGG
CCTACATTATTTTCTAAATGAGTTACTATTTAGGTTCATTTATTTTAGT
ATCCATTCTGCTTTTTATTAACTCTTGAAACGGTGAAAATGCTTTTCCAA
TATCATGAAATTCTATAACAAAGTCAAGTAATTGCCAAAATATCTCCTCT
TCTAGAAAATCTAAGCTATTTATATTTTTCCATAACTTTCTCTTAATAC
ATTCATTTGTTTTAAAAGTTCATCAGTATGTTCTCTAAGTGTTTCCACTG
GATTAGATTTAGCATATAACAT

TABLE 4

Sequences of Cas9 used to selectively kill E coli.

SEQ ID NO: 10 (Cas9 nucleotide sequence)

ATGGATAAGAAATACTCAATAGGCTTAGATATCGGCACAAATAGCGTCGG
ATGGGCGGTGATCACTGATGAATATAAGGTTCCGTCTAAAAAGTTCAAGG
TTCTGGGAAATACAGACCGCCACAGTATCAAAAAAATCTTATAGGGGCT
CTTTTATTTGACAGTGGAGAGACAGCGGAAGCGACTCGTCTCAAACGGAC
AGCTCGTAGAAGGTATACACGTCGGAAGAATCGTATTTGTTATCTACAGG
AGATTTTTTCAAATGAGATGGCGAAAGTAGATGATAGTTTCTTTCATCGA
CTTGAAGAGTCTTTTTTGGTGGAAGAAGACAAGAAGCATGAACGTCATCC
TATTTTTGGAAATATAGTAGATGAAGTTGCTTATCATGAGAAATATCCAA
CTATCTATCATCTGCGAAAAAATTGGTAGATTCTACTGATAAAGCGGAT
TTGCGCTTAATCTATTTGGCCTTAGCGCATATGATTAAGTTTCGTGGTCA
TTTTTTGATTGAGGGAGATTTAAATCCTGATAATAGTGATGTGGACAAAC
TATTTATCCAGTTGGTACAAACCTACAATCAATTATTTGAAGAAACCCT
ATTAACGCAAGTGGAGTAGATGCTAAAGCGATTCTTTCTGCACGATTGAG
TAAATCAAGACGATTAGAAAATCTCATTGCTCAGCTCCCCGGTGAGAAGA

TABLE 4-continued

Sequences of Cas9 used to selectively kill *E coli*.

AAAATGGCTTATTTGGGAATCTCATTGCTTTGTCATTGGGTTTGACCCCT

AATTTTAAATCAAATTTTGATTTGGCAGAAGATGCTAAATTACAGCTTTC

AAAAGATACTTACGATGATGATTTAGATAATTTATTGGCGCAAATTGGAG

ATCAATATGCTGATTTGTTTTGGCAGCTAAGAATTTATCAGATGCTATT

TTACTTTCAGATATCCTAAGAGTAAATACTGAAATAACTAAGGCTCCCCT

ATCAGCTTCAATGATTAAACGCTACGATGAACATCATCAAGACTTGACTC

TTTTAAAAGCTTTAGTTCGACAACAACTTCCAGAAAAGTATAAAGAAATC

TTTTTTGATCAATCAAAAAACGGATATGCAGGTTATATTGATGGGGGAGC

TAGCCAAGAAGAATTTTATAAATTTATCAAACCAATTTTAGAAAAAATGG

ATGGTACTGAGGAATTATTGGTGAAACTAAATCGTGAAGATTTGCTGCGC

AAGCAACGGACCTTTGACAACGGCTCTATTCCCCATCAAATTCACTTGGG

TGAGCTGCATGCTATTTTGAGAAGACAAGAAGACTTTTATCCATTTTTAA

AAGACAATCGTGAGAAGATTGAAAAAATCTTGACTTTTCGAATTCCTTAT

TATGTTGGTCCATTGGCGCGTGGCAATAGTCGTTTTGCATGGATGACTCG

GAAGTCTGAAGAAACAATTACCCCATGGAATTTTGAAGAAGTTGTCGATA

AAGGTGCTTCAGCTCAATCATTTATTGAACGCATGACAAACTTTGATAAA

AATCTTCCAAATGAAAAGTACTACCAAAACATAGTTTGCTTTATGAGTA

TTTTACGGTTTATAACGAATTGACAAAGGTCAAATATGTTACTGAAGGAA

TGCGAAAACCAGCATTTCTTTCAGGTGAACAGAAGAAAGCCATTGTTGAT

TTACTCTTCAAAACAAATCGAAAAGTAACCGTTAAGCAATTAAAAGAAGA

TTATTTCAAAAAAATAGAATGTTTTGATAGTGTTGAAATTTCAGGAGTTG

AAGATAGATTTAATGCTTCATTAGGTACCTACCATGATTTGCTAAAAATT

ATTAAAGATAAAGATTTTTTGGATAATGAAGAAAATGAAGATATCTTAGA

GGATATTGTTTTAACATTGACCTTATTTGAAGATAGGGAGATGATTGAGG

AAAGACTTAAAACATATGCTCACCTCTTTGATGATAAGGTGATGAAACAG

CTTAAACGTCGCCGTTATACTGGTTGGGGACGTTTGTCTCGAAAATTGAT

TAATGGTATTAGGGATAAGCAATCTGGCAAAACAATATTAGATTTTTGA

AATCAGATGGTTTTGCCAATCGCAATTTTATGCAGCTGATCCATGATGAT

AGTTTGACATTTAAAGAAGACATTCAAAAAGCACAAGTGTCTGGACAAGG

CGATAGTTTACATGAACATATTGCAAATTTAGCTGGTAGCCCTGCTATTA

AAAAAGGTATTTTACAGACTGTAAAAGTTGTTGATGAATTGGTCAAAGTA

ATGGGGCGGCATAAGCCAGAAAATATCGTTATTGAAATGGCACGTGAAAA

TCAGACAACTCAAAAGGGCCAGAAAAATTCGCGAGAGCGTATGAAACGAA

TCGAAGAAGGTATCAAAGAATTAGGAAGTCAGATTCTTAAAGAGCATCCT

GTTGAAAATACTCAATTGCAAAATGAAAAGCTCTATCTCTATTATCTCCA

AAATGGAAGAGACATGTATGTGGACCAAGAATTAGATATTAATCGTTTAA

GTGATTATGATGTCGATCACATTGTTCCACAAAGTTTCCTTAAAGACGAT

TCAATAGACAATAAGGTCTTAACGCGTTCTGATAAAAATCGTGGTAAATC

GGATAACGTTCCAAGTGAAGAAGTAGTCAAAAAGATGAAAAACTATTGGA

GACAACTTCTAAACGCCAAGTTAATCACTCAACGTAAGTTTGATAATTTA

ACGAAAGCTGAACGTGGAGGTTTGAGTGAACTTGATAAAGCTGGTTTTAT

CAAACGCCAATTGGTTGAAACTCGCCAAATCACTAAGCATGTGGCACAAA

TTTTGGATAGTCGCATGAATACTAAATACGATGAAAATGATAAACTTATT

CGAGAGGTTAAAGTGATTACCTTAAAATCTAAATTAGTTTCTGACTTCCG

AAAAGATTTCCAATTCTATAAAGTACGTGAGATTAACAATTACCATCATG

CCCATGATGCGTATCTAAATGCCGTCGTTGGAACTGCTTTGATTAAGAAA

TATCCAAAACTTGAATCGGAGTTTGTCTATGGTGATTATAAAGTTTATGA

TGTTCGTAAAATGATTGCTAAGTCTGAGCAAGAAATAGGCAAAGCAACCG

CAAAATATTTCTTTTACTCTAATATCATGAACTTCTTCAAAACAGAAATT

ACACTTGCAAATGGAGAGATTCGCAAACGCCCTCTAATCGAAACTAATGG

GGAAACTGGAGAAATTGTCTGGGATAAAGGGCGAGATTTTGCCACAGTGC

GCAAAGTATTGTCCATGCCCCAAGTCAATATTGTCAAGAAAACAGAAGTA

CAGACAGGCGGATTCTCCAAGGAGTCAATTTTACCAAAAAGAAATTCGGA

CAAGCTTATTGCTCGTAAAAAAGACTGGGATCCAAAAAAATATGGTGGTT

TTGATAGTCCAACGGTAGCTTATTCAGTCCTAGTGGTTGCTAAGGTGGAA

AAAGGGAAATCGAAGAAGTTAAAATCCGTTAAAGAGTTACTAGGGATCAC

AATTTATGGAAAGAAGTTCCTTTGAAAAAATCCGATTGACTTTTTAGAAG

CTAAAGGATAAGGAAGTTAAAAAAGACTTAATCATTAAACTACCTAAA

TATAGTCTTTTTGAGTTAGAAAACGGTCGTAAACGGATGCTGGCTAGTGC

CGGAGAATTACAAAAAGGAAATGAGCTGGCTCTGCCAAGCAAATATGTGA

ATTTTTTATATTTAGCTAGTCATTATGAAAAGTTGAAGGGTAGTCCAGAA

GATAACGAACAAAAACAATTGTTTGTGGAGCAGCATAAGCATTATTTAGA

TGAGATTATTGAGCAAATCAGTGAATTTTCTAAGCGTGTTATTTTAGCAG

ATGCCAATTTAGATAAAGTTCTTAGTGCATATAACAAACATAGAGACAAA

CCAATACGTGAACAAGCAGAAAATATTATTCATTTATTTACGTTGACGAA

TCTTGGAGCTCCCGCTGCTTTTAAATATTTTGATACAACAATTGATCGTA

AACGATATACGTCTACAAAAGAAGTTTTAGATGCCACTCTTATCCATCAA

TCCATCACTGGTCTTTATGAAACACGCATTGATTTGAGTCAGCTAGGAGG

TGACTGA

SEQ ID NO: 11 (Cas9 amino acid sequence)

MDKKYSIGLDIGTNSVGWAVITDEYKVPSKKFKVLGNTDRHSIKKNLIGA

LLFDSGETAEATRLKRTARRRYTRRKNRICYLQEIFSNEMAKVDDSFFHR

LEESFLVEEDKKHERHPIFGNIVDEVAYHEKYPTIYHLRKKLVDSTDKAD

LRLIYLALAHMIKFRGHFLIEGDLNPDNSDVDKLFIQLVQTYNQLFEENP

INASGVDAKAILSARLSKSRRLENLIAQLPGEKKNGLFGNLIALSLGLTP

NFKSNFDLAEDAKLQLSKDTYDDDLDNLLAQIGDQYADLFLAAKNLSDAI

LLSDILRVNTEITKAPLSASMIKRYDEHHQDLTLLKALVRQQLPEKYKEI

TABLE 4-continued

Sequences of Cas9 used to selectively kill E coli.

FFDQSKNGYAGYIDGGASQEEFYKFIKPILEKMDGTEELLVKLNREDLLR

KQRTFDNGSIPHQIHLGELHAILRRQEDFYPFLKDNREKIEKILTFRIPY

YVGPLARGNSRFAWMTRKSEETITPWNFEEVVDKGASAQSFIERMTNFDK

NLPNEKVLPKHSLLYEYFTVYNELTKVKYVTEGMRKPAFLSGEQKKAIVD

LLFKTNRKVTVKQLKEDYFKKIECFDSVEISGVEDRFNASLGTYHDLLKI

IKDKDFLDNEENEDILEDIVLTLTLFEDREMIEERLKTYAHLFDDKVMKQ

LKRRRYTGWGRLSRKLINGIRDKQSGKTILDFLKSDGFANRNFMQLIHDD

SLTFKEDIQKAQVSGQGDSLHEHIANLAGSPAIKKGILQTVKVVDELVKV

MGRHKPENIVIEMARENQTTQKGQKNSRERMKRIEEGIKELGSQILKEHP

VENTQLQNEKLYLYYLQNGRDMYVDQELDINRLSDYDVDHIVPQSFLKDD

SIDNKVLTRSDKNRGKSDNVPSEEVVKKMKNYWRQLLNAKLITQRKFDNL

TKAERGGLSELDKAGFIKRQLVETRQITKHVAQILDSRMNTKYDENDKLI

REVKVITLKSKLVSDFRKDFQFYKVREINNYHHAHDAYLNAVVGTALIKK

YPKLESEFVYGDYKVYDVRKMIAKSEQEIGKATAKYFFYSNIMNFFKTEI

TLANGEIRKRPLIETNGETGEIVWDKGRDFATVRKVLSMPQVNIVKKTEV

QTGGFSKESILPKRNSDKLIARKKDWDPKKYGGFDSPTVAYSVLVVAKVE

KGKSKKLKSVKELLGITIMERSSFEKNPIDFLEAKGYKEVKKDLIIKLPK

YSLFELENGRKRMLASAGELQKGNELALPSKYVNFLYLASHYEKLKGSPE

DNEQKQLFVEQHKHYLDEIIEQISEFSKRVILADANLDKVLSAYNKHRDK

PIREQAENIIHLFTLTNLGAPAAFKYFDTTIDRKRYTSTKEVLDATLIHQ

SITGLYETRIDLSQLGGD

TABLE 5

| Publication | Gram-neg. bacteria as causative infectious pathogen in cancer patients | E. coli/K. pneumoniae/P. aeruginosa as causative pathogens in bacteraemia in cancer patients [fraction of Gram-neg. cases] |
|---|---|---|
| Samonis et al | 65% | 54% [85%] |
| Velasco et al | 45% | 33% [74%] |
| Marin et al | 55% | 51% [92%] |
| Anatoliotaki et al | 47% | 34% [73%] |

What is claimed is:

1. A method of treating or reducing the risk of a urinary tract infection caused by first bacteria in a subject, the method comprising:
 selectively killing the first bacteria in the subject by cutting a target site comprised by the genomes of the first bacteria using an RNA-guided Cas nuclease,
 wherein the method comprises administering to the subject a nucleic acid sequence comprising or encoding one or more guide RNAs (gRNAs) at a first time (T1) and at a second time (T2), wherein T2 is at least 3 hours after T1,
 wherein the one or more gRNAs hybridize to the target site to guide the Cas nuclease to cut the target site, thereby killing the first bacteria,
 wherein the subject comprises second bacteria of one or more strains or species that are different from that of the first bacteria, wherein the genomes of the second bacteria do not comprise the target site, wherein the genomes of the second bacteria are not cut by the Cas nuclease in the subject, whereby second bacteria survive in the presence of the Cas nuclease in the subject, and
 wherein the number of the first bacteria is reduced at least 100-fold by the first 30 minutes after exposing the subject to the one or more gRNAs.

2. The method of claim 1, wherein the number of the first bacteria is reduced at least 1000-fold by the first 30 minutes after exposing the subject to the one or more gRNAs.

3. The method of claim 1, wherein the number of the first bacteria is reduced at least 100-fold by the first 15 minutes after exposing the subject to the one or more gRNAs.

4. The method of claim 1, wherein the number of the first bacteria is reduced at least 1000-fold by the first 15 minutes after exposing the subject to the one or more gRNAs.

5. The method of claim 1, wherein the reduction in the number of the first bacteria persists for at least 30 minutes immediately after the first 30 minutes after exposing the subject to the one or more gRNAs.

6. The method of claim 2, wherein the reduction in the number of the first bacteria by at least 100-fold is maintained for at least 120 minutes after exposing the subject to the one or more gRNAs.

7. The method of claim 1, wherein the gRNA comprises a sequence capable of hybridizing to a protospacer sequence comprising the target site, wherein the protospacer sequence is 15-45 nucleotides in length.

8. The method of claim 7, wherein the protospacer sequence is 15-25 nucleotides in length.

9. The method of claim 1, wherein the target site is in a protospacer sequence that is adjacent to an NGG, NAG, NGA, NGC, NGGNG, NNGRRT or NNAGAAW protospacer adjacent motif (PAM).

10. The method of claim 1, wherein the nucleic acid sequence is or is comprised by a vector.

11. The method of claim 10, wherein the vector is a phage, phagemid, viriophage, virus, plasmid, or transposon.

12. The method of claim 10, wherein the vector is a conjugative plasmid.

13. The method of claim 12, wherein the conjugative plasmid is delivered from carrier bacteria.

14. The method of claim 10, comprising A method of selectively killing first bacteria in a subject, the method comprising:
 selectively killing the first bacteria in the subject by cutting a target site comprised by the genomes of the first bacteria using an RNA-guided Cas nuclease,
 wherein the method comprises administering to the subject a nucleic acid sequence comprising or encoding one or more guide RNAs (gRNAs),
wherein the nucleic acid sequence is or is comprised by a first nucleic acid vector, and wherein the method comprises administering a second nucleic acid vector to the subject, wherein the second vector encodes the Cas nuclease,
 wherein the one or more gRNAs hybridize to the target site to guide the Cas nuclease to cut the target site, thereby killing the first bacteria,
 wherein the subject comprises second bacteria of one or more strains or species that are different from that of the first bacteria, wherein the genomes of the second bacteria do not comprise the target site, wherein the genomes of the second bacteria are not cut by the Cas nuclease in the subject, whereby second bacteria survive in the presence of the Cas nuclease in the subject, and
 wherein the number of the first bacteria is reduced at least 100-fold by the first 30 minutes after exposing the subject to the one or more gRNAs.

15. The method of claim 1, wherein the Cas nuclease is an endogenous Cas nuclease of the first bacteria.

16. The method of claim 1, wherein the Cas nuclease is a Cpf1, a Cas9, or a Cas3.

17. The method of claim 1, wherein the Cas nuclease is a Cas9.

18. The method of claim 1, wherein the Cas nuclease is a Cas3.

19. The method of claim 1, wherein the first bacteria are *Clostridium*.

20. A method of selectively killing treating or reducing the risk of a urinary tract infection caused by first bacteria in a subject, the method comprising:
 selectively killing the first bacteria in the subject by cutting a target site comprised by the genomes of the first bacteria using an RNA-guided Cas nuclease,
 wherein the method comprises administering to the subject a nucleic acid sequence comprising or encoding one or more guide RNAs (gRNAs) at a first time (T1) and at a second time (T2), wherein T2 is at least 3 hours after T1,
 wherein the one or more gRNAs hybridize to the target site to guide the Cas nuclease to cut the target site, thereby killing the first bacteria,
 wherein the subject comprises second bacteria of one or more strains or species that are different from that of the first bacteria, wherein the genomes of the second bacteria do not comprise the target site, wherein the genomes of the second bacteria are not cut by the Cas nuclease in the subject, whereby second bacteria survive in the presence of the Cas nuclease in the subject, and wherein the method comprises maintaining reduction in the number of the first bacteria by at least 100-fold for at least 60 minutes after exposing the subject to the one or more gRNAs.

21. The method of claim 1, wherein the second bacteria are of one or more species that are different from that of the first bacteria.

22. The method of claim 20, wherein the second bacteria are of one or more species that are different from that of the first bacteria.

23. The method of claim 20, wherein the nucleic acid sequence is or is comprised by a vector selected from the group consisting of a phage, phagemid, viriophage, virus, plasmid, and a transposon.

24. The method of claim 20, wherein the nucleic acid sequence is or is comprised by a conjugative plasmid.

25. The method of claim 20, wherein the Cas nuclease is a Cas9.

26. The method of claim 20, wherein the Cas nuclease is a Cas3.

27. The method of claim 1, wherein the subject has been administered an immunosuppressant medication.

28. The method of claim 20, wherein the subject has been administered an immunosuppressant medication.

* * * * *

SEQUENCE LISTING

```
<160> NUMBER OF SEQ ID NOS: 11

<210> SEQ ID NO 1
<211> LENGTH: 23
<212> TYPE: DNA
<213> ORGANISM: Artificial Sequence
<220> FEATURE:
<223> OTHER INFORMATION: Synthetic Construct

<400> SEQUENCE: 1
taggtgaagt ccctcgcgga tgg                                             23

<210> SEQ ID NO 2
<211> LENGTH: 23
<212> TYPE: DNA
<213> ORGANISM: Artificial Sequence
<220> FEATURE:
<223> OTHER INFORMATION: Synthetic Construct

<400> SEQUENCE: 2
cacccgcatt acctttatgc agg                                             23

<210> SEQ ID NO 3
<211> LENGTH: 23
<212> TYPE: DNA
<213> ORGANISM: Artificial Sequence
<220> FEATURE:
<223> OTHER INFORMATION: Synthetic Construct

<400> SEQUENCE: 3
gcgcgggtgt ggttgtgctt cgg                                             23

<210> SEQ ID NO 4
<211> LENGTH: 37
<212> TYPE: DNA
```

```
<213> ORGANISM: Artificial Sequence
<220> FEATURE:
<223> OTHER INFORMATION: Synthetic Construct

<400> SEQUENCE: 4
acaccttaac ccagccatag agtctgataa taacttc                                37

<210> SEQ ID NO 5
<211> LENGTH: 37
<212> TYPE: DNA
<213> ORGANISM: Artificial Sequence
<220> FEATURE:
<223> OTHER INFORMATION: Synthetic Construct

<400> SEQUENCE: 5
gacttatttg agtctataga gaaacctagt tcagtaa                                37

<210> SEQ ID NO 6
<211> LENGTH: 37
<212> TYPE: DNA
<213> ORGANISM: Artificial Sequence
<220> FEATURE:
<223> OTHER INFORMATION: Synthetic Construct

<400> SEQUENCE: 6
tcgacgactt cttccaaaag gttagataat cggcttc                                37

<210> SEQ ID NO 7
<211> LENGTH: 37
<212> TYPE: DNA
<213> ORGANISM: Artificial Sequence
<220> FEATURE:
<223> OTHER INFORMATION: Synthetic Construct

<400> SEQUENCE: 7
gtacaggatg gacccgcgtc tgattagcta gttggta                                37

<210> SEQ ID NO 8
<211> LENGTH: 37
<212> TYPE: DNA
<213> ORGANISM: Artificial Sequence
<220> FEATURE:
<223> OTHER INFORMATION: Synthetic Construct

<400> SEQUENCE: 8
tcctcatgga gatactgctg tttattatgc tatggta                                37

<210> SEQ ID NO 9
<211> LENGTH: 2322
<212> TYPE: DNA
<213> ORGANISM: Artificial Sequence
<220> FEATURE:
<223> OTHER INFORMATION: Synthetic Construct

<400> SEQUENCE: 9
tcaaataaat tggtctattt cattacttat aagcacacct ttaccaaata tctgttttgt        60
atgcttattt tcgtatatat catatttata taaaagtatt tttaaatctt caagaccttt       120
cacctgtatg tcaattacat tttgtttagc tttatatatt ggtaaattta cagttttttt       180
aattatctct cttcttgctt tttttctctt agactttatt ttatttatca attgtctatc       240
atcattacta tatgcattta taagctcttg tcccaactct tcataatctt tgattaaagt       300
ttcttcaatt ttattatata tatcctctgg aattactgta tatccttcaa tatttctaag       360
tatattttgt gcatctttag aacctaaact atatggcgtt atagtatcta aaatatttaa       420
```

```
agcactggta aatctctttt caaaagctgt accttctaga ctttctttag agtatagtat      480
cttaaccatt tctaccttat attttctttt catcttcaca cattctttc catttataaa       540 agttttcagt agctcaagtc cttttctac aatatcctta tcataaatac tacctattcc       600
tgtagctttt tctgtatata taaatatatt tgggctattt tcttcatact cacgacttct      660
ataacatcta ccaaatcgtt gaaatagact gtcaagtgtt gaattttctg tatgaagctc      720
atcaaaatca atatcaaggg atgcttccac taattgtgta gtaatccaaa taccattact      780
atcactatct gcaaattctt ttatatattt ttctaatttt gctctatctt cttgtatata      840
catagaatgt aaaagattta agttgacatc tattcctttt ggcttaacta tttcttctat      900
taactcatat ttttctacag cacttttaac tgtatttact attacaagaa cttttttatt      960
cattccactt tgtattattt tacctaagtt ttcatctatt gaattttcta caatagacac     1020
acaatgtctt attttttctg tattacatgt caattcagct aagttactat tcattacacc     1080 tcttttttt aattcatcta tatatatggt tggcatagta gctgtcatta tcataaatct      1140
gccacctatc ttatgtatca tttctatacc ttttaccaat acagctgcta tttctggtga     1200
atatgcttgt atctcatcta ttactacttt tgaaatatgct aatgttgagt cactttttc     1260 ataccctcta tacaaaaaag gaaatttaaa tatttggtct attgtagaaa atgtcagttt     1320
gcaagataat aactttgcta aatctacaat ctcacttgaa ttttcttgat tactttcttc     1380
tagataatct attgctgttg aatgtaacaa acctaagaat gtatcatttg attctccaac     1440
tccaactata tttttgctc tatcaaataa tgcatttata cttactctta atggaagtgt      1500
aaaaaatgcc ttgtctttat ctatccaaat taaggcagtt tctgtttttc ccattcctgt     1560
aggtgcaatc agtattatat tcttatttct attagattta gcaaatgatt gagcctctct     1620
caaactacca aactctttca ttaaataatt ttctgtctgt tctcctatat ttataacatt     1680
attgcattcc acaacttcat gagcagaagc actgtggtct aatctatgta gtattccttt     1740
taacataata tataaattat agtacttgtg attttatct attctttttt ctacactttg      1800
tagatatact ttactcaatt tttctgtttt tattggatat ctaactttaa attcatgctg     1860
tagttcataa actttattta ttaaatcttc atctaatatt ttttgtatta aatttttaaa     1920
atctttatct ataaagatat ctctttcatg atgatataca ataacttgat ttaatactgc     1980
tctaagttct ttatttttt tcctgtctat ataactataa tcaataaatg caggagaaag     2040
ataattatgg cctacattat tttctaaatg agttactatt ttaggttcat ttattttagt     2100
atccattctg cttttttatta actcttgaaa cggtgaaaat gctttccaa tatcatgaaa     2160 ttctataaca aagtcaagta attgccaaaa tatctcctct tctagaaaat ctaagctatt     2220 tatattttt ccataacttt ctcttaatac attcatttgt tttaaaagtt catcagtatg      2280
ttctctaagt gtttccactg gattagattt agcatataac at                       2322
```

<210> SEQ ID NO 10
<211> LENGTH: 4107
<212> TYPE: DNA
<213> ORGANISM: Artificial Sequence
<220> FEATURE:
<223> OTHER INFORMATION: Synthetic Construct

<400> SEQUENCE: 10

```
atggataaga aatactcaat aggcttagat atcggcacaa atagcgtcgg atgggcggtg       60
atcactgatg aatataaggt tccgtctaaa aagttcaagg ttctgggaaa tacagaccgc      120
```

```
cacagtatca aaaaaaatct tatagggget cttttatttg acagtggaga gacagcggaa       180
gcgactcgtc tcaaacggac agctcgtaga aggtatacac gtcggaagaa tcgtatttgt       240
tatctacagg agattttttc aaatgagatg gcgaaagtag atgatagttt ctttcatcga       300
cttgaagagt cttttttggt ggaagaagac aagaagcatg aacgtcatcc tatttttgga       360
aatatagtag atgaagttgc ttatcatgag aaatatccaa ctatctatca tctgcgaaaa       420
aaattggtag attctactga taaagcggat ttgcgcttaa tctatttggc cttagcgcat       480
atgattaagt ttcgtggtca tttttttgatt gagggagatt taaatcctga taatagtgat      540
gtggacaaac tatttatcca gttggtacaa acctacaatc aattatttga agaaaaccct       600
attaacgcaa gtggagtaga tgctaaagcg attcttctg cacgattgag taaatcaaga       660
cgattagaaa atctcattgc tcagctcccc ggtgagaaga aaaatggctt atttgggaat       720
ctcattgctt tgtcattggg tttgacccct aattttaaat caaattttga tttggcagaa       780
gatgctaaat tacagctttc aaaagatact tacgatgatg atttagataa tttattggcg       840
caaattggag atcaatatgc tgatttgttt ttggcagcta agaattatc agatgctatt        900 ttacttttcag atatcctaag agtaaatact gaaataacta aggctcccct atcagcttca     960
atgattaaac gctacgatga acatcatcaa gacttgactc ttttaaaagc tttagttcga     1020
caacaacttc cagaaaagta taagaaaatc ttttttgatc aatcaaaaaa cggatatgca     1080
ggttatattg atgggggagc tagccaagaa gaattttata aatttatcaa accaatttta     1140
gaaaaaatgg atggtactga ggaattattg gtgaaactaa atcgtgaaga tttgctgcgc     1200
aagcaacgga cctttgacaa cggctctatt ccccatcaaa ttcacttggg tgagctgcat     1260
gctattttga gaagacaaga agactttat ccatttttaa aagacaatcg tgagaagatt      1320
gaaaaaatct tgacttttcg aattccttat tatgttggtc cattggcgcg tggcaatagt    1380
cgttttgcat ggatgactcg gaagtctgaa gaaacaatta ccccatggaa ttttgaagaa    1440
gttgtcgata aaggtgcttc agctcaatca tttattgaac gcatgacaaa ctttgataaa    1500
aatcttccaa atgaaaaagt actaccaaaa catagtttgc tttatgagta ttttacggtt    1560
tataacgaat tgacaaaggt caaatatgtt actgaaggaa tgcgaaaacc agcatttctt    1620
tcaggtgaac agaagaaagc cattgttgat ttactcttca aaacaaatcg aaaagtaacc    1680
gttaagcaat aaaagaaga ttatttcaaa aaaatagaat gttttgatag tgttgaaatt    1740
tcaggagttg aagatagatt taatgcttca ttaggtacct accatgattt gctaaaaatt    1800
attaaagata aagatttttt ggataatgaa gaaaatgaag atatcttaga ggatattgtt    1860
ttaacattga ccttatttga agatagggag atgattgagg aaagacttaa aacatatgct    1920
cacctctttg atgataaggt gatgaaacag cttaaacgtc gccgttatac tggttggggga   1980 cgtttgtctc gaaaattgat taatggtatt agggataagc aatctggcaa aacaatatta    2040 gatttttga aatcagatgg ttttgccaat cgcaatttta tgcagctgat ccatgatgat    2100
agtttgacat ttaaagaaga cattcaaaaa gcacaagtgt ctggacaagg cgatagttta   2160
catgaacata ttgcaaattt agctggtagc cctgctatta aaaaaggtat tttacagact   2220
gtaaaagttg ttgatgaatt ggtcaaagta atggggcggc ataagccaga aaatatcgtt   2280
attgaaatgg cacgtgaaaa tcagacaact caaaagggcc agaaaaattc gcgagagcgt   2340
atgaaacgaa tcgaagaagg tatcaaagaa ttaggaagtc agattcttaa agagcatcct   2400
gttgaaaata ctcaattgca aaatgaaaag ctctatctct attatctcca aaatggaaga   2460
gacatgtatg tggaccaaga attagatatt aatcgtttaa gtgattatga tgtcgatcac   2520
```

```
attgttccac aaagtttcct taaagacgat tcaatagaca ataaggtctt aacgcgttct    2580
gataaaaatc gtggtaaatc ggataacgtt ccaagtgaag aagtagtcaa aaagatgaaa    2640
aactattgga gacaacttct aaacgccaag ttaatcactc aacgtaagtt tgataattta    2700
acgaaagctg aacgtggagg tttgagtgaa cttgataaag ctggttttat caaacgccaa    2760
ttggttgaaa ctcgccaaat cactaagcat gtggcacaaa ttttggatag tcgcatgaat    2820
actaaatacg atgaaaatga taaacttatt cgagaggtta aagtgattac cttaaaatct    2880
aaattagttt ctgacttccg aaaagatttc caattctata agtacgtga gattaacaat     2940
taccatcatg cccatgatgc gtatctaaat gccgtcgttg gaactgcttt gattaagaaa    3000
tatccaaaac ttgaatcgga gtttgtctat ggtgattata agtttatga tgttcgtaaa     3060
atgattgcta agtctgagca agaaataggc aaagcaaccg caaatatttt cttttactct    3120
aatatcatga acttcttcaa aacagaaatt acacttgcaa atggagagat tcgcaaacgc    3180
cctctaatcg aaactaatgg ggaaactgga gaaattgtct gggataaagg gcgagatttt    3240
gccacagtgc gcaaagtatt gtccatgccc caagtcaata ttgtcaagaa aacagaagta    3300
cagacaggcg gattctccaa ggagtcaatt ttaccaaaaa gaaattcgga caagcttatt    3360
gctcgtaaaa aagactggga tccaaaaaaa tatggtggtt ttgatagtcc aacggtagct    3420
tattcagtcc tagtggttgc taaggtggaa aaagggaaat cgaagaagtt aaaatccgtt    3480
aaagagttac tagggatcac aattatggaa agaagttcct ttgaaaaaaa tccgattgac    3540
tttttagaag ctaaaggata taggaagtt aaaaaagact taatcattaa actacctaaa     3600
tatagtcttt ttgagttaga aaacggtcgt aaacggatgc tggctagtgc cggagaatta    3660
caaaaaggaa atgagctggc tctgccaagc aaatatgtga ttttttata tttagctagt     3720
cattatgaaa agttgaaggg tagtccagaa gataacgaac aaaaacaatt gtttgtggag    3780
cagcataagc attatttaga tgagattatt gagcaaatca gtgaattttc taagcgtgtt    3840
attttagcag atgccaattt agataaagtt cttagtgcat ataacaaaca tagagacaaa    3900
ccaatacgtg aacaagcaga aaatattatt catttattta cgttgacgaa tcttggagct    3960
cccgctgctt ttaaatattt tgatacaaca attgatcgta aacgatatac gtctacaaaa    4020
gaagttttag atgccactct tatccatcaa tccatcactg gtctttatga aacacgcatt    4080
gatttgagtc agctaggagg tgactga                                        4107
```

<210> SEQ ID NO 11
<211> LENGTH: 1368
<212> TYPE: PRT
<213> ORGANISM: Artificial Sequence
<220> FEATURE:
<223> OTHER INFORMATION: Synthetic Construct

<400> SEQUENCE: 11

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

-continued

```
Tyr Leu Gln Glu Ile Phe Ser Asn Glu Met Ala Lys Val Asp Asp Ser
                85                  90                  95
Phe Phe His Arg Leu Glu Glu Ser Phe Leu Val Glu Glu Asp Lys Lys
            100                 105                 110
His Glu Arg His Pro Ile Phe Gly Asn Ile Val Asp Glu Val Ala Tyr
        115                 120                 125
His Glu Lys Tyr Pro Thr Ile Tyr His Leu Arg Lys Lys Leu Val Asp
    130                 135                 140
Ser Thr Asp Lys Ala Asp Leu Arg Leu Ile Tyr Leu Ala Leu Ala His
145                 150                 155                 160
Met Ile Lys Phe Arg Gly His Phe Leu Ile Glu Gly Asp Leu Asn Pro
                165                 170                 175
Asp Asn Ser Asp Val Asp Lys Leu Phe Ile Gln Leu Val Gln Thr Tyr
            180                 185                 190
Asn Gln Leu Phe Glu Glu Asn Pro Ile Asn Ala Ser Gly Val Asp Ala
        195                 200                 205
Lys Ala Ile Leu Ser Ala Arg Leu Ser Lys Ser Arg Arg Leu Glu Asn
    210                 215                 220
Leu Ile Ala Gln Leu Pro Gly Glu Lys Lys Asn Gly Leu Phe Gly Asn
225                 230                 235                 240
Leu Ile Ala Leu Ser Leu Gly Leu Thr Pro Asn Phe Lys Ser Asn Phe
                245                 250                 255
Asp Leu Ala Glu Asp Ala Lys Leu Gln Leu Ser Lys Asp Thr Tyr Asp
            260                 265                 270
Asp Asp Leu Asp Asn Leu Leu Ala Gln Ile Gly Asp Gln Tyr Ala Asp
        275                 280                 285
Leu Phe Leu Ala Ala Lys Asn Leu Ser Asp Ala Ile Leu Leu Ser Asp
    290                 295                 300
Ile Leu Arg Val Asn Thr Glu Ile Thr Lys Ala Pro Leu Ser Ala Ser
305                 310                 315                 320
Met Ile Lys Arg Tyr Asp Glu His His Gln Asp Leu Thr Leu Leu Lys
                325                 330                 335
Ala Leu Val Arg Gln Gln Leu Pro Glu Lys Tyr Lys Glu Ile Phe Phe
            340                 345                 350
Asp Gln Ser Lys Asn Gly Tyr Ala Gly Tyr Ile Asp Gly Gly Ala Ser
        355                 360                 365
Gln Glu Glu Phe Tyr Lys Phe Ile Lys Pro Ile Leu Glu Lys Met Asp
    370                 375                 380
Gly Thr Glu Glu Leu Leu Val Lys Leu Asn Arg Glu Asp Leu Leu Arg
385                 390                 395                 400
Lys Gln Arg Thr Phe Asp Asn Gly Ser Ile Pro His Gln Ile His Leu
                405                 410                 415
Gly Glu Leu His Ala Ile Leu Arg Arg Gln Glu Asp Phe Tyr Pro Phe
            420                 425                 430
Leu Lys Asp Asn Arg Glu Lys Ile Glu Lys Ile Leu Thr Phe Arg Ile
        435                 440                 445
Pro Tyr Tyr Val Gly Pro Leu Ala Arg Gly Asn Ser Arg Phe Ala Trp
    450                 455                 460
Met Thr Arg Lys Ser Glu Glu Thr Ile Thr Pro Trp Asn Phe Glu Glu
465                 470                 475                 480
Val Val Asp Lys Gly Ala Ser Ala Gln Ser Phe Ile Glu Arg Met Thr
                485                 490                 495
```

```
Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
            565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
            595                 600                 605

Asn Glu Glu Asn Glu Asp Ile Leu Glu Asp Ile Val Leu Thr Leu Thr
            610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
            645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
            675                 680                 685

Ala Asn Arg Asn Phe Met Gln Leu Ile His Asp Asp Ser Leu Thr Phe
            690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
            725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
            755                 760                 765

Thr Thr Gln Lys Gly Gln Lys Asn Ser Arg Glu Arg Met Lys Arg Ile
770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
            805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
    835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
            885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
```

```
                915                 920                 925
Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
                980                 985                 990

Val Gly Thr Ala Leu Ile Lys Lys Tyr Pro Lys Leu Glu Ser Glu Phe
        995                 1000                1005

Val Tyr Gly Asp Tyr Lys Val Tyr Asp Val Arg Lys Met Ile Ala Lys
    1010                1015                1020

Ser Glu Gln Glu Ile Gly Lys Ala Thr Ala Lys Tyr Phe Phe Tyr Ser
1025                1030                1035                1040

Asn Ile Met Asn Phe Phe Lys Thr Glu Ile Thr Leu Ala Asn Gly Glu
                1045                1050                1055

Ile Arg Lys Arg Pro Leu Ile Glu Thr Asn Gly Glu Thr Gly Glu Ile
                1060                1065                1070

Val Trp Asp Lys Gly Arg Asp Phe Ala Thr Val Arg Lys Val Leu Ser
    1075                1080                1085

Met Pro Gln Val Asn Ile Val Lys Lys Thr Glu Val Gln Thr Gly Gly
    1090                1095                1100

Phe Ser Lys Glu Ser Ile Leu Pro Lys Arg Asn Ser Asp Lys Leu Ile
1105                1110                1115                1120

Ala Arg Lys Lys Asp Trp Asp Pro Lys Lys Tyr Gly Gly Phe Asp Ser
                1125                1130                1135

Pro Thr Val Ala Tyr Ser Val Leu Val Val Ala Lys Val Glu Lys Gly
            1140                1145                1150

Lys Ser Lys Lys Leu Lys Ser Val Lys Glu Leu Leu Gly Ile Thr Ile
                1155                1160                1165

Met Glu Arg Ser Ser Phe Glu Lys Asn Pro Ile Asp Phe Leu Glu Ala
    1170                1175                1180

Lys Gly Tyr Lys Glu Val Lys Lys Asp Leu Ile Ile Lys Leu Pro Lys
1185                1190                1195                1200

Tyr Ser Leu Phe Glu Leu Glu Asn Gly Arg Lys Arg Met Leu Ala Ser
                1205                1210                1215

Ala Gly Glu Leu Gln Lys Gly Asn Glu Leu Ala Leu Pro Ser Lys Tyr
            1220                1225                1230

Val Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys His
        1250                1255                1260

Tyr Leu Asp Glu Ile Ile Glu Gln Ile Ser Glu Phe Ser Lys Arg Val
1265                1270                1275                1280

Ile Leu Ala Asp Ala Asn Leu Asp Lys Val Leu Ser Ala Tyr Asn Lys
                1285                1290                1295

His Arg Asp Lys Pro Ile Arg Glu Gln Ala Glu Asn Ile Ile His Leu
            1300                1305                1310

Phe Thr Leu Thr Asn Leu Gly Ala Pro Ala Ala Phe Lys Tyr Phe Asp
    1315                1320                1325

Thr Thr Ile Asp Arg Lys Arg Tyr Thr Ser Thr Lys Glu Val Leu Asp
        1330                1335                1340
```

```
Ala Thr Leu Ile His Gln Ser Ile Thr Gly Leu Tyr Glu Thr Arg Ile
1345                1350                1355                1360

Asp Leu Ser Gln Leu Gly Gly Asp
                1365
```